US012612360B2

(12) United States Patent
Bernardelli et al.

(10) Patent No.: US 12,612,360 B2
(45) Date of Patent: Apr. 28, 2026

(54) SUBSTITUTED 6,7-DIHYDRO-5H-BENZO[7]ANNULENE COMPOUNDS AND THEIR DERIVATIVES, PROCESSES FOR THEIR PREPARATION AND THERAPEUTIC USES THEREOF

(71) Applicant: Sanofi, Paris (FR)

(72) Inventors: Patrick Bernardelli, Paris (FR); Marc Bianciotto, Paris (FR); Youssef El Ahmad, Paris (FR); Frank Halley, Paris (FR); Patrick Mougenot, Paris (FR); Frédéric Petit, Paris (FR); Franck Slowinski, Paris (FR); Corinne Terrier, Paris (FR)

(73) Assignee: SANOFI, Paris (FR)

( * ) Notice: Subject to any disclaimer, the term of this patent is extended or adjusted under 35 U.S.C. 154(b) by 445 days.

(21) Appl. No.: 18/032,502

(22) PCT Filed: Oct. 19, 2021

(86) PCT No.: PCT/EP2021/078916

§ 371 (c)(1),
(2) Date: Apr. 18, 2023

(87) PCT Pub. No.: WO2022/084298

PCT Pub. Date: Apr. 28, 2022

(65) Prior Publication Data

US 2024/0101512 A1 Mar. 28, 2024

(30) Foreign Application Priority Data

Oct. 19, 2020 (EP) .................................... 20306236
Sep. 16, 2021 (EP) .................................... 21306282

(51) Int. Cl.
*C07D 205/10* (2006.01)
*A61P 19/10* (2006.01)
(Continued)

(52) U.S. Cl.
CPC ............ *C07D 205/10* (2013.01); *A61P 19/10* (2018.01); *A61P 35/00* (2018.01); *C07D 401/06* (2013.01);
(Continued)

(58) Field of Classification Search
None
See application file for complete search history.

(56) References Cited

U.S. PATENT DOCUMENTS 6,495,607 B2 12/2002 Bohlmann et al.
7,429,681 B2 9/2008 Pinney et al.
(Continued)

FOREIGN PATENT DOCUMENTS

CN 1309635 A 8/2001
CN 106924210 A 7/2017
(Continued)

OTHER PUBLICATIONS

André, F., et al., Alpelisib for PIK3CA-Mutated, Hormone Receptor-Positive Advanced Breast Cancer, The New England Journal of Medicine, vol. 380, No. 20, May 16, 2019, 12 pages (1929-1940).
Anstead, Gregory, M. et al., "2,3-Diarylindenes and 2,3-Diarylindenones: Synthesis, Molecular Structure, Photochemistry, Estrogen Receptor Binding Activity, and Comparisons with Related Triarylethylenes", Journal of Medicinal Chemistry, 1988, vol. 31, No. 7, pp. 1316-1326.
Bardia, A., et al., Dose-escalation study of SAR439859, an oral selective estrogen receptor (ER) degrader (SERD), in postmenopausal women with ER+/HER2-metastatic breast cancer (mBC), Journal of Clinical Oncology, vol. 37, Suppl. 15, p. 1054 (May 20, 2019).
Bernardelli, P., et al., Pending U.S. Appl. No. 18/032,500, filed Apr. 18, 2023.
Billot, P. et al., Pending U.S. Appl. No. 17/783,364, filed Jun. 8, 2022.
Boinsard, S., et al., Pending U.S. Appl. No. 17/765,169, filed Mar. 30, 2022.
Bouaboula, M. et al., Pending U.S. Appl. No. 18/037,949, filed May 19, 2023.
Bouaboula, M. et al., U.S. Appl. No. 16/414,558, filed May 16, 2019 (Issued).
Bouaboula, M., et al., Pending U.S. Appl. No. 16/634,089, filed Jan. 24, 2020. (Issued).
(Continued)

*Primary Examiner* — Sarah Pihonak
*Assistant Examiner* — Donna M Nestor
(74) *Attorney, Agent, or Firm* — McNeill PLLC

(57) ABSTRACT

The present application relates to compounds of formula (I), or pharmaceutically acceptable salts thereof: wherein R1 and R2 represent hydrogen or deuterium; R3 represents hydrogen, —COOH or —OH; R3' and R3" represent hydrogen, methyl, methoxy, chlorine, fluorine or cyano; R4 and R41 represent hydrogen or fluorine; R5 represents hydrogen, fluorine or (C1-C3)alkyl; R6 represents phenyl, fused phenyl, bicyclic group comprising 5 to 12 carbon atoms, heteroaryl group comprising 2 to 9 carbon atoms and comprising from 1 to 3 heteroatoms, cycloalkyl group comprising 3 to 7 carbon atoms, $(C_3-C_6)$cycloalkyl(C1-C3)alkyl group, 3 to 8 membered-heterocycloalkyl group comprising 1 or 2 heteroatoms, (C1-C6)alkyl, and phenyl(C1-C2)alkyl group; X represents $—CH_2—$, —O— or —S—; Y represents —CH=, —N= or —CR"=, wherein R" represents (C1-C3)alkyl, halogen, cyano, or (C1-C3)fluoroalkyl; R7 represents (C1-C3)alkyl, halogen atom, cyano, or (C1-C3)fluoroalkyl; R8 represents hydrogen or fluorine; R9 represents hydrogen, $(C1-C_3)$alkyl or a cyclopropyl; n is 0, 1 or 2; and m is 0 or 1. Further disclosed are process for preparing the same, pharmaceutical compositions comprising them as well as said compounds of formula (I) for use as an inhibitor and degrader of estrogen receptors, in particular in the treatment of ovulatory dysfunction, cancer, endometriosis, osteoporosis, benign prostatic hypertrophy or inflammation.

(Continued)

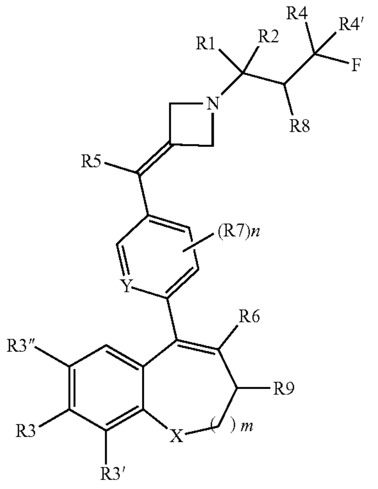

(I)

26 Claims, No Drawings

(51) Int. Cl.

| | |
|---|---|
| *A61P 35/00* | (2006.01) |
| *C07D 401/06* | (2006.01) |
| *C07D 401/10* | (2006.01) |
| *C07D 413/10* | (2006.01) |
| *C07D 417/10* | (2006.01) |

(52) U.S. Cl.
CPC ......... *C07D 401/10* (2013.01); *C07D 413/10* (2013.01); *C07D 417/10* (2013.01)

(56) References Cited

U.S. PATENT DOCUMENTS

| | | | |
|---|---|---|---|
| 7,612,114 | B2 | 11/2009 | Hamaoka et al. |
| 7,799,824 | B2 | 9/2010 | Lagu et al. |
| 8,299,112 | B2 | 10/2012 | Smith et al. |
| 9,309,211 | B2 | 4/2016 | Xiao et al. |
| 9,540,361 | B2 | 1/2017 | Dijcks et al. |
| 9,714,221 | B1 | 7/2017 | Bouaboula et al. |
| 9,845,291 | B2 | 12/2017 | Liang et al. |
| 10,570,090 | B2 | 2/2020 | Bouaboula et al. |
| 10,966,963 | B2 | 4/2021 | Labadie et al. |
| 11,149,031 | B2 | 10/2021 | Bouaboula et al. |
| 11,214,541 | B2 | 1/2022 | Bouaboula et al. |
| 11,260,057 | B2 | 3/2022 | Bouaboula et al. |
| 11,713,296 | B2 | 8/2023 | Malpart et al. |
| 12,157,721 | B2 | 12/2024 | Rabion et al. |
| 2012/0130219 | A1 | 5/2012 | Zhao et al. |
| 2013/0252890 | A1 | 9/2013 | Wintermantel et al. |
| 2015/0080438 | A1 | 3/2015 | Wintermantel et al. |
| 2015/0157606 | A1 | 6/2015 | Maneval et al. |
| 2016/0184311 | A1 | 6/2016 | Chen et al. |
| 2017/0197915 | A9 | 7/2017 | Liang et al. |
| 2017/0233340 | A1 | 8/2017 | Bouaboula et al. |
| 2018/0153828 | A1 | 6/2018 | Garner et al. |
| 2019/0167652 | A1 | 6/2019 | Abrams et al. |
| 2020/0155521 | A1 | 5/2020 | Schwartz et al. |
| 2020/0352905 | A1 | 11/2020 | Cartot-Cotton et al. |
| 2020/0361918 | A1 | 11/2020 | Bouaboula et al. |
| 2020/0392081 | A1 | 12/2020 | Bouaboula et al. |
| 2021/0188771 | A1 | 6/2021 | Rabion et al. |
| 2021/0188772 | A1 | 6/2021 | Malpart et al. |
| 2022/0073460 | A1 | 3/2022 | Bouaboula et al. |
| 2022/0204488 | A1 | 6/2022 | Bouaboula et al. |
| 2022/0362248 | A1 | 11/2022 | Bouaboula et al. |
| 2023/0028566 | A1 | 1/2023 | Billot et al. |
| 2023/0089371 | A1 | 3/2023 | Bouaboula et al. |
| 2023/0115865 | A1 | 4/2023 | Boisnard et al. |
| 2023/0382854 | A1 | 11/2023 | Bernardelli et al. |
| 2023/0404971 | A1 | 12/2023 | Bouaboula et al. |
| 2024/0091194 | A1 | 3/2024 | Cartot-Cotton et al. |
| 2024/0197692 | A1 | 6/2024 | Bouaboula et al. |
| 2024/0197739 | A1 | 6/2024 | Bouaboula et al. |
| 2025/0042849 | A1 | 2/2025 | Rabion et al. |

FOREIGN PATENT DOCUMENTS

| | | | |
|---|---|---|---|
| CN | 109896991 | A | 6/2019 |
| EA | 023947 | B1 | 7/2016 |
| EP | 1229036 | A1 | 8/2002 |
| EP | 3434272 | A1 | 1/2019 |
| JP | 2002520388 | A | 7/2002 |
| JP | 2005528320 | A | 9/2005 |
| JP | 2008512348 | A | 4/2008 |
| JP | 2008546706 | A | 12/2008 |
| JP | 2011500538 | A | 1/2011 |
| JP | 2013530973 | A | 8/2013 |
| JP | 2015500814 | A | 1/2015 |
| JP | 2018537406 | A | 12/2018 |
| WO | 1992015579 | A1 | 9/1992 |
| WO | 2000003979 | A1 | 1/2000 |
| WO | 2003016270 | A2 | 2/2003 |
| WO | 2003091239 | A1 | 11/2003 |
| WO | 2004058682 | A1 | 7/2004 |
| WO | 2006012135 | A1 | 2/2006 |
| WO | 2006138427 | A2 | 12/2006 |
| WO | 2009047343 | A1 | 4/2009 |
| WO | 2009101634 | A2 | 8/2009 |
| WO | 2012037410 | A2 | 3/2012 |
| WO | 2012037411 | A2 | 3/2012 |
| WO | 2012068284 | A2 | 5/2012 |
| WO | 2013097773 | A1 | 7/2013 |
| WO | 2015028409 | A1 | 3/2015 |
| WO | 2016051374 | A1 | 4/2016 |
| WO | 2016097071 | A1 | 6/2016 |
| WO | 2016097072 | A1 | 6/2016 |
| WO | 2016176666 | A1 | 11/2016 |
| WO | 2017140669 | A1 | 8/2017 |
| WO | 2018091153 | A1 | 5/2018 |
| WO | 2019020559 | A1 | 1/2019 |
| WO | 2019106604 | A1 | 6/2019 |
| WO | 2019144132 | | 7/2019 |
| WO | 2020014435 | A1 | 1/2020 |
| WO | 2020049153 | A1 | 3/2020 |
| WO | 2020112765 | A1 | 6/2020 |
| WO | 2020225375 | A1 | 11/2020 |
| WO | 2021116074 | A1 | 6/2021 |
| WO | 2021127043 | A1 | 6/2021 |
| WO | 2021170793 | A1 | 9/2021 |
| WO | 2021178846 | A1 | 9/2021 |
| WO | 2022084280 | A1 | 4/2022 |
| WO | 2022106711 | A1 | 5/2022 |
| WO | 2022218956 | A1 | 10/2022 |
| WO | 2022218958 | A1 | 10/2022 |

OTHER PUBLICATIONS

Bouaboula, M., et al., Pending U.S. Appl. No. 17/460,629, filed Aug. 30, 2021.

Bouaboula, M., et al., Pending U.S. Appl. No. 17/532,051, filed Nov. 22, 2021.

Bouaboula, M., et al., Pending U.S. Appl. No. 17/579,187, filed Jan. 19, 2022.

Bouaboula, M., et al., Pending U.S. Appl. No. 17/802,223, filed Aug. 25, 2022.

Bouaboula, M., et al., U.S. Appl. No. 16/743,504, filed Jan. 15, 2020 (Abandoned).

Bouaboula, M., et al., U.S. Appl. No. 17/124,852, filed Dec. 17, 2020. (Issued).

Campone, M., et al., "Abstract P5-11-02: Dose-escalation study of SAR439859, an oral selective estrogen receptor degrader, in post-menopausal women with estrogen receptor-positive and human

(56) References Cited

OTHER PUBLICATIONS epidermal growth factor receptor 2-negative metastatic breast cancer," Cancer Research, vol. 80, Suppl. 4, pp. 1-4 (Feb. 2020).
Cancer [online]—Medline Plus, [Retrieved on Jul. 6, 2007] Retrieved from the Internet, URL: http://www.nlm.nih.gov/medlineplus/cancer.html, pp. 1-10.
Cartot-Cotton, S., et al., Pending U.S. Appl. No. 16/870,031, filed May 8, 2020.
Chandarlapaty, S., et al., "277MO SAR439859, an oral selective estrogen receptor (ER) degrader (SERD), in ER+/ HER2-metastatic breast cancer (mBC): Biomarker analyses from a phase I/II study", Annals of Oncology, vol. 31, No. S4, Sep. 1, 2020, p. S351.
Deroo, B.J., et al., "Estrogen Receptors and Human Disease", The Journal of Clinical Investigation, vol. 116, No. 3, pp. 561-570 (2006).
El-Ahmad, Y., et al., "Discovery of 6-(2,4-Dichlorophenyl)-5-[4-[(3S)-1-(3-fluoropropyl)-pyrrolidin-3-yl]-oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," Journal of Medicinal Chemistry, vol. 63, No. 2, pp. 512-528 (2019).
Extended European Search Report issued in European Application No. 19305593.6 on Oct. 30, 2019, 7 pages.
Franks, et al., "Selective Estrogen Receptor Modulators: Cannabinoid Receptor Inverse Agonists with Differential CB1 and CB2 Selectively," Frontiers in Pharmacology, vol. 7, No. 503, pp. 1-16 (2016).
Golub et al., "Molecular Classification of Cancer: Class Discovery and Class Prediction by Gene Expression Monitoring", Science, vol. 286, pp. 531-537 (1999).
Gould, P., "Salt selection for basic drugs," International Journal of Pharmaceutics, vol. 33, pp. 201-217 (1986).
International Search Report for International Application No. PCT/EP2017/053282, mailed Jul. 6, 2017.
International Search Report for International Application No. PCT/EP2017/068446, mailed Sep. 12, 2017.
International Search Report for International Application No. PCT/EP2018/069901, mailed Oct. 12, 2018.
International Search Report for International Application No. PCT/EP2019/073823, mailed Oct. 10, 2019.
International Search Report for International Application No. PCT/EP2019/073827, mailed Oct. 9, 2019.
International Search Report for International Application No. PCT/EP2020/062743, mailed Aug. 10, 2020.
International Search Report for International Application No. PCT/EP2020/085011, mailed Jan. 25, 2021.
International Search Report for International Application No. PCT/EP2021/054815, mailed May 12, 2021.
International Search Report for International Application No. PCT/EP2021/078883, mailed Dec. 9, 2021.
International Search Report for International Application No. PCT/EP2021/082583, mailed Feb. 25, 2022.
Jordan, Craig V., "Antiestrogens and Selective Estrogen Receptor Modulators as Multifunctional Medicines. 1. Receptor Interactions," Journal of Medicinal Chemistry,vol. 46, No. 6, pp. 883-908 (2003).
Lala, P.K., et al., "Role of Nitric Oxide in Tumor Progression: Lessons From Experimental Tumors", Cancer Metastasis Reviews, Mar. 1998, vol. 17, No. 1, pp. 91-106.
Littke, A.F., et al., "Versatile Catalysts for the Suzuki Cross-Coupling of Arylboronic Acids with Aryl and Vinyl Halides and Triflates under Mild Conditions," Journal of the American Chemical Society, 122(17): 4020-4028 (2000).
Malpart, J., et al., Pending U.S. Appl. No. 17/193,776, filed Mar. 5, 2021.
Mannava, M.K.C., et al., "Enhanced Bioavailability in the Oxalate Salt of the Antituberculosis Drug Ethionamide," Crystal Growth & Design, vol. 16(3), pp. 1591-1598, (2016).
McCague, Raymond et al., "Nonisomerizable Analogues of (Z)- and (E)-4-Hydroxytamoxifen. Synthesis and Endocrinological Properties of Substituted Diphenylbenzocycloheptenes", Journal of Medicinal Chemistry, vol. 31, No. 7, pp. 1285-1290 (1988).
Miller, Chris P., "SERMs: Evolutionary Chemistry, Revolutionary Biology," Current Pharmaceutical Design, vol. 8, No. 23, pp. 2089-2111 (2002).
Pickar, et al., "SERMs: Progress and future perspectives," Maturitas, Elsevier, vol. 67, pp. 129-138 (2010).
Rabion, A., et al., Pending U.S. Appl. No. 17/193,706, filed Mar. 5, 2021.
RN 1861739-57-2, Registry Database Compound, 2016.
Ruff, et al., "Estrogen Receptor Transcription and Transactivation Structure-Function Relationship in DNA- and Ligand-Binding Domains of Estrogen Receptors", Breast Cancer Research, 2000, vol. 2, No. 5, pp. 353-359.
Translation of Office Action issued in Japanese Application No. 2018-515615, mailed on Sep. 18, 2018, 3 pages.
Translation of Search Report issued in Chinese Application No. 201780023008.0, mailed Apr. 23, 2020, 3 pages.
Ullrich, et al., "Estrogen receptor modulator review," Expert Opinion, vol. 16, No. 5, pp. 559-572 (2006).
Ashizawa, Kazuhide, "Optimization of salt and crystalline forms, and crystallization techniques," Pharm Tech Japan, 2002, vol. 18, No. 10, pp. 81-96 (machine translation of excerpts).
Hirayama, Noriaki, "Handbook for organic compounds crystal preparation," 2008, pp. 17-23, 37-40, 45-51, 57-65 (machine translation of excerpts).
Rabion, A., et al., Pending U.S. Appl. No. 18/924,400, filed Oct. 23, 2024.
Anonymous, "Phase 1 / 2 Study of Amcenestrant (SAR439859) Single Agent and in Combination With Other Anti-cancer Therapies in Postmenopausal Women With Estrogen Receptor Positive Advanced Breast Cancer," Sep. 15, 2017, URL: https://www.clinicaltrials.gov/ct2/show/NCT03284957.
Besret, et al., "Translational strategy using multiple nuclear imaging biomarkers to evaluate target engagement and early therapeutic efficacy of SAR439859, a novel selective estrogen receptor degrader", EJNMMI Research, Biomed Central Ltd, London, UK, vol. 10, No. 1, Jun. 29, 2020, pp. 1-13.
Bouaboula, M., et al., Pending U.S. Appl. No. 18/286,496, filed Oct. 11, 2023. (not enclosed).
Bouaboula, M., et al., Pending U.S. Appl. No. 18/286,510, filed Oct. 11, 2023. (not enclosed).
International Search Report for International Application No. PCT/EP2022/059700, mailed Jul. 8, 2022.
International Search Report for International Application No. PCT/EP2022/059704, mailed Jul. 21, 2022.
Robinson, Dan, R. et al., "Activating ESR1 mutations in hormone-resistant metastatic breast cancer", Nat. Genet., Dec. 2013, 45(12), 1446-1451.
Toy, Weiyi, et al., "Activating ESR1 mutations differentially impact the efficacy of ER antagonists", Cancer Discovery, Mar. 2017, 7(3), 277-287.
Iorfida, M., et al., Fulvestrant in combination with CDK4/6 inhibitors for HER2-metastatic breast cancers: current perspectives, Breast Cancer: Targets and Therapy, Mar. 18, 2020, 13 pages.

SUBSTITUTED 6,7-DIHYDRO-5H-BENZO[7]ANNULENE COMPOUNDS AND THEIR DERIVATIVES, PROCESSES FOR THEIR PREPARATION AND THERAPEUTIC USES THEREOF

CROSS-REFERENCE TO RELATED APPLICATIONS

This application is a national phase entry pursuant to 35 U.S.C. § 371 of International Application No. PCT/EP2021/078916, filed Oct. 19, 2021, which claims the benefit of priority to European Application No. 20306236.9, filed Oct. 19, 2020, and European Application No. 21306282.1, filed Sep. 16, 2021, the entire contents of each of which are incorporated by reference herein in their entirety for any purpose.

Disclosed herein are novel substituted 6,7-dihydro-5H-benzo[7]annulene derivatives, the processes for their preparation, as well as the therapeutic uses thereof, in particular as anticancer agents via selective antagonism and degradation of estrogen receptors.

The Estrogen Receptors (ER) belong to the steroid/nuclear receptor superfamily involved in the regulation of eukaryotic gene expression, cellular proliferation and differentiation in target tissues. ERs are in two forms: the estrogen receptor alpha (ERα) and the estrogen receptor beta (ERβ) respectively encoded by the ESR1 and the ESR2 genes. ERα and ERβ are ligand-activated transcription factors which are activated by the hormone estrogen (the most potent estrogen produced in the body is 17β-estradiol). In the absence of hormone, ERs are largely located in the cytosol of the cell. When the hormone estrogen binds to ERs, ERs migrate from the cytosol to the nucleus of the cell, form dimers and then bind to specific genomic sequences called Estrogen Response Elements (ERE). The DNA/ER complex interacts with co-regulators to modulate the transcription of target genes.

ERα is mainly expressed in reproductive tissues such as uterus, ovary, breast, bone and white adipose tissue. Abnormal ERα signaling leads to development of a variety of diseases, such as cancers, metabolic and cardiovascular diseases, neurodegenerative diseases, inflammation diseases and osteoporosis.

ERα is expressed in not more than 10% of normal breast epithelium but approximately 50-80% of breast tumors. Such breast tumors with high level of ERα are classified as ERα-positive breast tumors. The etiological role of estrogen in breast cancer is well established and modulation of ERα signaling remains the mainstay of breast cancer treatment for the majority ERα-positive breast tumors. Currently, several strategies for inhibiting the estrogen axis in breast cancer exist, including: 1—blocking estrogen synthesis by aromatase inhibitors that are used to treat early and advanced ERα-positive breast cancer patients; 2—antagonizing estrogen ligand binding to ERα by tamoxifen which is used to treat ERα-positive breast cancer patients in both pre- and post-menopausal setting; 3—antagonizing and downregulating ERα levels by fulvestrant, which is used to treat breast cancer in patients that have progressed despite endocrine therapies such as tamoxifen or aromatase inhibitors.

Although these endocrine therapies have contributed enormously to reduction in breast cancer development, about more than one-third of ERα-positive patients display de novo resistance or develop resistance over time to such existing therapies. Several mechanisms have been described to explain resistance to such hormone therapies. For example, hypersensitivity of ERα to low estrogen level in treatment with aromatase inhibitors, the switch of tamoxifen effects from antagonist to agonist effects in tamoxifen treatments or multiple growth factor receptor signaling pathways. Acquired mutations in ERα occurring after initiation of hormone therapies may also play a role in treatment failure and cancer progression. Certain mutations in ERα, particularly those identified in the Ligand Binding Domain (LBD), result in the ability to bind to DNA in the absence of ligand and confer hormone independence in cells harboring such mutant receptors.

Most of the endocrine therapy resistance mechanisms identified rely on ERα-dependent activity. One of the new strategies to counterforce such resistance is to shut down the ERα signaling by removing ERα from the tumor cells using Selective Estrogen Receptors Degraders (SERDs). Clinical and preclinical data showed that a significant number of the resistance pathways can be circumvented by the use of SERDs.

There is still a need to provide SERDs with good degradation efficacy.

Documents WO2017/140669 and WO2018/091153 disclose some substituted 6,7-dihydro-5H-benzo[7]annulene compounds and substituted N-(3-fluoropropyl)-pyrrolidine derivatives useful as SERDs.

The inventors have now found novel compounds able to selectively antagonize and degrade the estrogen receptors (SERDs compounds), for use in cancer treatment.

Disclosed herein are compounds of the formula (I), or pharmaceutically acceptable salts thereof:

(I)

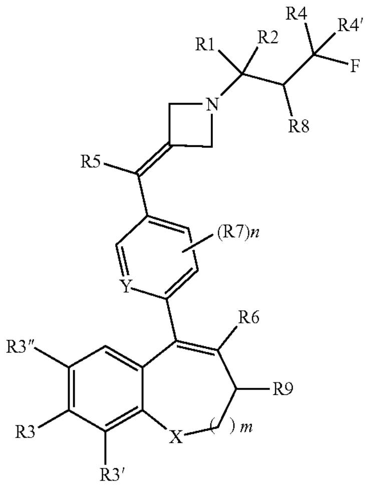

wherein:

R1 and R2 independently represent a hydrogen atom or a deuterium atom;

R3 represents a hydrogen atom, a —COOH group or a —OH group;

R3' and R3" independently represent a hydrogen atom, a methyl group, a methoxy group, a chlorine atom, a fluorine atom or a cyano group;

R4 and R4' independently represent a hydrogen atom or a fluorine atom;

R5 represents a hydrogen atom, a fluorine atom or a $(C_1-C_3)$alkyl group;

R6 represents a group selected from:

- a phenyl group, said phenyl group being optionally substituted by 1 to 3 substituents independently selected from a halogen atom; a $(C_1-C_6)$alkyl group, optionally substituted with a cyano group or a —OH group; a $(C_1-C_6)$fluoroalkyl group; a $(C_3-C_6)$cycloalkyl group; a $(C_1-C_6)$alkoxy group; a $(C_1-C_6)$fluoroalkoxy group; a cyano group; a trifluoromethylsulfonyl group; a $(C_1-C_4)$alkylthio group; a $(C_1-C_4)$fluoroalkylthio group; a $(C_1-C_4)$alkylsulfonyl group and a —OH group;
- a fused phenyl group, selected from phenyl groups fused with a $(C_3-C_6)$cycloalkyl, said $(C_3-C_6)$cycloalkyl optionally comprises an unsaturation, and wherein the fused phenyl group is optionally substituted with 1 to 3 substituents independently selected from a $(C_1-C_3)$alkyl group, a hydroxy group, a halogen atom, a $(C_1-C_6)$fluoroalkyl group and a $(C_1-C_3)$alkoxy group;
- a bicyclic group comprising 5 to 12 carbon atoms, optionally comprising 1 to 2 unsaturations; optionally substituted with 1 to 4 substituents independently selected from: a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group and an oxo group;
- a heteroaryl group comprising 2 to 9 carbon atoms and comprising from 1 to 3 heteroatoms independently selected from oxygen, nitrogen and sulfur, and at least 5 atoms including carbon atoms and heteroatoms, such as a pyridyl group, said heteroaryl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a cyano group, a carbamoyl group and a —OH group;
- a cycloalkyl group comprising 3 to 7 carbon atoms, said cycloalkyl group being saturated or partially saturated and being optionally substituted with 1 to 4 substituents independently selected from:
  - a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, an oxo group,
  - a $(C_3-C_6)$cycloalkyl group and a phenyl group, said $(C_3-C_6)$cycloalkyl or phenyl groups being optionally substituted with one or two halogen atom(s) or $(C_1-C_3)$alkyl group(s);
- a $(C_3-C_6)$cycloalkyl$(C_1-C_3)$alkyl group, optionally substituted on the cycloalkyl with 1 to 4 substituents independently selected from: a fluorine atom, a —OH group, a $(C_1-C_4)$alkyl group, a $(C_1-C_3)$fluoroalkyl group, a $(C_1-C_3)$fluoroalkoxy group and an oxo group;
- a 3 to 8 membered-heterocycloalkyl group comprising 1 or 2 heteroatoms independently selected from oxygen, nitrogen and sulfur, such as a tetrahydropyranyl group, said heterocycloalkyl group being saturated or partially saturated and being optionally substituted with 1 to 3 substituents independently selected from: a fluorine atom, a $(C_1-C_3)$alkyl group, a $(C_1-C_3)$fluoroalkyl group, a $(C_1-C_3)$fluoroalkoxy group, an oxo group, a $(C_1-C_3)$alkoxy group, and a —OH group;
- a $(C_1-C_6)$alkyl group, such as an isobutyl group, a methyl group or an ethyl group, said alkyl group being optionally substituted with 1 to 4 substituents independently selected from: a fluorine atom, a $(C_1-C_3)$alkoxy group, a $(C_1-C_3)$fluoroalkoxy group and a —OH group; and
- a phenyl$(C_1-C_2)$alkyl group, said phenyl group being optionally substituted with 1 to 3 substituents independently selected from a halogen atom; a $(C_1-C_3)$alkyl group; a $(C_1-C_3)$fluoroalkyl group; a $(C_1-C_3)$alkoxy group; a $(C_1-C_3)$ fluoroalkoxy group; a cyano group; and a —OH group;

X represents $—CH_2—$, —O— or —S—;

Y represents —CH═, —N═ or —CR"═, wherein R" represents a $(C_1-C_3)$alkyl group, a halogen atom, such as a fluorine or a chlorine atom, a cyano group, or a $(C_1-C_3)$fluoroalkyl group, such as trifluoromethyl;

R7 independently represents a $(C_1-C_3)$alkyl group such as methyl, a halogen atom such as a fluorine atom, a cyano group, or a $(C_1-C_3)$fluoroalkyl group such as trifluoromethyl;

R8 represents a hydrogen atom or a fluorine atom;

R9 represents a hydrogen atom, a $(C_1-C_3)$alkyl group or a cyclopropyl;

n is 0, 1 or 2; and m is 0 or 1.

The compounds of formula (I) can contain one or more asymmetric carbon atoms. They may therefore exist in the form of enantiomers.

The compounds of formula (I) may be present as well under tautomer forms.

The compounds of formula (I) may exist in the form of bases, acids, zwitterion or of addition salts with acids or bases. Hence, herein are provided compounds of formula (I) or pharmaceutically acceptable salts thereof.

These salts may be prepared with pharmaceutically acceptable acids or bases, although the salts of other acids or bases useful, for example, for purifying or isolating the compounds of formula (I) are also provided.

Among suitable salts of the compounds of formula (I), hydrochloride may be cited As used herein, the terms below have the following definitions unless otherwise mentioned throughout the instant specification:

- a halogen atom: a fluorine, a chlorine, a bromine or an iodine atom, and in particular a fluorine and a chlorine atom;
- an oxo: a "═O" group;
- an alkyl group: a linear or branched saturated hydrocarbon-based aliphatic group comprising, unless otherwise mentioned, from 1 to 6 carbon atoms (noted "$(C_1-C_6)$alkyl"). By way of examples, mention may be made of, but not limited to: methyl, ethyl, propyl, isopropyl, butyl, isobutyl, sec-butyl, tert-butyl, pentyl, isopentyl, hexyl and isohexyl groups, and the like;
- a cycloalkyl group: a monocyclic alkyl group comprising, unless otherwise mentioned, from 3 to 7 carbon atoms, saturated or partially unsaturated and unsubstituted or substituted. By way of examples, mention may be made of, but not limited to: cyclopropyl, cyclobutyl, cyclopentyl, cyclobutenyl, cyclopentenyl, cyclohexyl, cyclohexenyl, cycloheptyl and cycloheptenyl groups and the like, in particular a cyclopentyl, a cyclohexyl or a cyclohexenyl;
- a cycloalkylalkyl group: an alkyl group substituted with a cyclic alkyl group as defined above. Mention may be made of, but not limited to: cyclobutylmethyl;
- a heterocycloalkyl group: a 3 to 8-membered cycloalkyl group, saturated of partially unsaturated, comprising 1 to 2 heteroatoms independently selected from oxygen, nitrogen and sulfur, in particular being oxygen or nitrogen. By way of examples, mention may be made of, but not limited to: morpholinyl, piperazinyl, piperidinyl, pyrrolidinyl, aziridinyl, oxanyl, oxetanyl, tetrahydropyranyl, morpholinyl, tetrahydrofuranyl, oxepanyl, diazepanyl, dioxanyl, tetrahydropyranyl and tetrahydrothiopyranyl. The heterocycloalkyl is advantageously tetrahydropyranyl.

a fluoroalkyl group: an alkyl group as previously defined where the alkyl group is substituted with at least one fluorine atom. In other terms, at least one hydrogen atom of the alkyl group is replaced by a fluorine atom. By way of example, mention may be made of —CHF, —CHF, —$CH_2CHF_2$, —$CH_2CH_2F$ and the like. When all the hydrogen atoms belonging to the alkyl group are replaced by fluorine atoms, the fluoroalkyl group can be named perfluoroalkyl group. By way of example, mention may be made of trifluoromethyl group or trifluoroethyl group and the like, and in particular trifluoromethyl group;

an alkoxy group: an —O-alkyl group where the alkyl group is as previously defined. By way of examples, mention may be made of, but not limited to: methoxy, ethoxy, propoxy, isopropoxy, linear, secondary or tertiary butoxy, isobutoxy, pentoxy or hexoxy groups, and the like;

a fluoroalkoxy group: an —O-alkyl group where the alkyl group is as previously defined and where the alkyl group is substituted with at least one fluorine atom. In other terms, at least one hydrogen atom of the alkyl group is replaced by a fluorine atom. By way of example, mention may be made of —$OCH_2F$, —$OCHF_2$, —$OCH_2CH_2F$ and the like. When all the hydrogen atoms belonging to the alkyl group are replaced by fluorine atoms, the fluoroalkoxy group can be named perfluoroalkoxy group. By way of example, mention may be made of trifluoromethoxy group and the like;

a $(C_1\text{-}C_4)$alkylthio group also named $(C_1\text{-}C_4)$alkylsulfanyl: a —S-alkyl group where the alkyl group is as previously defined. By way of examples, mention may be made of, but not limited to: methylthio, ethylthio, propylthio, isopropylthio, linear, secondary or tertiary butylthio, isobutylthio, and the like;

a $(C_1\text{-}C_4)$alkylsulfonyl group: a —$SO_2$-alkyl group where the alkyl group is as previously defined. By way of examples, mention may be made of, but not limited to: —$SO_2CH_3$, —$SO_2CH_2CH_3$ and the like;

$(C_1\text{-}C_4)$fluoroalkylthio group also named a $(C_1\text{-}C_4)$fluoroalkylsulfanyl group: a —S-fluoroalkyl group where the fluoroalkyl group is as previously defined. By way of examples, mention may be made of, but not limited to: fluoromethylthio, difluoromethylthio, trifluoromethylthio and the like;

a fused phenyl: a bicyclic radical comprising from 8 to 10 carbon atoms and that contains a phenyl moiety. Said phenyl moiety may be fused to a $(C_3\text{-}C_6)$cycloalkyl group, i.e. the phenyl moiety may share a bond with said $(C_3\text{-}C_6)$cycloalkyl group. The fused phenyl group may be bound to the rest of the molecule by its phenyl moiety. It may be substituted. Examples are, but not limited to, indanyl, bicyclo[4.2.0]octa-1(6),2,4-trienyl, tetrahydronaphthalenyl and the like;

a heteroaryl group: a 5 to 10-membered cyclic aromatic group containing between 2 and 9 carbon atoms and containing between 1 and 3 heteroatoms, such as nitrogen, oxygen or sulfur. Such nitrogen atom may be substituted with an oxygen atom in order to form a —N—O bond. Such —N—O bond can be in a form of a N-oxide (—N+—O—). Said heteroaryl group may be monocyclic or bicyclic. By way of examples of heteroaryl groups, mention may be made of, but not limited to: thiophene, furan, thiadiazole, thiazole, imidazole, pyridazine, triazine, pyrazine, oxadiazole, pyrazole, isothiazole, oxazole, isoxazole, pyridine, pyrimidine, benzotriazole, benzoxazole, pyrrolo[2,3-b]pyridine, benzimidazole, benzoxadiazole, benzothiazole, benzothiadiazole, benzofuran, indole, isoquinoline, indazole, benzisoxazole, benzisothiazole, pyridone groups and the like. The heteroaryl is advantageously pyridine, pyrrole, imidazole, pyrazine, furane, thiazole, pyrazole, thiadiazole, pyridazine, pyridone and pyrimidine, and more particularly pyridine;

a bicyclic group, generally comprising 5 to 12 carbon atoms, is a hydrocarbon group selected from groups comprising two rings connected through:

a single common atom: a "spirobicyclic ring". Such spiro bicyclic alkyl generally comprises 5 to 11 carbon atoms referring to a "spiro$(C_5\text{-}C_{11})$bicyclic ring". The rings may be saturated or partially unsaturated. Such spirobicyclic ring may be unsubstituted or substituted, in particular by at least one $(C_1\text{-}C_3)$ alkyl group such as methyl or a fluorine. By way of examples of spiro$(C_5\text{-}C_{11})$bicyclic ring as for the definition of R6, mention may be made of, but not limited to: spiro[2.3]hexane, spiro[3.3]heptane, spiro[3.3]heptene, spiro[2.5]octane and 7-azaspiro[3.5]nonane. The spiro$(C_5\text{-}C_{11})$bicyclic ring is advantageously spiro[2.3]hexane, spiro[3.3]heptane or spiro[3.3]heptene still for the R6 group;

two common atoms. In that case the bicyclic group comprises 7 to 12 carbon atoms and optionally comprises 1 to 2 unsaturations. By way of examples of such bicyclic groups, mention may be made of, but not limited to: cis-1,3a,4,5,6,6a-hexahydropentalenyl group, bicyclo[3.1.0]hexan-1-yl, bicyclo[4.1.0]heptanyl and octahydropentalenyl, three or more common atoms. In that case the bicyclic group comprises 6 to 10 carbon atoms, such bicyclic group may be referred to as a "bridged $(C_6\text{-}C_{10})$ cycloalkyl" group, the rings share three or more atoms and the bridge contains at least one atom, for example 1, 2 or 3 atoms and preferentially 1 atom. By way of examples of such bridged cycloalkyl groups, mention may be made of, but not limited to bicyclo[3.2.1]octan-3-yl and bicyclo[2.2.1]heptan-2-yl.

a zwitterion means: a globally neutral molecule with a positive and a negative electrical charge and having an acidic group and a basic group.

In another embodiment, in the compounds of formula (I) as defined above, R1 and R2 are a hydrogen atom.

In another embodiment, in the compounds of formula (I) as defined above, R3 is —COOH.

In another embodiment, in the compounds of formula (I) as defined above, R3' and R3" represent a hydrogen atom.

In another embodiment, in the compounds of formula (I) as defined above, X represents —$CH_2$—.

In another embodiment, in the compounds of formula (I) as defined above, R4 and R4' represent a hydrogen atom.

In another embodiment, in the compounds of formula (I) as defined above, R5 represents a hydrogen atom.

In another embodiment, in the compounds of formula (I) as defined above, R5 represents a hydrogen atom, a $—NH_2$ group, a methyl group, a methoxy group, an ethoxy group.

In another embodiment, in the compounds of formula (I) as defined above, R6 represents a phenyl group, said phenyl group being optionally substituted with 1 to 3 substituents independently selected from a chlorine atom, a fluorine atom, a methyl group, an ethyl group, a trifluoromethyl group, a cyclopropyl group, a methoxy group and a cyano group.

In another embodiment, in the compounds of formula (I) as defined above, R6 represents a fused phenyl group, selected from a bicyclo[4.2.0]octatrienyl group, a indanyl group or a tetrahydronaphthalenyl group, optionally substituted with one or two fluorine atom.

In another embodiment, in the compounds of formula (I) as defined above, R6 represents a bicyclic group selected from a bicyclo[4.1.0]heptanyl, a bicyclo[3.1.0]hexanyl, a spiro[2.3]hexanyl and a bicyclo[3.2.1]octan-3-yl, optionally substituted with 1 to 4 substituents independently selected from: a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group and an oxo group; advantageously said bicyclic group is unsubstituted.

In another embodiment, in the compounds of formula (I) as defined above, R6 represents a pyridyl group, said pyridyl group being optionally substituted with 1 to 3 substituents independently selected from a halogen atom, a $(C_1-C_6)$alkyl group, a $(C_1-C_6)$fluoroalkyl group and a $(C_1-C_6)$alkoxy group, and more particularly selected from a fluorine atom, a chlorine atom, a methyl group, a trifluoromethyl group and a methoxy group.

In another embodiment, in the compounds of formula (I) as defined above, R6 represents a cycloalkyl chosen from a cyclohexyl or a cyclopropyl group, said cycloalkyl being optionally substituted with 1 to 4 substituents independently selected from:

- a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, an oxo group
- a $(C_1-C_6)$cycloalkyl group and a phenyl group said $(C_3-C_6)$cycloalkyl or phenyl group being optionally substituted with one or two halogen atom(s) or $(C_1-C_3)$alkyl group(s), said cycloalkyl being advantageously substituted with 1 to 2 substituents independently selected from:

- a methyl group, a phenyl group and
- a cyclohexyl group substituted by two halogen atoms, in particular fluor atoms.

In another embodiment, in the compounds of formula (I) as defined above, R6 represents a cyclobutylmethyl, optionally substituted on the cycloalkyl with 1 to 4 substituents independently selected from: a fluorine atom, a OH group, a $(C_1-C_4)$alkyl group, a $(C_1-C_3)$fluoroalkyl group, a $(C_1-C_3)$ fluoroalkoxy group and an oxo group; advantageously said cyclobutylmethyl is unsubstituted.

In another embodiment, in the compounds of formula (I) as defined above, R6 represents a tetrahydropyranyl group, said tetrahydropyranyl group being optionally substituted with 1 to 3 substituents independently selected from: a fluorine atom, a $(C_1-C_3)$alkoxy group, a $(C_1-C_3)$fluoroalkyl group, a $(C_1-C_3)$fluoroalkoxy group and a —OH group; advantageously said tetrahydropyranyl group is unsubstituted.

In another embodiment, in the compounds of formula (I) as defined above, R6 represents an isobutyl group, said isobutyl group being optionally substituted with 1 to 4 substituents independently selected from: a fluorine atom, a $(C_1-C_3)$alkoxy group, a $(C_1-C_3)$fluoroalkoxy group and a —OH group, and in particular optionally substituted with 1 or 3 fluorine atoms; advantageously said isobutyl group is unsubstituted.

In another embodiment, in the compounds of formula (I) as defined above, R6 represents a phenyl$(C_1-C_2)$alkyl group, in particular chosen from a phenylmethyl or a phenylethyl.

In another embodiment, in the compounds of formula (I) as defined above, R7 independently represents a methyl group, a cyano group, a trifluoromethyl group or a fluorine atom and n is 0, 1 or 2.

In another embodiment, in the compounds of formula (I) as defined above, Y represents —CH═, —N═ or —CR"═, R" representing a fluorine atom, a cyano group, or a trifluoromethyl group.

In another embodiment, in the compounds of formula (I) as defined above, m is 1.

In another embodiment, in the compounds of formula (I) as defined above, R3 is a COOH group and R6 is a phenyl group comprising two substitutions independently selected from a chlorine atom, a fluorine atom, a trifluoromethyl group and a methyl group, at least one of the substitutions comprising a halogen atom. In such embodiment, R3' and R3" are in particular hydrogen atoms. Still in such embodiment, R1, R2, R4, R4', R5, R8 and R9 are hydrogen atoms. In such embodiment, Y is a —CH═ group, m is equal to 1 and n is equal to 0. Still in such embodiment, X is a $—CH_2—$ group.

In addition to said embodiment, further embodiments are herein provided.

A further embodiment provides compounds of the formula (I'), or pharmaceutically acceptable salts thereof:

(I')

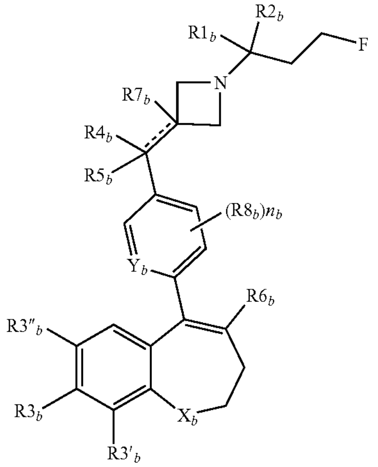

wherein:

- ═══ represents a double or single bond, and when it is a double bond, then $R4_b$ and $R7_b$ do not exist;
- $R1_b$ and $R2_b$ represent independently a hydrogen atom or a deuterium atom;
- $R3_b$ represents a hydrogen atom, a —COOH group or a —OH group;
- $R3'_b$ and $R3''_b$ independently represent a hydrogen atom, a methyl, a chlorine or a fluorine atom;
- $R4_b$ and $R5_b$ represent independently a hydrogen atom, a halogen atom, a $—NH_2$ group, a methyl group or a —OH group; or R4 and R5 together form an oxo group;

$R6_b$ represents a group selected from:

- a phenyl group, said phenyl group being optionally substituted with 1 to 3 substituents independently selected from a halogen atom, a $(C_1-C_6)$alkyl group, a $(C_1-C_6)$haloalkyl group, a $(C_1-C_6)$alkoxy group, a $(C_1-C_6)$haloalkoxy group and a —OH group;
- a heteroaryl group comprising 2 to 9 carbon atoms and comprising from 1 to 3 heteroatoms independently selected from oxygen, nitrogen and sulfur, and at least 5 atoms including carbon atoms and heteroatoms, such as a pyridyl group, said heteroaryl group being optionally substituted by 1 to 3 substituents independently selected from a halogen atom, a $(C_1-C_6)$alkyl group, a $(C_1-C_6)$haloalkyl group, a $(C_1-C_6)$ alkoxy group, a $(C_1-C_6)$haloalkoxy group and a —OH group;
- a cycloalkyl group comprising 3 to 9 carbon atoms, said cycloalkyl group being saturated or partially saturated and being optionally substituted with 1 to 4 substituents independently selected from: a fluorine atom, a —OH group, a $(C_1-C_6)$alkyl group and an oxo group;
- a 4 to 7 membered-heterocycloalkyl group comprising 1 or 2 heteroatoms independently selected from oxygen, nitrogen and sulfur, such as a tetrahydropyran group, said heterocycloalkyl group being optionally substituted with 1 to 3 substituents independently selected from: a fluorine atom, a $(C_1-C_6)$ alkoxy group, a $(C_1-C_6)$haloalkoxy group and a —OH group;
- a spiro$(C_5-C_{11})$bicyclic ring, such as a spiro[3.3]heptane or spiro[3.3]heptane), said spiro$(C_5-C_{11})$bicyclic ring being optionally substituted with 1 to 4 substituents independently selected from: a $(C_1-C_6)$ alkyl group, a fluorine atom, a $(C_1-C_6)$alkoxy group, a $(C_1-C_6)$haloalkoxy group and a —OH group;
- a $(C_1-C_6)$alkyl group, such as isobutyl, said alkyl group being optionally substituted with 1 to 4 substituents independently selected from: a fluorine atom, a $(C_1-C_6)$alkoxy group, a $(C_1-C_6)$haloalkoxy group and a —OH group;

$R7_b$ represents a hydrogen atom or a halogen atom;

$X_b$ represents $—CH_2—$, —O— or —S—;

$Y_b$ represents —CH—, —N— or $—CR''_b—$, wherein R"b represents a $(C_1-C_4)$alkyl group or a halogen atom, such as a fluorine or a chlorine atom;

$R8_b$ independently represents a $(C_1-C_4)$alkyl group, such as methyl, or a halogen atom, such as fluorine; and $n_b$ is 0, 1 or 2.

The compounds of formula (I') can contain one or more asymmetric carbon atoms. They may therefore exist in the form of enantiomers.

The compounds of formula (I') may be present as well under tautomer forms.

The compounds of formula (I') may exist in the form of bases, acids, zwitterion or of addition salts with acids or bases. Hence, herein are provided compounds of formula (I') or pharmaceutically acceptable salts thereof.

These salts may be prepared with pharmaceutically acceptable acids or bases, although the salts of other acids or bases useful, for example, for purifying or isolating the compounds of formula (I') are also provided.

Among suitable salts of the compounds of formula (I'), hydrochloride may be cited.

In an embodiment, in the compound of formula (I') as defined above, ═══ represents a single bond.

In another embodiment, in the compounds of formula (I') as defined above, $R1_b$ and $R2_b$ are a hydrogen atom.

In another embodiment, in the compounds of formula (I) as defined above, $R3_b$ is —COOH.

In another embodiment, in the compounds of formula (I') as defined above, $X_b$ represents $—CH_2—$.

In another embodiment, in the compounds of formula (I') as defined above, $R4_b$ and $R5_b$ represent independently a hydrogen atom, a fluorine atom, a $—NH_2$ group, a methyl group or a —OH group, in particular represent independently a hydrogen atom, a fluorine atom or a —OH group; or $R4_b$ and $R5_b$ together form an oxo group, in particular both of $R4_b$ and $R5_b$ represent hydrogen atoms or a fluorine atom, or one of $R4_b$ and $R5_b$ represents a hydrogen atom and the other a fluorine atom or a —OH group, more particularly $R4_b$ and $R5_b$ both represent a hydrogen atom.

In another embodiment, in the compounds of formula (I') as defined above, $R7_b$ represents a hydrogen atom or a fluorine atom, more particularly a hydrogen atom.

In another embodiment, in the compounds of formula (I') as defined above, $R6_b$ represents a phenyl group, said phenyl group being optionally substituted with 1 to 3 substituents independently selected from a chlorine atom, a fluorine atom, a methyl group, a trifluoromethyl group, a methoxy group and a difluoromethoxy group.

In another embodiment, in the compounds of formula (I') as defined above, $R6_b$ represents a pyridyl group, said pyridyl group being optionally substituted by 1 to 3 substituents independently selected from a halogen atom, a $(C_1-C_6)$alkyl group, a $(C_1-C_6)$haloalkyl group, a $(C_1-C_6)$ alkoxy group, a $(C_1-C_6)$haloalkoxy group and a —OH group, and more particularly selected from a methoxy group.

In another embodiment, in the compounds of formula (I') as defined above, $R6_b$ represents a cycloalkyl group selected from a cyclohexyl group, a cyclopentyl group and a cyclohexenyl group, said cycloalkyl group being optionally substituted with 1 to 4 substituents independently selected from: a fluorine atom and a methyl group.

In another embodiment, in the compounds of formula (I') as defined above, $R6_b$ represents a tetrahydropyran group, said tetrahydropyran group being optionally substituted with 1 to 3 substituents independently selected from: a fluorine atom, a $(C_1-C_6)$alkoxy group, a $(C_1-C_6)$haloalkoxy group and a —OH group.

In another embodiment, in the compounds of formula (I') as defined above, $R6_b$ represents a spiro[3.3]hept-1-ene or a spiro[3.3]hept-2-ane group, said spiro[3.3]hept-1-ene or spiro[3.3]hept-2-ane group being optionally substituted with 1 to 4 substituents independently selected from: a $(C_1-C_6)$ alkyl group, a fluorine atom, a $(C_1-C_6)$alkoxy group, a $(C_1-C_6)$haloalkoxy group and a —OH group, and in particular optionally substituted with 1 or 2 fluorine atoms.

In another embodiment, in the compounds of formula (I') as defined above, $R6_b$ represents an isobutyl group, said isobutyl group being optionally substituted with 1 to 4 substituents independently selected from: a fluorine atom, a $(C_1-C_6)$alkoxy group, a $(C_1-C_6)$haloalkoxy group and a —OH group, and in particular optionally substituted with 1 to 3 fluorine atoms.

In another embodiment, in the compounds of formula (I') as defined above, $R8_b$ independently represents a methyl group or a fluorine atom and n is 0, 1 or 2.

In another embodiment, in the compounds of formula (I') as defined above, $Y_b$ represents —CH—, $—C(CH_3)—$, —CF— or —N—, and in particular —CH— or —N—.

Among the compounds of formula (I) described herein, mention may be made in particular of the following compounds or a pharmaceutically acceptable salt thereof, in particular hydrochloride salt thereof:

8-(2,4-dichlorophenyl)-9-(4-((1-(3-fluoropropyl)azetidin-3-ylidene)methyl)phenyl)-6,7-dihydro-5H-benzo[7]annulene-3-carboxylic acid, (1)

8-(3-fluoro-2-methoxypyridin-4-yl)-9-(4-((1-(3-fluoropropyl)azetidin-3-ylidene)methyl)phenyl)-6,7-dihydro-5H-benzo[7]annulene-3-carboxylic acid, (2)

9-(4-((1-(3-fluoropropyl)azetidin-3-ylidene)methyl)phenyl)-8-(2-methyl-4-(trifluoromethyl)phenyl)-6,7-dihydro-5H-benzo[7]annulene-3-carboxylic acid, (3)

8-(6-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, (4)

8-(4-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (5)

8-(5-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, (6)

8-(4-fluoro-2,3-dihydro-1H-inden-5-yl)-9-(4-((1-(3-fluoropropyl)azetidin-3-ylidene)methyl)phenyl)-6,7-dihydro-5H-benzo[7]annulene-3-carboxylic acid, (7)

8-(bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylic acid, (8)

8-(1,1-difluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, (9)

8-(2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, (10)

8-(4-fluoro-2-methylphenyl)-9-(2-fluoro-4-((1-(3-fluoropropyl)azetidin-3-ylidene)methyl)phenyl)-6,7-dihydro-5H-benzo[7]annulene-3-carboxylic acid, (11)

8-(7-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, (12)

8-(3-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, (13)

9-(4-((1-(3-fluoropropyl)azetidin-3-ylidene)methyl)phenyl)-8-(3-methyl-2-(trifluoromethyl)phenyl)-6,7-dihydro-5H-benzo[7]annulene-3-carboxylic acid, (14)

8-(2,4-difluorophenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride, (15)

8-(2,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (16)

8-(2,4-difluorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid hydrochloride, (17)

8-(5-fluoro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid, (18)

9-(4-((1-(3,3-difluoropropyl)azetidin-3-ylidene)methyl)phenyl)-8-(4-fluoro-2-methylphenyl)-6,7-dihydro-5H-benzo[7]annulene-3-carboxylic acid, (19)

8-(2,4-difluorophenyl)-9-(4-((1-(3,3-difluoropropyl)azetidin-3-ylidene)methyl)phenyl)-6,7-dihydro-5H-benzo[7]annulene-3-carboxylic acid, (20)

8-(2,6-difluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (21)

8-(3,4-difluoro-2-methylphenyl)-9-(4-((1-(3,3-difluoropropyl)azetidin-3-ylidene)methyl)phenyl)-6,7-dihydro-5H-benzo[7]annulene-3-carboxylic acid, (22)

8-(3-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (23)

8-(3-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (24)

9-(4-((1-(3,3-difluoropropyl)azetidin-3-ylidene)methyl)phenyl)-8-(4-fluoro-2-(trifluoromethyl)phenyl)-6,7-dihydro-5H-benzo[7]annulene-3-carboxylic acid, (25)

9-(4-((1-(3,3-difluoropropyl)azetidin-3-ylidene)methyl)phenyl)-8-(3-fluoro-2-(trifluoromethyl)phenyl)-6,7-dihydro-5H-benzo[7]annulene-3-carboxylic acid, (26)

8-(2,4-difluorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid, (27)

8-(4-fluoro-2-methylphenyl)-9-(3-fluoro-4-((1-(3-fluoropropyl)azetidin-3-ylidene)methyl)-5-methylphenyl)-6,7-dihydro-5H-benzo[7]annulene-3-carboxylic acid, (28)

8-(3,4-difluoro-2-methylphenyl)-9-(4-((1-(3-fluoropropyl)azetidin-3-ylidene)methyl)phenyl)-6,7-dihydro-5H-benzo[7]annulene-3-carboxylic acid, (29)

8-(4-fluoro-2-methylphenyl)-9-(3-fluoro-4-((1-(3-fluoropropyl)azetidin-3-ylidene)methyl)-2-methylphenyl)-6,7-dihydro-5H-benzo[7]annulene-3-carboxylic acid, (30)

8-(2,4-difluorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid, (31)

8-(5-fluoro-3-methylpyridin-2-yl)-9-(4-((1-(3-fluoropropyl)azetidin-3-ylidene)methyl)phenyl)-6,7-dihydro-5H-benzo[7]annulene-3-carboxylic acid, (32)

9-(4-((1-(3-fluoropropyl)azetidin-3-ylidene)methyl)phenyl)-8-(2,4,6-trifluorophenyl)-6,7-dihydro-5H-benzo[7]annulene-3-carboxylic acid, (33)

8-(4-cyclopropyl-2-fluorophenyl)-9-(4-((1-(3-fluoropropyl)azetidin-3-ylidene)methyl)phenyl)-6,7-dihydro-5H-benzo[7]annulene-3-carboxylic acid, (34)

8-(5-chloro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid, (35)

9-(3,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, (36)

8-(4-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (37)

8-(5-fluoro-2-methylphenyl)-9-(4-((1-(3-fluoropropyl)azetidin-3-ylidene)methyl)phenyl)-6,7-dihydro-5H-benzo[7]annulene-3-carboxylic acid, (38)

8-(4-cyclopropyl-2-methylphenyl)-9-(4-((1-(3-fluoropropyl)azetidin-3-ylidene)methyl)phenyl)-6,7-dihydro-5H-benzo[7]annulene-3-carboxylic acid, (39)

8-(2-cyclopropyl-4-fluorophenyl)-9-(4-((1-(3-fluoropropyl)azetidin-3-ylidene)methyl)phenyl)-6,7-dihydro-5H-benzo[7]annulene-3-carboxylic acid, (40)

8-(2-chloro-4-methylphenyl)-9-(4-((1-(3-fluoropropyl)azetidin-3-ylidene)methyl)phenyl)-6,7-dihydro-5H-benzo[7]annulene-3-carboxylic acid, (41)

8-(2-chloro-6-fluorophenyl)-9-(4-((1-(3-fluoropropyl)azetidin-3-ylidene)methyl)phenyl)-6,7-dihydro-5H-benzo[7]annulene-3-carboxylic acid, (42)

9-(2,3-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid, (43)

8-(4-fluoro-2-methylphenyl)-9-(4-((1-(3-fluoropropyl)azetidin-3-ylidene)methyl)-3-methylphenyl)-6,7-dihydro-5H-benzo[7]annulene-3-carboxylic acid hydrochloride, (44)

8-(4-fluoro-2-methylphenyl)-9-(4-((1-(3-fluoropropyl)azetidin-3-ylidene)methyl)-2,5-dimethylphenyl)-6,7-dihydro-5H-benzo[7]annulene-3-carboxylic acid, (45)

9-(3-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, (46)

8-(3-chloro-2-fluorophenyl)-9-(4-((1-(3-fluoropropyl)azetidin-3-ylidene)methyl)phenyl)-6,7-dihydro-5H-benzo[7]annulene-3-carboxylic acid, (47)

8-(2-fluoro-3-methylphenyl)-9-(4-((1-(3-fluoropropyl)azetidin-3-ylidene)methyl)phenyl)-6,7-dihydro-5H-benzo[7]annulene-3-carboxylic acid, (48)

8-(2-fluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (49)

8-(2-chloro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (50)

8-(2,6-difluoro-4-methylphenyl)-9-(4-((1-(3-fluoropropyl)azetidin-3-ylidene)methyl)phenyl)-6,7-dihydro-5H-benzo[7]annulene-3-carboxylic acid, (51)

9-(2,6-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid, (52)

8-(2,4-difluorophenyl)-9-(3-fluoro-4-((1-(3-fluoropropyl)azetidin-3-ylidene)methyl)phenyl)-6,7-dihydro-5H-benzo[7]annulene-3-carboxylic acid, (53)

8-(2,4-difluorophenyl)-9-(4-((1-(3-fluoropropyl)azetidin-3-ylidene)methyl)phenyl)-6,7-dihydro-5H-benzo[7]annulene-3-carboxylic acid, (54)

8-(2,3-difluorophenyl)-9-(4-((1-(3-fluoropropyl)azetidin-3-ylidene)methyl)phenyl)-6,7-dihydro-5H-benzo[7]annulene-3-carboxylic acid, (55)

8-(2-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (56)

8-(2-fluoro-4-methylphenyl)-9-(4-((1-(3-fluoropropyl)azetidin-3-ylidene)methyl)phenyl)-6,7-dihydro-5H-benzo[7]annulene-3-carboxylic acid, (57)

8-(4-chloro-2-fluorophenyl)-9-(4-((1-(3-fluoropropyl)azetidin-3-ylidene)methyl)phenyl)-6,7-dihydro-5H-benzo[7]annulene-3-carboxylic acid, (58)

9-(3,5-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid, (59)

9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylic acid, (60)

8-(4-fluoro-2-methylphenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride, (61)

8-(4-fluoro-2-methylphenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride, (62)

8-(2,4-dichlorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid, (63)

8-(2,4-dichlorophenyl)-9-(4-((1-(3-fluoropropyl)azetidin-3-ylidene)methyl)-3-methylphenyl)-6,7-dihydro-5H-benzo[7]annulene-3-carboxylic acid, (64)

9-(2,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid hydrochloride, (65)

8-(2,4-dichlorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride, (66)

8-(4-fluoro-2-methylphenyl)-9-(2-fluoro-4-((1-(3-fluoropropyl)azetidin-3-ylidene)methyl)-3-methylphenyl)-6,7-dihydro-5H-benzo[7]annulene-3-carboxylic acid, (67)

9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid, (68)

9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid, (69)

9-(4-((1-(3-fluoropropyl)azetidin-3-ylidene)methyl)phenyl)-8-(4-methyl-2-(trifluoromethyl)phenyl)-6,7-dihydro-5H-benzo[7]annulene-3-carboxylic acid, (70)

8-(2,4-dichlorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid hydrochloride, (71)

8-(3-chloro-2-methylphenyl)-9-(4-((1-(3-fluoropropyl)azetidin-3-ylidene)methyl)phenyl)-6,7-dihydro-5H-benzo[7]annulene-3-carboxylic acid, (72)

8-(2,4-dichlorophenyl)-9-(2,6-difluoro-4-((1-(3-fluoropropyl)azetidin-3-ylidene)methyl)phenyl)-6,7-dihydro-5H-benzo[7]annulene-3-carboxylic acid, (73)

8-(2,4-dichlorophenyl)-9-(2-fluoro-4-((1-(3-fluoropropyl)azetidin-3-ylidene)methyl)-3-methylphenyl)-6,7-dihydro-5H-benzo[7]annulene-3-carboxylic acid hydrochloride, (74)

8-(2-chloro-4-methoxyphenyl)-9-(4-((1-(3-fluoropropyl)azetidin-3-ylidene)methyl)phenyl)-6,7-dihydro-5H-benzo[7]annulene-3-carboxylic acid, (75)

8-(2-chloro-3-methylphenyl)-9-(4-((1-(3-fluoropropyl)azetidin-3-ylidene)methyl)phenyl)-6,7-dihydro-5H-benzo[7]annulene-3-carboxylic acid, (76)

8-(2,4-dimethylphenyl)-9-(4-((1-(3-fluoropropyl)azetidin-3-ylidene)methyl)phenyl)-6,7-dihydro-5H-benzo[7]annulene-3-carboxylic acid, (77)

8-(2-chloro-3-fluorophenyl)-9-(4-((1-(3-fluoropropyl)azetidin-3-ylidene)methyl)phenyl)-6,7-dihydro-5H-benzo[7]annulene-3-carboxylic acid, (78)

8-(2-chloro-4-fluorophenyl)-9-(4-((1-(3-fluoropropyl)azetidin-3-ylidene)methyl)phenyl)-6,7-dihydro-5H-benzo[7]annulene-3-carboxylic acid, (79)

8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylic acid hydrochloride, (80)

8-(4-chloro-3-fluoro-2-methylphenyl)-9-(4-((1-(3-fluoropropyl)azetidin-3-ylidene)methyl)phenyl)-6,7-dihydro-5H-benzo[7]annulene-3-carboxylic acid, (81)

8-(4-chloro-2,3-dimethylphenyl)-9-(4-((1-(3-fluoropropyl)azetidin-3-ylidene)methyl)phenyl)-6,7-dihydro-5H-benzo[7]annulene-3-carboxylic acid, (82)

8-(4-chloro-2,6-dimethylphenyl)-9-(4-((1-(3-fluoropropyl)azetidin-3-ylidene)methyl)phenyl)-6,7-dihydro-5H-benzo[7]annulene-3-carboxylic acid, (83)

8-(4-cyano-2-methylphenyl)-9-(4-((1-(3-fluoropropyl)azetidin-3-ylidene)methyl)phenyl)-6,7-dihydro-5H-benzo[7]annulene-3-carboxylic acid, (84)

8-(3-fluoro-2-methylphenyl)-9-(4-((1-(3-fluoropropyl)azetidin-3-ylidene)methyl)phenyl)-6,7-dihydro-5H-benzo[7]annulene-3-carboxylic acid, (85)

8-(2-ethylphenyl)-9-(4-((1-(3-fluoropropyl)azetidin-3-ylidene)methyl)phenyl)-6,7-dihydro-5H-benzo[7]annulene-3-carboxylic acid, (86)

8-(4-fluoro-2,3-dimethylphenyl)-9-(4-((1-(3-fluoropropyl)azetidin-3-ylidene)methyl)phenyl)-6,7-dihydro-5H-benzo[7]annulene-3-carboxylic acid, (87)

8-(2-cyano-3-methylphenyl)-9-(4-((1-(3-fluoropropyl)azetidin-3-ylidene)methyl)phenyl)-6,7-dihydro-5H-benzo[7]annulene-3-carboxylic acid, (88)

8-(4-chloro-2-methylphenyl)-9-(4-((1-(3-fluoropropyl)azetidin-3-ylidene)methyl)phenyl)-6,7-dihydro-5H-benzo[7]annulene-3-carboxylic acid, (89)

8-(4-fluoro-2,6-dimethylphenyl)-9-(4-((1-(3-fluoropropyl)azetidin-3-ylidene)methyl)phenyl)-6,7-dihydro-5H-benzo[7]annulene-3-carboxylic acid, (90)

8-(3-cyano-2-methylphenyl)-9-(4-((1-(3-fluoropropyl)azetidin-3-ylidene)methyl)phenyl)-6,7-dihydro-5H-benzo[7]annulene-3-carboxylic acid, (91)

8-(2,4-dichlorophenyl)-9-(2,5-difluoro-4-((1-(3-fluoropropyl)azetidin-3-ylidene)methyl)phenyl)-6,7-dihydro-5H-benzo[7]annulene-3-carboxylic acid hydrochloride, (92)

8-(2,4-dichlorophenyl)-9-(4-((1-(3-fluoropropyl)azetidin-3-ylidene)methyl)-2-methylphenyl)-6,7-dihydro-5H-benzo[7]annulene-3-carboxylic acid hydrochloride, (93)

8-(2,3-dimethylphenyl)-9-(4-((1-(3-fluoropropyl)azetidin-3-ylidene)methyl)phenyl)-6,7-dihydro-5H-benzo[7]annulene-3-carboxylic acid, (94)

8-(4-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (95)

8-(2-ethyl-4-fluorophenyl)-9-(4-((1-(3-fluoropropyl)azetidin-3-ylidene)methyl)phenyl)-6,7-dihydro-5H-benzo[7]annulene-3-carboxylic acid, (96)

8-(2,6-dimethylphenyl)-9-(4-((1-(3-fluoropropyl)azetidin-3-ylidene)methyl)phenyl)-6,7-dihydro-5H-benzo[7]annulene-3-carboxylic acid, (97)

8-(4-fluoro-2-methylphenyl)-9-(4-((1-(3-fluoropropyl)azetidin-3-ylidene)methyl)phenyl)-6,7-dihydro-5H-benzo[7]annulene-3-carboxylic acid, (98)

9-(4-((1-(3-fluoropropyl)azetidin-3-ylidene)methyl)phenyl)-8-(o-tolyl)-6,7-dihydro-5H-benzo[7]annulene-3-carboxylic acid, (99)

9-(4-((1-(3-fluoropropyl)azetidin-3-ylidene)methyl)phenyl)-8-isobutyl-6,7-dihydro-acid, (100)

8-(2,4-dichlorophenyl)-9-(2-fluoro-4-((1-(3-fluoropropyl)azetidin-3-ylidene)methyl)phenyl)-6,7-dihydro-5H-benzo[7]annulene-3-carboxylic acid hydrochloride, (101)

8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylic acid, (102)

8-(2,4-dichlorophenyl)-9-(3-fluoro-4-((1-(3-fluoropropyl)azetidin-3-ylidene)methyl)phenyl)-6,7-dihydro-5H-benzo[7]annulene-3-carboxylic acid hydrochloride, (103)

8-(2,4-dichlorophenyl)-9-(4-((1-(3-fluoropropyl)azetidin-3-ylidene)methyl)-3,5-dimethylphenyl)-6,7-dihydro-5H-benzo[7]annulene-3-carboxylic acid hydrochloride, (104)

8-(2,4-dichlorophenyl)-9-(3,5-difluoro-4-((1-(3-fluoropropyl)azetidin-3-ylidene)methyl)phenyl)-6,7-dihydro-5H-benzo[7]annulene-3-carboxylic acid, (105)

6-(2,4-dichlorophenyl)-5-(4-((1-(3-fluoropropyl)azetidin-3-ylidene)methyl)phenyl)-7,8-dihydronaphthalene-2-carboxylic acid hydrochloride, (106)

8-(3-chloro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, (107)

8-(4-fluoro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, (108)

8-(2,4-dichlorophenyl)-9-(4-((1-(3,3,3-trifluoropropyl)azetidin-3-ylidene)methyl)phenyl)-6,7-dihydro-5H-benzo[7]annulene-3-carboxylic acid, (109)

8-(3-methyl-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, (110)

8-(4-chloro-3-fluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid, (111)

8-(3,4-difluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid, (112)

8-(2-methyl-4-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, (113)

4-(2,4-dichlorophenyl)-5-(4-((1-(3-fluoropropyl)azetidin-3-ylidene)methyl)phenyl)-2,3-dihydrobenzo[b]oxepine-8-carboxylic acid hydrochloride, (114)

4-(2,4-dichlorophenyl)-5-[4-[[1-(3-fluoropropyl)azetidin-3-ylidene]methyl]phenyl]-2,3-dihydro-1-benzothiepine-8-carboxylic acid; hydrochloride, (115)

9-(4-((1-(3,3-difluoropropyl)azetidin-3-ylidene)methyl)phenyl)-8-(3-methyl-2-(trifluoromethyl)phenyl)-6,7-dihydro-5H-benzo[7]annulene-3-carboxylic acid, (116)

8-(2,4-dichlorophenyl)-9-(4-((1-(3,3-difluoropropyl-1,1-d2)azetidin-3-ylidene)methyl)phenyl)-6,7-dihydro-5H-benzo[7]annulene-3-carboxylic acid, (117)

9-(4-((1-(3-fluoropropyl)azetidin-3-ylidene)methyl)phenyl)-8-(3-methyl-2-(trifluoromethyl)phenyl)-6,7-dihydro-5H-benzo[7]annulene-3-carboxylic acid, (118)

9-(4-((1-(3-fluoropropyl)azetidin-3-ylidene)methyl)phenyl)-8-(5-methyl-2-(trifluoromethyl)phenyl)-6,7-dihydro-5H-benzo[7]annulene-3-carboxylic acid, (119)

3-(4-(8-(2-chlorophenyl)-6,7-dihydro-5H-benzo[7]annulen-9-yl)benzylidene)-1-(3-fluoropropyl)azetidine, (120)

8-(2-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (121)

8-(2,4-dichlorophenyl)-9-(4-((1-(3-fluoropropyl-1,1-d2)azetidin-3-ylidene)methyl)phenyl)-6,7-dihydro-5H-benzo[7]annulene-3-carboxylic acid, (122)

8-(2-chloro-5-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (123)

8-(2,4-difluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (124)

8-(5-chloro-3-(trifluoromethyl)pyridin-2-yl)-9-(4-((1-(3,3-difluoropropyl)azetidin-3-ylidene)methyl)phenyl)-6,7-dihydro-5H-benzo[7]annulene-3-carboxylic acid, (125)

8-(3-chloro-2-methylphenyl)-9-(4-((1-(3,3-difluoropropyl)azetidin-3-ylidene)methyl)phenyl)-6,7-dihydro-5H-benzo[7]annulene-3-carboxylic acid, (126)

8-(4-chloro-3-fluoro-2-methylphenyl)-9-(4-((1-(3,3-difluoropropyl)azetidin-3-ylidene)methyl)phenyl)-6,7-dihydro-5H-benzo[7]annulene-3-carboxylic acid, (127)

8-(4-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, (128)

9-(4-((1-(3,3-difluoropropyl)azetidin-3-ylidene)methyl)phenyl)-8-(2-fluoro-3-(trifluoromethyl)phenyl)-6,7-dihydro-5H-benzo[7]annulene-3-carboxylic acid, (129)

9-(4-((1-(3,3-difluoropropyl)azetidin-3-ylidene)methyl)phenyl)-8-(4-fluoro-2,3-dimethylphenyl)-6,7-dihydro-5H-benzo[7]annulene-3-carboxylic acid, (130)

8-(2-chloro-3-methylphenyl)-9-(4-((1-(3,3-difluoropropyl)azetidin-3-ylidene)methyl)phenyl)-6,7-dihydro-5H-benzo[7]annulene-3-carboxylic acid, (131)

8-(4-chloro-2-methylphenyl)-9-(4-((1-(3,3-difluoropropyl)azetidin-3-ylidene)methyl)phenyl)-6,7-dihydro-5H-benzo[7]annulene-3-carboxylic acid, (132)

8-(2-chloro-3-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, (133)

9-(4-((1-(3,3-difluoropropyl)azetidin-3-ylidene)methyl)phenyl)-8-(2-methyl-3-(trifluoromethyl)phenyl)-6,7-dihydro-5H-benzo[7]annulene-3-carboxylic acid, (134)

9-(4-((1-(3-fluoropropyl)azetidin-3-ylidene)methyl)phenyl)-8-(2,3,4-trifluorophenyl)-6,7-dihydro-5H-benzo[7]annulene-3-carboxylic acid, (135)

9-(4-((1-(3-fluoropropyl)azetidin-3-ylidene)methyl)phenyl)-8-(2-methyl-5-(trifluoromethyl)phenyl)-6,7-dihydro-5H-benzo[7]annulene-3-carboxylic acid, (136)

9-(4-((1-(3-fluoropropyl)azetidin-3-ylidene)methyl)phenyl)-8-(2-methoxy-5-(137)

8-(4-fluoro-2-methylphenyl)-9-(4-((1-(3-fluoropropyl)azetidin-3-ylidene)methyl)-2-(trifluoromethyl)phenyl)-6,7-dihydro-5H-benzo[7]annulene-3-carboxylic acid, (138)

9-(2-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, (139)

8-(2-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (140)

8-(4-cyclopropyl-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (141)

Sodium 8-(2,4-difluorophenyl)-9-(2-fluoro-4-((1-(3-fluoropropyl)azetidin-3-ylidene)methyl)phenyl)-6,7-dihydro-5H-benzo[7]annulene-3-carboxylate, (142)

8-(3-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (143)

9-(4-((1-(3-fluoropropyl)azetidin-3-ylidene)methyl)phenyl)-8-(4-methyl-3-(trifluoromethyl)phenyl)-6,7-dihydro-5H-benzo[7]annulene-3-carboxylic acid, (144)

9-(4-((1-(3-fluoropropyl)azetidin-3-ylidene)methyl)phenyl)-8-(3-methyl-5-(trifluoromethyl)phenyl)-6,7-dihydro-5H-benzo[7]annulene-3-carboxylic acid, (145)

8-(3,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (146)

8-(2-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (147)

9-(4-((1-(3-fluoropropyl)azetidin-3-ylidene)methyl)phenyl)-8-(4-methoxy-3-(trifluoromethyl)phenyl)-6,7-dihydro-5H-benzo[7]annulene-3-carboxylic acid, (148)

8-(4-ethoxy-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (149)

9-(4-((1-(3-fluoropropyl)azetidin-3-ylidene)methyl)phenyl)-8-(3-methoxy-5-(150)

8-(2,5-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (151)

9-(2,3-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, (152)

8-(5-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (153)

8-(4-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (154)

8-(3-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, (155)

8-(5-fluoro-2-methoxypyridin-4-yl)-9-(4-((1-(3-fluoropropyl)azetidin-3-ylidene)methyl)phenyl)-6,7-dihydro-5H-benzo[7]annulene-3-carboxylic acid, (156)

8-(4-fluoro-2-methylphenyl)-9-(4-((1-(3-fluoropropyl)azetidin-3-ylidene)methyl)-3-(trifluoromethyl)phenyl)-6,7-dihydro-5H-benzo[7]annulene-3-carboxylic acid, (157)

8-(2,4-dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylic acid, (158)

8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylic acid, trifluoroacetic acid, (159)

9-(4-((1-(3,3-difluoropropyl)azetidin-3-ylidene)methyl)phenyl)-8-(5-fluoro-2,3-dihydro-1H-inden-4-yl)-6,7-dihydro-5H-benzo[7]annulene-3-carboxylic acid (160)

9-(4-((1-(3,3-difluoropropyl)azetidin-3-ylidene)methyl)phenyl)-8-(4-fluoro-2,3-dihydro-1H-inden-5-yl)-6,7-dihydro-5H-benzo[7]annulene-3-carboxylic acid (161)

9-(4-((1-(3,3-difluoropropyl)azetidin-3-ylidene)methyl)phenyl)-8-(6-fluoro-2,3-dihydro-1H-inden-4-yl)-6,7-dihydro-5H-benzo[7]annulene-3-carboxylic acid (162)

9-(4-((1-(3,3-difluoropropyl)azetidin-3-ylidene)methyl)phenyl)-8-(2,3-dihydro-1H-inden-4-yl)-6,7-dihydro-5H-benzo[7]annulene-3-carboxylic acid (163)

8-(1,1-difluoro-2,3-dihydro-1H-inden-4-yl)-9-(4-((1-(3,3-difluoropropyl)azetidin-3-ylidene)methyl)phenyl)-6,7-dihydro-5H-benzo[7]annulene-3-carboxylic acid (164)

9-(4-((1-(3,3-difluoropropyl)azetidin-3-ylidene)methyl)phenyl)-8-(7-fluoro-2,3-dihydro-1H-inden-4-yl)-6,7-dihydro-5H-benzo[7]annulene-3-carboxylic acid (165)

8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylic acid, racemic mixture (166)

8-benzyl-9-(4-((1-(3-fluoropropyl)azetidin-3-ylidene)methyl)phenyl)-6,7-dihydro-acid (167)

9-(4-((1-(3-fluoropropyl)azetidin-3-ylidene)methyl)phenyl)-8-phenethyl-6,7-dihydro-5H-benzo[7]annulene-3-carboxylic acid (168)

8-(cyclobutylmethyl)-9-(4-((1-(3-fluoropropyl)azetidin-3-ylidene)methyl)phenyl)-6,7-dihydro-5H-benzo[7]annulene-3-carboxylic acid (169)

8-(2,4-dichlorophenyl)-9-(4-((1-(3-fluoropropyl)azetidin-3-ylidene)methyl)phenyl)-6,7-dihydro-5H-benzo[7]annulen-3-ol (170)

8-(3,3-dimethylcyclohexyl)-9-(4-((1-(3-fluoropropyl)azetidin-3-ylidene)methyl)phenyl)-6,7-dihydro-5H-benzo[7]annulene-3-carboxylic acid, Isomer 1 (171)

8-(3,3-dimethylcyclohexyl)-9-(4-((1-(3-fluoropropyl)azetidin-3-ylidene)methyl)phenyl)-6,7-dihydro-5H-benzo[7]annulene-3-carboxylic acid, Isomer 2 (172)

9-(4-((1-(3-fluoropropyl)azetidin-3-ylidene)methyl)phenyl)-8-((trans)-2-phenylcyclopropyl)-6,7-dihydro-5H-benzo[7]annulene-3-carboxylic acid, racemic mixture (173)

84(1R,6S,70-bicyclo[4.1.0]heptan-7-yl)-9-(4-((1-(3-fluoropropyl)azetidin-3-ylidene)methyl)phenyl)-6,7-dihydro-5H-benzo[7]annulene-3-carboxylic acid (174)

8-(bicyclo[3.1.0]hexan-1-yl)-9-(4-((1-(3-fluoropropyl)azetidin-3-ylidene)methyl)phenyl)-6,7-dihydro-5H-benzo[7]annulene-3-carboxylic acid (175)

9-(4-((1-(3-fluoropropyl)azetidin-3-ylidene)methyl)phenyl)-8-(spiro[2.3]hexan-1-yl)-6,7-dihydro-5H-benzo[7]annulene-3-carboxylic acid (176)

9-(4-((1-(3-fluoropropyl)azetidin-3-ylidene)methyl)phenyl)-8-(5,6,7,8-tetrahydronaphthalen-1-yl)-6,7-dihydro-5H-benzo[7]annulene-3-carboxylic acid (177)

8-(bicyclo[3.2.1]octan-3-yl)-9-(4-((1-(3-fluoropropyl)azetidin-3-ylidene)methyl)phenyl)-6,7-dihydro-5H-benzo[7]annulene-3-carboxylic acid (178)

8-(4-chlorophenyl)-9-(4-((1-(3-fluoropropyl)azetidin-3-ylidene)methyl)phenyl)-7-methyl-6,7-dihydro-5H-benzo[7]annulene-3-carboxylic acid, Isomer 1 (179)

8-(3-chlorophenyl)-9-(4-((1-(3-fluoropropyl)azetidin-3-ylidene)methyl)phenyl)-6,7-dihydro-5H-benzo[7]annulene-3-carboxylic acid (180)

8-(4-chlorophenyl)-9-(4-((1-(3-fluoropropyl)azetidin-3-ylidene)methyl)phenyl)-6,7-dihydro-5H-benzo[7]annulene-3-carboxylic acid (181)

9-(4-((1-(3-fluoropropyl)azetidin-3-ylidene)methyl)phenyl)-8-(3-(trifluoromethyl)phenyl)-6,7-dihydro-5H-benzo[7]annulene-3-carboxylic acid hydrochloride (182)

9-(4-((1-(3-fluoropropyl)azetidin-3-ylidene)methyl)phenyl)-8-(2-(trifluoromethyl)phenyl)-6,7-dihydro-5H-benzo[7]annulene-3-carboxylic acid hydrochloride (183)

8-(4-chlorophenyl)-9-(4-((1-(3-fluoropropyl)azetidin-3-ylidene)methyl)phenyl)-7-methyl-6,7-dihydro-5H-benzo[7]annulene-3-carboxylic acid, Isomer 2 (184)

9-(4-((1-(3-fluoropropyl)azetidin-3-ylidene)methyl)phenyl)-8-(4-(trifluoromethyl)phenyl)-6,7-dihydro-5H-benzo[7]annulene-3-carboxylic acid hydrochloride (185)

8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid (186)

8-(trans-2-(4,4-difluorocyclohexyl)cyclopropyl)-9-(4-((1-(3-fluoropropyl)azetidin-3-ylidene)methyl)phenyl)-6,7-dihydro-5H-benzo[7]annulene-3-carboxylic acid, racemic mixture (187)

9-(3-fluoro-5-((1-(3-fluoropropyl)azetidin-3-ylidene)methyl)pyridin-2-yl)-8-(4-methylcyclohexyl)-6,7-dihydro-5H-benzo[7]annulene-3-carboxylic acid, mixture of isomers (188).

Another embodiment is a compound selected from the above list, or a pharmaceutically acceptable salt thereof, for use in therapy, especially as an inhibitor and degrader of estrogen receptors.

Another embodiment is a compound selected from the above list, or a pharmaceutically acceptable salt thereof, for use in the treatment of cancer, especially breast cancer.

Another embodiment is a method of inhibiting and degrading estrogen receptors, comprising administering to a subject in need thereof, in particular a human, a therapeutically effective amount of a compound selected from the above list, or a pharmaceutically acceptable salt thereof.

Another embodiment is a method of treating ovulatory dysfunction, cancer, endometriosis, osteoporosis, benign prostatic hypertrophy or inflammation, comprising administering to a subject in need thereof, in particular a human, a therapeutically effective amount of a compound selected from the above list, or a pharmaceutically acceptable salt thereof.

Another embodiment is a method of treating cancer, comprising administering to a subject in need thereof, in particular a human, a therapeutically effective amount of a compound selected from the above list, or a pharmaceutically acceptable salt thereof.

Another embodiment is a pharmaceutical composition comprising as active principle an effective dose of a compound selected from the above list, or a pharmaceutically acceptable salt thereof, and also at least one pharmaceutically acceptable excipient.

The compounds of the formula (I) can be prepared by the following processes.

The compounds of the formula (I) and other related compounds having different substituents are synthesized using techniques and materials described below or otherwise known by the skilled person in the art. In addition, solvents, temperatures and other reaction conditions presented below may vary as deemed appropriate to the skilled person in the art.

General below methods for the preparation of compounds of formula (I) optionally modified by the use of appropriate reagents and conditions for the introduction of the various moieties found in the formula (I) as described below.

The following abbreviations and empirical formulae are used:

| | |
|---|---|
| MeCN | Acetonitrile |
| $NH_4Cl$ | Ammonium chloride |
| BuLi | Butyl lithium |
| CO | Carbon monoxide |
| $Cs_2CO_3$ | Cesium carbonate |
| DBU | 1,8-Diazabicyclo[5.4.0]undec-7-ene |
| DCM | Dichloromethane |
| $Et_2O$ | Diethyl ether |
| DIEA | Diisopropylethylamine |
| DMF | N,N-dimethylformamide |
| DMSO | Dimethyl sulfoxide |
| Dppf | 1,1'-Bis(diphenylphosphino)ferrocene |
| EtOH | Ethanol |
| EtOAc | Ethyl acetate |
| h | hour |
| $H_2$ | Hydrogen |
| HCl | Hydrochloric acid |
| HPLC | High performance liquid chromatography |
| LiOH | Lithium hydroxide |
| LiHMDS | Lithium hexamethyldisilazane |
| MeOH | Methanol |
| $MgSO_4$ | Magnesium sulfate |
| MTBE | Methyl tert-butyl ether |
| MeTHF | 2-Methyltetrahydrofuran |
| min | minute |
| n-BuLi | n-Butyllithium |
| Pd/C | Palladium on carbon |
| KOAc | Potassium acetate |
| $K_2CO_3$ | Potassium carbonate |
| KHMDS | Potassium hexamethyldisilazane |
| KOH | Potassium hydroxide |
| $NaBH_4$ | Sodium borohydride |
| $NaHCO_3$ | Sodium bicarbonate |
| NaH | Sodium hydride |
| NaOH | Sodium hydroxide |
| $Na_2SO_4$ | Sodium sulfate |
| $NaHSO_3$ | Sodium bisulfate |
| SCX | Strong cation exchange |
| $Pd(dppf)Cl_2$ | [1,1'-Bis(diphenylphosphino)ferrocene]dichloropalladium(II) |
| $Pd(PPh_3)_2Cl_2$ | bis (triphenylphosphine) palladium(II) dichloride |
| $Pd(PPh_3)_4$ | tetrakis(triphenylphosphine)palladium(0) |
| $Pd_2(dba)_3$ | tris(dibenzylideneacetone)dipalladium(0) |
| PhOK | Potassium phenolate |
| SFC | Supercritical Fluid Chromatography |
| TEA | Triethylamine |
| TFA | Trifluoroacetic acid |
| THF | Tetrahydrofuran |
| $PPh_3$ | Triphenylphosphine |
| RT | Room temperature |
| Ar | Argon |
| DABCO | 1,4-diazabicyclo[2.2.2]octane |

Scheme 1a - Part I: Preparation of compounds of the formula (I) - General process
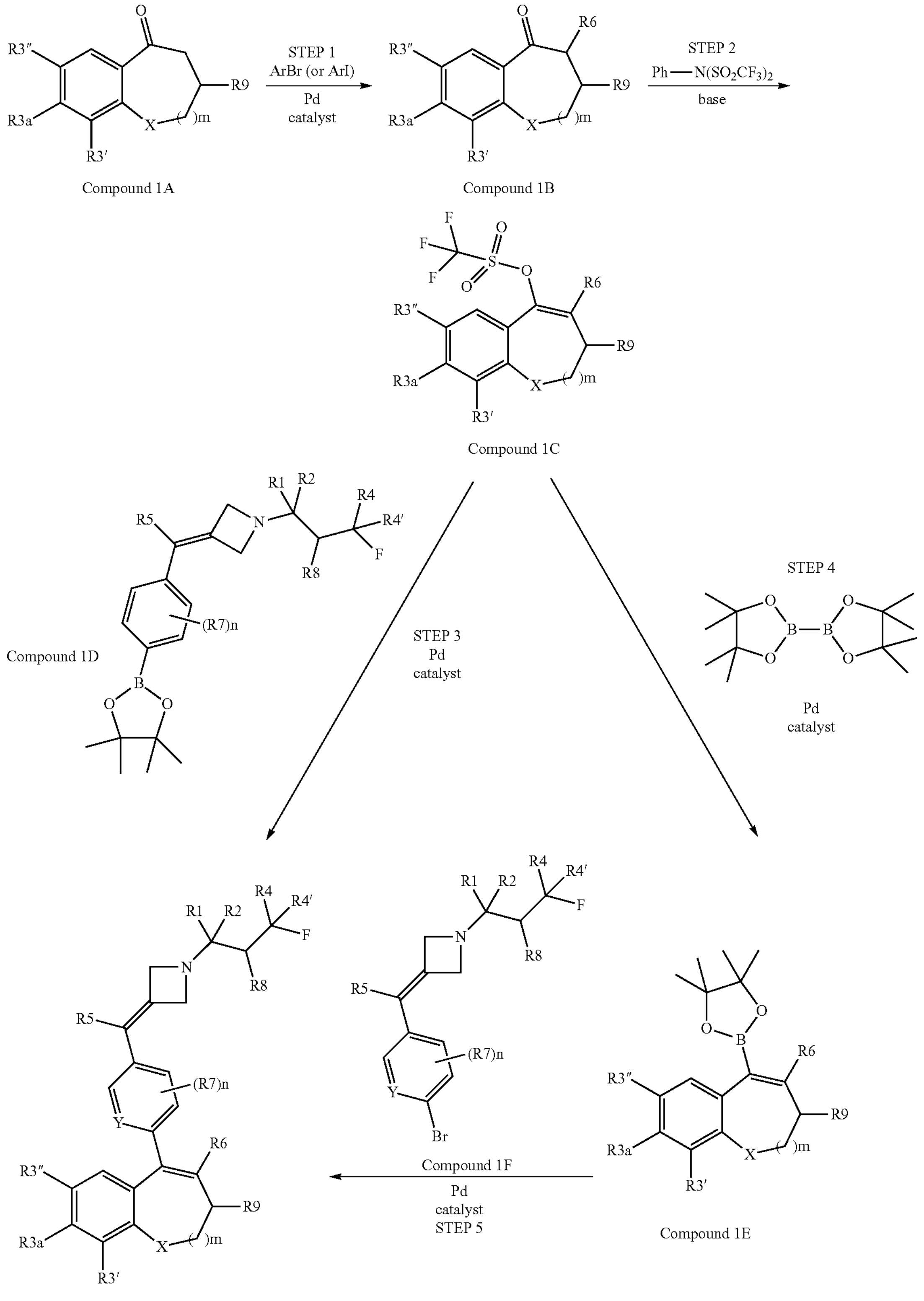
Compound 1A
Compound 1B
Compound 1C
Compound 1D
Compound 1F
Compound 1E
Compound 1K -continued

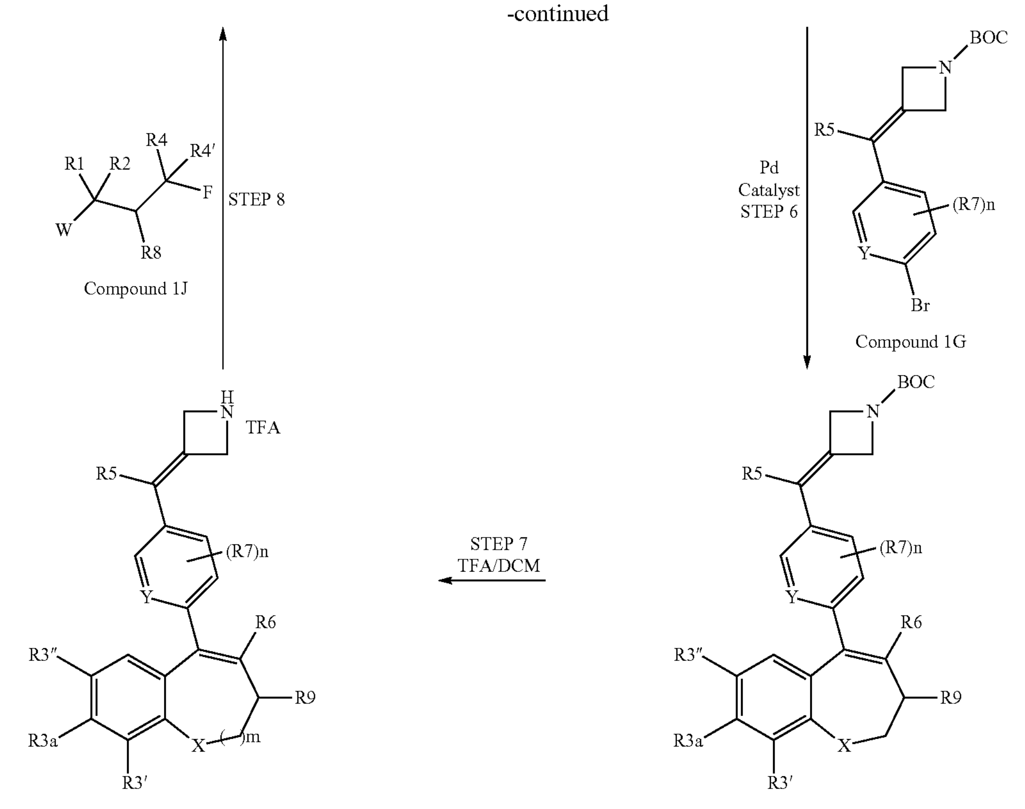

Compound 1J

Compound 1G

Compound 1I

Compound 1H

SCHEME 1a - Part-2

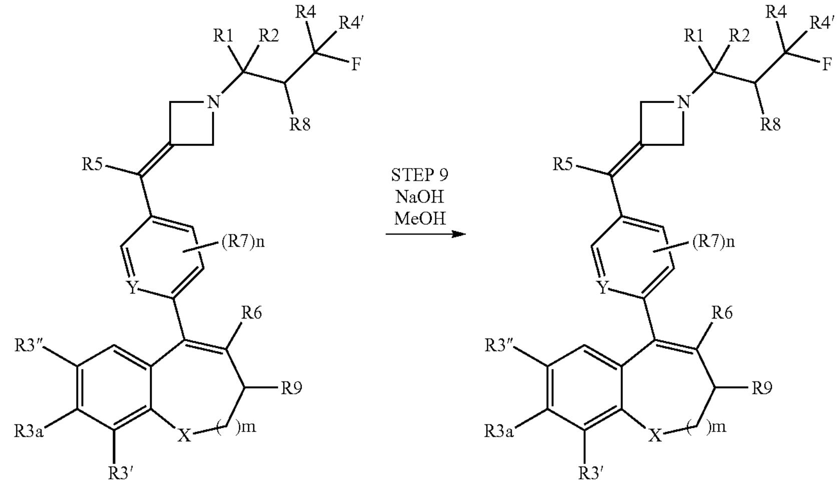

Compound 1K

Compound 1

According to SCHEME 1a-Part-1 and Part-2, in which R3a is H or a carboxylic ester such as COOMe, COOEt, or protected OH with O-pivaloyl for example, and R9 is a hydrogen atom, R1, R2, R3, R3', R3", R4, R4', R5, R6, R7, R8, X, m, n and Y are defined as described above, compound 1A can be converted in STEP 1 to compound 1B by treatment with aryl bromide or iodide in the presence of a palladium catalyst, for example tris(dibenzylideneacetone) dipalladium(0) $Pd_2(dba)_3$, and a phosphine such as (9,9-dimethyl-9H-xanthene-4,5-diyl)bis(diphenylphosphane) (XANTPHOS) in solution in toluene by heating up to reflux of solvent, in presence of a base such as $K_2CO_3$ or $Cs_2CO_3$.

Compound 1B can be converted in STEP 2 to compound 1C by treatment with N,N-bis(trifluoromethylsulfonyl)aniline in the presence of base such as DBU or NaH, or KHMDS at −50° C., in a solvent such as MeTHF.

Compound 1C, can be converted in STEP 4 to compound 1E by treatment for example with bis(pinacolato)diboron, and with a palladium catalyst, for example bis (triphenylphosphine) palladium(II) dichloride $Pd(PPh_3)_2Cl_2$, and a phosphine, such as triphenylphosphine, in solution in toluene by heating up to reflux of solvent, in presence of a base such as KOPh.

Compound 1K can be prepared in a Suzuki coupling reaction either between compounds 1C and 1D in STEP 3 or between compounds 1E and 1F in STEP 5 using for example [1,1'-bis(diphenylphosphino) ferrocene]dichloropalladium (II) (Pd(dppf)$Cl_2$), complex with DCM, as catalyst, in a mixture of dioxane and water and in the presence of a base, for example cesium carbonate ($Cs_2CO_3$), by heating up to reflux of solvent.

Alternatively, compound 1E can be converted in STEP 6 to compound 1H in a Suzuki coupling reaction with compound 1G using for example [1,1'-bis(diphenylphosphino) ferrocene]dichloropalladium(II) (Pd(dppf)$Cl_2$), complex with DCM, as catalyst, in a mixture of dioxane and water and in the presence of a base, for example cesium carbonate ($Cs_2CO_3$), by heating up to reflux of solvent. Compound 1H can be converted in STEP 7 to compound 1I by treatment with TFA in solution in DCM or HCl in solution in dioxane. Compound 1I can be converted in STEP 8 to compound 1K by treatment with compound 1J, wherein W is Br, I or $OSO_2R$ with R=$CH_3$, PhMe, $CF_3$ or $CF_2CF_2CF_2CF_3$, in presence of a base such as potassium carbonate in DMF at 70° C. or in presence of sodium hydroxide or potassium hydroxide in THF at room temperature or in presence of aqueous sodium hydroxide in DCM at room temperature.

When R3a is COOMe, COOEt, or a protected OH such as O-pivaloyl, compound 1K can be deprotected into compound I in STEP 9 by treating with an aqueous solution of sodium hydroxide (NaOH) or lithium hydroxide (LiOH), in MeOH. When R3 is COOH, extraction of compound could give the sodium salt of compound I. The acidification with an aqueous solution of HCl 2N to pH 6-7 could give the neutral form. The acidification with an aqueous solution of HCl 2N to pH 1-2 could give the hydrochloride salt. The purification using HPLC could give the formate or trifluoroacetate salt.

SCHEME 1B - Part 1: Preparation of compounds of the formula (I) - General process

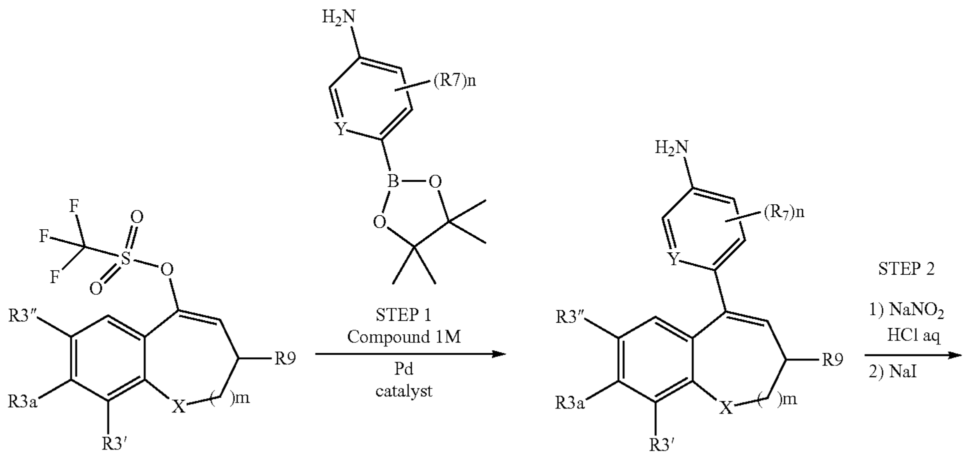

Compound 1L

Compound 1N

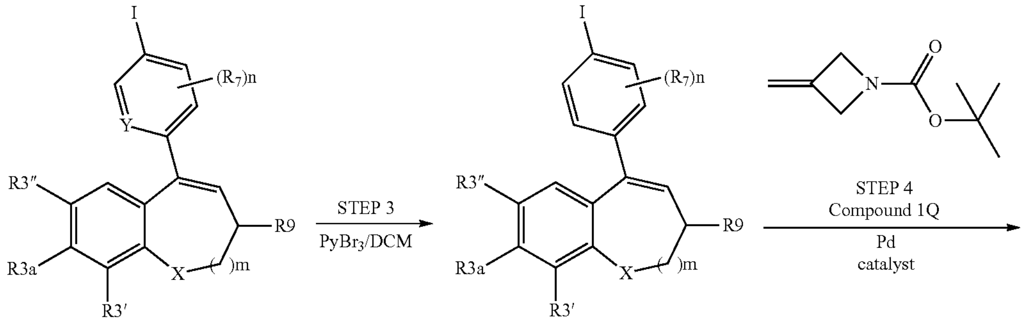

Compound 1O

Compound 1P

-continued
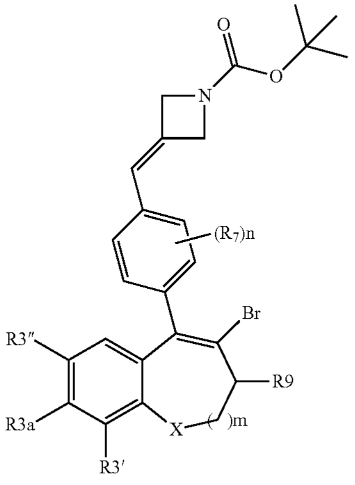
Compound 1R
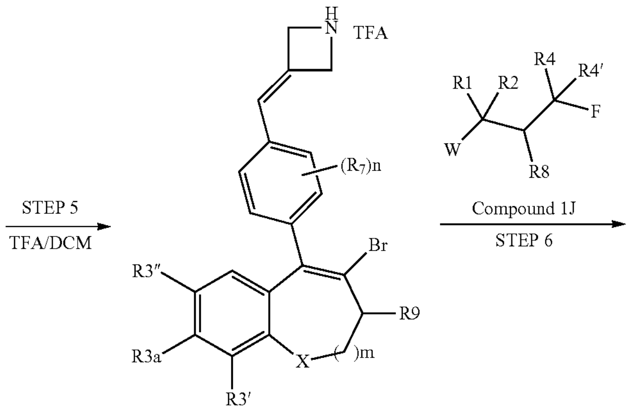
Compound 1S
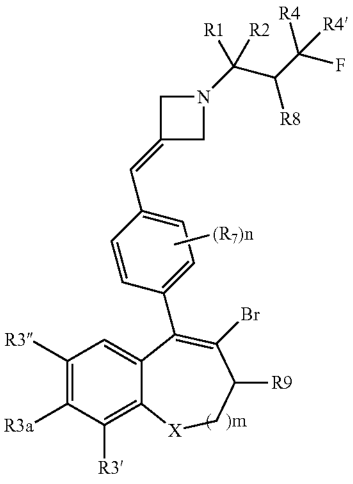
Compound 1T
SCHEME 1b - Part 2
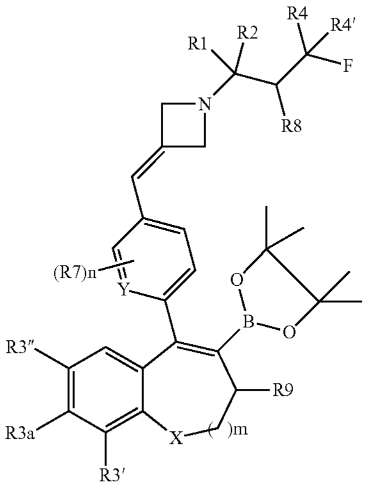
Compound 1U -continued

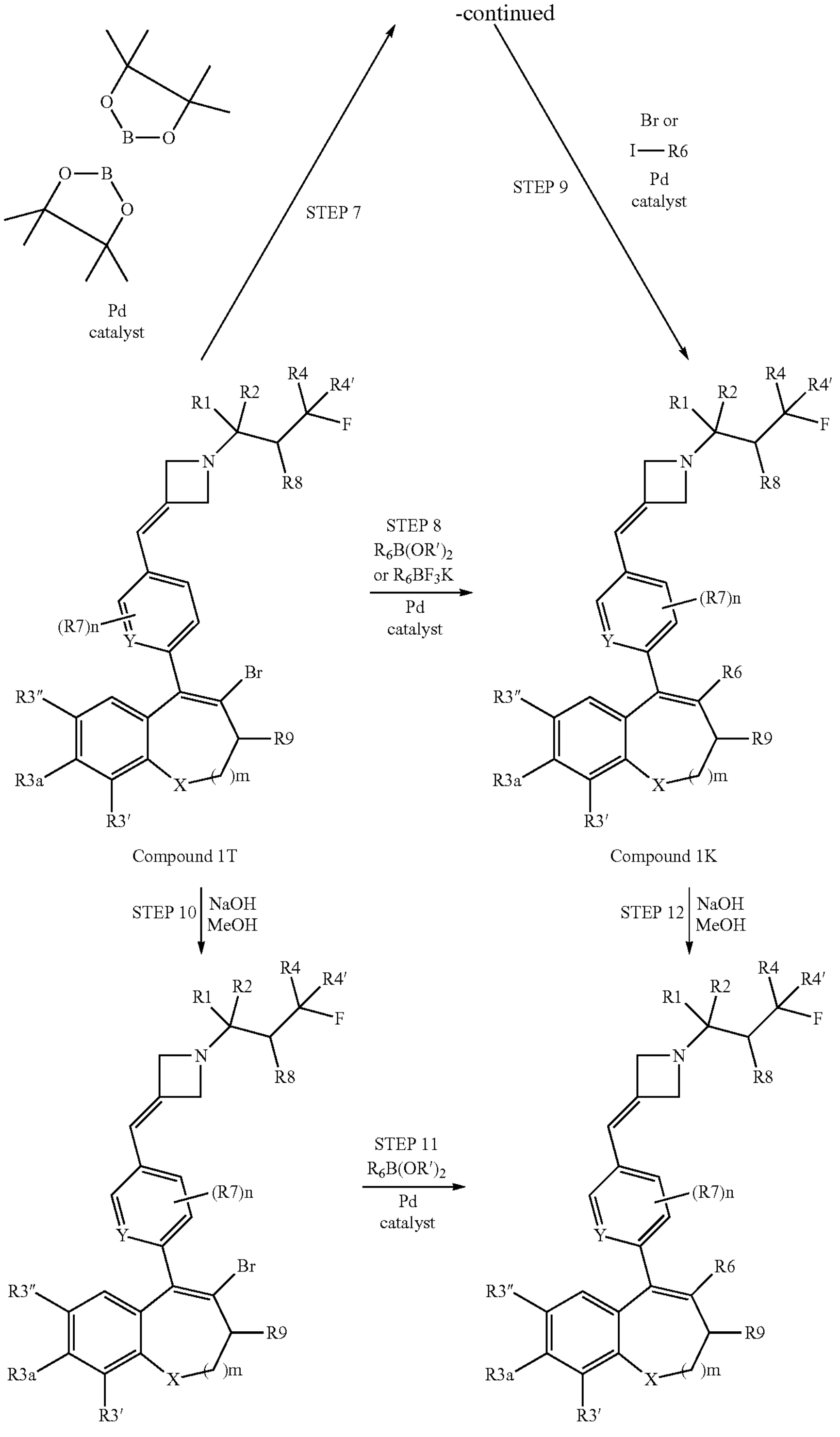

Compound 1T

Compound 1K

Compound 1Ta

Compound 1

According to SCHEME 1b-Part-1 and Part-2, in which R3a is H, a carboxylic ester such as COOMe, COOEt, or protected OH with O-pivaloyl for example, R1, R2, R3, R3', R3", R4, R4', R6, R7, R8, R9, X, n, m and Y are defined as described above, compound 1L can be converted in STEP 1 to compound 1N in a Suzuki coupling reaction with compound 1M using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Compound 1N can be converted in STEP 2 to compound 1O by treatment with sodium nitrite followed by a treatment with sodium iodide in solvents such as a mixture of water and acetonitrile.

Compound 1O can be converted in STEP 3 to compound 1P by treatment for example with pyridinium tribromide in DCM or THF at room temperature. Compound 1P can be converted in STEP 4 to compound 1R in a Heck coupling reaction with compound 1Q using for example palladium (II) acetate as catalyst in a solvent such as DMF.

Compound 1R can be converted in STEP 5 to compound 1S by treatment with TFA in solution in DCM or HCl in solution in dioxane.

Compound 1S can be converted in STEP 6 to compound 1T by treatment with compound 1J, wherein W is Cl, Br or I or $OSO_2R$ with R═$CH_3$, PhMe, $CF_3$ or $CF_2CF_2CF_2CF_3$, in presence of a base such as potassium carbonate in DMF at 70° C. or in presence of sodium hydroxide or potassium hydroxide in THF at room temperature or in presence of aqueous sodium hydroxide in DCM at room temperature.

Compound 1T can be converted in STEP 7 to compound 1U by treatment for example with bis(pinacolato)diboron, and with a palladium catalyst, for example bis (triphenylphosphine) palladium(II) dichloride $Pd(PPh_3)_2Cl_2$, and a phosphine such as triphenylphosphine in solution in toluene by heating up to reflux of solvent in presence of a base such as KOPh.

Compound 1K can be prepared in a Suzuki coupling reaction either between compounds 1T and $R6B(OR')_2$ or $R6BF_3K$ in STEP 8 or between compounds 1U and R6Br or R6I in STEP 9 using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Compound 1K can be converted in STEP 12 to compound of formula (I) in presence of a source of hydroxide ions such as NaOH in solution in methanol (MeOH).

Intermediate 1T can be converted in STEP 10 to compound 1Ta in the presence of a source of hydroxide ions such as NaOH in solution in methanol (MeOH).

This compound 1Ta can be converted in STEP 11 to compound I through Suzuki conditions using a suitable boronic reagent $R6B(OR')_2$ or $R6BF_3K$, wherein —$B(OR')_2$ is a boronic acid or a pinacolate ester and R6 is as above defined, using for example $Pd(dppf)Cl_2$, complex with DCM, as catalyst, in a mixture of dioxane and water as solvent and in the presence of a base, for example $Cs_2CO_3$, at room temperature or by heating up to reflux of solvents.

When R3a is COOMe, COOEt, or a protected OH such as O-pivaloyl, compound 1K can be deprotected into compound I in STEPS 12 by treating with an aqueous solution of sodium hydroxide (NaOH) or lithium hydroxide (LiOH), in MeOH. When R3 is COOH, extraction of compound could give the sodium salt of compound I. The acidification with an aqueous solution of HCl 2N to pH 6-7 could give the neutral form. The acidification with an aqueous solution of HCl 2N to pH 1-2 could give the hydrochloride salt. The purification using HPLC could give the formate or trifluoroacetate salt.

SCHEME 1c - Part - 1: Alternative process to prepare Intermediate 1T

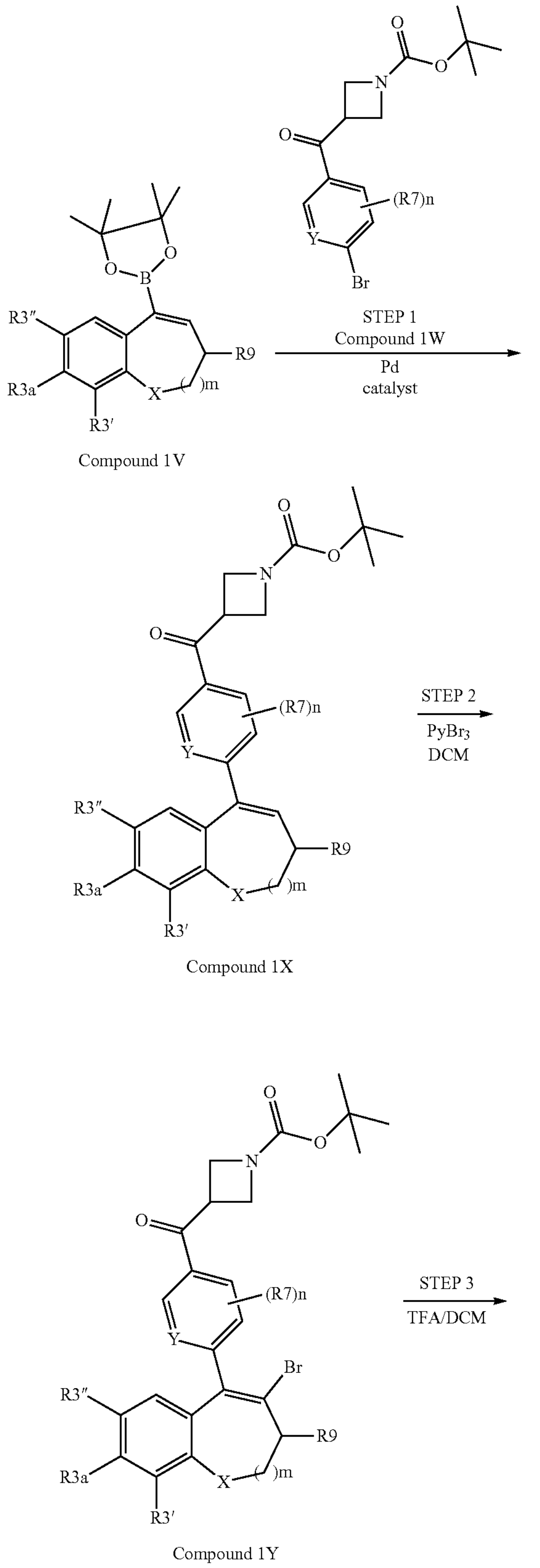

Compound 1V

Compound 1X

Compound 1Y

-continued
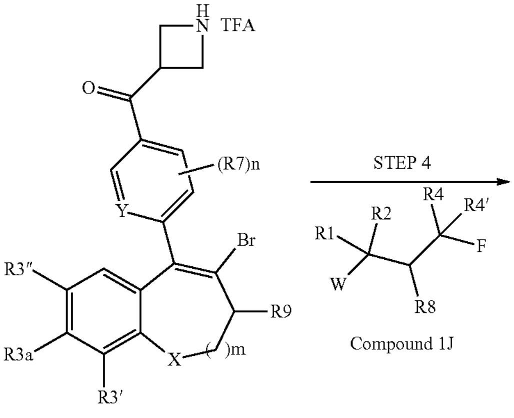
Compound 1Z Compound 1J
-continued
SCHEME 1c - Part - 2
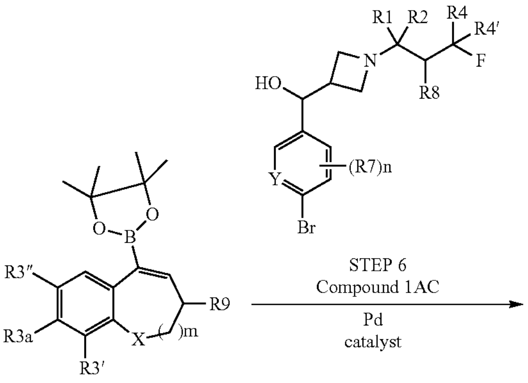
Compound IV
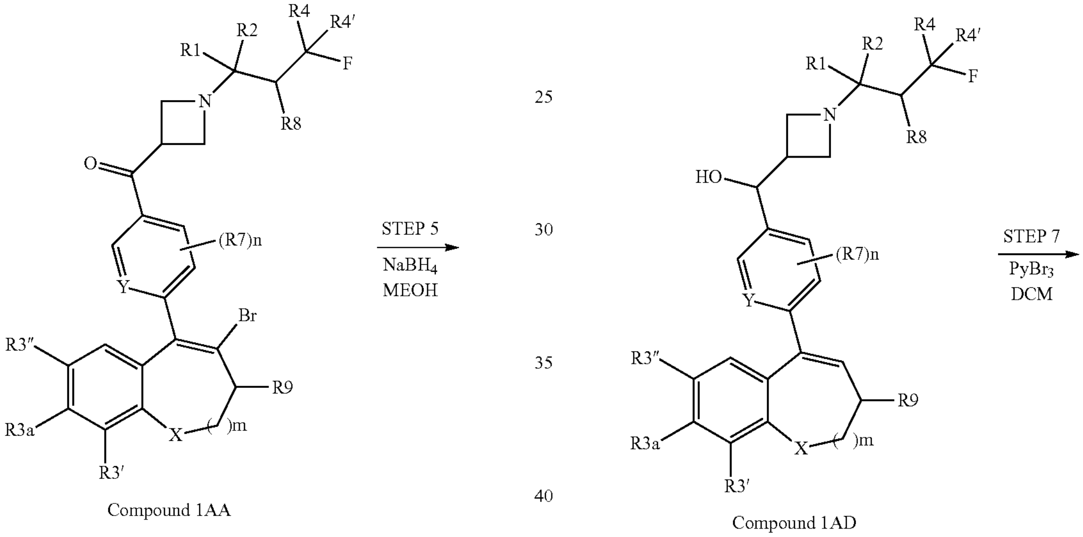
Compound 1AA Compound 1AD
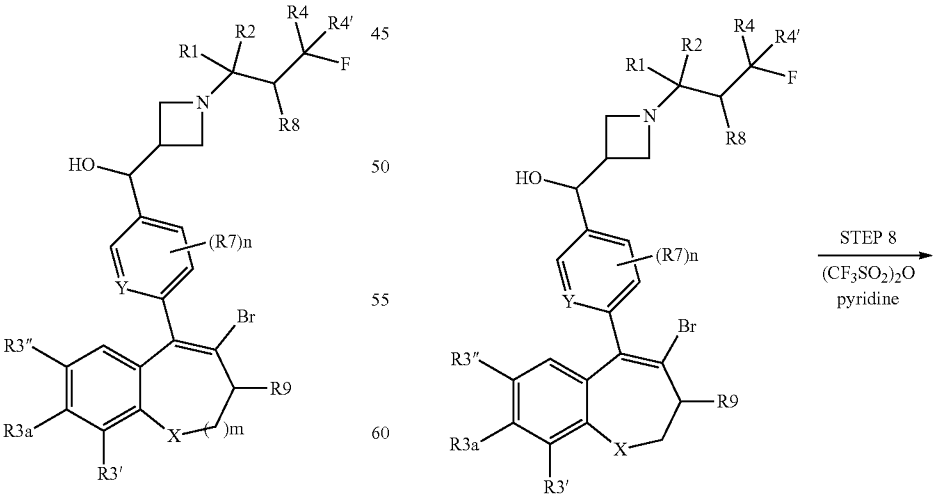
Compound 1AB Compound 1AB -continued

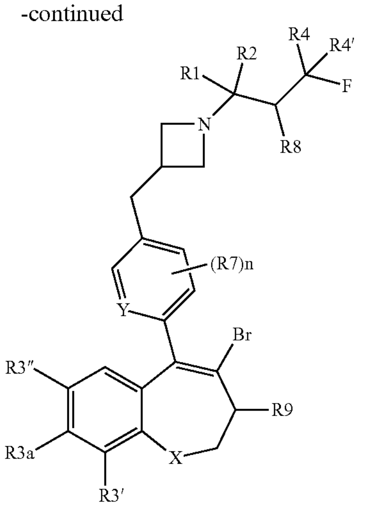

Compound 1T

According to SCHEME 1c-Part-1 and Part-2, in which R3a is H, carboxylic ester such as COOMe, COOEt, or protected OH with O-pivaloyl for example, R1, R2, R3, R3', R3", R4, R7, R8, R9, X, n, m and Y are defined as described above, compound 1V can be converted in STEP 1 to compound 1X in a Suzuki coupling reaction with compound 1W using for example [1,1'-bis(diphenylphosphino) ferrocene]dichloropalladium(II) (Pd(dppf)$Cl_2$), complex with DCM, as catalyst, in a mixture of dioxane and water and in the presence of a base, for example cesium carbonate ($Cs_2CO_3$), by heating up to reflux of solvent.

Compound 1X can be converted in STEP 2 to compound 1Y by treatment for example with pyridinium tribromide in DCM or THF at room temperature.

Compound 1Y can be converted in STEP 3 to compound 1Z by treatment with with TFA in solution in DCM or HCl in solution in dioxane.

Compound 1Z can be converted in STEP 4 to compound 1AA by treatment with compound 1J, wherein W is Cl, Br or I or $OSO_2R$ with R=$CH_3$, PhMe, $CF_3$ or $CF_2CF_2CF_2CF_3$, in presence of a base such as potassium carbonate in DMF at 70° C. or in presence of sodium hydroxide of potassium hydroxide in THF at room temperature.

Compound 1AA can be converted in STEP 5 to compound 1AB by treatment with sodium borohydride in solution in MeOH.

Compound 1AB can also be prepared from compound 1V using Suzuki coupling reaction with compounds 1AC in STEP 6 using for example [1,1'-bis(diphenylphosphino) ferrocene]dichloropalladium(II) (Pd(dppf)$Cl_2$), complex with DCM, as catalyst, in a mixture of dioxane and water and in the presence of a base, for example cesium carbonate ($Cs_2CO_3$), by heating up to reflux of solvent followed by bromination of the resulting compound 1AD in STEP 7 by treatment for example with pyridinium tribromide in DCM or THF at room temperature.

Compound 1AB can be converted in STEP 8 to compound 1T by treatment with trifluoromethanesulfonic anhydride and pyridine in DCM.

SCHEME 1d:
Preparation of compounds of the formula (I) - General process

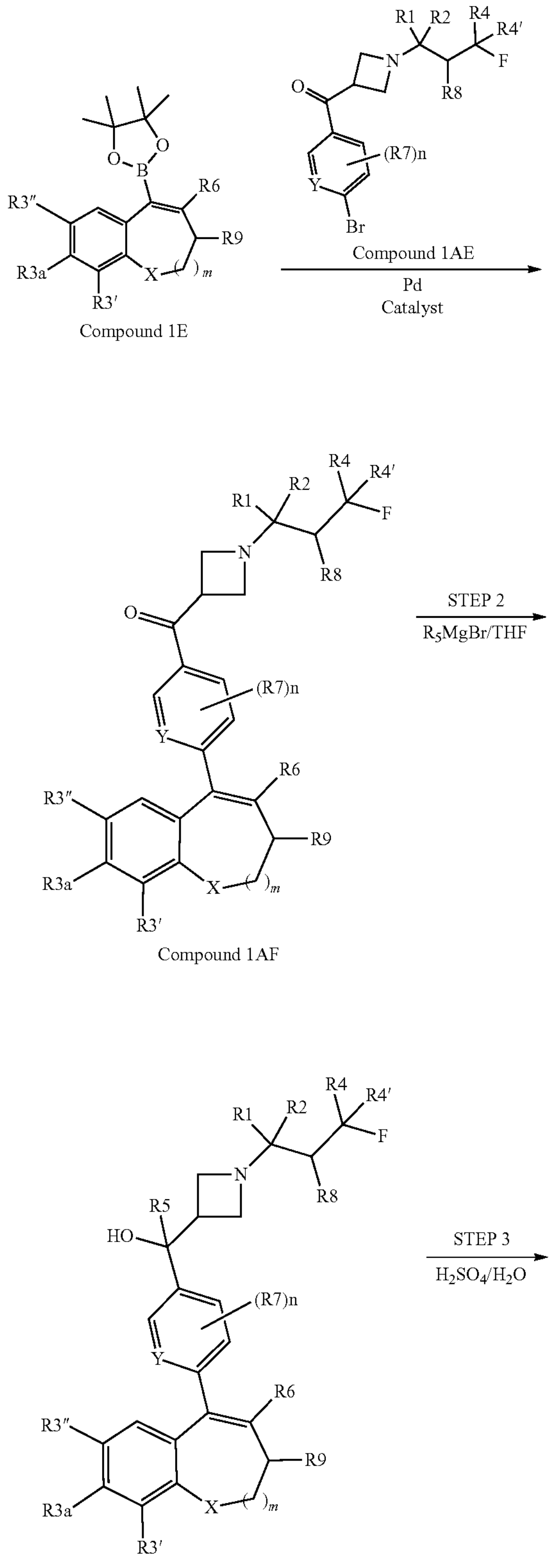

Compound 1E

Compound 1AE

Compound 1AF

Compound 1AG

-continued

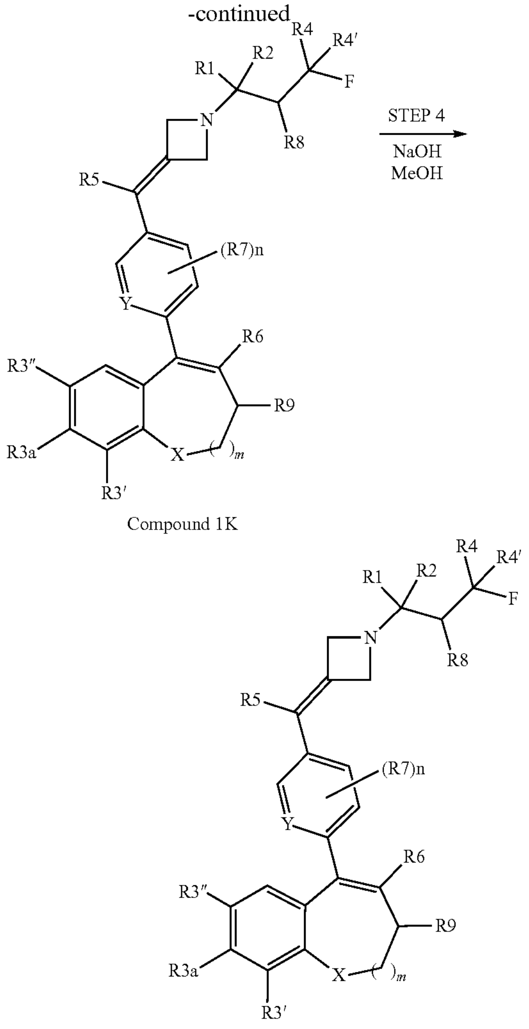

Compound 1K

Compound I

According to SCHEME 1d, in which R3a is H, carboxylic ester such as COOMe, COOEt, or protected OH with O-pivaloyl for example, and R9 is a hydrogen atom R1, R2, R3, R3', R3", R4, R4', R5, R6, R7, R8, X, n, m and Y are defined as described above, compound 1E can be converted in STEP 1 to compound 1AF in a Suzuki coupling reaction by treatment with compound 1AE using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Compound 1AF can be converted in STEP 2 to compound 1AG by treatment with alkyl magnesium bromide in a solvent such as THF.

Compound 1AG can be converted in STEP 3 to compound 1K by treatment with sulfuric acid in water.

When R3a is COOMe, COOEt, or a protected OH such as O-pivaloyl, compound 1K can be deprotected into compound I in STEP 4 by treating with an aqueous solution of sodium hydroxide (NaOH) or lithium hydroxide (LiOH), in MeOH. When R3 is COOH, extraction of compound could give the sodium salt of compound I. The acidification with an aqueous solution of HCl 2N to pH 6-7 could give the neutral form. The acidification with an aqueous solution of HCl 2N to pH 1-2 could give the hydrochloride salt. The purification using HPLC could give the formate or trifluoroacetate salt.

SCHEME 1e:
Alternative preparation of compounds of the formula (1B) - General process

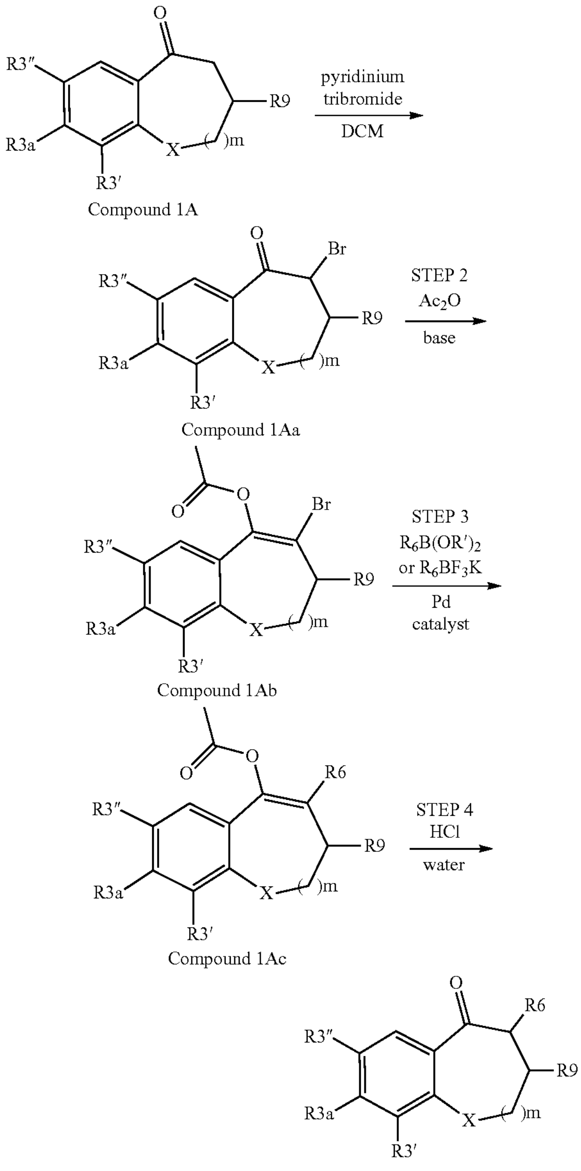

Compound 1A

Compound 1Aa

Compound 1Ab

Compound 1Ac

Compound 1B

According to SCHEME 1e, in which R3a is H, a carboxylic ester such as COOMe, COOEt, or protected OH with O-pivaloyl for example, R3', R3", R9, X and m are defined as described above, compound 1B could alternatively be prepared as follows: compound 1A can be converted in STEP 1 to compound 1Aa by treatment with pyridinium tribromide in DCM or THF at room temperature for example.

Compound 1Aa can be converted in STEP 2 to compound 1Ab by deprotonation with a base such as LiHMDS in THF followed by treatment with acetic anhydride.

Compound 1Ac can be prepared in STEP 3 in a Suzuki coupling reaction between compounds 1 Ab and $R6B(OR')_2$ or $R6BF_3K$ using for example [1,1'-bis(diphenylphosphino) ferrocene]dichloropalladium(II) ($Pd(dppf)Cl_2$), complex with DCM, as catalyst, in a mixture of toluene and water and in the presence of a base, for example cesium carbonate ($Cs_2CO_3$), by heating up to reflux of solvent. When R6 is a substituted cycloalkene, heterocycloalkene or aliphatic ethylene, it may be reduced by hydrogenation with a catalyst such as Pd/C under hydrogen pressure ($H_2$) around 5 bars for example at temperature up to 70° C. to give the corresponding saturated compound 1Ac.

Compound 1Ac can be converted in STEP 4 to compound 1B by hydrolysis with aqueous HCl solution by heating in methanol and DCM for example.

Herein is also provided a process for preparing a compound of formula (I) as defined above, wherein a compound of formula 1K

1K

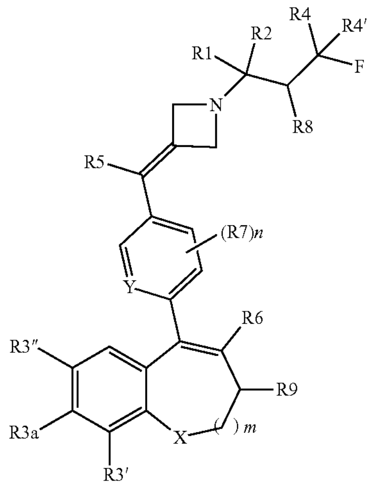

wherein R1, R2, R3', R3", R4, R4', R5, R6, R7, R8, R9, m, n, X and Y are as defined above and R3a is carboxylic ester such as COOMe, COOEt, or protected OH with for example, is converted to compound of formula (I), in presence of a source of hydroxide ions, such as NaOH in solution in methanol, said step being optionally preceded by a step for obtaining compound 1K, wherein a compound of formula 1T

1T

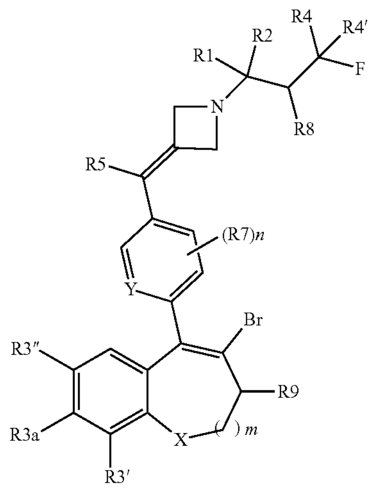

wherein, R1, R2, R3', R3", R4, R4', R5, R7, R8, R9, m, n, X and Y are as described above and R3a is as defined above, is subjected to a Suzuki coupling with a boronic reagent $R6B(OR')_2$ or $R6BF_3K$, wherein $—B(OR')_2$ is a boronic acid or a pinacolate ester and R6 is as defined above.

Herein is also provided a process for preparing a compound of formula (I) as described above, wherein a compound of formula 1Ta 1Ta

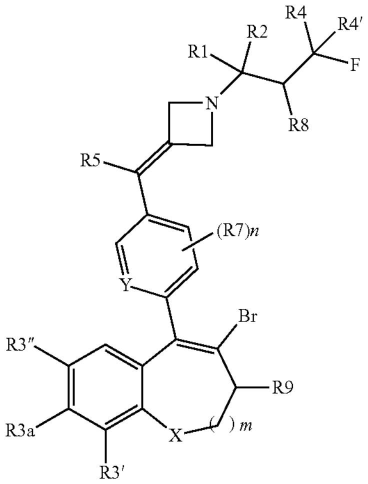

wherein R1, R2, R3a, R3', R3", R4, R4', R5, R7, R8, R9, m, n, X and Y are as described above, is submitted to a Suzuki coupling with a boronic reagent $R6B(OR')_2$ or $R6BF_3K$, wherein $—B(OR')_2$ is a boronic acid or a pinacolate ester and R6 is defined above, said step being optionally preceded by a step for obtaining compound 1Ta, wherein a compound of formula 1T

1T

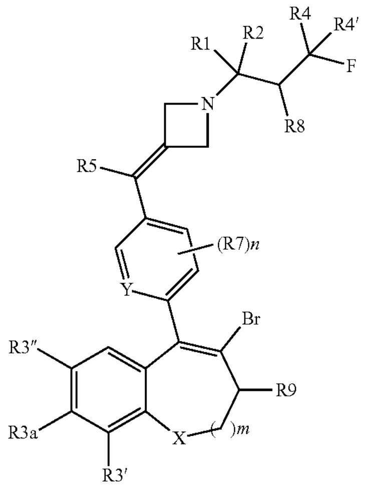

wherein R1, R2, R3', R3", R4, R4', R5, R7, R8, R9, m, n, X and Y are as described above and R3a is as defined above, is converted to a compound 1Ta in the presence of a source of hydroxide ions, such as NaOH in solution in methanol.

Herein are also provided the intermediate compounds selected from compounds of formula 1T, 1K and 1Ta, or any of their pharmaceutically acceptable salt,

1T

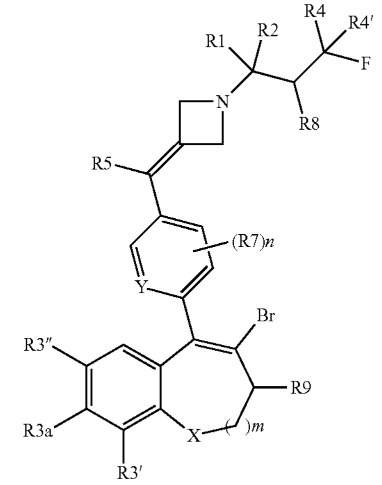

1K

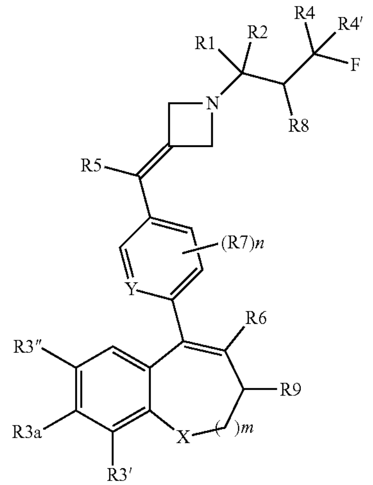

and

1Ta

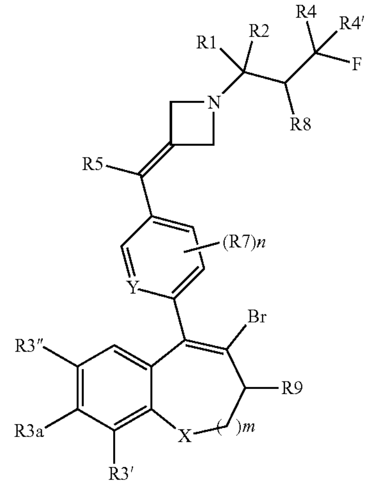

wherein R1, R2, R3', R3", R4, R4', R5, R7, R8, R9, m, n, X and Y are as defined above and R3a is carboxylic ester such as COOMe, COOEt, or protected OH with 0-pivaloyl.

Herein is further provided the intermediate compound of formula 1F, or any of its pharmaceutically acceptable salt

1F

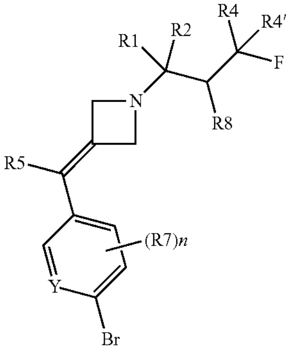

wherein R1, R2, R4, R4', R5, R7, R8, Y and n are as described above.

The present application also describes the intermediate compound of formula 1E, or any of its pharmaceutically acceptable salt

IE

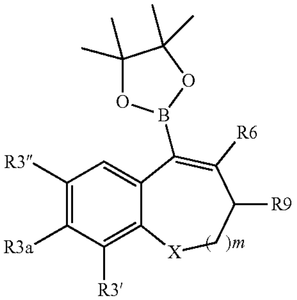

wherein R3a, R3', R3", X, m, R6 and R9 is a hydrogen atom are as described above.

In another aspect, herein is also provided a process for the preparation of a compound of formula (I), wherein R3 is a —COOH group, comprising a deprotection step of a compound of formula IG as defined above, optionally followed by a purification step.

Said purification step may for example consist, as illustrated in step 6 of example 1 herein after, in an acidification step, for example with an aqueous solution of hydrochloric acid.

The $^{1}H$ NMR Spectra at 400 and 500 MHz were performed on a Bruker Avance DRX-400 and Bruker Avance DPX-500 spectrometer, respectively, with the chemical shifts (δ in ppm) in the solvent dimethyl sulfoxide-d6 (d6-DMSO) referenced at 2.5 ppm at a temperature of 303 K. Coupling constants (J) are given in Hertz.

The liquid chromatography/mass spectra (LC/MS) were obtained on a UPLC Acquity Waters instrument, light scattering detector Sedere and SQD Waters mass spectrometer using UV detection DAD 210-400 nm and flash Acquity UPLC CSH C18 1.7 μm, dimension 2.1×30 mm, mobile phase $H_2O$+0.1% $HCO_2H/CH_3CN$+0.1% $HCO_2H$.

The following tables 1a and 1b comprise respectively specific compounds of formula (I) (name and structure) in accordance with the present disclosure as well their characterization ($^{1}H$ NMR and liquid chromatography/mass).

TABLE 1a

| Ex. or compounds | Structure | Name |
| --- | --- | --- |
| 1 | 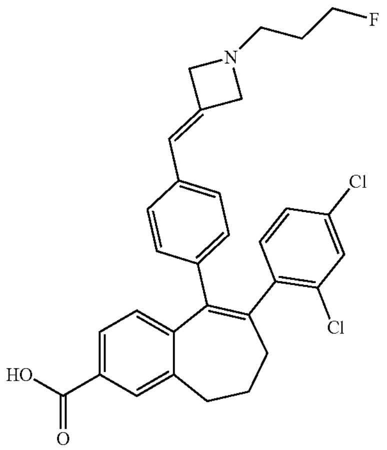 [SMILES: O=C(O)c1ccc2c(c1)CCCC(c1ccc(Cl)cc1Cl)=C2c1ccc(C=C2CN(CCCF)C2)cc1] | 8-(2,4-dichlorophenyl)-9-(4-((1-(3-fluoropropyl)azetidin-3-ylidene)methyl)phenyl)-6,7-dihydro-5H-benzo[7]annulene-3-carboxylic acid |
| 2 | 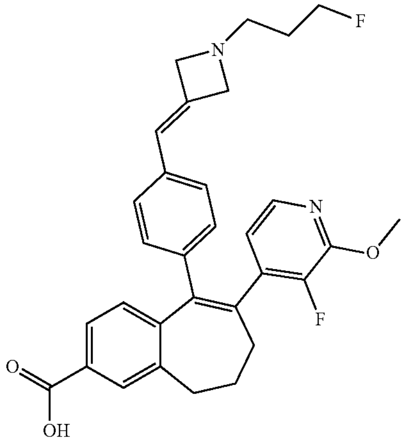 [SMILES: COc1nccc(C2=C(c3ccc(C=C4CN(CCCF)C4)cc3)c3ccc(C(=O)O)cc3CCC2)c1F] | 8-(3-fluoro-2-methoxypyridin-4-yl)-9-(4-((1-(3-fluoropropyl)azetidin-3-ylidene)methyl)phenyl)-6,7-dihydro-5H-benzo[7]annulene-3-carboxylic acid |
| 3 | 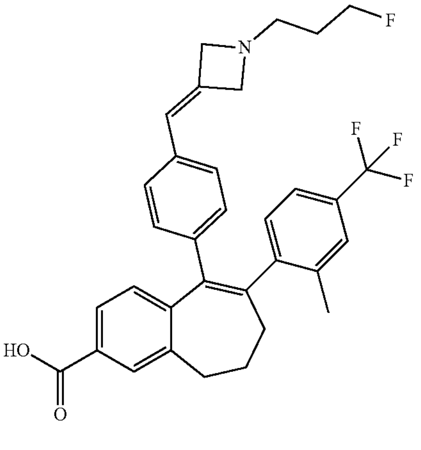 [SMILES: Cc1cc(C(F)(F)F)ccc1C1=C(c2ccc(C=C3CN(CCCF)C3)cc2)c2ccc(C(=O)O)cc2CCC1] | 9-(4-((1-(3-fluoropropyl)azetidin-3-ylidene)methyl)phenyl)-8-(2-methyl-4-(trifluoromethyl)phenyl)-6,7-dihydro-5H-benzo[7]annulene-3-carboxylic acid |

TABLE 1a-continued
| Ex. or compounds | Structure | Name |
| --- | --- | --- |
| 4 | 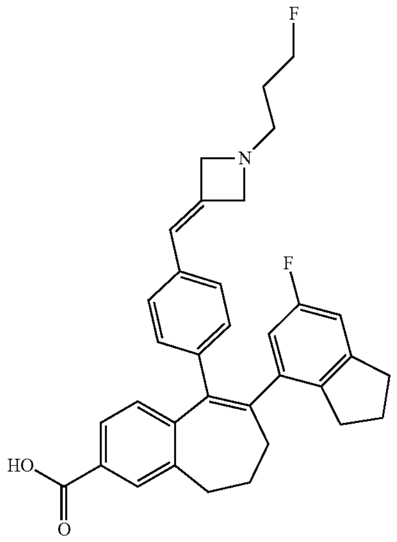 [SMILES: O=C(O)c1ccc2c(c1)CCCC(c1cc(F)cc3c1CCC3)=C2c1ccc(C=C2CN(CCCF)C2)cc1] | 8-(6-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid |
| 5 | 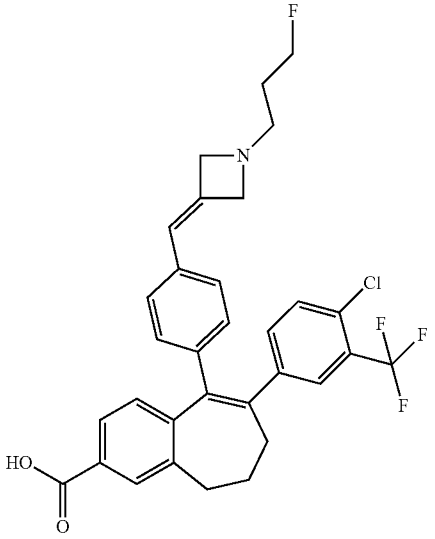 [SMILES: O=C(O)c1ccc2c(c1)CCCC(c1ccc(Cl)c(C(F)(F)F)c1)=C2c1ccc(C=C2CN(CCCF)C2)cc1] | 8-(4-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 6 | 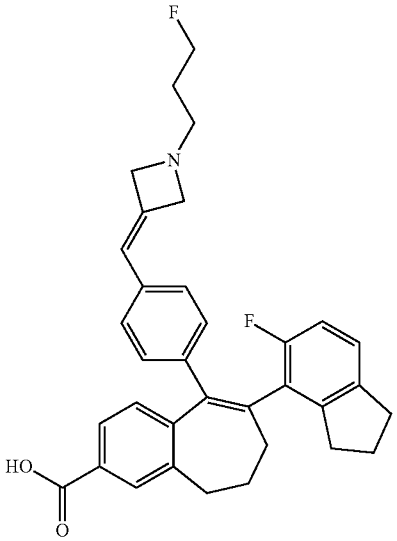 [SMILES: O=C(O)c1ccc2c(c1)CCCC(c1c(F)ccc3c1CCC3)=C2c1ccc(C=C2CN(CCCF)C2)cc1] | 8-(5-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid |
| 7 | 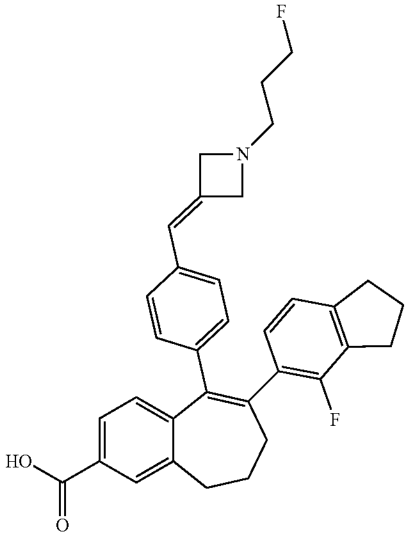 [SMILES: O=C(O)c1ccc2c(c1)CCCC(c1ccc3c(c1F)CCC3)=C2c1ccc(C=C2CN(CCCF)C2)cc1] | 8-(4-fluoro-2,3-dihydro-1H-inden-5-yl)-9-(4-((1-(3-fluoropopyl)azetidin-3-ylidene)methyl)phenyl)-6,7-dihydro-5H-benzo[7]annulene-3-carboxylic acid |

TABLE 1a-continued
| Ex. or compounds | Structure | Name |
| --- | --- | --- |
| 8 | 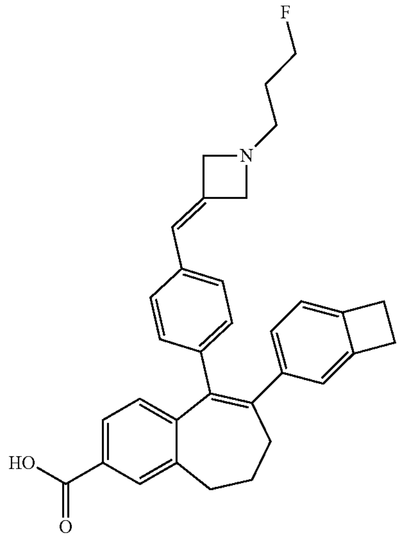 [SMILES: O=C(O)c1ccc2c(c1)CCCC(c1ccc3c(c1)CC3)=C2c1ccc(C=C2CN(CCCF)C2)cc1] | 8-(bicyclo[4.2.0]octan-1,3,5-trien-3-yl)-9-(4-((1-(3-fluoropropyl)azetidin-3-ylidene)methyl)phenyl)-6,7-dihydro-5H-benzo[7]annulene-3-carboxylic acid |
| 9 | 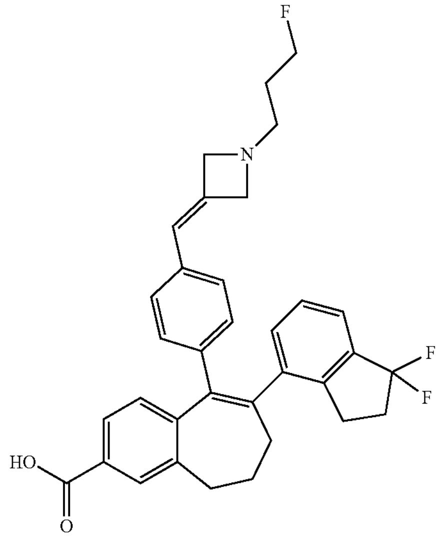 [SMILES: O=C(O)c1ccc2c(c1)CCCC(c1cccc3c1CCC3(F)F)=C2c1ccc(C=C2CN(CCCF)C2)cc1] | 8-(1,1-difluoro-2,3-dihydro-1H-indene-4-yl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 10 | 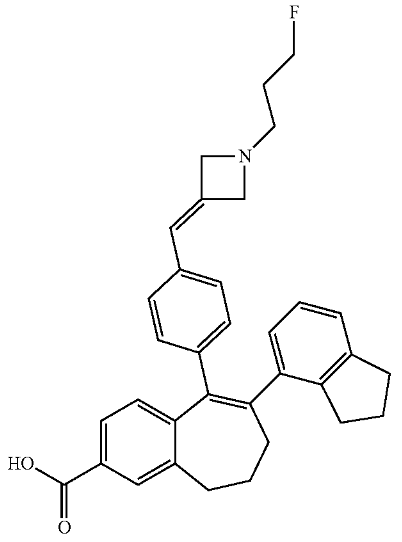 [SMILES: O=C(O)c1ccc2c(c1)CCCC(c1cccc3c1CCC3)=C2c1ccc(C=C2CN(CCCF)C2)cc1] | 8-(2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid |
| 11 | 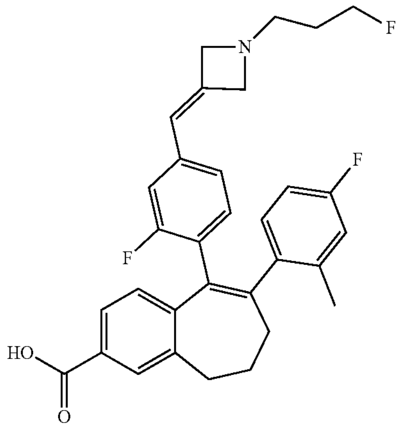 [SMILES: Cc1cc(F)ccc1C1=C(c2ccc(C=C3CN(CCCF)C3)cc2F)c2ccc(C(=O)O)cc2CCC1] | 8-(4-fluoro-2-methylphenyl)-9-(2-fluoro-4-((1-(3-fluoropropyl)azetidin-3-ylidene)methyl)phenyl)-6,7-dihydro-5H-benzo[7]annulene-3-carboxylic acid |
| 12 | 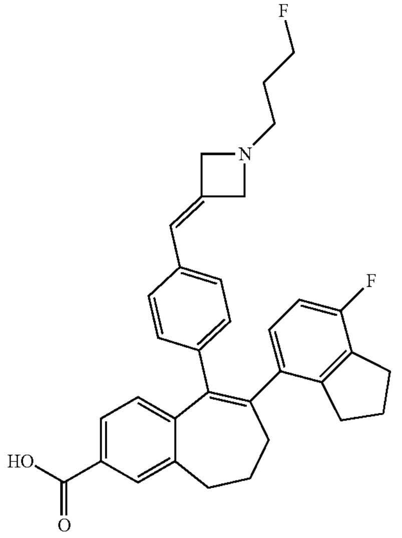 [SMILES: O=C(O)c1ccc2c(c1)CCCC(c1ccc(F)c3c1CCC3)=C2c1ccc(C=C2CN(CCCF)C2)cc1] | 8-(7-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 13 | 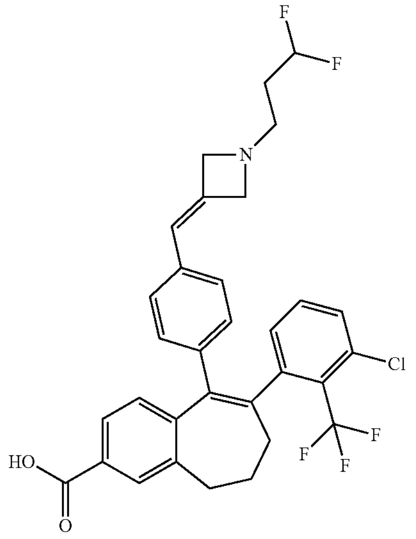 [SMILES: O=C(O)c1ccc2c(c1)CCCC(c1cccc(Cl)c1C(F)(F)F)=C2c1ccc(C=C2CN(CCC(F)F)C2)cc1] | 8-(3-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid |
| 14 | 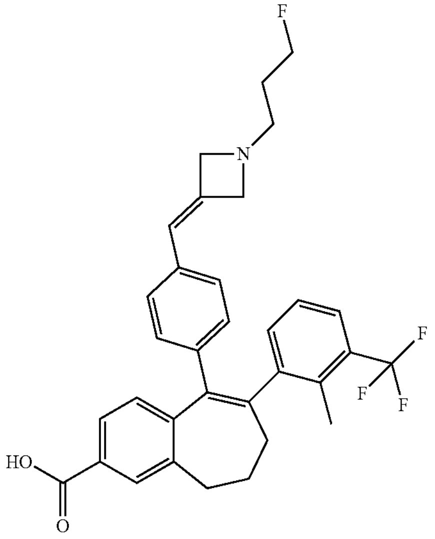 [SMILES: Cc1c(C2=C(c3ccc(C=C4CN(CCCF)C4)cc3)c3ccc(C(=O)O)cc3CCC2)cccc1C(F)(F)F] | 9-(4-((1-(3-fluoropropyl)azetidin-3-ylidene)methyl)phenyl)-8-(2-methyl-3-(trifluoromethyl)phenyl)-6,7-dihydro-5H-benzo[7]annulene-3-carboxylic acid |
| 15 | 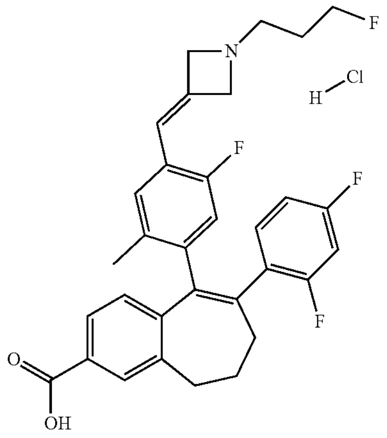 | 8-(2,4-difluorophenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride |

TABLE 1a-continued

| Ex. or compounds | Structure | Name |
|---|---|---|
| 16 | 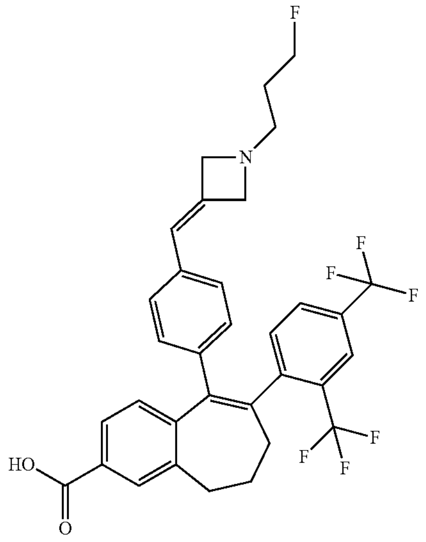 [SMILES: O=C(O)c1ccc2c(c1)CCCC(c1ccc(C(F)(F)F)cc1C(F)(F)F)=C2c1ccc(C=C2CN(CCCF)C2)cc1] | 8-(2,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 17 | 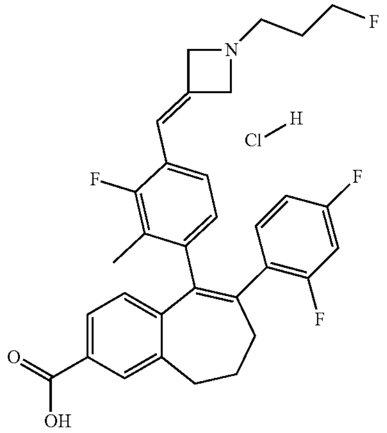 | 8-(2,4-difluorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid hydrochloride |
| 18 | 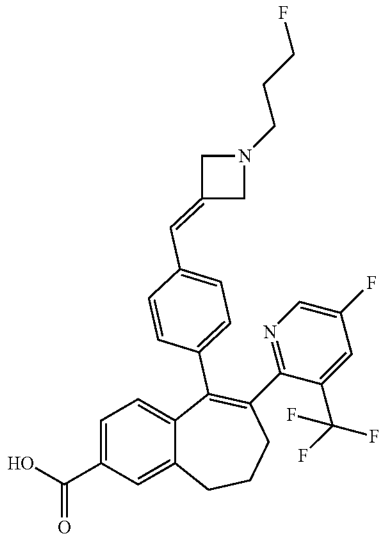 [SMILES: O=C(O)c1ccc2c(c1)CCCC(c1ncc(F)cc1C(F)(F)F)=C2c1ccc(C=C2CN(CCCF)C2)cc1] | 8-(5-fluoro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
| --- | --- | --- |
| 19 | 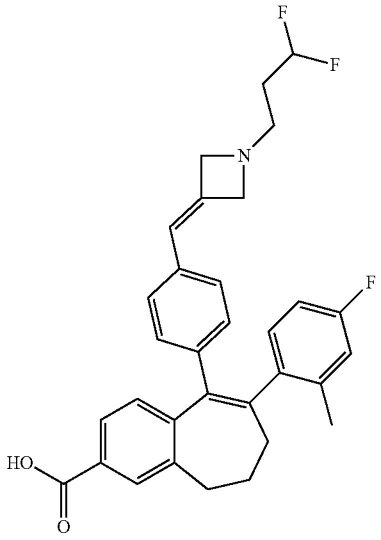 [SMILES: Cc1cc(F)ccc1C1=C(c2ccc(C=C3CN(CCC(F)F)C3)cc2)c2ccc(C(=O)O)cc2CCC1] | 9-(4-((1-(3,3-difluoropropyl)azetidin-3-ylidene)methyl)phenyl)-8-(4-fluoro-2-methylphenyl)-6,7-dihydro-5H-benzo[7]annulene-3-carboxylic acid |
| 20 | 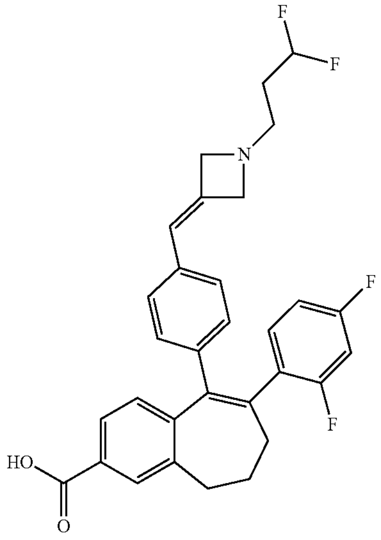 [SMILES: O=C(O)c1ccc2c(c1)CCCC(c1ccc(F)cc1F)=C2c1ccc(C=C2CN(CCC(F)F)C2)cc1] | 8-(2,4-difluorophenyl)-9-(4-((1-(3,3-difluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 21 | 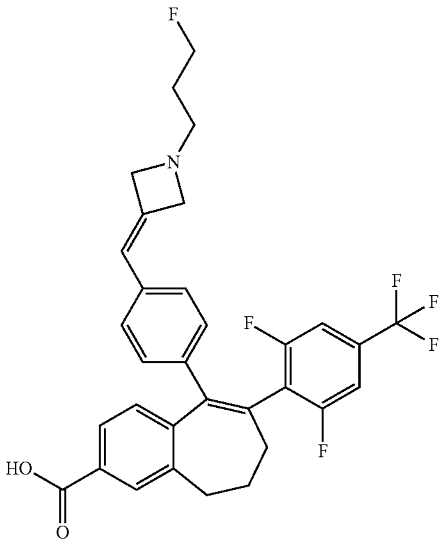 [SMILES: O=C(O)c1ccc2c(c1)CCCC(c1c(F)cc(C(F)(F)F)cc1F)=C2c1ccc(C=C2CN(CCCF)C2)cc1] | 8-(2,6-difluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 22 | 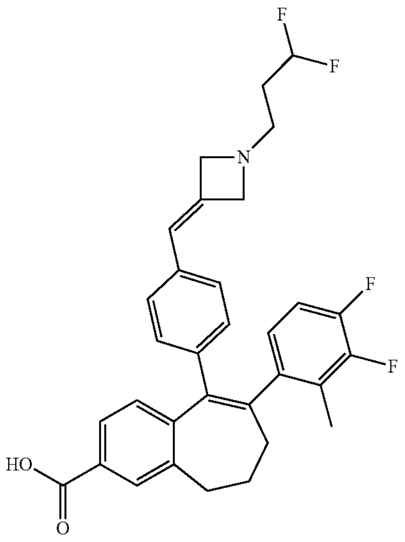 [SMILES: Cc1c(C2=C(c3ccc(C=C4CN(CCC(F)F)C4)cc3)c3ccc(C(=O)O)cc3CCC2)ccc(F)c1F] | 8-(3,4-difluro-4-methylphenyl)-9-(4-((1-(3,3-difluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 23 | 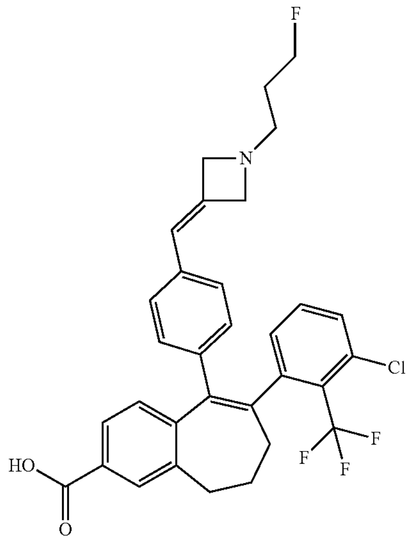 [SMILES: O=C(O)c1ccc2c(c1)CCCC(c1cccc(Cl)c1C(F)(F)F)=C2c1ccc(C=C2CN(CCCF)C2)cc1] | 8-(3-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 24 | 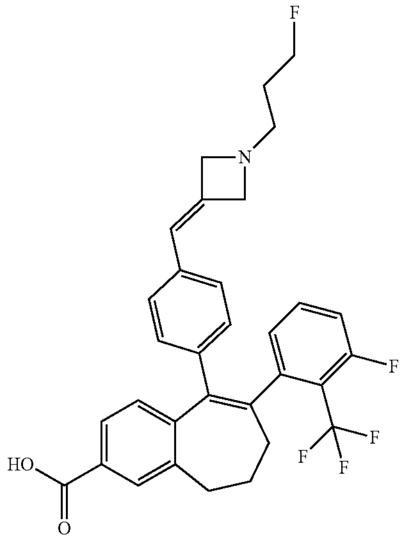 [SMILES: O=C(O)c1ccc2c(c1)CCCC(c1cccc(F)c1C(F)(F)F)=C2c1ccc(C=C2CN(CCCF)C2)cc1] | 8-(3-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
| --- | --- | --- |
| 25 | 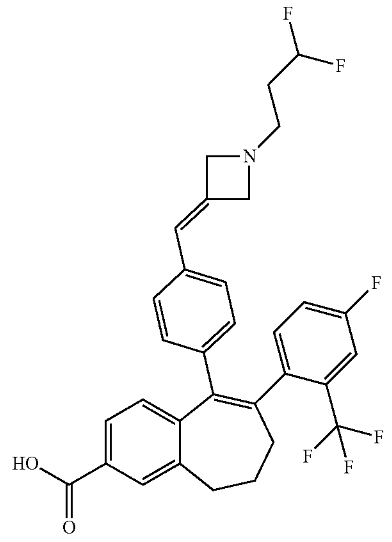 [SMILES: O=C(O)c1ccc2c(c1)CCCC(c1ccc(F)cc1C(F)(F)F)=C2c1ccc(C=C2CN(CCC(F)F)C2)cc1] | 9-(4-((1-(3,3-difluoropropyl)azetidin-3-ylidene)methyl)phenyl)-8-(4-fluoro-2-(trifluoromethyl)phenyl)-6,7-dihydro-5H-benzo[7]annulene-3-carboxylic acid |
| 26 | 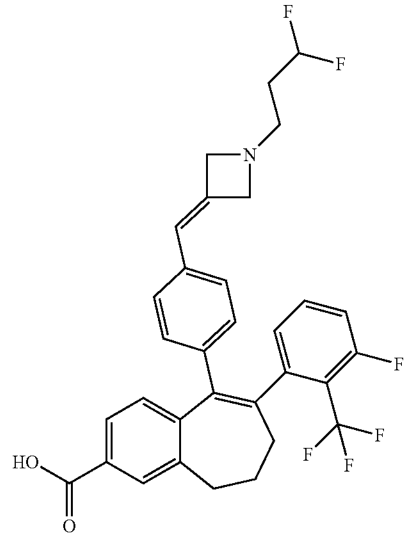 [SMILES: O=C(O)c1ccc2c(c1)CCCC(c1cccc(F)c1C(F)(F)F)=C2c1ccc(C=C2CN(CCC(F)F)C2)cc1] | 9-(4-((1-(3,3-difluoropropyl)azetidin-3-ylidene)methyl)phenyl)-8-(3-fluoro-2-(trifluoromethyl)phenyl)-6,7-dihydro-5H-benzo[7]annulene-3-carboxylic acid |
| 27 | 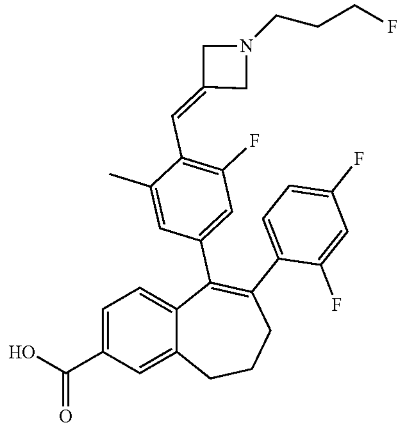 [SMILES: Cc1cc(C2=C(c3ccc(F)cc3F)CCCc3cc(C(=O)O)ccc32)cc(F)c1C=C1CN(CCCF)C1] | 8-(2,4-difluorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid |

TABLE 1a-continued

| Ex. or compounds | Structure | Name |
|---|---|---|
| 28 | 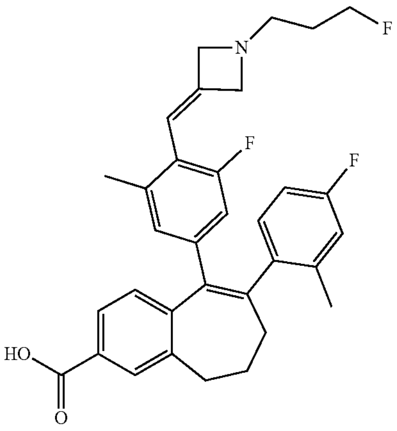 [SMILES: Cc1cc(F)ccc1C1=C(c2cc(C)c(C=C3CN(CCCF)C3)c(F)c2)c2ccc(C(=O)O)cc2CCC1] | 8-(4-fluoro-2-methylphenyl)-9-(3-fluoro-4-((1-(3-fluoropropyl)azetidin-3-ylidene)methyl)-5-methylphenyl)-6,7-dihydro-5H-benzo[7]annulene-3-carboxylic acid |
| 29 | 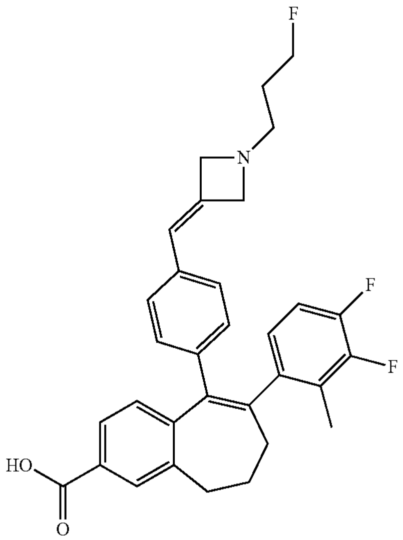 [SMILES: Cc1c(C2=C(c3ccc(C=C4CN(CCCF)C4)cc3)c3ccc(C(=O)O)cc3CCC2)ccc(F)c1F] | 8-(3,4-difluoro-2-methylphenyl)-9-(4-((1-(3-fluoropropyl)azetidin-3-ylidene)methyl)phenyl)-6,7-dihydro-5H-benzo[7]annulene-3-carboxylic acid |
| 30 | 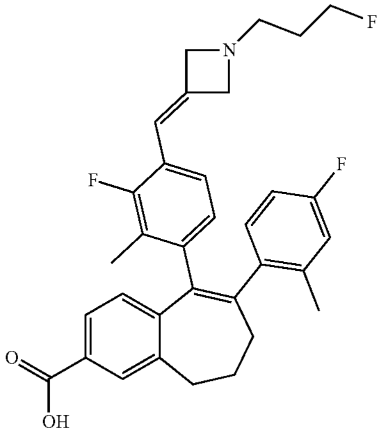 [SMILES: Cc1cc(F)ccc1C1=C(c2ccc(C=C3CN(CCCF)C3)c(F)c2C)c2ccc(C(=O)O)cc2CCC1] | 8-(4-fluoro-2-methylphenyl)-9-(3-fluoro-4-((1-(3-fluoropropyl)azetidin-3-ylidene)methyl)-2-methylphenyl)-6,7-dihydro-5H-benzo[7]annulene-3-carboxylic acid |

TABLE 1a-continued

| Ex. or compounds | Structure | Name |
|---|---|---|
| 31 | 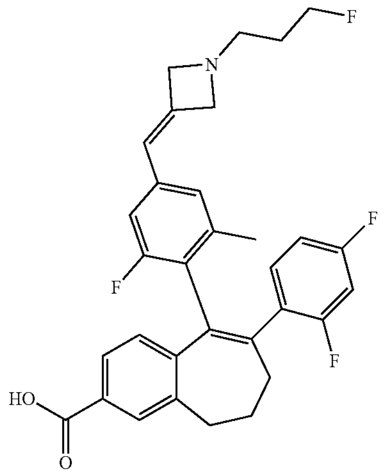 [SMILES: Cc1cc(C=C2CN(CCCF)C2)cc(F)c1C1=C(c2ccc(F)cc2F)CCCc2cc(C(=O)O)ccc21] | 8-(2,4-difluorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid |
| 32 | 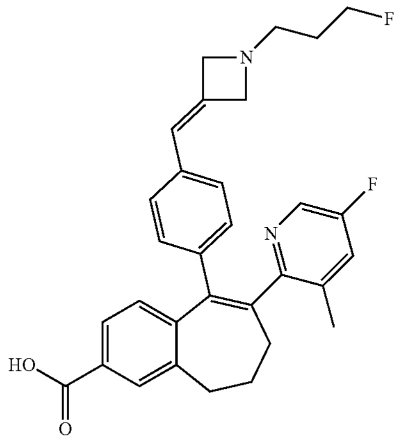 [SMILES: Cc1cc(F)cnc1C1=C(c2ccc(C=C3CN(CCCF)C3)cc2)c2ccc(C(=O)O)cc2CCC1] | 8-(5-fluoro-3-methylpyridin-2-yl)-9-(4-((1-(3-fluoropropyl)azetidin-3-ylidene)methyl)phenyl)-6,7-dihydro-5H-benzo[7]annulene-3-carboxylic acid |
| 33 | 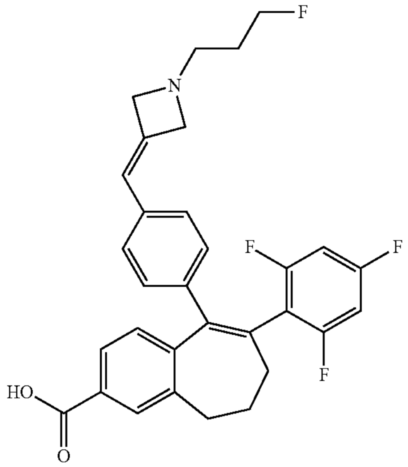 [SMILES: O=C(O)c1ccc2c(c1)CCCC(c1c(F)cc(F)cc1F)=C2c1ccc(C=C2CN(CCCF)C2)cc1] | 9-(4-((1-(3-fluoropropyl)azetidin-3-ylidene)methyl)phenyl)-8-(2,4,6-trifluorophenyl)-6,7-dihydro-5H-benzo[7]annulene-3-carboxylic acid |

TABLE 1a-continued

| Ex. or compounds | Structure | Name |
|---|---|---|
| 34 | 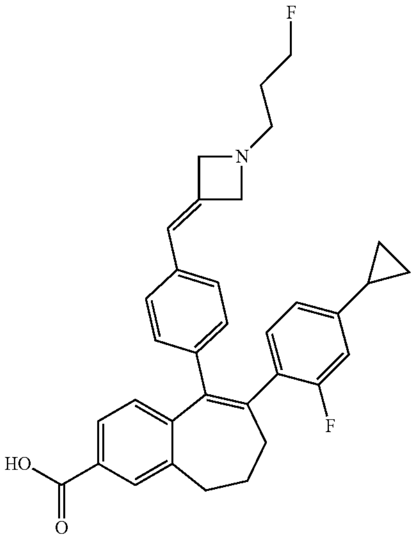 | 8-(4-cyclopropyl-2-fluorophenyl)-9-(4-((1-(3-fluoropropyl)azetidin-3-ylidene)methyl)phenyl)-6,7-dihydro-5H-benzo[7]annulene-3-carboxylic acid |
| 35 | 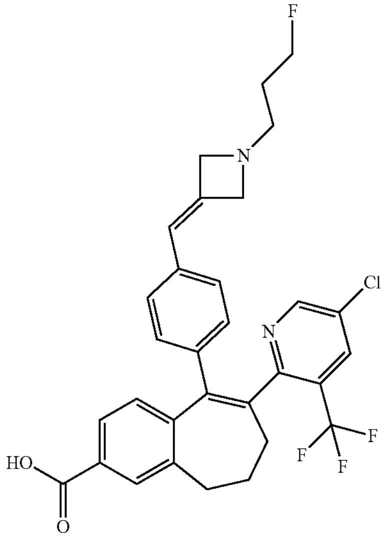 [SMILES: O=C(O)c1ccc2c(c1)CCCC(c1ncc(Cl)cc1C(F)(F)F)=C2c1ccc(C=C2CN(CCCF)C2)cc1] | 8-(5-chloro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid |
| 36 | 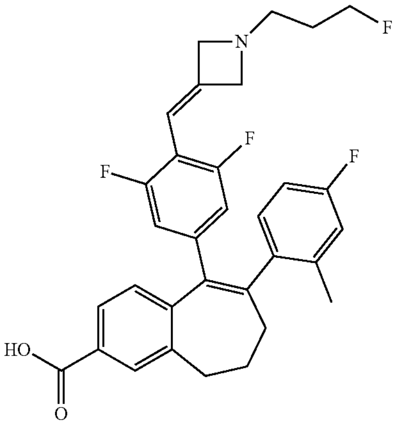 [SMILES: Cc1cc(F)ccc1C1=C(c2cc(F)c(C=C3CN(CCCF)C3)c(F)c2)c2ccc(C(=O)O)cc2CCC1] | 9-(3,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid |

TABLE 1a-continued

| Ex. or compounds | Structure | Name |
| --- | --- | --- |
| 37 | 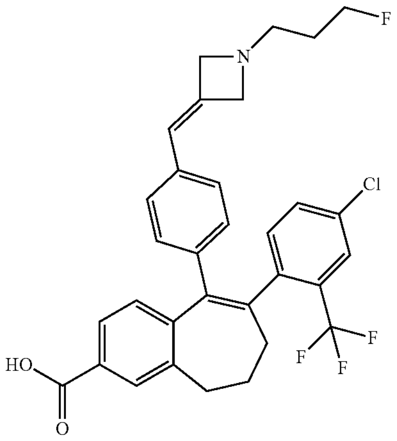 [SMILES: O=C(O)c1ccc2c(c1)CCCC(c1ccc(Cl)cc1C(F)(F)F)=C2c1ccc(C=C2CN(CCCF)C2)cc1] | 8-(4-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 38 | 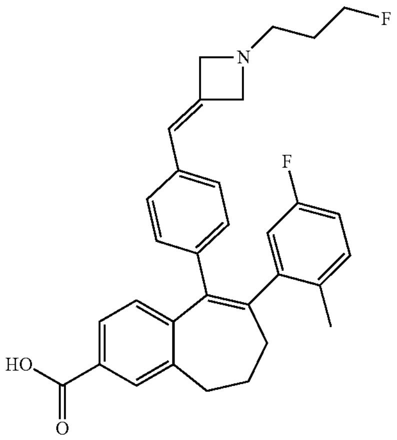 [SMILES: Cc1ccc(F)cc1C1=C(c2ccc(C=C3CN(CCCF)C3)cc2)c2ccc(C(=O)O)cc2CCC1] | 8-(5-fluoro-2-methylphenyl)-9-(4-((1-(3-fluoropropyl)azetidin-3-ylidene)methyl)phenyl)-6,7-dihydro-5H-benzo[7]annulene-3-carboxylic acid |
| 39 | 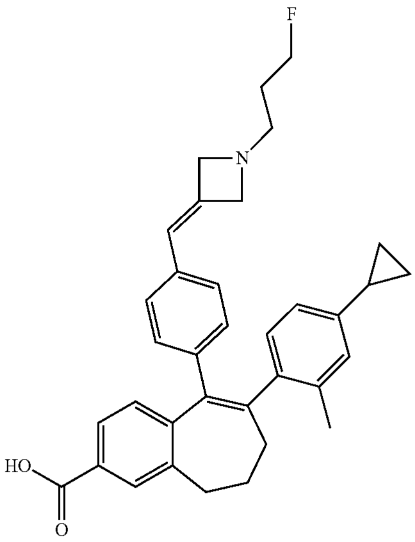 [SMILES: Cc1cc(C2CC2)ccc1C1=C(c2ccc(C=C3CN(CCCF)C3)cc2)c2ccc(C(=O)O)cc2CCC1] | 8-(4-cyclopropyl-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 40 | 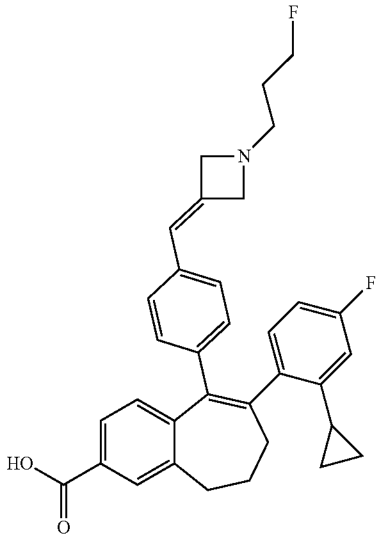 [SMILES: O=C(O)c1ccc2c(c1)CCCC(c1ccc(F)cc1C1CC1)=C2c1ccc(C=C2CN(CCCF)C2)cc1] | 8-(2-cyclopropyl-4-fluorophenyl)-9-(4-((1-(3-fluoropropyl)azetidin-3-ylidene)methyl)phenyl)-6,7-dihydro-5H-benzo[7]annulene-3-carboxylic acid |
| 41 | 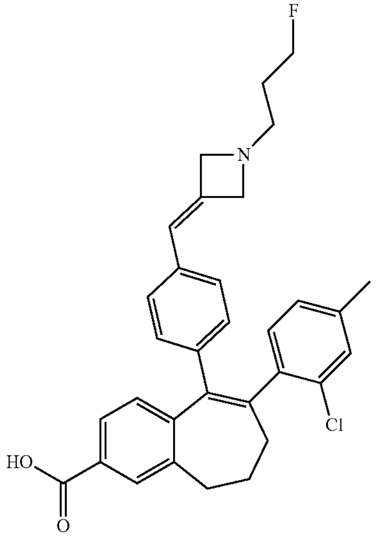 [SMILES: Cc1ccc(C2=C(c3ccc(C=C4CN(CCCF)C4)cc3)c3ccc(C(=O)O)cc3CCC2)c(Cl)c1] | 8-(2-chloro-4-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 42 | 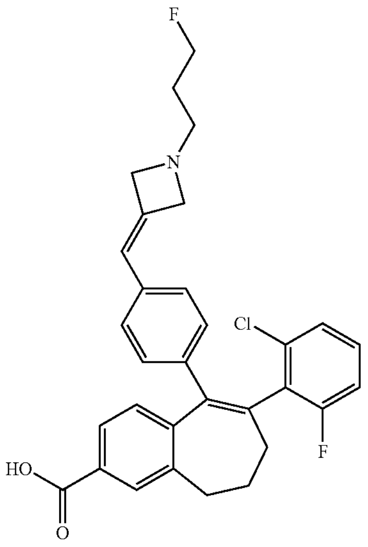 [SMILES: O=C(O)c1ccc2c(c1)CCCC(c1c(F)cccc1Cl)=C2c1ccc(C=C2CN(CCCF)C2)cc1] | 8-(2-chloro-6-fluorophenyl)-9-(4-((1-(3-fluoropropyl)azetidin-3-ylidene)methyl)phenyl)-6,7-dihydro-5H-benzo[7]annulene-3-carboxylic acid |
| 43 | 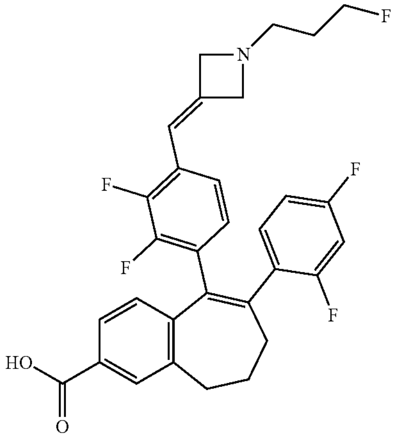 [SMILES: O=C(O)c1ccc2c(c1)CCCC(c1ccc(F)cc1F)=C2c1ccc(C=C2CN(CCCF)C2)c(F)c1F] | 9-(2,3-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid |
| 44 | 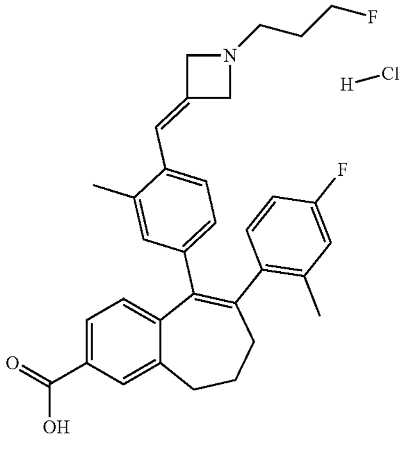 | 8-(4-fluoro-2-methylphenyl)-9-(4-((1-(3-fluoropropyl)azetidin-3-ylidene)methyl)-3-methylphenyl)-6,7-dihydro-5H-benzo[7]annulene-3-carboxylic acid hydrochloride |

TABLE 1a-continued

| Ex. or compounds | Structure | Name |
|---|---|---|
| 45 | 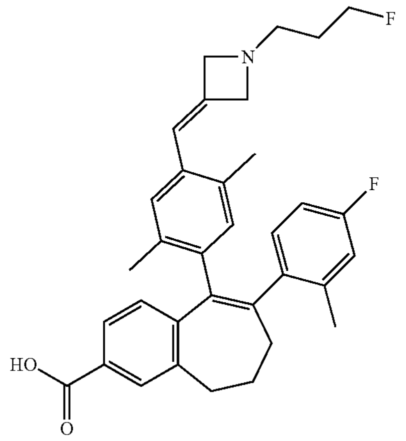 [SMILES: Cc1cc(C2=C(c3ccc(F)cc3C)CCCc3cc(C(=O)O)ccc32)c(C)cc1C=C1CN(CCCF)C1] | 8-(4-fluoro-2-methylphenyl)-9-(4-((1-(3-fluoropropyl)azetidin-3-ylidene)methyl)-2,5-dimethylphenyl)-6,7-dihydro-5H-benzo[7]annulene-3-carboxylic acid |
| 46 | 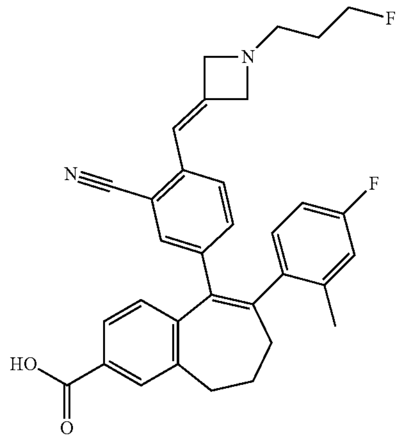 [SMILES: Cc1cc(F)ccc1C1=C(c2ccc(C=C3CN(CCCF)C3)c(C#N)c2)c2ccc(C(=O)O)cc2CCC1] | 9-(3-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid |
| 47 | 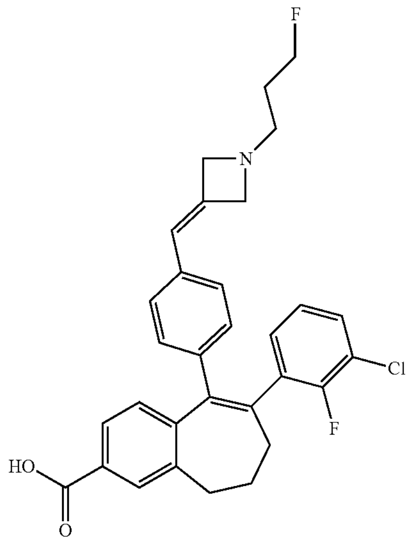 [SMILES: O=C(O)c1ccc2c(c1)CCCC(c1cccc(Cl)c1F)=C2c1ccc(C=C2CN(CCCF)C2)cc1] | 8-(3-chloro-2-fluorophenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 48 | 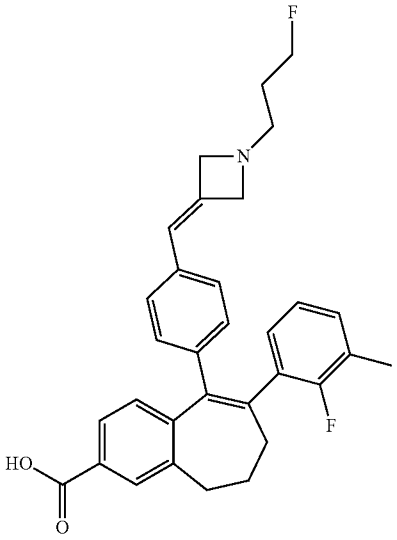 | 8-(2-fluoro-3-methylphenyl)-9-(4-((1-(3-fluoropropyl)azetidin-3-ylidene)methyl)phenyl)-6,7-dihydro-5H-benzo[7]annulene-3-carboxylic acid |
| 49 | 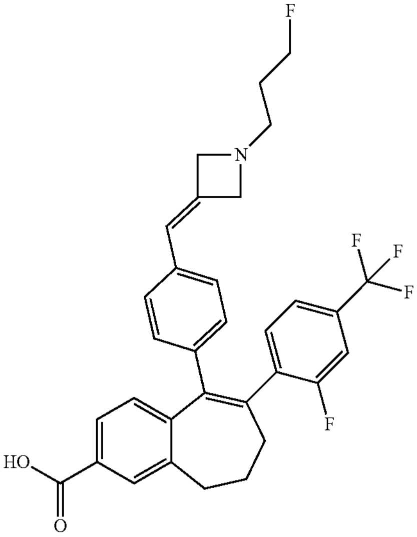 [SMILES: O=C(O)c1ccc2c(c1)CCCC(c1ccc(C(F)(F)F)cc1F)=C2c1ccc(C=C2CN(CCCF)C2)cc1] | 8-(2-fluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
| --- | --- | --- |
| 50 | 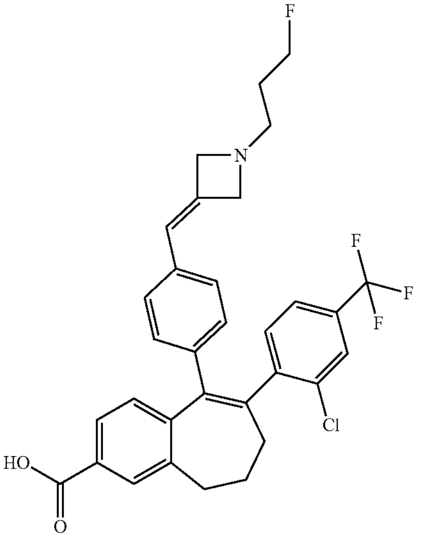 [SMILES: O=C(O)c1ccc2c(c1)CCCC(c1ccc(C(F)(F)F)cc1Cl)=C2c1ccc(C=C2CN(CCCF)C2)cc1] | 8-(2-chloro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 51 | 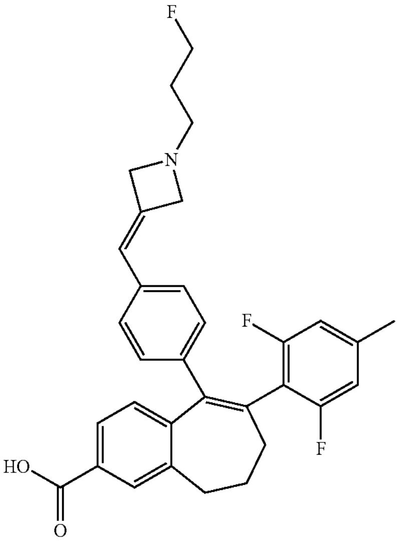 [SMILES: Cc1cc(F)c(C2=C(c3ccc(C=C4CN(CCCF)C4)cc3)c3ccc(C(=O)O)cc3CCC2)c(F)c1] | 8-(2,6-difluoro-4-methylphenyl)-9-(4-((1-(3-fluoropropyl)azetidin-3-ylidene)methyl)phenyl)-6,7-dihydro-5H-benzo[7]annulene-3-carboxylic acid |
| 52 | 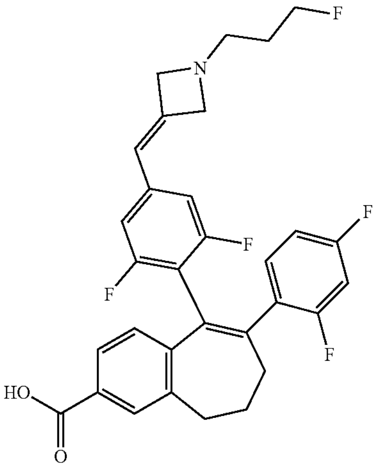 [SMILES: O=C(O)c1ccc2c(c1)CCCC(c1ccc(F)cc1F)=C2c1c(F)cc(C=C2CN(CCCF)C2)cc1F] | 9-(2,6-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid |

TABLE 1a-continued

| Ex. or compounds | Structure | Name |
|---|---|---|
| 53 | 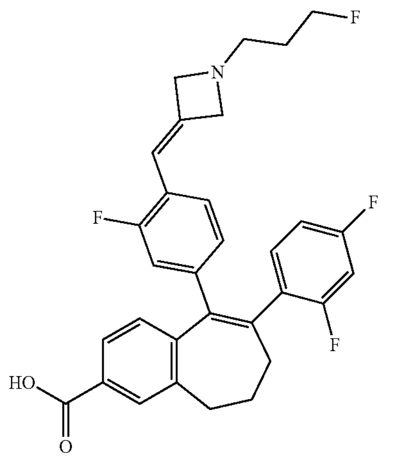 [SMILES: O=C(O)c1ccc2c(c1)CCCC(c1ccc(F)cc1F)=C2c1ccc(C=C2CN(CCCF)C2)c(F)c1] | 8-(2,4-difluorophenyl)-9-(3-fluoro-4-((1-(3-fluoropropyl)azetidin-3-ylidene)methyl)phenyl)-6,7-dihydro-5H-benzo[7]annulene-3-carboxylic acid |
| 54 | 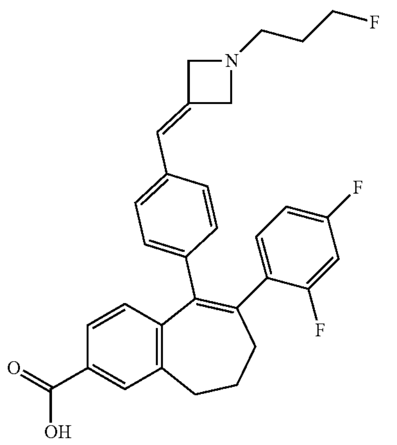 [SMILES: O=C(O)c1ccc2c(c1)CCCC(c1ccc(F)cc1F)=C2c1ccc(C=C2CN(CCCF)C2)cc1] | 8-(2,4-difluorophenyl)-9-(4-((1-(3-fluoropropyl)azetidin-3-ylidene)methyl)phenyl)-6,7-dihydro-5H-benzo[7]annulene-3-carboxylic acid |
| 55 | 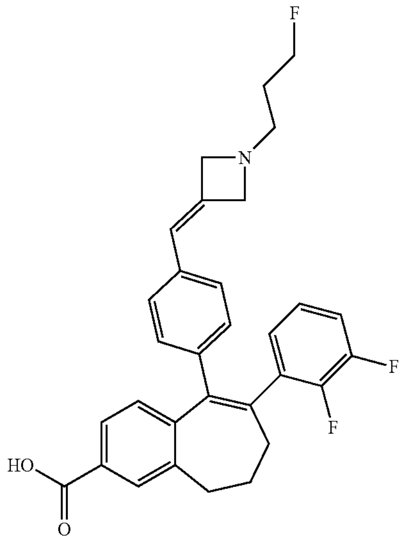 [SMILES: O=C(O)c1ccc2c(c1)CCCC(c1cccc(F)c1F)=C2c1ccc(C=C2CN(CCCF)C2)cc1] | 8-(2,3-difluorophenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 56 | 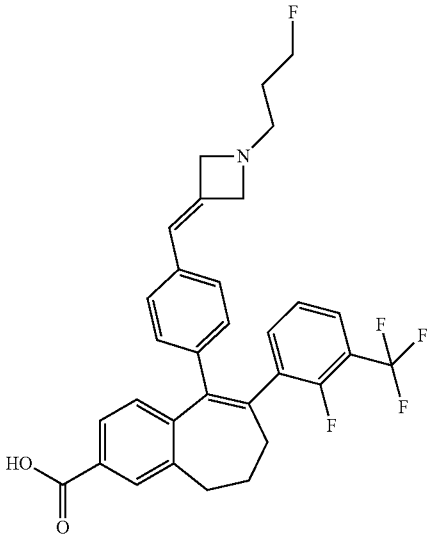 [SMILES: O=C(O)c1ccc2c(c1)CCCC(c1cccc(C(F)(F)F)c1F)=C2c1ccc(C=C2CN(CCCF)C2)cc1] | 8-(2-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 57 | 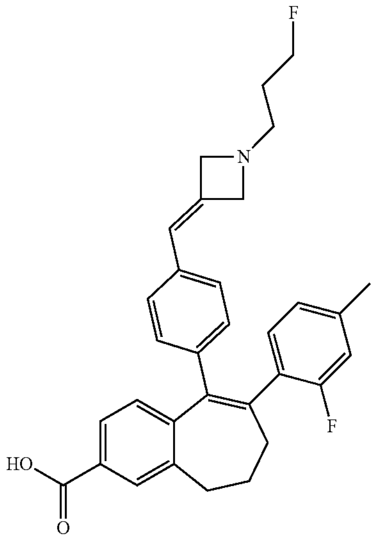 [SMILES: Cc1ccc(C2=C(c3ccc(C=C4CN(CCCF)C4)cc3)c3ccc(C(=O)O)cc3CCC2)c(F)c1] | 8-(2-fluoro-4-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
| --- | --- | --- |
| 58 | 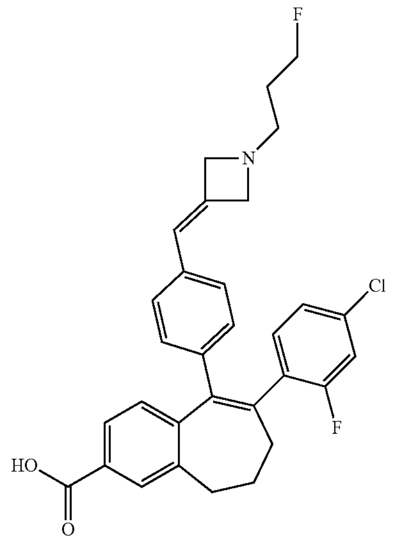 [SMILES: O=C(O)c1ccc2c(c1)CCCC(c1ccc(Cl)cc1F)=C2c1ccc(C=C2CN(CCCF)C2)cc1] | 8-(4-chloro-2-fluorophenyl)-9-(4-((1-(3-fluororpopyl)azetidin-3-ylidene)methyl)phenyl)-6,7-dihydro-5H-benzo[7]annulene-3-carboxylic acid |
| 59 | 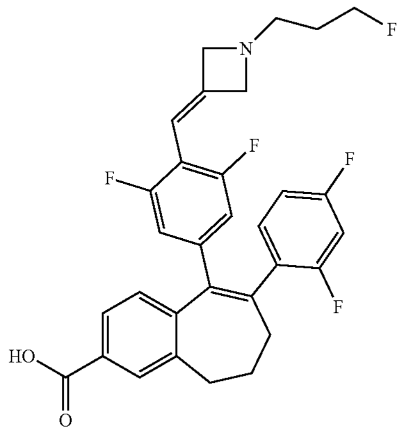 [SMILES: O=C(O)c1ccc2c(c1)CCCC(c1ccc(F)cc1F)=C2c1cc(F)c(C=C2CN(CCCF)C2)c(F)c1] | 9-(3,5-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid |
| 60 | 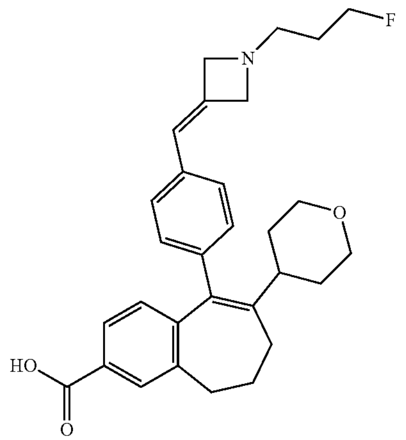 [SMILES: O=C(O)c1ccc2c(c1)CCCC(C1CCOCC1)=C2c1ccc(C=C2CN(CCCF)C2)cc1] | 9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylic acid |

TABLE 1a-continued

| Ex. or compounds | Structure | Name |
|---|---|---|
| 61 | 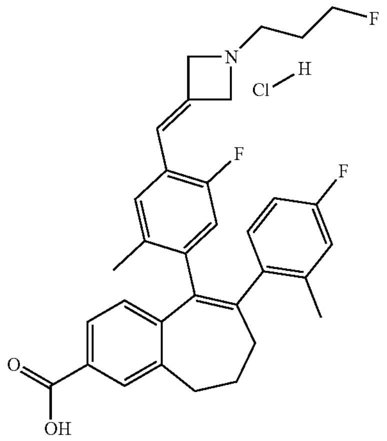 | 8-(4-fluoro-2-methylphenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride |
| 62 | 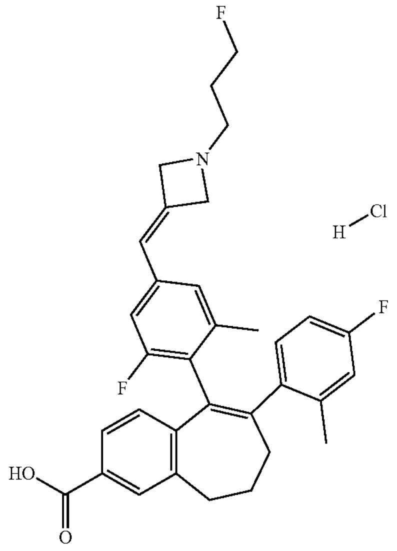 [SMILES: Cc1cc(F)ccc1C1=C(c2c(C)cc(C=C3CN(CCCF)C3)cc2F)c2ccc(C(=O)O)cc2CCC1 ; Cl] | 8-(4-fluoro-2-methylphenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride |
| 63 | 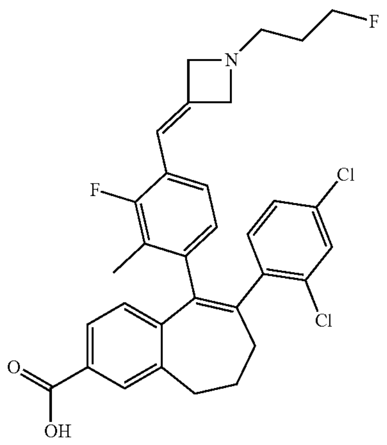 [SMILES: Cc1c(C2=C(c3ccc(Cl)cc3Cl)CCCc3cc(C(=O)O)ccc32)ccc(C=C2CN(CCCF)C2)c1F] | 8-(2,4-dichlorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid |

TABLE 1a-continued

| Ex. or compounds | Structure | Name |
|---|---|---|
| 64 | 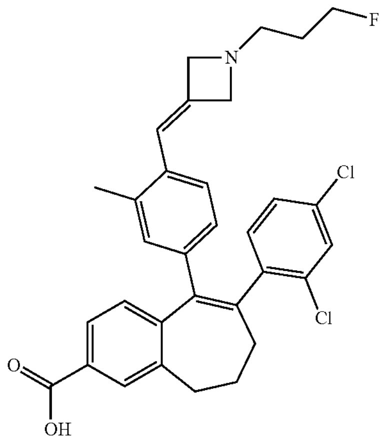 [SMILES: Cc1cc(C2=C(c3ccc(Cl)cc3Cl)CCCc3cc(C(=O)O)ccc32)ccc1C=C1CN(CCCF)C1] | 8-(2,4-dichlorophenyl)-9-(4-((1-(3-fluoropropyl)azetidin-3-ylidene)methyl)-3-methylphenyl)-6,7-dihydro-5H-benzo[7]annulene-3-carboxylic acid |
| 65 | 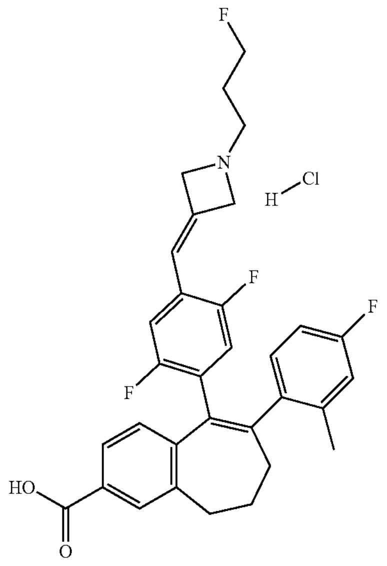 | 9-(2,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid hydrochloride |
| 66 | 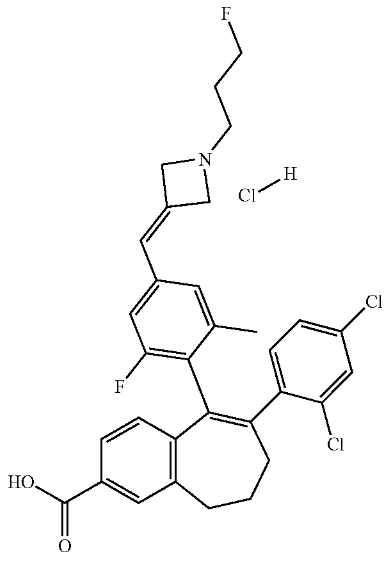 | 8-(2,4-dichlorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride |

TABLE 1a-continued

| Ex. or compounds | Structure | Name |
|---|---|---|
| 67 | 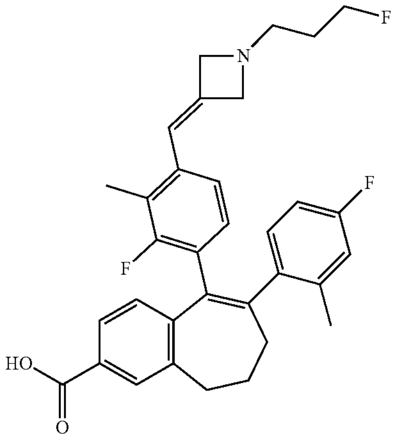 [SMILES: Cc1cc(F)ccc1C1=C(c2ccc(C=C3CN(CCCF)C3)c(C)c2F)c2ccc(C(=O)O)cc2CCC1] | 8-(4-fluoro-2-methylphenyl)-9-(2-fluoro-4-((1-(3-fluoropropyl)azetidin-3-ylidene)methyl)-3-methylphenyl)-6,7-dihydro-5H-benzo[7]annulene-3-carboxylic acid |
| 68 | 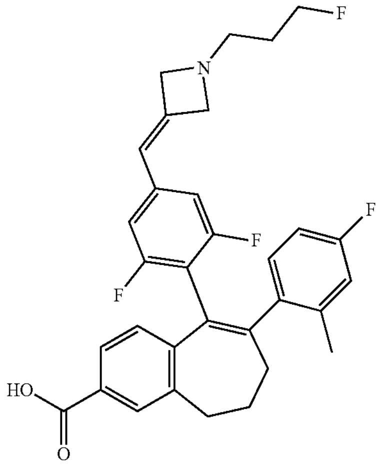 [SMILES: Cc1cc(F)ccc1C1=C(c2c(F)cc(C=C3CN(CCCF)C3)cc2F)c2ccc(C(=O)O)cc2CCC1] | 9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid |
| 69 | 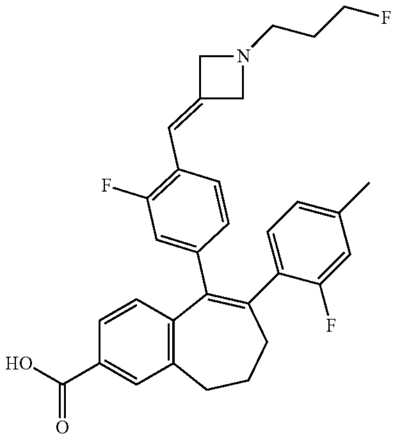 [SMILES: Cc1ccc(C2=C(c3ccc(C=C4CN(CCCF)C4)c(F)c3)c3ccc(C(=O)O)cc3CCC2)c(F)c1] | 9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid |

TABLE 1a-continued

| Ex. or compounds | Structure | Name |
|---|---|---|
| 70 | 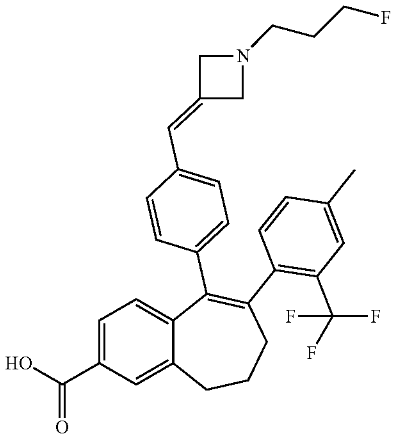 [SMILES: Cc1ccc(C2=C(c3ccc(C=C4CN(CCCF)C4)cc3)c3ccc(C(=O)O)cc3CCC2)c(C(F)(F)F)c1] | 9-(4-((1-(3-dlfluoropropyl)azetidin-3-ylidene)methyl)phenyl)-8-(4-methyl-2-(trifluoromethyl)phenyl)-6,7-dihydro-5H-benzo[7]annulene-3-carboxylic acid |
| 71 | 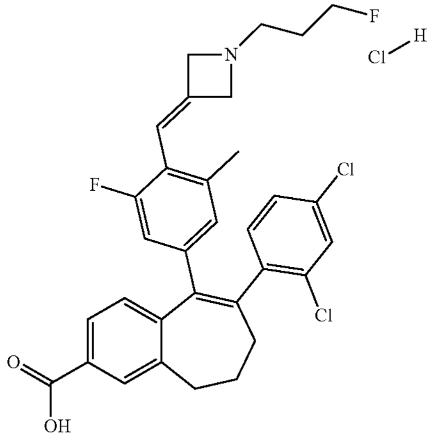 | 8-(2,4-dichlorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid hydrochloride |
| 72 | 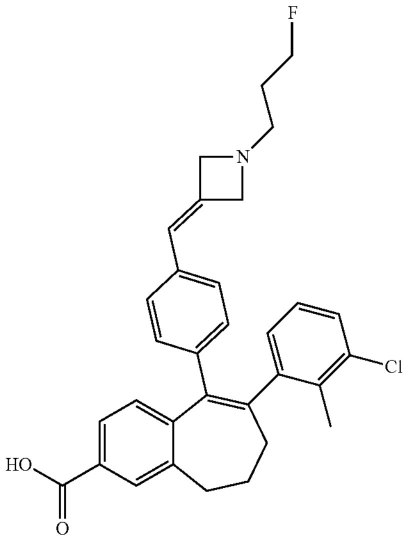 [SMILES: Cc1c(Cl)cccc1C1=C(c2ccc(C=C3CN(CCCF)C3)cc2)c2ccc(C(=O)O)cc2CCC1] | 8-(3-chloro-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 73 | 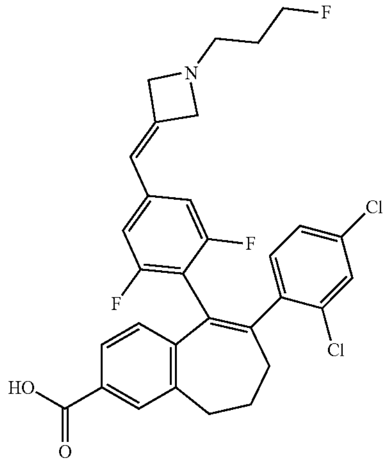 [SMILES: O=C(O)c1ccc2c(c1)CCCC(c1ccc(Cl)cc1Cl)=C2c1c(F)cc(C=C2CN(CCCF)C2)cc1F] | 8-(2,4-dichlorophenyl)-9-(2,6-difluoro-4-((1-(3-fluoropropyl)azetidin-3-ylidene)methyl)phenyl)-6,7-dihydro-5H-benzo[7]annulene-3-carboxylic acid |
| 74 | 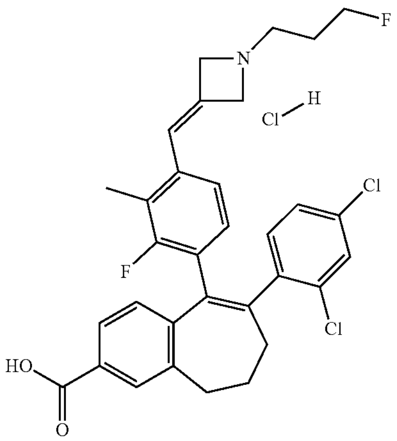 | 8-(2,4-dichlorophenyl)-9-(2-fluoro-4-((1-(3-fluoropropyl)azetidin-3-ylidene)methyl)-3-methylphenyl)-6,7-dihydro-5H-benzo[7]annulene-3-carboxylic acid hydrochloride |
| 75 | 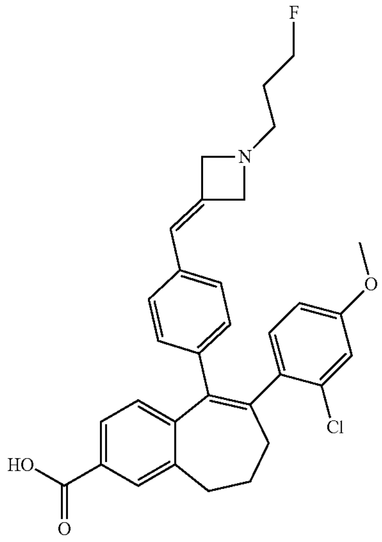 [SMILES: COc1ccc(C2=C(c3ccc(C=C4CN(CCCF)C4)cc3)c3ccc(C(=O)O)cc3CCC2)c(Cl)c1] | 8-(2-chloro-4-methoxyphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 76 | 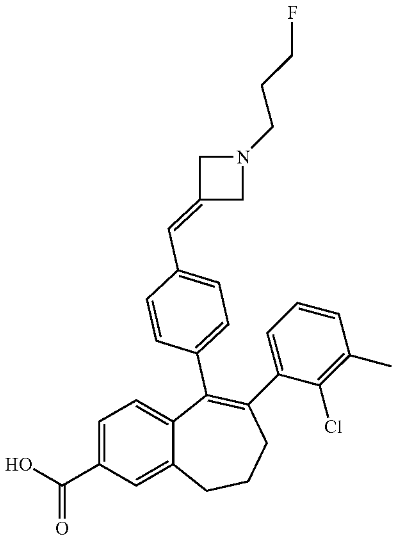 [SMILES: Cc1cccc(C2=C(c3ccc(C=C4CN(CCCF)C4)cc3)c3ccc(C(=O)O)cc3CCC2)c1Cl] | 8-(2-chloro-3-methylphenyl)-9-(4-((1-(3-fluoropropyl)azetidin-3-ylidene)methyl)phenyl)-6,7-dihydro-5H-benzo[7]annulene-3-carboxylic acid |
| 77 | 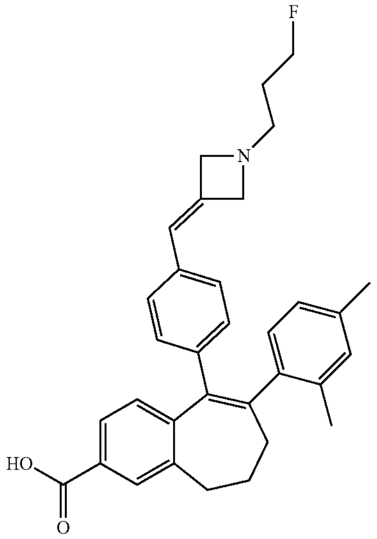 [SMILES: Cc1ccc(C2=C(c3ccc(C=C4CN(CCCF)C4)cc3)c3ccc(C(=O)O)cc3CCC2)c(C)c1] | 8-(2,4-dimethylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
| --- | --- | --- |
| 78 | 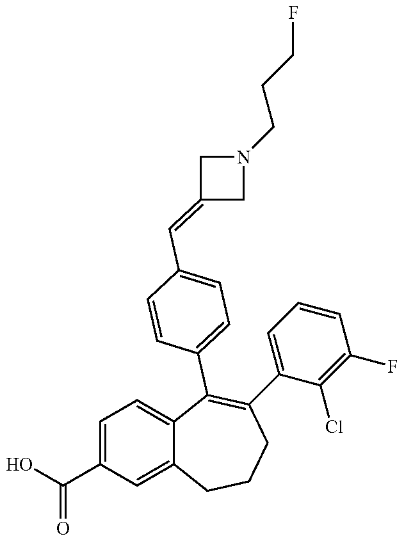 [SMILES: O=C(O)c1ccc2c(c1)CCCC(c1cccc(F)c1Cl)=C2c1ccc(C=C2CN(CCCF)C2)cc1] | 8-(2-chloro-3-fluorophenyl)-9-(4-((1-(3-fluoropropyl)azetidin-3-ylidene)methyl)phenyl)-6,7-dihydro-5H-benzo[7]annulene-3-carboxylic acid |
| 79 | 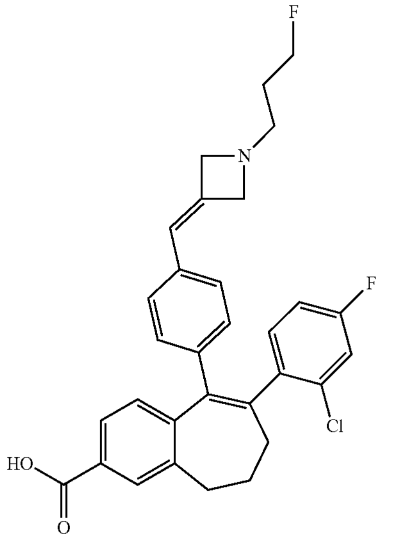 [SMILES: O=C(O)c1ccc2c(c1)CCCC(c1ccc(F)cc1Cl)=C2c1ccc(C=C2CN(CCCF)C2)cc1] | 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 80 | 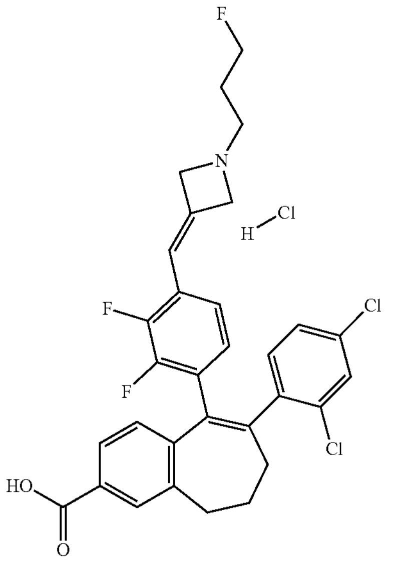 | 8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylic acid hydrochloride |
| 81 | 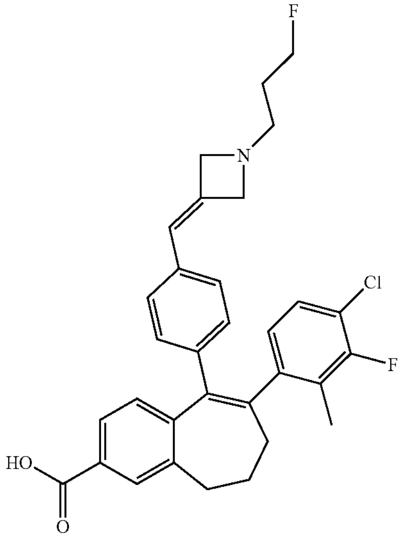 [SMILES: Cc1c(C2=C(c3ccc(C=C4CN(CCCF)C4)cc3)c3ccc(C(=O)O)cc3CCC2)ccc(Cl)c1F] | 8-(4-chloro-3-fluoro-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 82 | 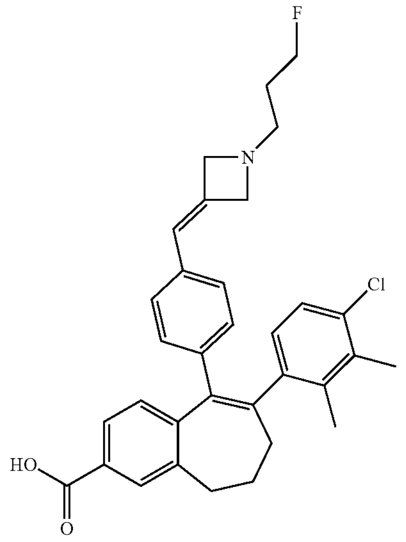 [SMILES: Cc1c(Cl)ccc(C2=C(c3ccc(C=C4CN(CCCF)C4)cc3)c3ccc(C(=O)O)cc3CCC2)c1C] | 8-(4-chloro-2,3-dimethylphenyl)-9-(4-((1-(3-fluoropropyl)azetidin-3-ylidene)methyl)phenyl)-6,7-dihydro-5H-benzo[7]annulene-3-carboxylic acid |
| 83 | 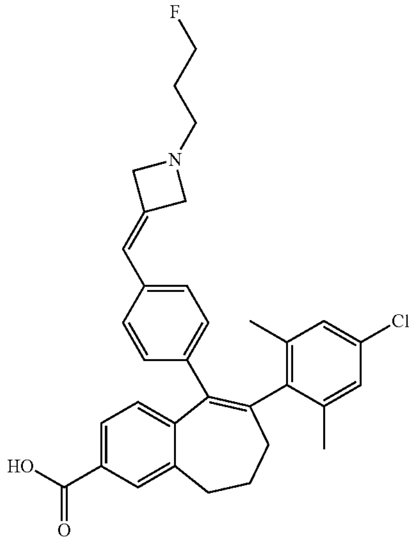 [SMILES: Cc1cc(Cl)cc(C)c1C1=C(c2ccc(C=C3CN(CCCF)C3)cc2)c2ccc(C(=O)O)cc2CCC1] | 8-(4-chloro-2,6-dimethyphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
| --- | --- | --- |
| 84 | 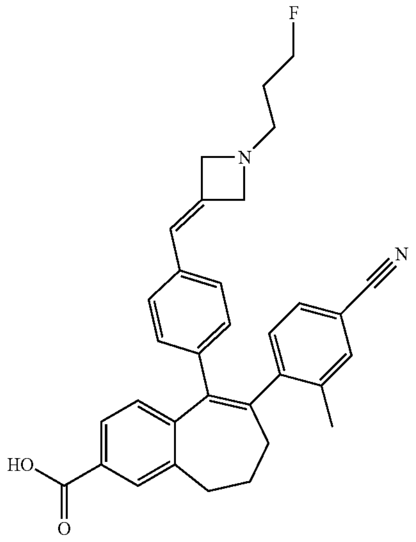 [SMILES: Cc1cc(C#N)ccc1C1=C(c2ccc(C=C3CN(CCCF)C3)cc2)c2ccc(C(=O)O)cc2CCC1] | 8-(4-cyano-2-methylphenyl)-9-(4-((1-(3-fluoropropyl)azetidin-3-ylidene)methyl)phenyl)-6,7-dihydro-5H-benzo[7]annulene-3-carboxylic acid |
| 85 | 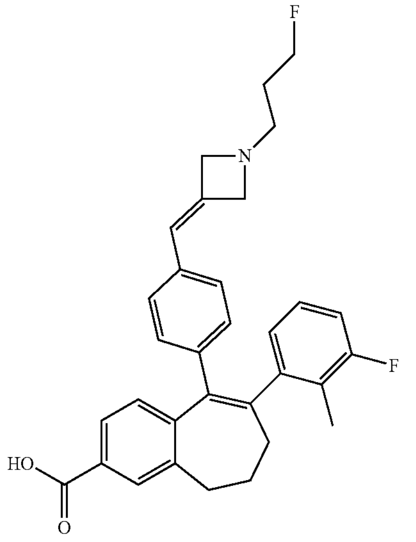 [SMILES: Cc1c(F)cccc1C1=C(c2ccc(C=C3CN(CCCF)C3)cc2)c2ccc(C(=O)O)cc2CCC1] | 8-(3-fluoro-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 86 | 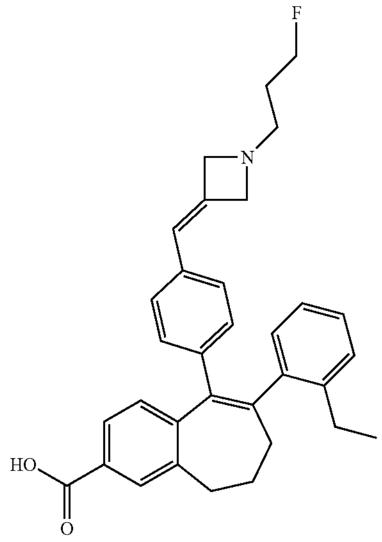 [SMILES: CCc1ccccc1C1=C(c2ccc(C=C3CN(CCCF)C3)cc2)c2ccc(C(=O)O)cc2CCC1] | 8-(2-ethylphenyl)-9-(4-((1-(3-fluoropropyl)azetidin-3-ylidene)methyl)phenyl)-6,7-dihydro-5H-benzo[7]annulene-3-carboxylic acid |
| 87 | 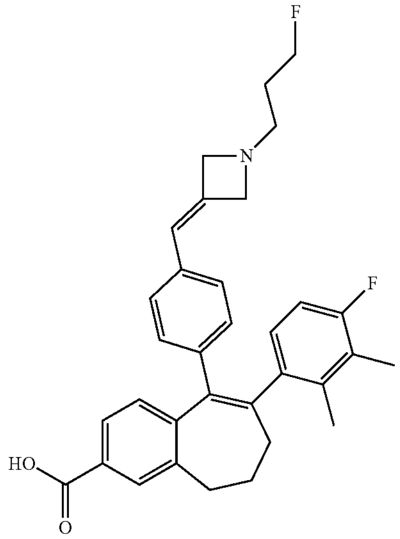 [SMILES: Cc1c(F)ccc(C2=C(c3ccc(C=C4CN(CCCF)C4)cc3)c3ccc(C(=O)O)cc3CCC2)c1C] | 8-(4-fluoro-2,3-dimethylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 88 | 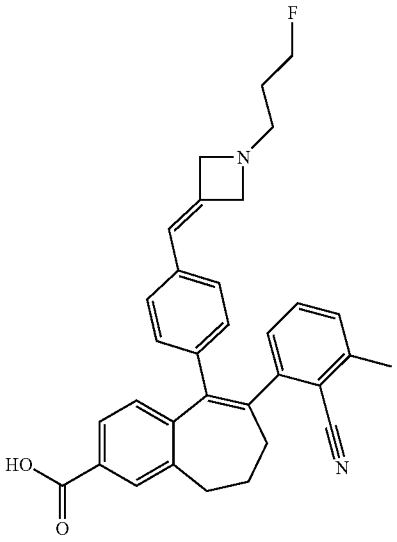 [SMILES: Cc1cccc(C2=C(c3ccc(C=C4CN(CCCF)C4)cc3)c3ccc(C(=O)O)cc3CCC2)c1C#N] | 8-(2-cyano-3-methylphenyl)-9-(4-((1-(3-fluoropropyl)azetidin-3-ylidene)methyl)phenyl)-6,7-dihydro-5H-benzo[7]annulene-3-carboxylic acid |
| 89 | 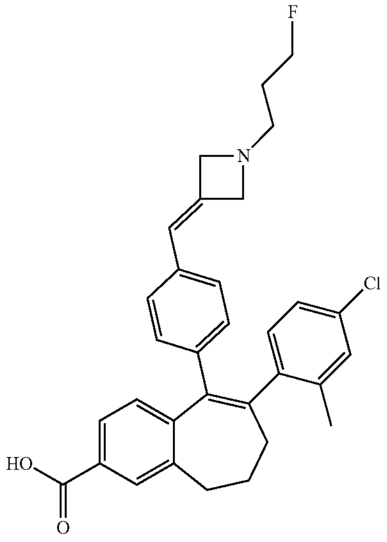 [SMILES: Cc1cc(Cl)ccc1C1=C(c2ccc(C=C3CN(CCCF)C3)cc2)c2ccc(C(=O)O)cc2CCC1] | 8-(4-chloro-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 90 | 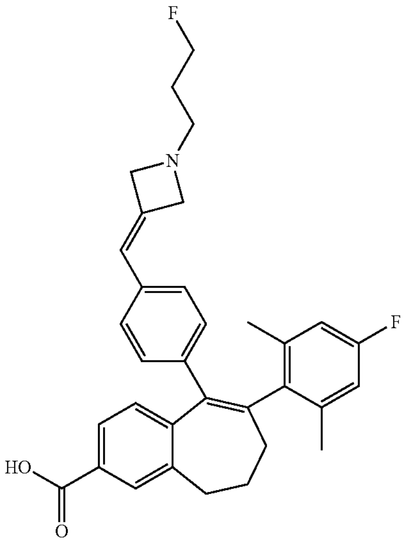 [SMILES: Cc1cc(F)cc(C)c1C1=C(c2ccc(C=C3CN(CCCF)C3)cc2)c2ccc(C(=O)O)cc2CCC1] | 8-(4-fluoro-2,6-dimethylphenyl)-9-(4-((1-(3-fluoropropyl)azetidin-3-ylidene)methyl)phenyl)-6,7-dihydro-5H-benzo[7]annulene-3-carboxylic acid |
| 91 | 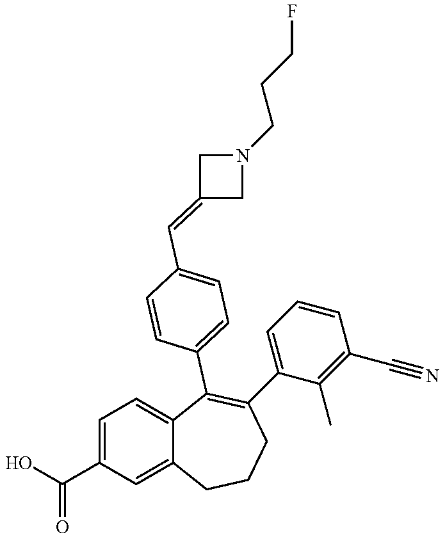 [SMILES: Cc1c(C#N)cccc1C1=C(c2ccc(C=C3CN(CCCF)C3)cc2)c2ccc(C(=O)O)cc2CCC1] | 8-(3-cyano-2-methylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 92 | 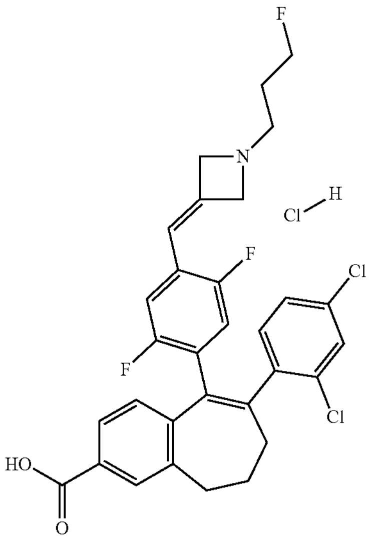 | 8-(2,4-dichlorophenyl)-9-(2,5-difluoro-4-((1-(3-fluoropropyl)azetidin-3-ylidene)methyl)phenyl)-6,7-dihydro-5H-benzo[7]annulene-3-carboxylic acid hydrochloride |
| 93 | 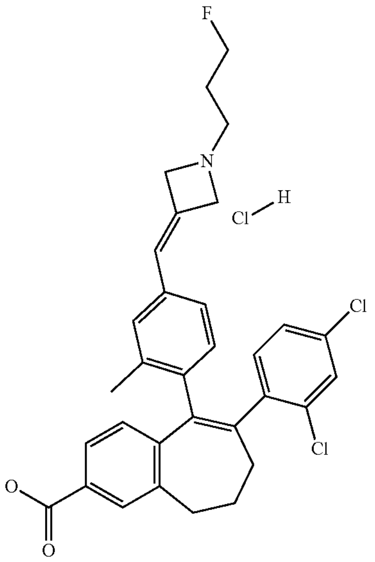 | 8-(2,4-dichlororphenyl)-9-(4-((1-(3-fluoropropyl)azetidin-3-ylidene)methyl)-2-methylphenyl)-6,7-dihydro-5H-benzo[7]annulene-3-carboxylic acid hydrochloride |

TABLE 1a-continued
| Ex. or compounds | Structure | Name |
|---|---|---|
| 94 | 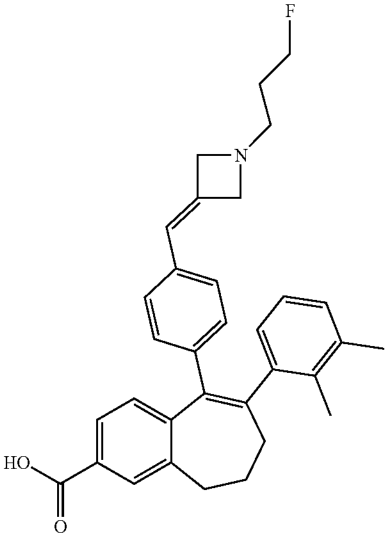 [SMILES: Cc1cccc(C2=C(c3ccc(C=C4CN(CCCF)C4)cc3)c3ccc(C(=O)O)cc3CCC2)c1C] | 8-(2,3-dimethylphenyl)-9-(4-((1-(3-fluoropropyl)azetidin-3-ylidene)methyl)phenyl)-6,7-dihydro-5H-benzo[7]annulene-3-carboxylic acid |
| 95 | 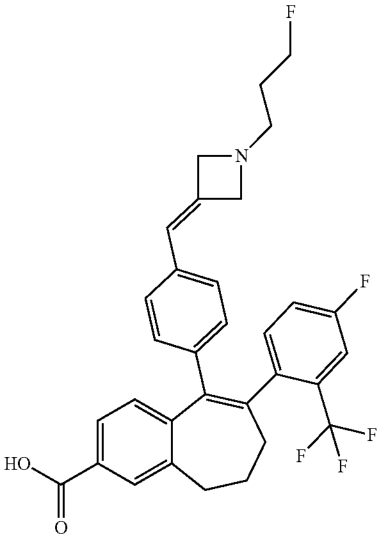 [SMILES: O=C(O)c1ccc2c(c1)CCCC(c1ccc(F)cc1C(F)(F)F)=C2c1ccc(C=C2CN(CCCF)C2)cc1] | 8-(4-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
| --- | --- | --- |
| 96 | 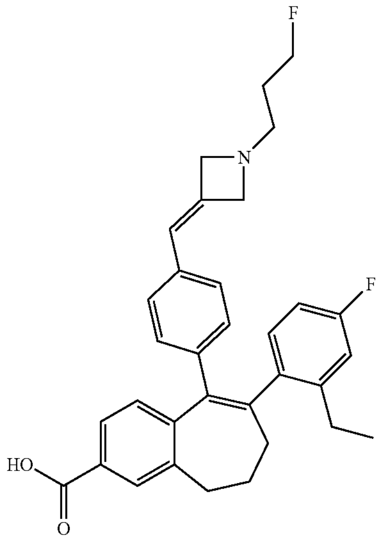 [SMILES: CCc1cc(F)ccc1C1=C(c2ccc(C=C3CN(CCCF)C3)cc2)c2ccc(C(=O)O)cc2CCC1] | 8-(2-ethyl-4-fluoropehnyl)-9-(4-((1-(3-fluoropropyl)azetidin-3-ylidene)methyl)phenyl)-6,7-dihydro-5H-benzo[7]annulene-3-carboxylic acid |
| 97 | 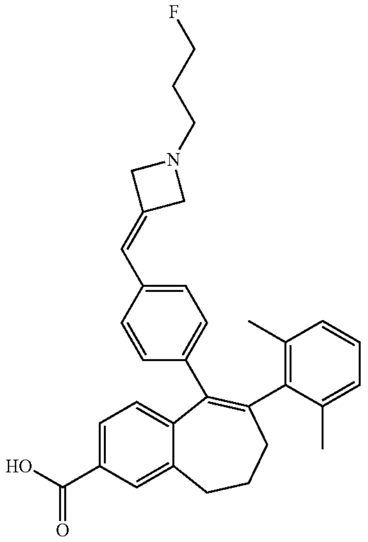 [SMILES: Cc1cccc(C)c1C1=C(c2ccc(C=C3CN(CCCF)C3)cc2)c2ccc(C(=O)O)cc2CCC1] | 8-(2,6-dimethylphenyl)-9-(4-((1-(3-fluoropropyl)azetidin-3-ylidene)methyl)phenyl)-6,7-dihydro-5H-benzo[7]annulene-3-carboxylic acid |

TABLE 1a-continued
| Ex. or compounds | Structure | Name |
|---|---|---|
| 98 | 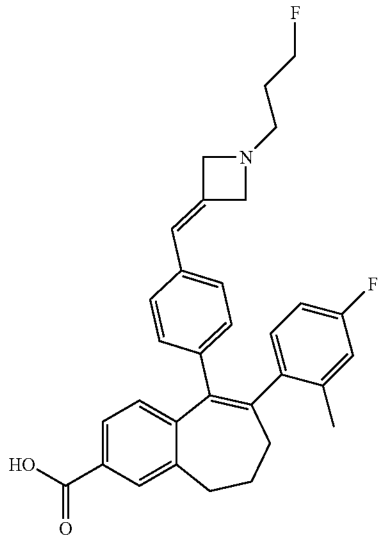 [SMILES: Cc1cc(F)ccc1C1=C(c2ccc(C=C3CN(CCCF)C3)cc2)c2ccc(C(=O)O)cc2CCC1] | 8-(4-fluoro-2-methylphenyl)-9-(4-((1-(3-fluoropropyl)azetidin-3-ylidene)methyl)phenyl)-6,7-dihydro-5H-benzo[7]annulene-3-carboxylic acid |
| 99 | 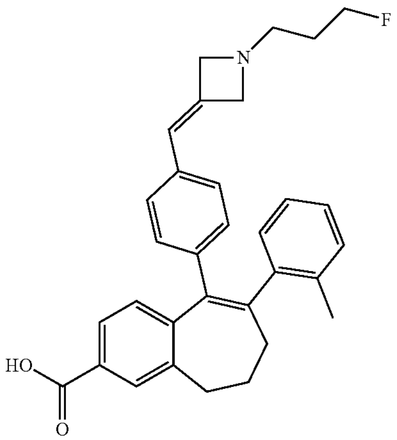 [SMILES: Cc1ccccc1C1=C(c2ccc(C=C3CN(CCCF)C3)cc2)c2ccc(C(=O)O)cc2CCC1] | 9-(4-((1-(3-fluoropropyl)azetidin-3-ylidene)methyl)phenyl)-8-(o-tolyl)-6,7-dihydro-5H-benzo[7]annulene-3-carboxylic acid |
| 100 | 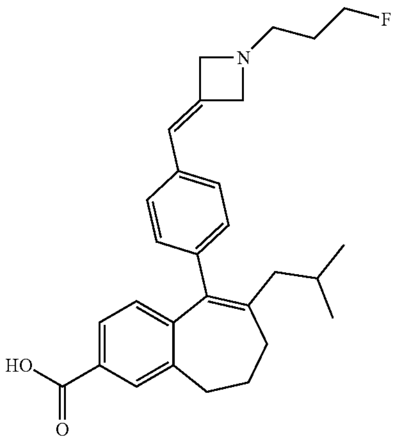 [SMILES: CC(C)CC1=C(c2ccc(C=C3CN(CCCF)C3)cc2)c2ccc(C(=O)O)cc2CCC1] | 9-(4-((1-(3-fluoropropyl)azetidin-3-ylidene)methyl)phenyl)-8-isobutyl-6,7-dihydro-5H-benzo[7]annulene-3-carboxylic acid |

TABLE 1a-continued

| Ex. or compounds | Structure | Name |
|---|---|---|
| 101 | 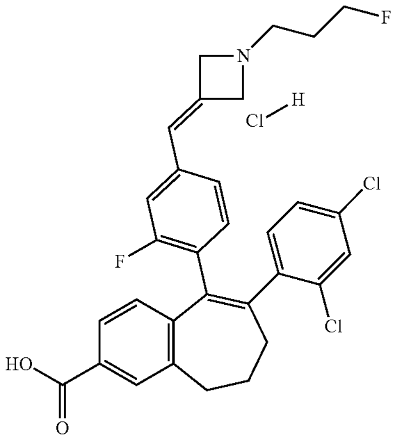 | 8-(2,4-dichlorophenyl)-9-(2-fluoro-4-((1-(3-fluoropropyl)azetidin-3-ylidene)methyl)phenyl)-6,7-dihydro-5H-benzo[7]annulene-3-carboxylic acid hydrochloride |
| 102 | 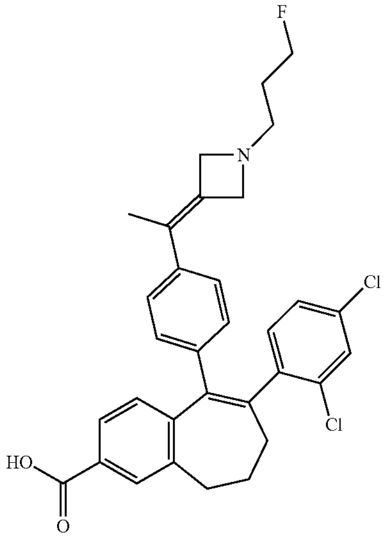 [SMILES: CC(=C1CN(CCCF)C1)c1ccc(C2=C(c3ccc(Cl)cc3Cl)CCCc3cc(C(=O)O)ccc32)cc1] | 8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylic acid |
| 103 | 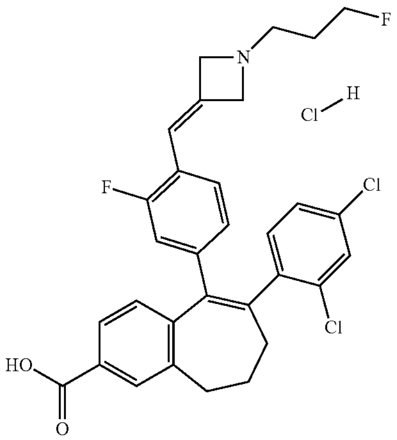 [SMILES: O=C(O)c1ccc2c(c1)CCCC(c1ccc(Cl)cc1Cl)=C2c1ccc(C=C2CN(CCCF)C2)c(F)c1 ; Cl] | 8-(2,4-dichlorophenyl)-9-(3-fluoro-4-((1-(3-fluoropropyl)azetidin-3-ylidene)methyl)phenyl)-6,7-dihydro-5H-benzo[7]annulene-3-carboxylic acid hydrochloride |

TABLE 1a-continued

| Ex. or compounds | Structure | Name |
| --- | --- | --- |
| 104 | 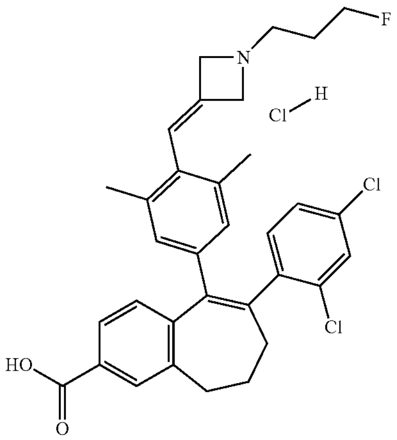 | 8-(2,4-dichlorophenyl)-9-(4-((1-(3-fluoropropyl)azetidin-3-ylidene)methyl)-3,5-dimethylphenyl)-6,7-dihydro-5H-benzo[7]annulene-3-carboxylic acid hydrochloride |
| 105 | 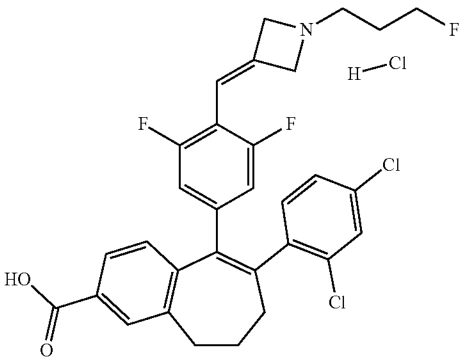 | 8-(2,4-dichlorophenyl)-9-(3,5-difluoro-4-((1-(3-fluoropropyl)azetidin-3-ylidene)methyl)phenyl)-6,7-dihydro-5H-benzo[7]annulene-3-carboxylic acid hydrochloride |
| 106 | 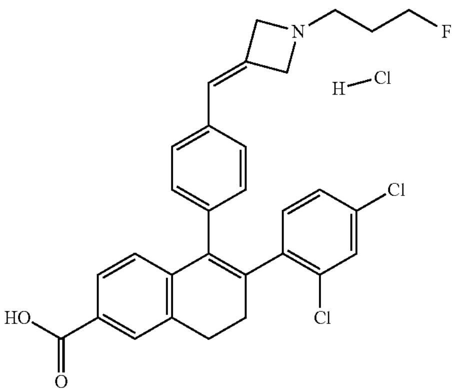 | 6-(2,4-dichlorophenyl)-5-(4-((1-(3-fluoropropyl)azetidin-3-ylidene)methyl)phenyl)-7,8-dihydronaphthalene-2-carboxylic acid hydrochloride |

TABLE 1a-continued

| Ex. or compounds | Structure | Name |
|---|---|---|
| 107 | 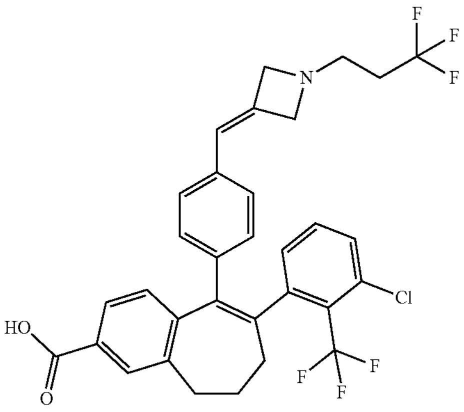 [SMILES: O=C(O)c1ccc2c(c1)CCCC(c1cccc(Cl)c1C(F)(F)F)=C2c1ccc(C=C2CN(CCC(F)(F)F)C2)cc1] | 8-(3-chloro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid |
| 108 | 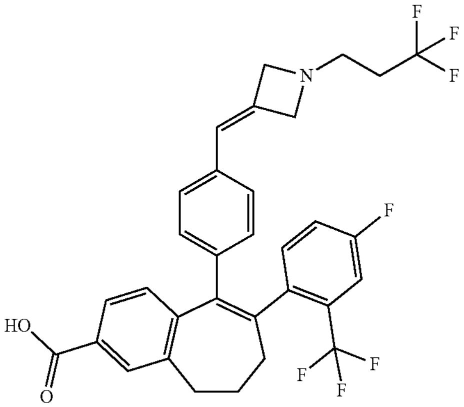 [SMILES: O=C(O)c1ccc2c(c1)CCCC(c1ccc(F)cc1C(F)(F)F)=C2c1ccc(C=C2CN(CCC(F)(F)F)C2)cc1] | 8-(4-fluoro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid |
| 109 | 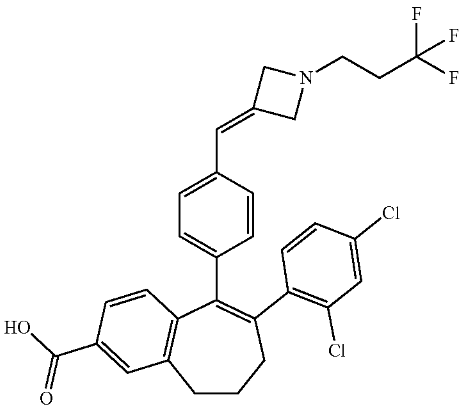 [SMILES: O=C(O)c1ccc2c(c1)CCCC(c1ccc(Cl)cc1Cl)=C2c1ccc(C=C2CN(CCC(F)(F)F)C2)cc1] | 8-(2,4-dichlorophenyl)-9-(4-((1-(3,3,3-trifluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 110 | 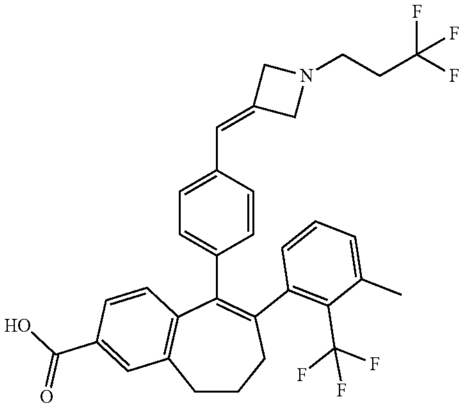 [SMILES: Cc1cccc(C2=C(c3ccc(C=C4CN(CCC(F)(F)F)C4)cc3)c3ccc(C(=O)O)cc3CCC2)c1C(F)(F)F] | 8-(3-methyl-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid |
| 111 | 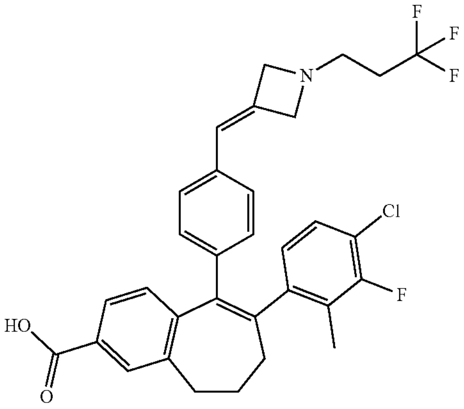 [SMILES: Cc1c(C2=C(c3ccc(C=C4CN(CCC(F)(F)F)C4)cc3)c3ccc(C(=O)O)cc3CCC2)ccc(Cl)c1F] | 8-(4-chloro-3-fluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid |
| 112 | 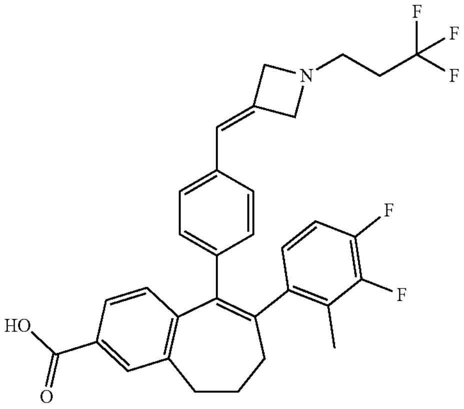 [SMILES: Cc1c(C2=C(c3ccc(C=C4CN(CCC(F)(F)F)C4)cc3)c3ccc(C(=O)O)cc3CCC2)ccc(F)c1F] | 8-(3,4-difluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 113 | 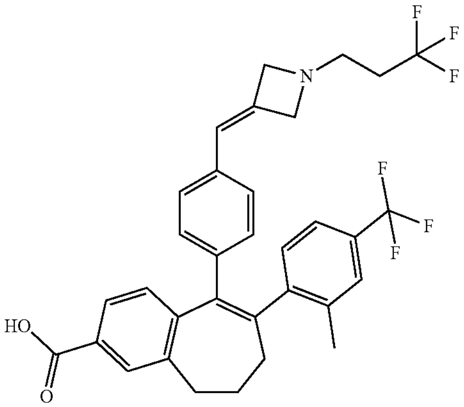 [SMILES: Cc1cc(C(F)(F)F)ccc1C1=C(c2ccc(C=C3CN(CCC(F)(F)F)C3)cc2)c2ccc(C(=O)O)cc2CCC1] | 8-(2-methyl-4-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid |
| 114 | 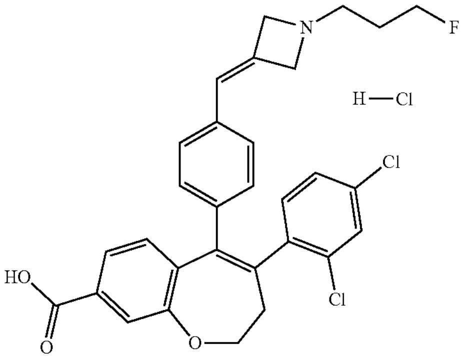 [SMILES: O=C(O)c1ccc2c(c1)OCCC(c1ccc(Cl)cc1Cl)=C2c1ccc(C=C2CN(CCCF)C2)cc1 ; Cl] | 4-(2,4-dichlorophenyl)-5-(4-((1-(3-fluoropropyl)azetidin-3-ylidene)methyl)phenyl)-2,3-dihydrobenzo[b]oxepine-8-carboxylic acid hydrochloride |
| 115 | 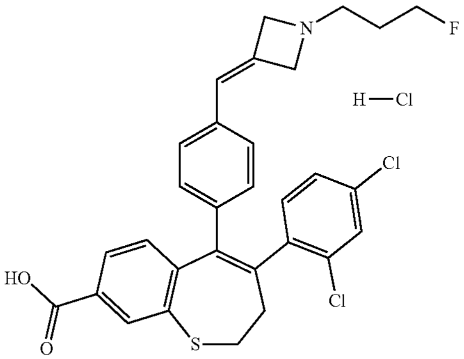 | 4-(2,4-dichlorophenyl)-5-[4-[[1-(3-fluoropropyl)azetidin-3-ylidene]methyl]phenyl]-2,3-dihydro-1-benzothiepine-8-carboxylic acid hydrochloride |
| 116 | 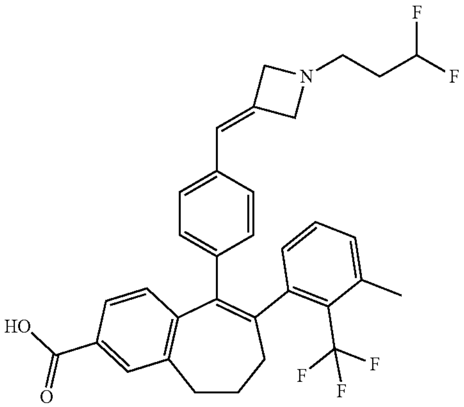 [SMILES: Cc1cccc(C2=C(c3ccc(C=C4CN(CCC(F)F)C4)cc3)c3ccc(C(=O)O)cc3CCC2)c1C(F)(F)F] | 9-(4-((1-(3,3-difluoropropyl)azetidin-3-ylidene)methyl)phenyl)-8-(3-methyl-2-(trifluoromethyl)phenyl)-6,7-dihydro-5H-benzo[7]annulene-3-carboxylic acid |

TABLE 1a-continued

| Ex. or compounds | Structure | Name |
|---|---|---|
| 117 | 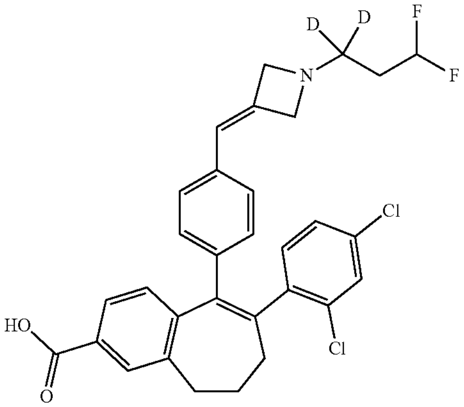 [SMILES: [2H]C([2H])(CC(F)F)N1CC(=Cc2ccc(C3=C(c4ccc(Cl)cc4Cl)CCCc4cc(C(=O)O)ccc43)cc2)C1] | 8-(2,4-dichlorophenyl)-9-(4-((1-(3,3-difluoropropyl-1,1-d2)azetidin-3-ylidene)methyl)phenyl)-6,7-dihydro-5H-benzo[7]annulene-3-carboxylic acid |
| 118 | 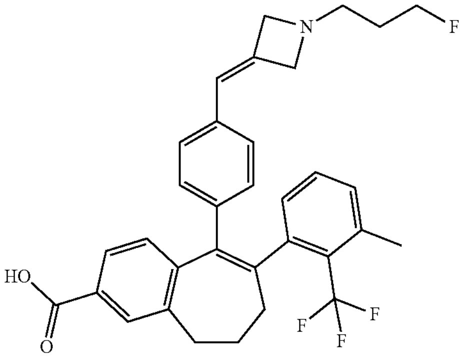 [SMILES: Cc1cccc(C2=C(c3ccc(C=C4CN(CCCF)C4)cc3)c3ccc(C(=O)O)cc3CCC2)c1C(F)(F)F] | 9-(4-((1-(3-fluoropropyl)azetidin-3-ylidene)methyl)phenyl)-8-(3-methyl-2-(trifluoromethyl)phenyl)-6,7-dihydro-5H-benzo[7]annulene-3-carboxylic acid |
| 119 | 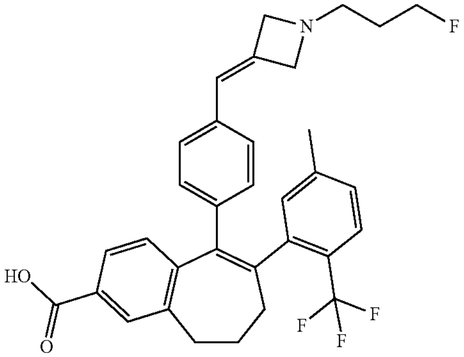 [SMILES: Cc1ccc(C(F)(F)F)c(C2=C(c3ccc(C=C4CN(CCCF)C4)cc3)c3ccc(C(=O)O)cc3CCC2)c1] | 9-(4-((1-(3-fluoropropyl)azetidin-3-ylidene)methyl)phenyl)-8-(5-methyl-2-(trifluoromethyl)phenyl)-6,7-dihydro-5H-benzo[7]annulene-3-carboxylic acid |
| 120 | 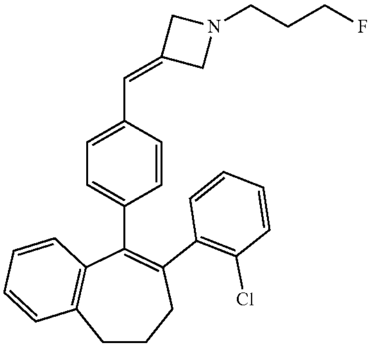 [SMILES: FCCCN1CC(=Cc2ccc(C3=C(c4ccccc4Cl)CCCc4ccccc43)cc2)C1] | 3-(4-(8-(2-chlorophenyl)-6,7-dihydro-5H-benzo[7]annulen-9-yl)benzylidene)-1-(3-fluoropropyl)azetidine |

TABLE 1a-continued

| Ex. or compounds | Structure | Name |
|---|---|---|
| 121 | 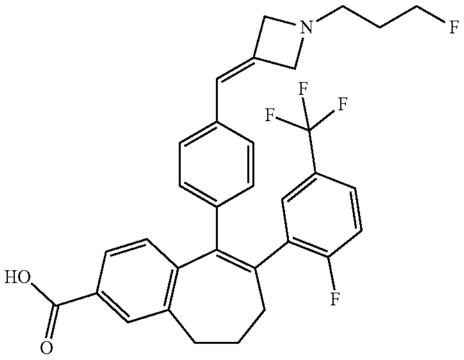 [SMILES: O=C(O)c1ccc2c(c1)CCCC(c1cc(C(F)(F)F)ccc1F)=C2c1ccc(C=C2CN(CCCF)C2)cc1] | 8-(2-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 122 | 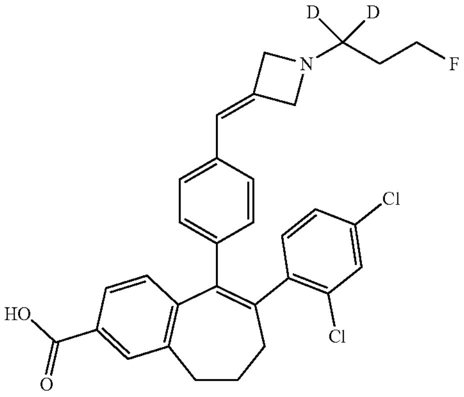 [SMILES: [2H]C([2H])(CCF)N1CC(=Cc2ccc(C3=C(c4ccc(Cl)cc4Cl)CCCc4cc(C(=O)O)ccc43)cc2)C1] | 8-(2,4-dichlorophenyl)-9-(4-((1-(3-fluoropropyl-1,1-d2)azetidin-3-ylidene)methyl)phenyl)-6,7-dihydro-5H-benzo[7]annulene-3-carboxylic acid |
| 123 | 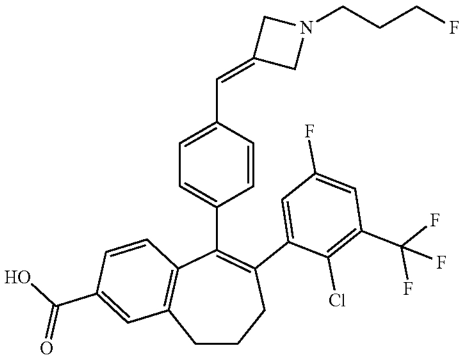 [SMILES: O=C(O)c1ccc2c(c1)CCCC(c1cc(F)cc(C(F)(F)F)c1Cl)=C2c1ccc(C=C2CN(CCCF)C2)cc1] | 8-(2-chloro-5-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 124 | 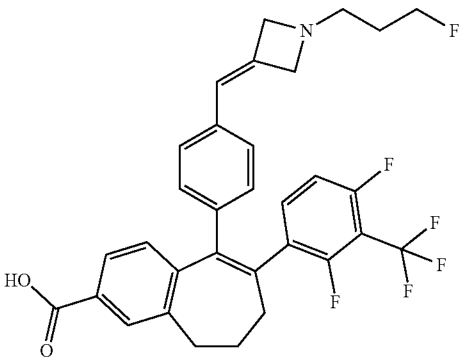 [SMILES: O=C(O)c1ccc2c(c1)CCCC(c1ccc(F)c(C(F)(F)F)c1F)=C2c1ccc(C=C2CN(CCCF)C2)cc1] | 8-(2,4-difluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 125 | 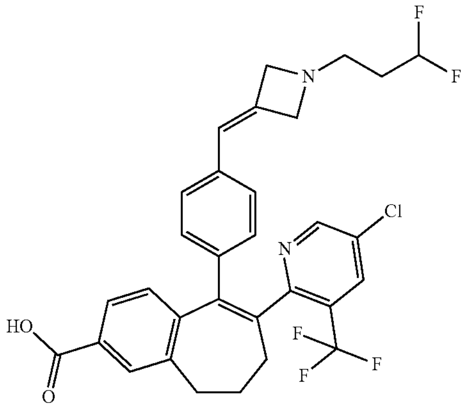 [SMILES: O=C(O)c1ccc2c(c1)CCCC(c1ncc(Cl)cc1C(F)(F)F)=C2c1ccc(C=C2CN(CCC(F)F)C2)cc1] | 8-(5-chloro-3-(trifluoromethyl)pyridin-2-yl)-9-(4-((1-(3,3-difluoropropyl)azetidin-3-ylidene)methyl)phenyl)-6,7-dihydro-5H-benzo[7]annulene-3-carboxylic acid |
| 126 | 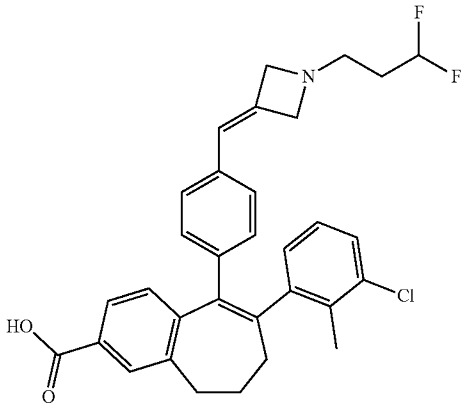 [SMILES: Cc1c(Cl)cccc1C1=C(c2ccc(C=C3CN(CCC(F)F)C3)cc2)c2ccc(C(=O)O)cc2CCC1] | 8-(3-chloro-2-methylphenyl)-9-(4-((1-(3,3-difluoropropyl)azetidin-3-ylidene)methyl)phenyl)-6,7-dihydro-5H-benzo[7]annulene-3-carboxylic acid |
| 127 | 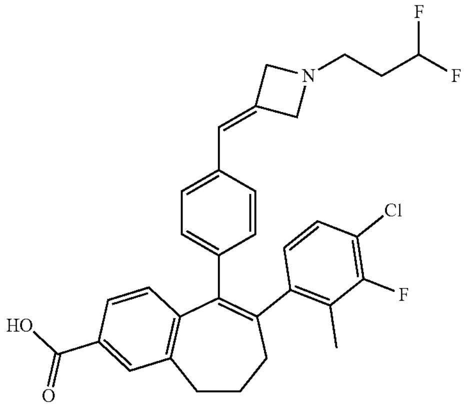 [SMILES: Cc1c(C2=C(c3ccc(C=C4CN(CCC(F)F)C4)cc3)c3ccc(C(=O)O)cc3CCC2)ccc(Cl)c1F] | 8-(4-chloro-3-fluoro-2-methylphenyl)-9-(4-((1-(3,3-difluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 128 | 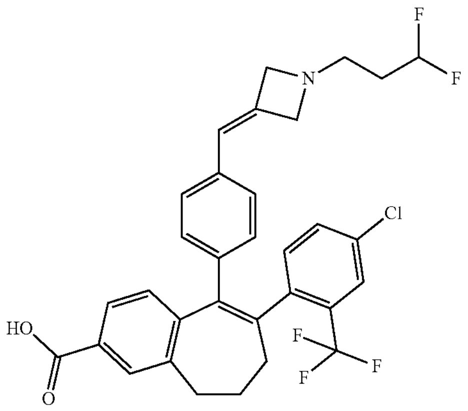 [SMILES: O=C(O)c1ccc2c(c1)CCCC(c1ccc(Cl)cc1C(F)(F)F)=C2c1ccc(C=C2CN(CCC(F)F)C2)cc1] | 8-(4-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid |
| 129 | 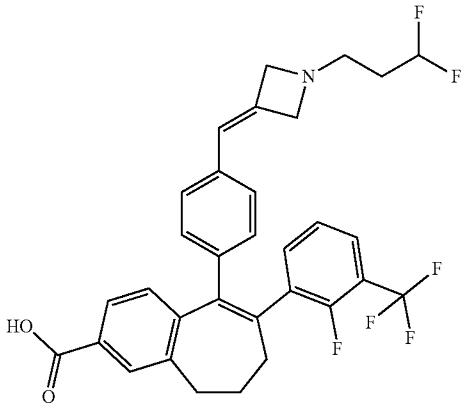 [SMILES: O=C(O)c1ccc2c(c1)CCCC(c1cccc(C(F)(F)F)c1F)=C2c1ccc(C=C2CN(CCC(F)F)C2)cc1] | 9-(4-((1-(3,3-difluoropropyl)azetidin-3-ylidene)methyl)phenyl)-8-(2-fluoro-3-(trifluoromethyl)phenyl)-6,7-dihydro-5H-benzo[7]annulene-3-carboxylic acid |
| 130 | 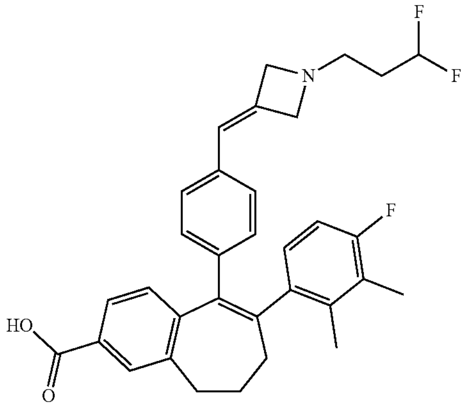 [SMILES: Cc1c(F)ccc(C2=C(c3ccc(C=C4CN(CCC(F)F)C4)cc3)c3ccc(C(=O)O)cc3CCC2)c1C] | 9-(4-((1-(3,3-difluoropropyl)azetidin-3-ylidene)methyl)phenyl)-8-(4-fluoro-2,3-dimethylphenyl)-6,7-dihydro-5H-benzo[7]annulene-3-carboxylic acid |

TABLE 1a-continued

| Ex. or compounds | Structure | Name |
| --- | --- | --- |
| 131 | 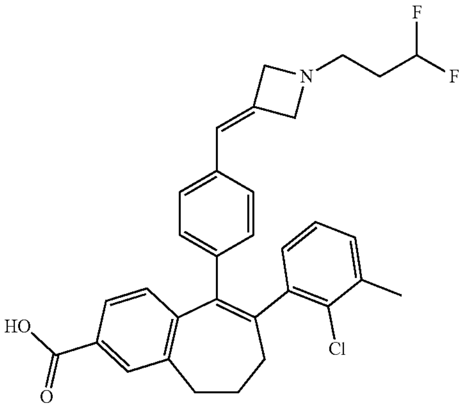 [SMILES: Cc1cccc(C2=C(c3ccc(C=C4CN(CCC(F)F)C4)cc3)c3ccc(C(=O)O)cc3CCC2)c1Cl] | 8-(2-chloro-3-methylphenyl)-9-(4-((1-(3,3-difluoropropyl)azetidin-3-ylidene)methyl)phenyl)-6,7-dihydro-5H-benzo[7]annulene-3-carboxylic acid |
| 132 | 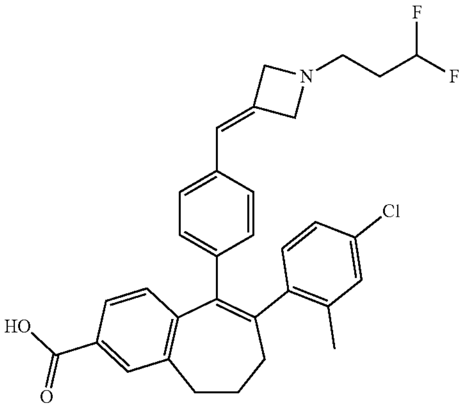 [SMILES: Cc1cc(Cl)ccc1C1=C(c2ccc(C=C3CN(CCC(F)F)C3)cc2)c2ccc(C(=O)O)cc2CCC1] | 8-(4-chloro-2-methylphenyl)-9-(4-((1-(3,3-difluoropropyl)azetidin-3-ylidene)methyl)phenyl)-6,7-dihydro-5H-benzo[7]annulene-3-carboxylic acid |
| 133 | 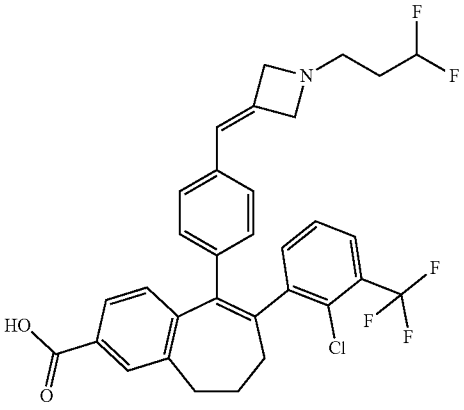 [SMILES: O=C(O)c1ccc2c(c1)CCCC(c1cccc(C(F)(F)F)c1Cl)=C2c1ccc(C=C2CN(CCC(F)F)C2)cc1] | 8-(2-chloro-3-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 134 | 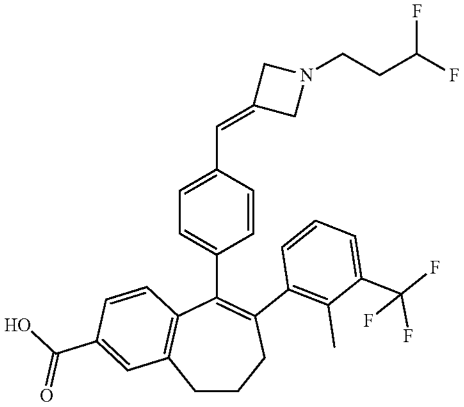 [SMILES: Cc1c(C2=C(c3ccc(C=C4CN(CCC(F)F)C4)cc3)c3ccc(C(=O)O)cc3CCC2)cccc1C(F)(F)F] | 9-(4-((1-(3,3-difluoropropyl)azetidin-3-ylidene)methyl)phenyl)-8-(2-methyl-3-(trifluoromethyl)phenyl)-6,7-dihydro-5H-benzo[7]annulene-3-carboxylic acid |
| 135 | 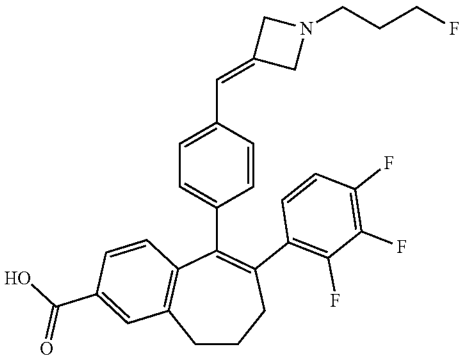 [SMILES: O=C(O)c1ccc2c(c1)CCCC(c1ccc(F)c(F)c1F)=C2c1ccc(C=C2CN(CCCF)C2)cc1] | 9-(4-((1-(3-fluoropropyl)azetidin-3-ylidene)methyl)phenyl)-8-(2,3,4-trifluorophenyl)-6,7-dihydro-5H-benzo[7]annulene-3-carboxylic acid |
| 136 | 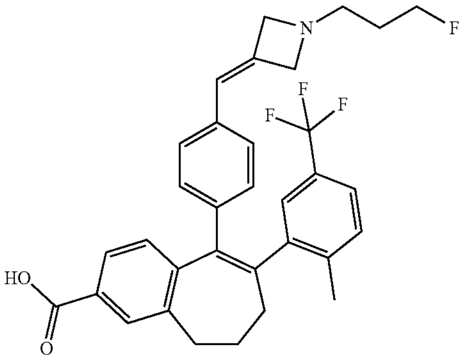 [SMILES: Cc1ccc(C(F)(F)F)cc1C1=C(c2ccc(C=C3CN(CCCF)C3)cc2)c2ccc(C(=O)O)cc2CCC1] | 9-(4-((1-(3-fluoropropyl)azetidin-3-ylidene)methyl)phenyl)-8-(2-methyl-5-(trifluoromethyl)phenyl)-6,7-dihydro-5H-benzo[7]annulene-3-carboxylic acid |
| 137 | 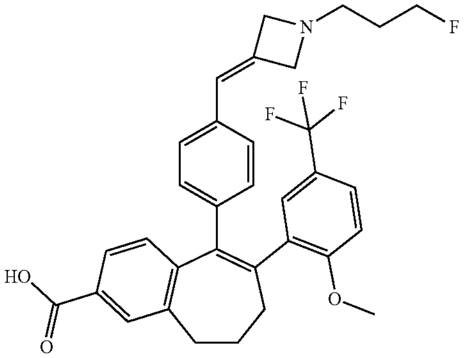 [SMILES: COc1ccc(C(F)(F)F)cc1C1=C(c2ccc(C=C3CN(CCCF)C3)cc2)c2ccc(C(=O)O)cc2CCC1] | 9-(4-((1-(3-fluoropropyl)azetidin-3-ylidene)methyl)phenyl)-8-(2-methoxy-5-(trifluoromethyl)phenyl)-6,7-dihydro-5H-benzo[7]annulene-3-carboxylic acid |

TABLE 1a-continued

| Ex. or compounds | Structure | Name |
|---|---|---|
| 138 | 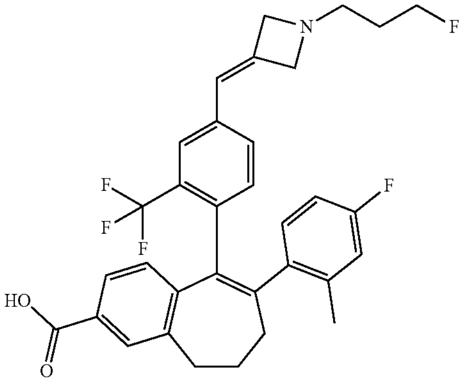 [SMILES: Cc1cc(F)ccc1C1=C(c2ccc(C=C3CN(CCCF)C3)cc2C(F)(F)F)c2ccc(C(=O)O)cc2CCC1] | 8-(4-fluoro-2-methylphenyl)-9-(4-((1-(3-fluoropropyl)azetidin-3-ylidene)methyl)-2-(trifluoromethyl)phenyl)-6,7-dihydro-5H-benzo[7]annulene-3-carboxylic acid |
| 139 | 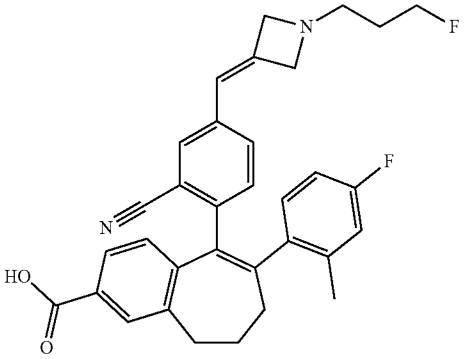 [SMILES: Cc1cc(F)ccc1C1=C(c2ccc(C=C3CN(CCCF)C3)cc2C#N)c2ccc(C(=O)O)cc2CCC1] | 9-(2-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid |
| 140 | 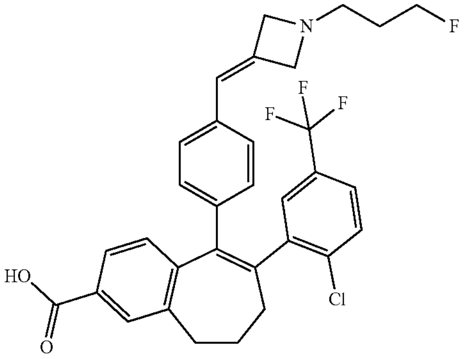 [SMILES: O=C(O)c1ccc2c(c1)CCCC(c1cc(C(F)(F)F)ccc1Cl)=C2c1ccc(C=C2CN(CCCF)C2)cc1] | 8-(2-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 141 | 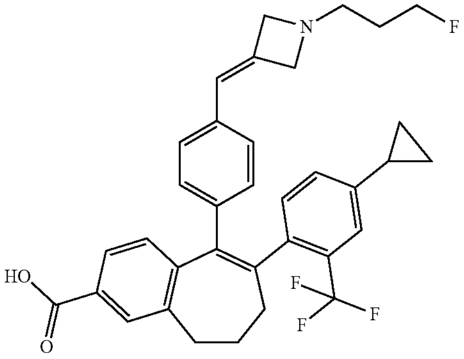 [SMILES: O=C(O)c1ccc2c(c1)CCCC(c1ccc(C3CC3)cc1C(F)(F)F)=C2c1ccc(C=C2CN(CCCF)C2)cc1] | 8-(4-cyclopropyl-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 142 | 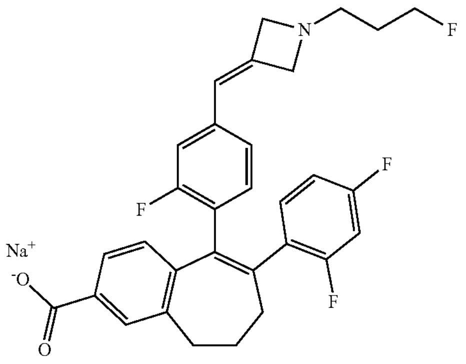 | Sodium 8-(2,4-difluorophenyl)-9-(2-fluoro-4-((1-(3-fluoropropyl)azetidin-3-ylidene)methyl)phenyl)-6,7-dihydro-5H-benzo[7]annulene-3-carboxylate |
| 143 | 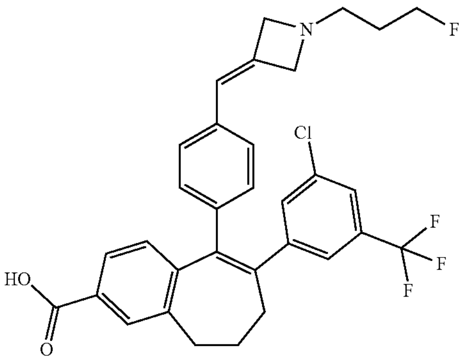 [SMILES: O=C(O)c1ccc2c(c1)CCCC(c1cc(Cl)cc(C(F)(F)F)c1)=C2c1ccc(C=C2CN(CCCF)C2)cc1] | 8-(3-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 144 | 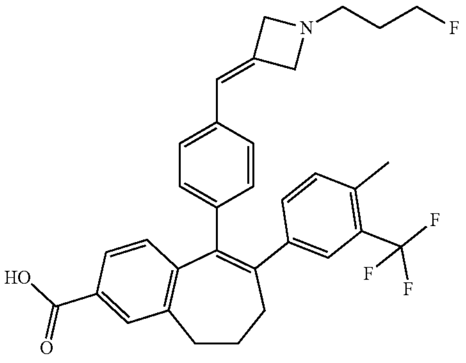 [SMILES: Cc1ccc(C2=C(c3ccc(C=C4CN(CCCF)C4)cc3)c3ccc(C(=O)O)cc3CCC2)cc1C(F)(F)F] | 9-(4-((1-(3-fluoropropyl)azetidin-3-ylidene)methyl)phenyl)-8-(4-methyl-3-(trifluoromethyl)phenyl)-6,7-dihydro-5H-benzo[7]annulene-3-carboxylic acid |
| 145 | 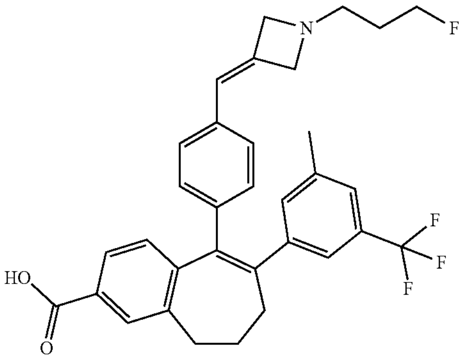 [SMILES: Cc1cc(C2=C(c3ccc(C=C4CN(CCCF)C4)cc3)c3ccc(C(=O)O)cc3CCC2)cc(C(F)(F)F)c1] | 9-(4-((1-(3-fluoropropyl)azetidin-3-ylidene)methyl)phenyl)-8-(3-methyl-5-(trifluoromethyl)phenyl)-6,7-dihydro-5H-benzo[7]annulene-3-carboxylic acid |

TABLE 1a-continued

| Ex. or compounds | Structure | Name |
|---|---|---|
| 146 | 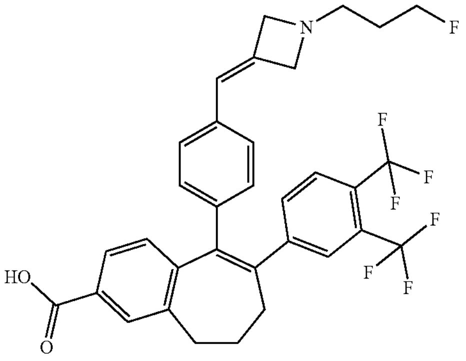 [SMILES: O=C(O)c1ccc2c(c1)CCCC(c1ccc(C(F)(F)F)c(C(F)(F)F)c1)=C2c1ccc(C=C2CN(CCCF)C2)cc1] | 8-(3,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 147 | 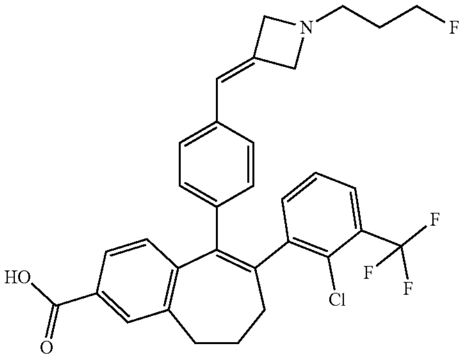 [SMILES: O=C(O)c1ccc2c(c1)CCCC(c1cccc(C(F)(F)F)c1Cl)=C2c1ccc(C=C2CN(CCCF)C2)cc1] | 8-(2-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 148 | 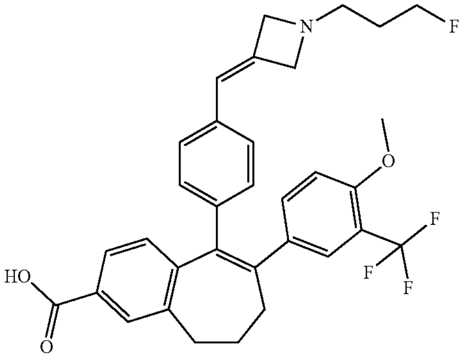 [SMILES: COc1ccc(C2=C(c3ccc(C=C4CN(CCCF)C4)cc3)c3ccc(C(=O)O)cc3CCC2)cc1C(F)(F)F] | 9-(4-((1-(3-fluoropropyl)azetidin-3-ylidene)methyl)phenyl)-8-(4-methoxy-3-(trifluoromethyl)phenyl)-6,7-dihydro-5H-benzo[7]annulene-3-carboxylic acid |
| 149 | 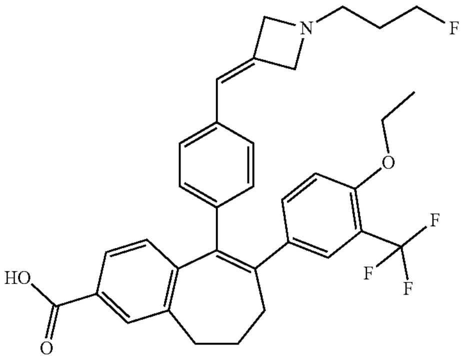 [SMILES: CCOc1ccc(C2=C(c3ccc(C=C4CN(CCCF)C4)cc3)c3ccc(C(=O)O)cc3CCC2)cc1C(F)(F)F] | 8-(4-ethoxy-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
| --- | --- | --- |
| 150 | 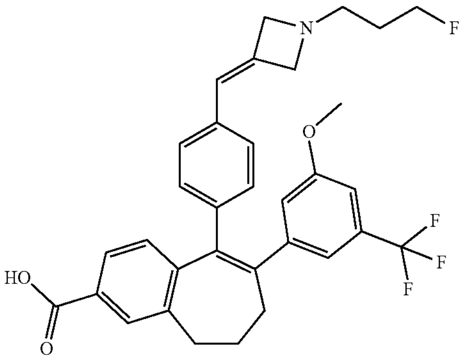 [SMILES: COc1cc(C2=C(c3ccc(C=C4CN(CCCF)C4)cc3)c3ccc(C(=O)O)cc3CCC2)cc(C(F)(F)F)c1] | 9-(4-((1-(3-fluoropropyl)azetidin-3-ylidene)methyl)phenyl)-8-(3-methoxy-5-(trifluoromethyl)phenyl)-6,7-dihydro-5H-benzo[7]annulene-3-carboxylic acid |
| 151 | 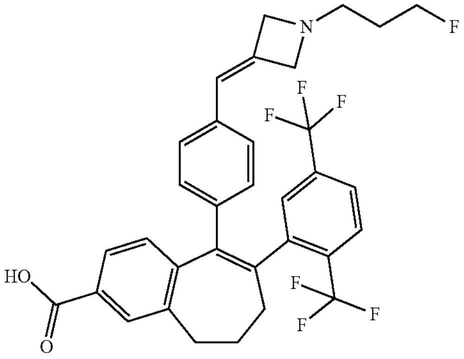 [SMILES: O=C(O)c1ccc2c(c1)CCCC(c1cc(C(F)(F)F)ccc1C(F)(F)F)=C2c1ccc(C=C2CN(CCCF)C2)cc1] | 8-(2,5-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 152 | 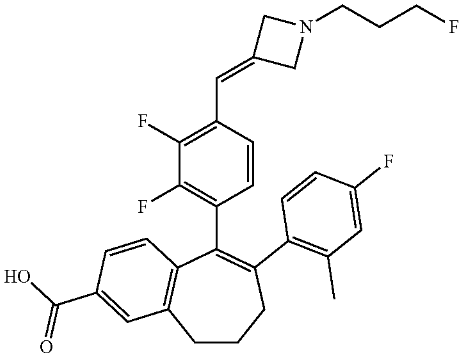 [SMILES: Cc1cc(F)ccc1C1=C(c2ccc(C=C3CN(CCCF)C3)c(F)c2F)c2ccc(C(=O)O)cc2CCC1] | 9-(2,3-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid |
| 153 | 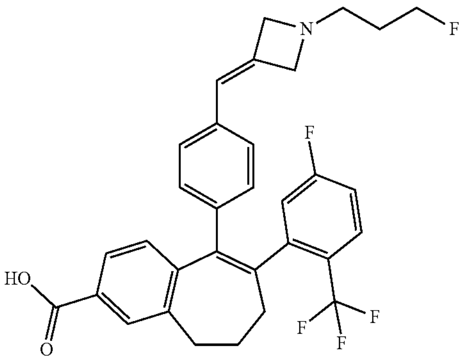 | 8-(5-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 154 | 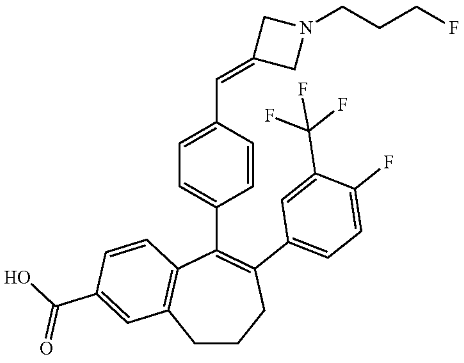 [SMILES: O=C(O)c1ccc2c(c1)CCCC(c1ccc(F)c(C(F)(F)F)c1)=C2c1ccc(C=C2CN(CCCF)C2)cc1] | 8-(4-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 155 | 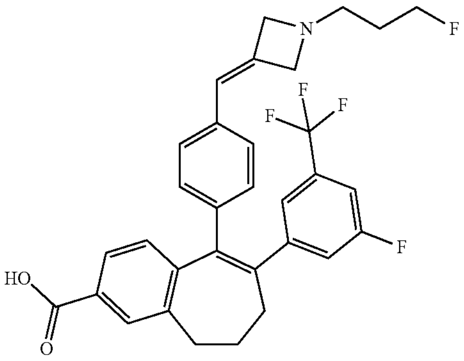 [SMILES: O=C(O)c1ccc2c(c1)CCCC(c1cc(F)cc(C(F)(F)F)c1)=C2c1ccc(C=C2CN(CCCF)C2)cc1] | 8-(3-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid |
| 156 | 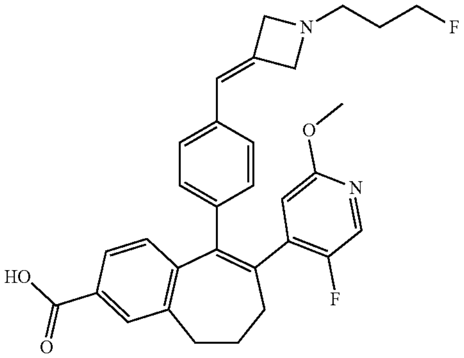 [SMILES: COc1cc(C2=C(c3ccc(C=C4CN(CCCF)C4)cc3)c3ccc(C(=O)O)cc3CCC2)c(F)cn1] | 8-(5-fluoro-2-methoxypyridin-4-yl)-9-(4-((1-(3-fluoropropyl)azetidin-3-yidene)methyl)phenyl)-6,7-dihydro-5H-benzo[7]annulene-3-carboxylic acid |
| 157 | 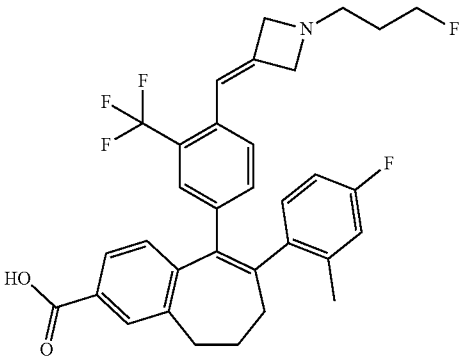 [SMILES: Cc1cc(F)ccc1C1=C(c2ccc(C=C3CN(CCCF)C3)c(C(F)(F)F)c2)c2ccc(C(=O)O)cc2CCC1] | 8-(4-fluoro-2-methylphenyl)-9-(4-((1-(3-fluoropropyl)azetidin-3-ylidene)methyl)-3-(trifluoromethyl)phenyl)-6,7-dihydro-5H-benzo[7]annulene-3-carboxylic acid |

TABLE 1a-continued

| Ex. or compounds | Structure | Name |
|---|---|---|
| 158 | 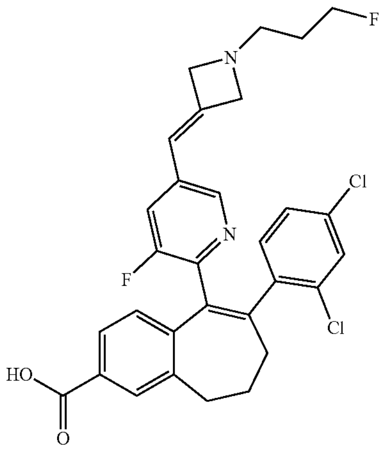 [SMILES: O=C(O)c1ccc2c(c1)CCCC(c1ccc(Cl)cc1Cl)=C2c1ncc(C=C2CN(CCCF)C2)cc1F] | 8-(2,4-dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylic acid |
| 159 | 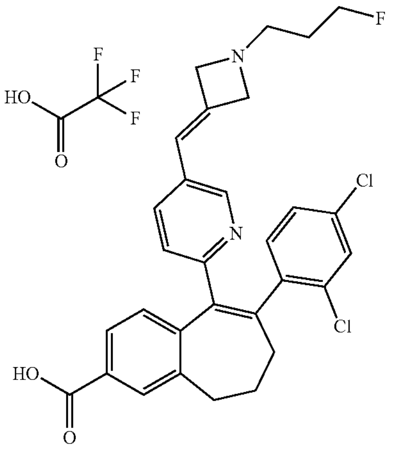 | 8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylic acid, trifluoroacetic acid |
| 160 | 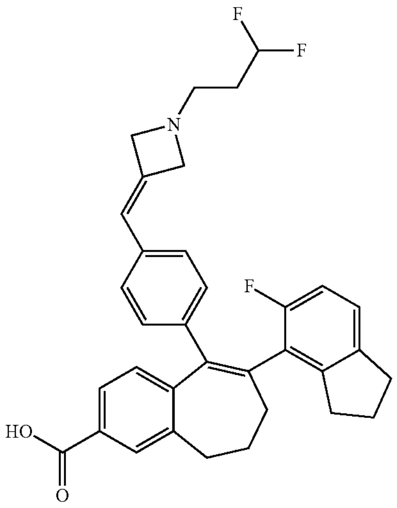 [SMILES: O=C(O)c1ccc2c(c1)CCCC(c1c(F)ccc3c1CCC3)=C2c1ccc(C=C2CN(CCC(F)F)C2)cc1] | 9-(4-((1-(3,3-difluoropropyl)azetidin-3-ylidene)methyl)phenyl)-8-(5-fluoro-2,3-dihydro-1H-inden-4-yl)-6,7-dihydro-5H-benzo[7]annulene-3-carboxylic acid |

TABLE 1a-continued

| Ex. or compounds | Structure | Name |
|---|---|---|
| 161 | 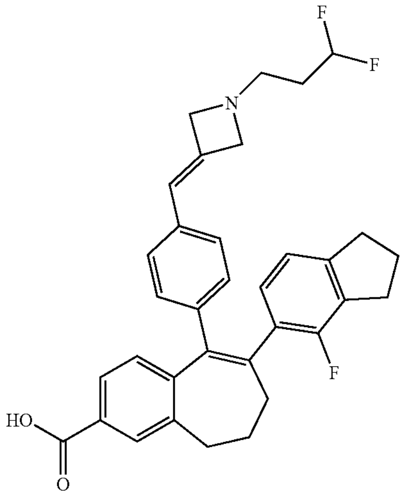 [SMILES: O=C(O)c1ccc2c(c1)CCCC(c1ccc3c(c1F)CCC3)=C2c1ccc(C=C2CN(CCC(F)F)C2)cc1] | 9-(4-((1-(3,3-difluoropropyl)azetidin-3-ylidene)methyl)phenyl)-8-(4-fluoro-2,3-dihydro-1H-inden-5-yl)-6,7-dihydro-5H-benzo[7]annulene-3-carboxylic acid |
| 162 | 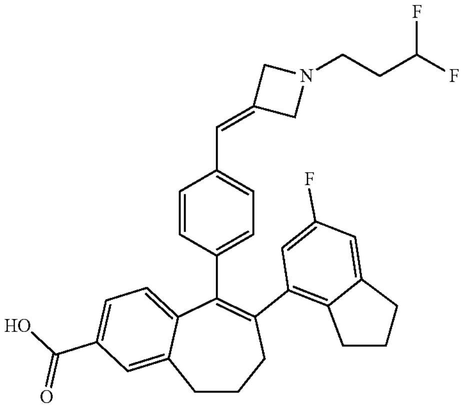 [SMILES: O=C(O)c1ccc2c(c1)CCCC(c1cc(F)cc3c1CCC3)=C2c1ccc(C=C2CN(CCC(F)F)C2)cc1] | 9-(4-((1-(3,3-difluoropropyl)azetidin-3-ylidene)methyl)phenyl)-8-(6-fluoro-2,3-dihydro-1H-inden-4-yl)-6,7-dihydro-5H-benzo[7]annulene-3-carboxylic acid |
| 163 | 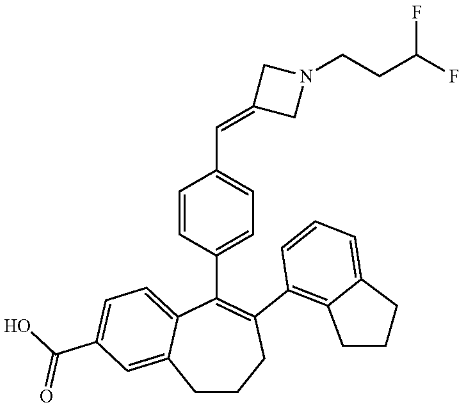 [SMILES: O=C(O)c1ccc2c(c1)CCCC(c1cccc3c1CCC3)=C2c1ccc(C=C2CN(CCC(F)F)C2)cc1] | 9-(4-((1-(3,3-difluoropropyl)azetidin-3-ylidene)methyl)phenyl)-8-(2,3-dihydro-1H-inden-4-yl)-6,7-dihydro-5H-benzo[7]annulene-3-carboxylic acid |

TABLE 1a-continued

| Ex. or compounds | Structure | Name |
| --- | --- | --- |
| 164 | 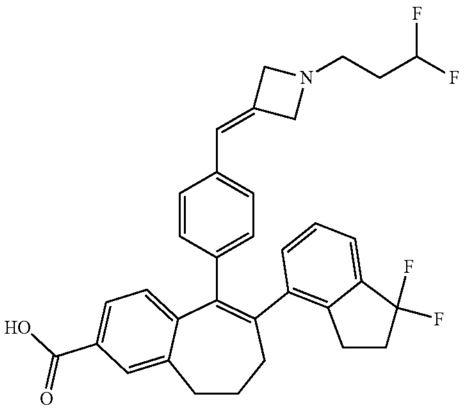 [SMILES: O=C(O)c1ccc2c(c1)CCCC(c1cccc3c1CCC3(F)F)=C2c1ccc(C=C2CN(CCC(F)F)C2)cc1] | 8-(1,1-difluoro-2,3-dihydro-1H-inden-4-yl)-9-(4-((1-(3,3-difluoropropyl)azetidin-3-ylidene)methyl)phenyl)-6,7-dihydro-5H-benzo[7]annulene-3-carboxylic acid |
| 165 | 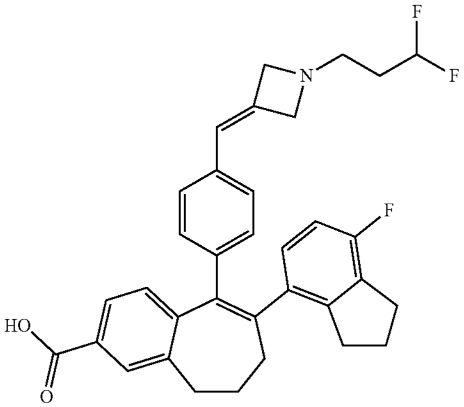 [SMILES: O=C(O)c1ccc2c(c1)CCCC(c1ccc(F)c3c1CCC3)=C2c1ccc(C=C2CN(CCC(F)F)C2)cc1] | 9-(4-((1-(3,3-difluoropropyl)azetidin-3-ylidene)methyl)phenyl)-8-(7-fluoro-2,3-dihydro-1H-inden-4-yl)-6,7-dihydro-5H-benzo[7]annulene-3-carboxylic acid |
| 166 | 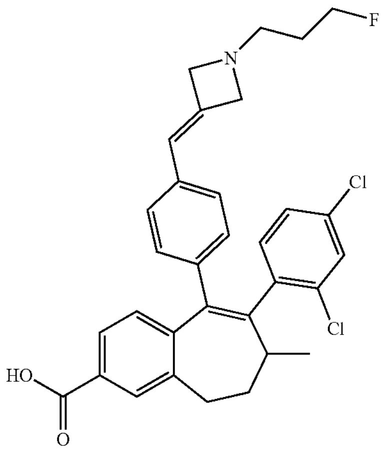 [SMILES: CC1CCc2cc(C(=O)O)ccc2C(c2ccc(C=C3CN(CCCF)C3)cc2)=C1c1ccc(Cl)cc1Cl] | 8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylic acid<br>racemic mixture |

TABLE 1a-continued
| Ex. or compounds | Structure | Name |
|---|---|---|
| 167 | 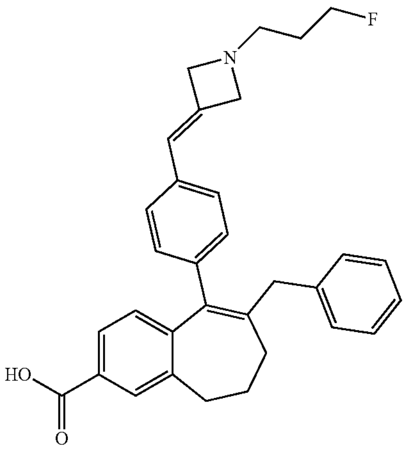 [SMILES: O=C(O)c1ccc2c(c1)CCCC(Cc1ccccc1)=C2c1ccc(C=C2CN(CCCF)C2)cc1] | 8-benzyl-9-(4-((1-(3-fluoropropyl)azetidin-3-ylidene)methyl)phenyl)-6,7-dihydro-5H-benzo[7]annulene-3-carboxylic acid |
| 168 | 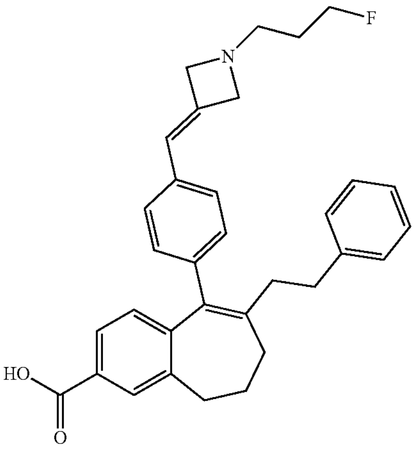 [SMILES: O=C(O)c1ccc2c(c1)CCCC(CCc1ccccc1)=C2c1ccc(C=C2CN(CCCF)C2)cc1] | 9-(4-((1-(3-fluoropropyl)azetidin-3-ylidene)methyl)phenyl)-8-phenethyl-6,7-dihydro-5H-benzo[7]annulene-3-carboxylic acid |
| 169 | 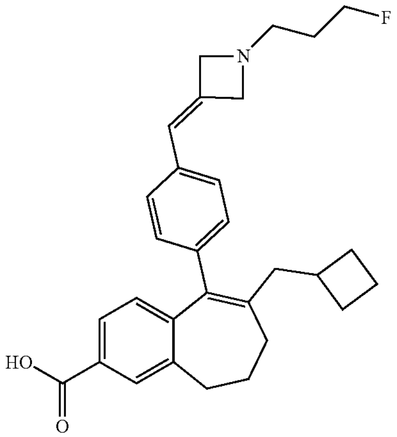 [SMILES: O=C(O)c1ccc2c(c1)CCCC(CC1CCC1)=C2c1ccc(C=C2CN(CCCF)C2)cc1] | 8-(cyclobutylmethyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 170 | 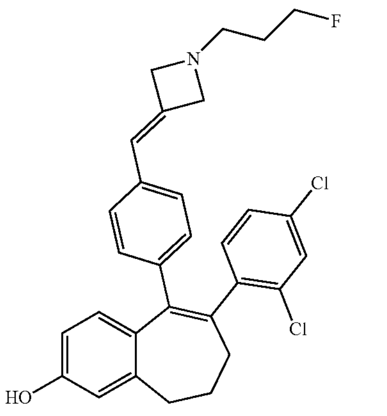 [SMILES: Oc1ccc2c(c1)CCCC(c1ccc(Cl)cc1Cl)=C2c1ccc(C=C2CN(CCCF)C2)cc1] | 8-(2,4-dichlorophenyl)-9-(4-((1-(3-fluoropropyl)azetidin-3-ylidene)methyl)phenyl)-6,7-dihydro-5H-benzo[7]annulen-3-ol |
| 171 | 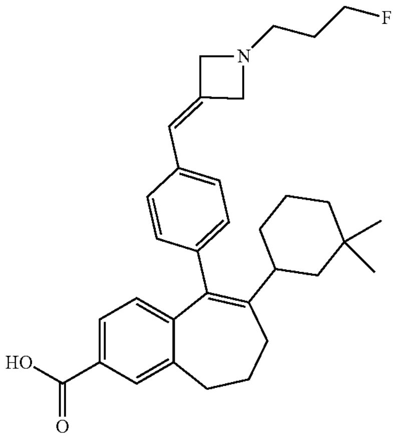 Isomer 1 | 8-(3,3-dimethylcyclohexyl)-9-(4-((1-(3-fluoropropyl)azetidin-3-ylidene)methyl)phenyl)-6,7-dihydro-5H-benzo[7]annulene-3-carboxylic acid, Isomer 1 |
| 172 | 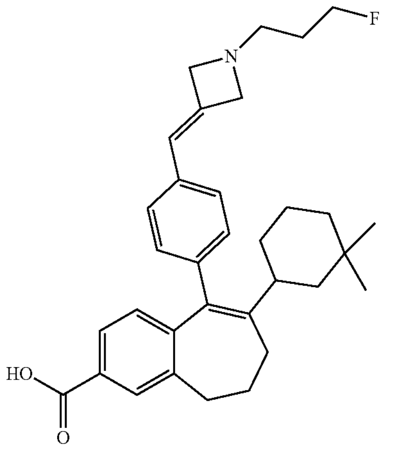 Isomer 2 | 8-(3,3-dimethylcyclohexyl)-9-(4-((1-(3-fluoropropyl)azetidin-3-ylidene)methyl)phenyl)-6,7-dihydro-5H-benzo[7]annulene-3-carboxylic acid, Isomer 2 |

TABLE 1a-continued

| Ex. or compounds | Structure | Name |
| --- | --- | --- |
| 173 | 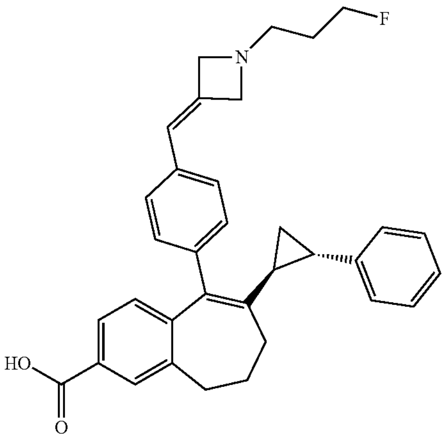 racemic mixture | 9-(4-((1-(3-fluoropropyl)azetidin-3-ylidene)methyl)phenyl)-8-((trans)-2-phenylcyclopropyl)-6,7-dihydro-5H-benzo[7]annulene-3-carboxylic acid, racemic mixture |
| 174 | 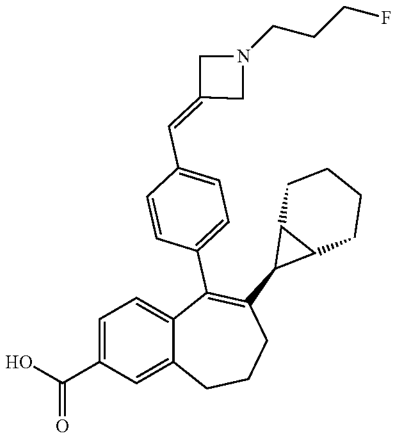 | 8-((1R,6S,7r)-bicyclo[4.1.0]heptan-7-yl)-9-(4-((1-(3-fluoropropyl)azetidin-3-ylidene)methyl)phenyl)-6,7-dihydro-5H-benzo[7]annulene-3-carboxylic acid |
| 175 | 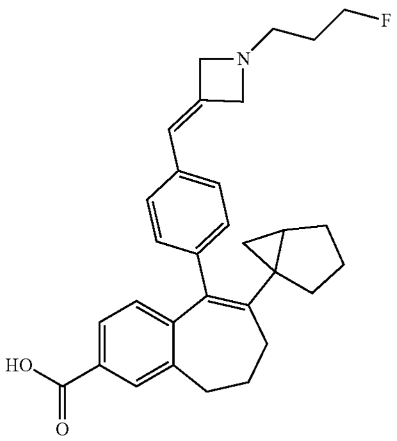 [SMILES: O=C(O)c1ccc2c(c1)CCCC(C13CCCC1C3)=C2c1ccc(C=C2CN(CCCF)C2)cc1] | 8-(bicyclo[3.1.0]hexan-1-yl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 176 | 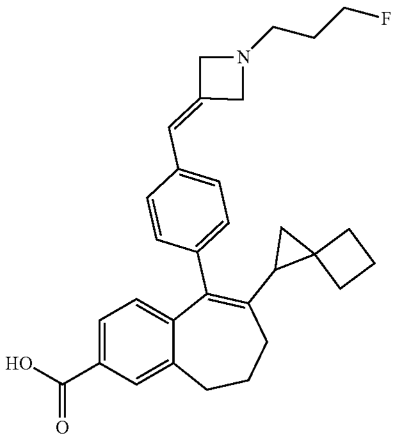 [SMILES: O=C(O)c1ccc2c(c1)CCCC(C1CC13CCC3)=C2c1ccc(C=C2CN(CCCF)C2)cc1] | 9-(4-((1-(3-fluoropropyl)azetidin-3-ylidene)methyl)phenyl)-8-(spiro[2.3]hexan-1-yl)-6,7-dihydro-5H-benzo[7]annulene-3-carboxylic acid |
| 177 | 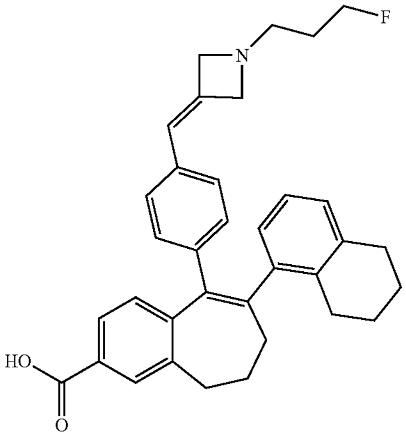 [SMILES: O=C(O)c1ccc2c(c1)CCCC(c1cccc3c1CCCC3)=C2c1ccc(C=C2CN(CCCF)C2)cc1] | 9-(4-((1-(3-fluoropropyl)azetidin-3-ylidene)methyl)phenyl)-8-(5,6,7,8-tetrahydronaphthalen-1-yl)-6,7-dihydro-5H-benzo[7]annulene-3-carboxylic acid |
| 178 | 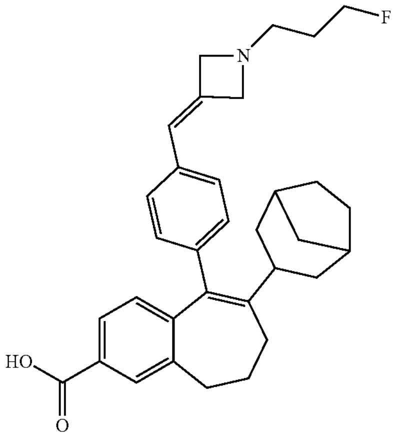 [SMILES: O=C(O)c1ccc2c(c1)CCCC(C1CC3CCC(C3)C1)=C2c1ccc(C=C2CN(CCCF)C2)cc1] | 8-(bicyclo[3.2.1]octan-3-yl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 179 | 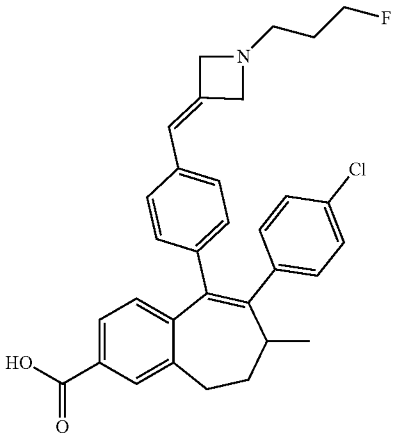 Isomer 1 | 8-(4-chlorophenyl)-9-(4-((1-(3-fluoropropyl)azetidin-3-ylidene)methyl)phenyl)-7-methyl-6,7-dihydro-5H-benzo[7]annulene-3-carboxylic acid, Isomer 1 |
| 180 | 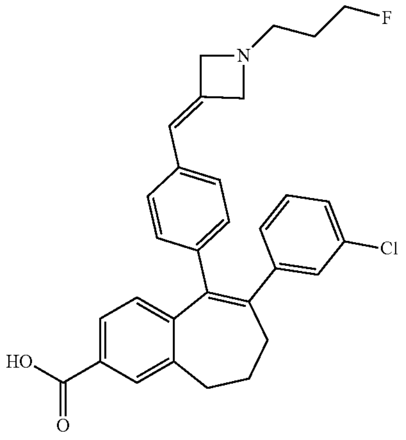 [SMILES: O=C(O)c1ccc2c(c1)CCCC(c1cccc(Cl)c1)=C2c1ccc(C=C2CN(CCCF)C2)cc1] | 8-(3-chlorophenyl)-9-(4-((1-(3-fluoropropyl)azetidin-3-ylidene)methyl)phenyl)-6,7-dihydro-5H-benzo[7]annulene-3-carboxylic acid |
| 181 | 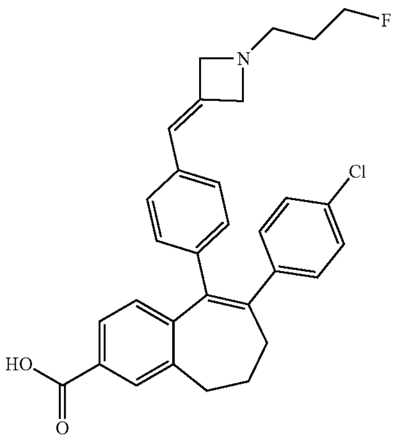 [SMILES: O=C(O)c1ccc2c(c1)CCCC(c1ccc(Cl)cc1)=C2c1ccc(C=C2CN(CCCF)C2)cc1] | 8-(4-chlorophenyl)-9-(4-((1-(3-fluoropropyl)azetidin-3-ylidene)methyl)phenyl)-6,7-dihydro-5H-benzo[7]annulene-3-carboxylic acid |

TABLE 1a-continued

| Ex. or compounds | Structure | Name |
|---|---|---|
| 182 | 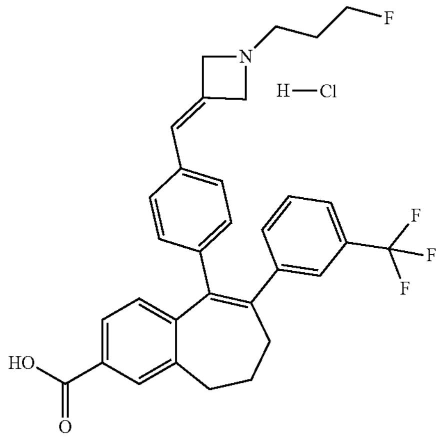 | 9-(4-((1-(3-fluoropropoyl)azetidin-3-ylidene)methyl)phenyl)-8-(3-(trifluoromethyl)phenyl)-6,7-dihydro-5H-benzo[7]annulene-3-carboxylic acid hydrochloride |
| 183 | 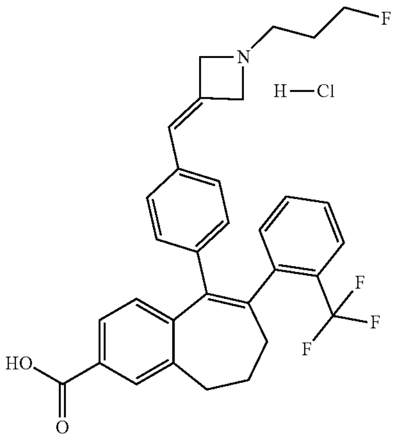 | 9-(4-((1-(3-fluoropropyl)azetidin-3-ylidene)methyl)phenyl)-8-(2-(trifluoromethyl)phenyl)-6,7-dihydro-5H-benzo[7]annulene-3-carboxylic acid hydrochloride |
| 184 | 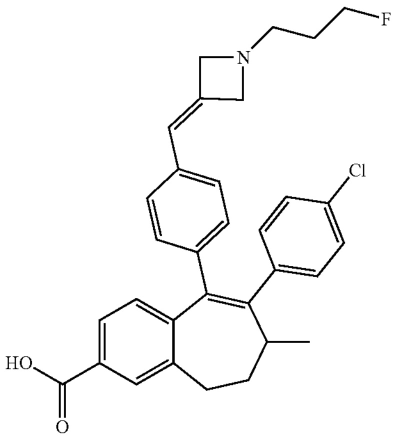 Isomer 2 | 8-(4-chlorophenyl)-9-(4-((1-(3-fluoropropyl)azetidin-3-ylidene)methyl)phenyl)-7-methyl-6,7-dihydro-5H-benzo[7]annulene-3-carboxylic acid, Isomer 2 |

TABLE 1a-continued

| Ex. or compounds | Structure | Name |
|---|---|---|
| 185 | 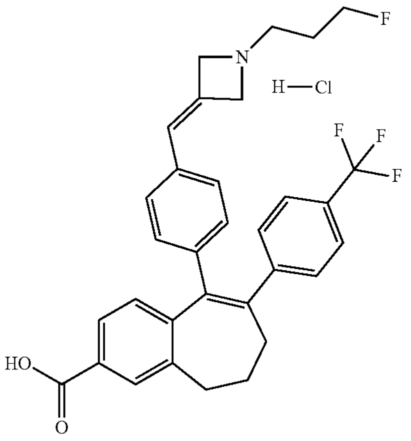 | 9-(4-((1-(3-fluoropropyl)azetidin-3-ylidene)methyl)phenyl)-8-(4-(trifluoromethyl)phenyl)-6,7-dihydro-5H-benzo[7]annulene-3-carboxylic acid hydrochloride |
| 186 | 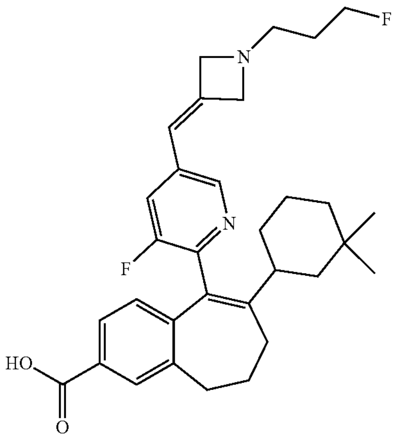 [SMILES: CC1(C)CCCC(C2=C(c3ncc(C=C4CN(CCCF)C4)cc3F)c3ccc(C(=O)O)cc3CCC2)C1] | 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid, racmic mixture |
| 187 | 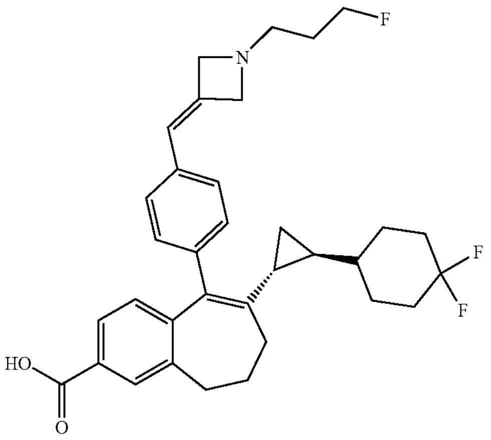 [SMILES: O=C(O)c1ccc2c(c1)CCCC([C@@H]1C[C@H]1C1CCC(F)(F)CC1)=C2c1ccc(C=C2CN(CCCF)C2)cc1] | 8-(trans-2-(4,4-difluorocyclohexyl)cyclopropyl)-9-(4-((1-(3-fluoropropyl)azetidin-3-ylidene)methyl)phenyl)-6,7-dihydro-5H-benzo[7]annulene-3-carboxylic acid, racemic mixture |

TABLE 1a-continued

| Ex. or compounds | Structure | Name |
| --- | --- | --- |
| 188 | 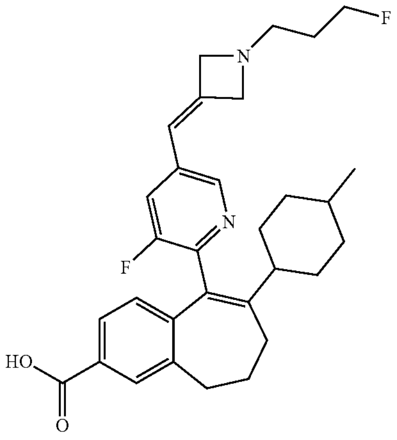 Mixture of isomers | 9-(3-fluoro-5-((1-(3-fluoropropyl)azetidin-3-ylidene)methyl)pyridin-2-yl)-8-(4-methylcyclohexyl)-6,7-dihydro-5H-benzo[7]annulene-3-carboxylic acid, mixture of isomers |

TABLE 1b

| Ex. or cmpds | Preparation Method | NMR | MASS: LC/MS (m/z, MH+): |
| --- | --- | --- | --- |
| 1 | A | 1H NMR (400 MHz, DMSO-d6) δ ppm: 1.68 (dquin, J = 25, 6 Hz, 2 H); 2.18 (m, 4 H); 2.61 (m, 2 H); 2.94 (t, J = 6 Hz, 3 H); 3.88 (br s, 3 H); 4.04 (br s, 2 H); 4.47 (dt, J = 47, 6 Hz, 2 H); 6.08 (quin, J = 2 Hz, 1 H); 6.80 (d, J = 8 Hz, 2 H); 6.85 (d, J = 8 Hz, 1 H); 6.90 (d, J = 8 Hz, 2 H); 7.22 (d, J = 8 Hz, 1 H); 7.28 (dd, J = 8, 2 Hz, 1 H); 7.60 (d, J = 2 Hz, 1 H); 7.75 (dd, J = 8, 2 Hz, 1 H); 7.92 (d, J = 2 Hz, 1 H) | 536 |
| 2 | B | 1H NMR (500 MHz, DMSO-d6) δ ppm 1.73 (dquin, J = 25, 6 Hz, 2 H), 2.09-2.26 (m, 4 H), 2.67-2.79 (m, 2 H), 2.87 (t, J = 7 Hz, 2 H), 3.87 (s, 3 H), 3.98-4.13 (m, 2 H), 4.14-4.28 (m, 2 H), 4.48 (dt, J = 47, 6 Hz, 2 H), 6.15 (br s, 1 H), 6.81-6.89 (m, 4 H), 6.94 (d, J = 9 Hz, 2 H), 7.76 (dd, J = 8, 2 Hz, 1 H), 7.81 (d, J = 5 Hz, 1 H), 7.93 (d, J = 2 Hz, 1 H), 12.78 (br s, 1 H) | 517 |
| 3 | B | 1H NMR (400 MHz, DMSO-d6) δ ppm 1.65-1.86 (m, 2 H), 2.15-2.23 (m, 4 H), 2.27 (s, 3 H), 2.77-2.87 (m, 2 H), 2.87-3.00 (m, 2 H), 4.16 (br s, 2 H), 4.32 (br s, 2 H), 4.48 (dt, J = 47, 6 Hz, 2 H), 6.15 (br s, 1 H), 6.77 (d, J = 9 Hz, 2 H), 6.88 (dd, J = 8, 5 Hz, 3 H), 7.27 (d, J = 8 Hz, 1 H), 7.41 (d, J = 8 Hz, 1 H), 7.51 (s, 1 H), 7.76 (dd, J = 8, 2 Hz, 1 H), 7.93 (d, J = 2 Hz, 1 H) | 550 |
| 4 | C | 1H NMR (500 MHz, DMSO-d6) δ ppm 1.68 (dquin, J = 25, 7 Hz, 2 H), 1.75-1.91 (m, 2 H), 2.08-2.22 (m, 4 H), 2.49-2.57 (m hidden, 2 H), 2.59 (t, J = 7 Hz, 2 H), 2.74 (t, J = 7 Hz, 2 H), 2.87 (t, J = 7 Hz, 2 H), 3.85-3.89 (m, 2 H), 4.00-4.05 (m, 2 H), 4.46 (dt, J = 47, 6 Hz, 2 H), 6.08 (t, J = 2 Hz, 1 H), 6.77 (d, J = 8 Hz, 2 H), 6.80 (dd, J = 11, 2 Hz, 1 H), 6.85 (d, J = 8 Hz, 1 H), 6.86-6.91 (m, 3 H), 7.74 (dd, J = 8, 2 Hz, 1 H), 7.91 (d, J = 2 Hz, 1 H), 12.93 (br s, 1 H) | 526 |
| 5 | B | 1H NMR (400 MHz, DMSO-d6) δ ppm 1.68 (dquin, J = 25, 7 Hz, 2 H), 2.10-2.21 (m, 2 H), 2.28-2.33 (m, 2 H), 2.60 (t, J = 7 Hz, 2 H), 2.87 (br t, J = 7 Hz, 2 H), 3.89 (br s, 2 H), 4.03 (br s, 2 H), 4.47 (dt, J = 47, 6 Hz, 2 H), 6.11 (t, J = 2 Hz, 1 H), 6.83 (d, J = 8 Hz, 2 H), 6.86 (d, J = 8 Hz, 1 H), 6.93 (d, J = 8 Hz, 2 H), 7.49 (dd, J = 9, 2 Hz, 1 H), 7.53-7.59 (m, 2 H), 7.74 (dd, J = 8, 2 Hz, 1 H), 7.91 (d, J = 2 Hz, 1 H) | 570 |

TABLE 1b-continued

| Ex. or cmpds | Preparation Method | NMR | MASS: LC/MS (m/z, MH+): |
|---|---|---|---|
| 6 | C | 1H NMR (400 MHz, DMSO-d6) δ ppm 1.68 (dquin, J = 26, 7 Hz, 2 H), 1.96 (m, 1 H), 2.09-2.21 (m, 3 H), 2.34-2.44 (m, 2 H), 2.59 (t, J = 7 Hz, 2 H), 2.63-2.82 (m, 4 H), 2.90 (t, J = 5 Hz, 2 H), 3.88 (br s, 2 H), 4.03 (br s, 2 H), 4.46 (dt, J = 47, 6 Hz, 2 H), 6.07 (t, J = 2 Hz, 1 H), 6.78 (d, J = 8 Hz, 2 H), 6.83-6.93 (m, 4 H), 7.07 (dd, J = 8, 5 Hz, 1 H), 7.74 (dd, J = 8, 2 Hz, 1 H), 7.92 (d, J = 2 Hz, 1 H), 12.67 (br s, 1 H) | 526 |
| 7 | C | 1H NMR (400 MHz, DMSO-d6) δ ppm 1.68 (dquin, J = 25, 6 Hz, 2 H), 2.03 (quin, J = 8 Hz, 2 H), 2.07-2.24 (m, 4 H), 2.60 (t, J = 7 Hz, 2 H), 2.75-2.92 (m, 6 H), 3.88 (br s, 2 H), 4.04 (br s, 2 H), 4.46 (dt, J = 47, 6 Hz, 2 H), 6.08 (t, J = 2 Hz, 1 H), 6.81 (d, J = 9 Hz, 2 H), 6.85 (d, J = 8 Hz, 1 H), 6.87-6.95 (m, 4 H), 7.74 (dd, J = 8, 2 Hz, 1 H), 7.90 (d, J = 2 Hz, 1 H), 12.72 (br s, 1 H) | 526 |
| 8 | C | 1H NMR (500 MHz, DMSO-d6) δ ppm 1.69 (dquin, J = 25, 7 Hz, 2 H), 2.06-2.17 (m, 2 H), 2.25 (t, J = 8 Hz, 2 H), 2.61 (t, J = 7 Hz, 2 H), 2.84 (t, J = 7 Hz, 2 H), 3.01-3.11 (m, 4 H), 3.90 (br s, 2 H), 4.07 (br s, 2 H), 4.47 (dt, J = 47, 6 Hz, 2 H), 6.09 (t, J = 2 Hz, 1 H), 6.78-6.84 (m, 3 H), 6.85-6.91 (m, 3 H), 6.92 (s, 1 H), 6.97 (dd, J = 8, 1 Hz, 1 H), 7.72 (dd, J = 8, 2 Hz, 1 H), 7.88 (d, J = 2 Hz, 1 H), 12.63 (br s, 1 H) | 494 |
| 9 | C | 1H NMR (500 MHz, DMSO-d6) δ ppm 1.67 (dquin, J = 25, 6 Hz, 2 H), 2.10-2.20 (m, 2 H), 2.20-2.26 (m, 2 H), 2.36 (dt, J = 4, 2 Hz, 4 H), 2.59 (t, J = 7 Hz, 2 H), 2.88 (t, J = 7 Hz, 2 H), 3.87 (br s, 2 H), 4.01 (br s, 2 H), 4.46 (dt, J = 47, 6 Hz, 2 H), 6.07 (t, J = 2 Hz, 1 H), 6.74 (d, J = 8 Hz, 2 H), 6.84 (d, J = 8 Hz, 2 H), 6.87 (d, J = 8 Hz, 1 H), 7.30-7.42 (m, 3 H), 7.68-7.83 (m, 1 H), 7.93 (d, J = 2 Hz, 1 H), 12.84 (br s, 1 H) | 544 |
| 10 | B | 1H NMR (500 MHz, DMSO-d6) δ ppm 1.67 (dquin, J = 25, 6 Hz, 2 H), 1.74-1.88 (m, 2 H), 2.07-2.23 (m, 4 H), 2.45(m hidden, 4 H), 2.58 (t, J = 7 Hz, 2 H), 2.75 (t, J = 7 Hz, 2 H), 2.87 (t, J = 7 Hz, 2 H), 3.87 (br d, J = 2 Hz, 2 H), 4.02 (br d, J = 2 Hz, 2 H), 4.46 (dt, J = 47, 6 Hz, 2 H), 6.06 (t, J = 2 Hz, 1 H), 6.74 (d, J = 9 Hz, 2 H), 6.83 (d, J = 9 Hz, 2 H), 6.85 (d, J = 8 Hz, 1 H), 6.96 (dd, J = 7, 2 Hz, 1 H), 7.01-7.08 (m, 2 H), 7.74 (dd, J = 8, 2 Hz, 1 H), 7.91 (d, J = 2 Hz, 1 H) | 508 |
| 11 | A | 1H NMR (500 MHz, DMSO-d6) δ ppm 1.67 (dquin, J = 25, 7 Hz, 2 H), 2.12-2.20 (m, 4 H), 2.22 (s, 3 H), 2.57 (t, J = 7 Hz, 2 H), 2.76-2.97 (m, 2 H), 3.82-3.89 (m, 2 H), 3.99-4.06 (m, 2 H), 4.46 (dt, J = 47, 6 Hz, 2 H), 6.07 (t, J = 2 Hz, 1 H), 6.64-6.76 (m, 3 H), 6.83 (td, J = 8, 2 Hz, 1 H), 6.88 (t, J = 9 Hz, 1 H), 6.95 (dd, J = 10, 2 Hz, 1 H), 7.03 (br s, 1 H), 7.66 (br s, 1 H), 7.83 (br s, 1 H) | 518 |
| 12 | C | 1H NMR (400 MHz, DMSO-d6) δ ppm 1.67 (dquin, J = 25, 7 Hz, 2 H), 1.77-1.92 (m, 4 H), 2.05-2.24 (m, 4 H), 2.58 (t, J = 7 Hz, 2 H), 2.77 (t, J = 7 Hz, 2 H), 2.86 (t, J = 6 Hz, 2 H), 3.87 (br s, 2 H), 4.02 (br s, 2 H), 4.46 (dt, J = 47, 6 Hz, 2 H), 6.07 (t, J = 2 Hz, 1 H), 6.74 (d, J = 9 Hz, 2 H), 6.78-6.92 (m, 4 H), 7.01 (dd, J = 8, 5 Hz, 1 H), 7.73 (dd, J = 8, 2 Hz, 1 H), 7.89 (d, J = 2 Hz, 1 H) | 526 |
| 13 | B | 1H NMR (400 MHz, DMSO-d6) δ ppm 1.74-1.95 (m, 2 H), 2.03-2.30 (m, 4 H), 2.62 (t, J = 7 Hz, 2 H), 2.83 (m, 1 H), 3.01 (m, 1 H), 3.88 (br s, 2 H), 4.05 (br s, 2 H), 6.08 (tt, J = 57, 5 Hz, 1 H), 6.07 (t, J = 2 Hz, 1 H), 6.80 (d, J = 8 Hz, 2 H), 6.86 (d, J = 8 Hz, 1 H), 6.91 (d, J = 9 Hz, 2 H), 7.14 (d, J = 8 Hz, 1 H), 7.41 (t, J = 8 Hz, 1 H), 7.55 (d, J = 8 Hz, 1 H), 7.75 (dd, J = 8, 2 Hz, 1 H), 7.91 (d, J = 2 Hz, 1 H) | 588 |
| 14 | B | 1H NMR (400 MHz, DMSO-d6) δ ppm 1.67 (dquin, J = 25, 6 Hz, 2 H), 2.11-2.26 (m, 3 H), 2.30-2.38 (m, 4 H), 2.58 (t, J = 7 Hz, 2 H), 2.84-3.03 (m, 2 H), 3.86 (br s, 2 H), 4.01 (br s, 2 H), 4.46 (dt, J = 47, 6 Hz, 2 H), 6.06 (t, J = 2 Hz, 1 H), | 550 |

TABLE 1b-continued

| Ex. or cmpds | Preparation Method | NMR | MASS: LC/MS (m/z, MH+): |
|---|---|---|---|
| | | 6.73 (d, J = 9 Hz, 2 H), 6.85 (d, J = 8 Hz, 2 H), 6.88 (d, J = 8 Hz, 1 H), 7.24 (t, J = 8 Hz, 1 H), 7.33 (d, J = 7 Hz, 1 H), 7.52 (dd, J = 8, 1 Hz, 1 H), 7.75 (dd, J = 8, 2 Hz, 1 H), 7.92 (d, J = 2 Hz, 1 H) | |
| 15 | A | 1H NMR (500 MHz, DMSO-d6) δ ppm 1.79-2.01 (m, 5 H), 2.11-2.32 (m, 4 H), 2.82-3.09 (m, 2 H), 3.25-3.28 (m, 2 H), 4.53 (dt, J = 47, 6 Hz, 2 H), 4.65-5.17 (m, 4 H), 6.41 (br s, 1 H), 6.75 (d, J = 11 Hz, 1 H), 6.80 (d, J = 8 Hz, 1 H), 6.88 (d, J = 8 Hz, 1 H), 6.97 (td, J = 8, 2 Hz, 1 H), 7.12 (td, J = 10, 3 Hz, 1 H), 7.30 (td, J = 9, 7 Hz, 1 H), 7.74 (dd, J = 8, 2 Hz, 1 H), 7.94 (d, J = 2 Hz, 1 H), 10.45 (br s, 1 H), 12.96 (br s, 1 H) | 536 |
| 16 | B | 1H NMR (400 MHz, DMSO-d6) δ ppm 1.67 (dquin, J = 25, 6 Hz, 2 H), 2.08-2.29 (m, 4 H), 2.58 (t, J = 7 Hz, 2 H), 2.77-3.08 (m, 4 H), 3.84-3.89 (m, 2 H), 4.01 (br s, 2 H), 4.46 (dt, J = 47, 6 Hz, 2 H), 6.06 (t, J = 2 Hz, 1 H), 6.78 (d, J = 8 Hz, 2 H), 6.87 (d, J = 4 Hz, 2 H), 6.89 (d, J = 5 Hz, 1 H), 7.49 (d, J = 8 Hz, 1 H), 7.76 (dd, J = 8, 2 Hz, 1 H), 7.87 (dd, J = 8, 2 Hz, 1 H), 7.93 (d, J = 2 Hz, 1 H), 8.05 (d, J = 1 Hz, 1 H) | 604 |
| 17 | A | 1H NMR (500 MHz, DMSO-d6) δ ppm 1.79 (d, J = 2 Hz, 3 H), 1.86-2.02 (m, 2 H), 2.18-2.35 (m, 4 H), 2.94 (t, J = 5 Hz, 2 H), 3.32-3.36 (m hidden, 2 H), 4.53 (dt, J = 47, 6 Hz, 2 H), 4.70-5.14 (m, 4 H), 6.48 (t, J = 2 Hz, 1 H), 6.72-6.79 (m, 2 H), 6.84 (t, J = 8 Hz, 1 H), 6.95 (td, J = 8, 2 Hz, 1 H), 7.12 (ddd, J = 11, 9, 3 Hz, 1 H), 7.27 (td, J = 9, 7 Hz, 1 H), 7.74 (dd, J = 8, 2 Hz, 1 H), 7.94 (d, J = 2 Hz, 1 H), 10.49 (br s, 1 H), 12.89 (br s, 1 H) | 536 |
| 18 | C | 1H NMR (500 MHz, DMSO-d6) δ ppm 1.68 (dquin, J = 25, 7 Hz, 2 H), 2.13-2.35 (m, 4 H), 2.59 (t, J = 7 Hz, 2 H), 2.92 (t, J = 6 Hz, 2 H), 3.87 (br s, 2 H), 4.02 (br s, 2 H), 4.46 (dt, J = 47, 6 Hz, 2 H), 6.06 (t, J = 2 Hz, 1 H), 6.65 (d, J = 8 Hz, 2 H), 6.80-6.88 (m, 3 H), 7.75 (dd, J = 8, 2 Hz, 1 H), 7.93 (d, J = 2 Hz, 1 H), 8.16 (dd, J = 9, 3 Hz, 1 H), 8.88 (d, J = 3 Hz, 1 H), 12.76 (br s, 1 H) | 555 |
| 19 | B | 1H NMR (400 MHz, DMSO-d6) δ ppm 1.71-1.95 (m, 2 H), 2.12-2.17 (m, 4 H), 2.17 (s, 3 H), 2.63 (t, J = 7 Hz, 2 H), 2.80-3.04 (m, 2 H), 3.89 (br s, 2 H), 4.05 (br s, 2 H), 6.08 (tt, J = 57, 5 Hz, 1 H), 6.07 (t, J = 2 Hz, 1 H), 6.73 (d, J = 8 Hz, 2 H), 6.81-6.91 (m, 4 H), 6.98 (dd, J = 10, 3 Hz, 1 H), 7.07 (dd, J = 9, 6 Hz, 1 H), 7.74 (dd, J = 8, 2 Hz, 1 H), 7.91 (d, J = 2 Hz, 1 H), 12.95 (br s, 1 H) | 518 |
| 20 | B | 1H NMR (400 MHz, DMSO-d6) δ ppm 1.74-1.97 (m, 2 H), 2.06-2.26 (m, 4 H), 2.65 (t, J = 6 Hz, 2 H), 2.87 (t, J = 7 Hz, 2 H), 3.92 (br s, 2 H), 4.08 (br s, 2 H), 6.09 (tt, J = 57, 5 Hz, 1 H), 6.09 (t, J = 2 Hz, 1 H), 6.79 (d, J = 8 Hz, 2 H), 6.86 (d, J = 8 Hz, 1 H), 6.90 (d, J = 8 Hz, 2 H), 6.96 (td, J = 8, 2 Hz, 1 H), 7.12 (ddd, J = 11, 9, 3 Hz, 1 H), 7.26 (td, J = 9, 7 Hz, 1 H), 7.75 (dd, J = 8, 2 Hz, 1 H), 7.92 (d, J = 2 Hz, 1 H), 12.76 (br s, 1 H) | 522 |
| 21 | C | 1H NMR (400 MHz, DMSO-d6) δ ppm 1.69 (dquin, J = 25, 6 Hz, 2 H), 2.11-2.28 (m, 4 H), 2.63 (t, J = 7 Hz, 2 H), 2.90 (t, J = 6 Hz, 2 H), 3.93 (br s, 2 H), 4.08 (br s, 2 H), 4.46 (dt, J = 47, 6 Hz, 2 H), 6.11 (t, J = 2 Hz, 1 H), 6.82 (d, J = 8 Hz, 2 H), 6.89 (d, J = 8 Hz, 1 H), 6.93 (d, J = 9 Hz, 2 H), 7.49-7.61 (m, 2 H), 7.77 (dd, J = 8, 2 Hz, 1 H), 7.95 (d, J = 2 Hz, 1 H), 12.61 (br s, 1 H) | 572 |
| 22 | B | 1H NMR (400 MHz, DMSO-d6) δ ppm 1.77-1.95 (m, 2 H), 2.13 (d, J = 2 Hz, 3 H), 2.14-2.24 (m, 4 H), 2.66 (t, J = 7 Hz, 2 H), 2.80-3.01 (m, 2 H), 3.93 (br s, 2 H), 4.10 (br s, 2 H), 6.09 (tt, J = 57, 5 Hz, 1 H), 6.09 (t, J = 2 Hz, 1 H), 6.74 (d, J = 9 Hz, 2 H), 6.84-6.94 (m, 4 H), 7.11 (q, J = 8 Hz, 1 H), 7.75 (dd, J = 8, 2 Hz, 1 H), 7.92 (d, J = 2 Hz, 1 H), 12.67 (br s, 1 H) | 536 |
| 23 | B | 1H NMR (400 MHz, DMSO-d6) δ ppm 1.68 (dquin, J = 25, 7 Hz, 2 H), 2.00-2.28 (m, 4 H), | 570 |

TABLE 1b-continued

| Ex. or cmpds | Preparation Method | NMR | MASS: LC/MS (m/z, MH+): |
|---|---|---|---|
| | | 2.58 (t, J = 7 Hz, 2 H), 2.79-2.89 (m, 1 H), 3.01 (br d, J = 13 Hz, 1 H), 3.83-3.89 (m, 2 H), 4.00-4.06 (m, 2 H), 4.46 (dt, J = 47, 6 Hz, 2 H), 6.06 (t, J = 2 Hz, 1 H), 6.80 (d, J = 8 Hz, 2 H), 6.86 (d, J = 8 Hz, 1 H), 6.92 (d, J = 9 Hz, 2 H), 7.14 (d, J = 8 Hz, 1 H), 7.41 (t, J = 8 Hz, 1 H), 7.55 (d, J = 8 Hz, 1 H), 7.75 (dd, J = 8, 2 Hz, 1 H), 7.91 (d, J = 2 Hz, 1 H) | |
| 24 | B | 1H NMR (500 MHz, DMSO-d6) δ ppm 1.68 (dquin, J = 25, 7 Hz, 2 H), 2.05-2.29 (m, 4 H), 2.58 (t, J = 7 Hz, 2 H), 2.85 (m, 1 H), 3.00 (dt, J = 13, 9 Hz, 1 H), 3.84-3.89 (m, 2 H), 3.99-4.07 (m, 2 H), 4.46 (dt, J = 47, 6 Hz, 2 H), 6.06 (quin, J = 2 Hz, 1 H), 6.80 (d, J = 9 Hz, 2 H), 6.86 (d, J = 8 Hz, 1 H), 6.91 (d, J = 9 Hz, 2 H), 7.01 (d, J = 8 Hz, 1 H), 7.32 (dd, J = 11, 8 Hz, 1 H), 7.48 (td, J = 8, 6 Hz, 1 H), 7.75 (dd, J = 8, 2 Hz, 1 H), 7.91 (d, J = 2 Hz, 1 H) | 554 |
| 25 | B | 1H NMR (400 MHz, DMSO-d6) δ ppm 1.66-1.97 (m, 2 H), 2.10-2.23 (m, 4 H), 2.62 (t, J = 7 Hz, 2 H), 2.84(m, 1 H), 2.99 (m, 1 H), 3.88 (br s, 2 H), 4.04 (br s, 2 H), 6.08 (tt, J = 57, 5 Hz, 1 H), 6.06 (br t, J = 2 Hz, 1 H), 6.77 (d, J = 8 Hz, 2 H), 6.82-6.93 (m, 3 H), 7.27 (dd, J = 9, 6 Hz, 1 H), 7.35 (td, J = 9, 3 Hz, 1 H), 7.63 (dd, J = 9, 3 Hz, 1 H), 7.75 (dd, J = 8, 2 Hz, 1 H), 7.91 (d, J = 2 Hz, 1 H), 12.86 (br s, 1 H) | 572 |
| 26 | B | 1H NMR (400 MHz, DMSO-d6) δ ppm 1.76-1.95 (m, 2 H), 2.07-2.27 (m, 4 H), 2.62 (t, J = 7 Hz, 2 H), 2.80-3.07 (m, 2 H), 3.88 (br s, 2 H), 4.05 (br s, 2 H), 6.08 (tt, J = 57, 5 Hz, 1 H), 6.07 (t, J = 2 Hz, 1 H), 6.80 (d, J = 9 Hz, 2 H), 6.87 (d, J = 8 Hz, 1 H), 6.91 (d, J = 8 Hz, 2 H), 7.01 (d, J = 8 Hz, 1 H), 7.32 (dd, J = 11, 8 Hz, 1 H), 7.48 (td, J = 8, 6 Hz, 1 H), 7.75 (dd, J = 8, 2 Hz, 1 H), 7.92 (d, J = 2 Hz, 1 H), 12.95 (br s, 1 H) | 572 |
| 27 | A | 1H NMR (400 MHz, DMSO-d6) δ ppm 1.65 (dquin, J = 25, 6 Hz, 2 H), 1.96-2.28 (m, 7 H), 2.55 (m hidden, 2 H), 2.74-2.91 (m, 2 H), 3.56-3.72 (m, 2 H), 3.76-3.90 (m, 2 H), 4.45 (dt, J = 47, 6 Hz, 2 H), 6.03 (m, 1 H), 6.31-6.61 (m, 2 H), 6.78 (m, 1 H), 6.98 (td, J = 9, 2 Hz, 1 H), 7.14 (m, 1 H), 7.25 (m, 1 H), 7.74 (m, 1 H), 7.88 (m, 1 H) | 536 |
| 28 | A | 1H NMR (400 MHz, DMSO-d6) δ ppm 1.65 (dquin, J = 25, 6 Hz, 2 H), 2.04 (s, 3 H), 2.11-2.18 (m, 4 H), 2.19 (s, 3 H), 2.55 (t, J = 7 Hz, 2 H), 2.83-2.98 (m, 2 H), 3.58-3.68 (m, 2 H), 3.80-3.87 (m, 2 H), 4.45 (dt, J = 47, 6 Hz, 2 H), 6.03 (t, J = 2 Hz, 1 H), 6.35 (dd, J = 12, 1 Hz, 1 H), 6.46 (s, 1 H), 6.84-6.95 (m, 2 H), 7.01 (dd, J = 10, 3 Hz, 1 H), 7.08 (dd, J = 9, 6 Hz, 1 H), 7.76 (dd, J = 8, 2 Hz, 1 H), 7.91 (d, J = 2 Hz, 1 H), 11.55-15.32 (m, 1 H) | 532 |
| 29 | B | 1H NMR (500 MHz, DMSO-d6) δ ppm 1.63-1.73 (m, 2 H), 2.08-2.18 (m, 7 H), 2.59 (t, J = 7 Hz, 2 H), 2.87 (m, 1 H), 2.94 (m, 1 H), 3.88 (br s, 2 H), 4.04 (br s, 2 H), 4.46 (dt, J = 47, 6 Hz, 2 H), 6.07 (t, J = 2 Hz, 1 H), 6.74 (d, J = 8 Hz, 2 H), 6.85-6.92 (m, 4 H), 7.11 (q, J = 10 Hz, 1 H), 7.75 (dd, J = 8, 2 Hz, 1 H), 7.92 (d, J = 2 Hz, 1 H) | 518 |
| 30 | A | 1H NMR (400 MHz, DMSO-d6) δ ppm 1.57-1.86 (m, 5 H), 2.05-2.38 (m, 7 H), 2.59 (t, J = 7 Hz, 2 H), 2.86-3.11 (m, 2 H), 3.81 (m, 2 H), 4.01 (br s, 2 H), 4.47 (dt, J = 47, 6 Hz, 2 H), 6.20 (t, J = 2 Hz, 1 H), 6.59-6.85 (m, 4 H), 6.85-7.24 (m, 2 H), 7.73 (dd, J = 8, 2 Hz, 1 H), 7.93 (d, J = 2 Hz, 1 H), 12.78 (br s, 1 H) | 532 |
| 31 | A | 1H NMR (400 MHz, DMSO-d6) δ ppm 1.65-1.84 (m, 2 H), 1.98 (m, J = 6 Hz, 3 H), 2.16-2.31 (m, 4 H), 2.71-2.83 (m, 2 H), 2.84-3.01 (m, 2 H), 4.06-4.20 (m, 2 H), 4.25-4.37 (m, 2 H), 4.48 (dt, J = 47, 6 Hz, 2 H), 6.13 (br s, 1 H), 6.61 (d, J = 11 Hz, 1 H), 6.71 (s, 1 H), 6.79 (d, J = 8 Hz, 1 H), 6.92 (td, J = 8, 3 Hz, 1 H), 7.08- | 536 |

TABLE 1b-continued

| Ex. or cmpds | Preparation Method | NMR | MASS: LC/MS (m/z, MH+): |
|---|---|---|---|
| | | 7.23 (m, 2 H), 7.74 (dd, J = 8, 2 Hz, 1 H), 7.92 (d, J = 2 Hz, 1 H), 12.30 (br s, 1 H) | |
| 32 | C | 1H NMR (400 MHz, DMSO-d6) δ ppm 1.68 (dquin, J = 25, 6 Hz, 2 H), 1.96 (s, 3 H), 2.08-2.45 (m, 4 H), 2.60 (t, J = 7 Hz, 2 H), 2.91 ( t, J = 6 Hz, 2 H), 3.88 (br s, 2 H), 4.03 (br s, 2 H), 4.46 (dt, J = 47, 6 Hz, 2 H), 6.08 (t, J = 2 Hz, 1 H), 6.66 (d, J = 8 Hz, 2 H), 6.84-6.90 (m, 3 H), 7.41 (dd, J = 10, 3 Hz, 1 H), 7.76 (dd, J = 8, 2 Hz, 1 H), 7.94 (d, J = 2 Hz, 1 H), 8.44 (d, J = 3 Hz, 1 H) | 501 |
| 33 | C | 1H NMR (400 MHz, DMSO-d6) δ ppm 1.68 (dquin, J = 25, 6 Hz, 2 H), 2.11-2.24 (m, 4 H), 2.60 (t, J = 7 Hz, 2 H), 2.88 (t, J = 7 Hz, 2 H), 3.89 (br s, 2 H), 4.05 (br s, 2 H), 4.47 (dt, J = 47, 6 Hz, 2 H), 6.10 (t, J = 2 Hz, 1 H), 6.81 (d, J = 8 Hz, 2 H), 6.88 (d, J = 8 Hz, 1 H), 6.93 (d, J = 9 Hz, 2 H), 7.06-7.17 (m, 2 H), 7.76 (dd, J = 8, 2 Hz, 1 H), 7.93 (d, J = 2 Hz, 1 H), 12.75 (br s, 1 H) | 522 |
| 34 | B | 1H NMR (400 MHz, DMSO-d6) δ ppm 0.62-0.68 (m, 2 H), 0.88-0.97 (m, 2 H), 1.70 (dquin, J = 25, 7 Hz, 2 H), 1.86 (m, 1 H), 2.09-2.23 (m, 4 H), 2.65 (t, J = 6 Hz, 2 H), 2.86 (t, J = 7 Hz, 2 H), 3.94 (br s, 2 H), 4.11 (br s, 2 H), 4.47 (dt, J = 47, 6 Hz, 2 H), 6.10 (t, J = 2 Hz, 1 H), 6.76 (dd, J = 7, 2 Hz, 1 H), 6.78-6.82 (m, 3 H), 6.84 (d, J = 8 Hz, 1 H), 6.88 (d, J = 9 Hz, 2 H), 7.04 (t, J = 8 Hz, 1 H), 7.74 (dd, J = 8, 2 Hz, 1 H), 7.90 (d, J = 2 Hz, 1 H) | 526 |
| 35 | C | 1H NMR (400 MHz, DMSO-d6) δ ppm 1.78 (dquin, J = 26, 6 Hz, 2 H), 2.13-2.32 (m, 4 H), 2.82-2.98 (m, 4 H), 4.25 (br s, 2 H), 4.44 (br s, 2 H), 4.49 (dt, J = 47, 6 Hz, 2 H), 6.18 (br s, 1 H), 6.69 (d, J = 8 Hz, 2 H), 6.84 (d, J = 8 Hz, 1 H), 6.90 (d, J = 9 Hz, 2 H), 7.76 (dd, J = 8, 2 Hz, 1 H), 7.94 (d, J = 2 Hz, 1 H), 8.32 (d, J = 2 Hz, 1 H), 8.91 (d, J = 3 Hz, 1 H | 571 |
| 36 | A | 1H NMR (400 MHz, DMSO-d6) δ ppm 1.66 (dquin, J = 25, 6 Hz, 2 H), 2.09-2.25 (m, 7 H), 2.57 (t, J = 7 Hz, 2 H), 2.82-3.01 (m, 2 H), 3.78 (br s, 2 H), 3.86 (br s, 2 H), 4.45 (dt, J = 47, 6 Hz, 2 H), 6.05 (t, J = 2 Hz, 1 H), 6.39-6.49 (m, 2 H), 6.89-6.98 (m, 2 H), 7.04 (dd, J = 10, 3 Hz, 1 H), 7.10 (dd, J = 8, 6 Hz, 1 H), 7.77 (dd, J = 8, 2 Hz, 1 H), 7.92 (d, J = 2 Hz, 1 H), 12.83 (br s, 1 H) | 536 |
| 37 | B | 1H NMR (400 MHz, DMSO-d6) δ ppm 1.64-1.80 (m, 2 H), 2.11-2.26 (m, 4 H), 2.69-2.80 (m, 2 H), 2.82-3.04 (m, 2 H), 4.00-4.14 (m, 2 H), 4.16-4.32 (m, 2 H), 4.48 (dt, J = 47, 6 Hz, 2 H), 6.12 (br s, 1 H), 6.79 (d, J = 9 Hz, 2 H), 6.86 (d, J = 8 Hz, 1 H), 6.91 (d, J = 8 Hz, 2 H), 7.25 (d, J = 8 Hz, 1 H), 7.56 (dd, J = 8, 2 Hz, 1 H), 7.75 (dd, J = 8, 2 Hz, 1 H), 7.81 (d, J = 2 Hz, 1 H), 7.92 (d, J = 2 Hz, 1 H), 12.59 (br s, 1 H) | 570 |
| 38 | B | 1H NMR (400 MHz, DMSO-d6) δ ppm 1.60-1.80 (m, 2 H), 2.05-2.25 (m, 7 H), 2.64-2.70 (m, 2 H), 2.80-3.01 (m, 2 H), 3.90-4.04 (m, 2 H), 4.05-4.21 (m, 2 H), 4.47 (dt, J = 47, 6 Hz, 2 H), 6.10 (t, J = 2 Hz, 1 H), 6.77 (d, J = 8 Hz, 2 H), 6.82-6.98 (m, 5 H), 7.14 (dd, J = 8, 6 Hz, 1 H), 7.75 (dd, J = 8, 2 Hz, 1 H), 7.92 (d, J = 2 Hz, 1 H), 12.29 (br s, 1 H) | 500 |
| 39 | B | 1H NMR (400 MHz, DMSO-d6) δ ppm 0.56-0.64 (m, 2 H), 0.85-0.93 (m, 2 H), 1.68 (dquin, J = 25, 6, 6, 6, 6 Hz, 2 H), 1.81(m, 1 H), 2.11 (s, 3 H), 2.12-2.19 (m, 4 H), 2.60 (t, J = 7 Hz, 2 H), 2.80-2.97 (m, 2 H), 3.88 (br s, 2 H), 4.04 (br s, 2 H), 4.46 (dt, J = 47, 6 Hz, 2 H), 6.06 (t, J = 2 Hz, 1 H), 6.70-6.77 (m, 3 H), 6.79-6.87 (m, 4 H), 6.91 (d, J = 8 Hz, 1 H), 7.73 (dd, J = 8, 2 Hz, 1 H), 7.90 (d, J = 2 Hz, 1 H), 12.75 (br s, 1 H) | 522 |
| 40 | B | 1H NMR (400 MHz, DMSO-d6) δ ppm 0.60-0.81 (m, 2 H), 0.86-1.02 (m, 2 H), 1.68 (dquin, J = 25, 7 Hz, 2 H), 1.92 (m, 1 H), 2.07-2.31 (m, 4 H), 2.59 (t, J = 7 Hz, 2 H), 2.79-3.02 (m, 2 H), 3.87 (br d, J = 2 Hz, 2 H), 3.97-4.08 (m, 2 H), 4.46 (dt, J = 47, 6 Hz, 2 H), 6.06 (t, J = 2 Hz, 1 H), | 526 |

TABLE 1b-continued

| Ex. or cmpds | Preparation Method | NMR | MASS: LC/MS (m/z, MH+): |
|---|---|---|---|
| | | 6.58 (dd, J = 11, 3 Hz, 1 H), 6.76 (td, J = 8, 2 Hz, 1 H), 6.80 (d, J = 8 Hz, 2 H), 6.83-6.90 (m, 3 H), 6.96 (dd, J = 8, 6 Hz, 1 H), 7.74 (dd, J = 8, 2 Hz, 1 H), 7.91 (d, J = 2 Hz, 1 H), 12.82 (br s, 1 H) | |
| 41 | B | 1H NMR (500 MHz, DMSO-d6) δ ppm 1.68 (dquin, J = 25, 7 Hz, 2 H), 2.09-2.23 (m, 4 H), 2.24 (s, 3 H), 2.61 (t, J = 7 Hz, 2 H), 2.93 (br t, J = 6 Hz, 2 H), 3.90 (br s, 2 H), 4.06 (br s, 2 H), 4.46 (dt, J = 47, 6 Hz, 2 H), 6.07 (t, J = 2 Hz, 1 H), 6.80 (d, J = 8 Hz, 2 H), 6.83-6.89 (m, 3 H), 6.98 (dd, J = 8, 1 Hz, 1 H), 7.02-7.07 (m, 1 H), 7.24 (s, 1 H), 7.74 (dd, J = 8, 2 Hz, 1 H), 7.91 (d, J = 2 Hz, 1 H), 12.74 (br s, 1 H) | 516 |
| 42 | B | 1H NMR (500 MHz, DMSO-d6) δ ppm 1.69 (dquin, J = 25, 6 Hz, 2 H), 2.07-2.29 (m, 4 H), 2.58-2.63 (m, 2 H), 2.87-3.07 (m, 2 H), 3.92 (br s, 2 H), 4.08 (br s, 2 H), 4.46 (dt, J = 47, 6 Hz, 2 H), 6.08 (t, J = 2 Hz, 1 H), 6.82 (d, J = 8 Hz, 2 H), 6.87 (d, J = 8 Hz, 1 H), 6.89 (d, J = 8 Hz, 2 H), 7.10 (ddd, J = 9, 6, 4 Hz, 1 H), 7.24-7.35 (m, 2 H), 7.75 (dd, J = 8, 2 Hz, 1 H), 7.94 (d, J = 2 Hz, 1 H), 12.76 (br s, 1 H) | 520 |
| 43 | A | 1H NMR (400 MHz, DMSO-d6) δ ppm 1.68 (dquin, J = 25, 6 Hz, 2 H), 2.12-2.31 (m, 4 H), 2.59 (t, J = 7 Hz, 2 H), 2.89 (t, J = 7 Hz, 2 H), 3.85-3.94 (m, 2 H), 3.96-4.06 (m, 2 H), 4.46 (dt, J = 47, 6 Hz, 2 H), 6.23 (t, J = 2 Hz, 1 H), 6.67-6.82 (m, 2 H), 6.89 (d, J = 8 Hz, 1 H), 6.98 (td, J = 8, 2 Hz, 1 H), 7.15 (ddd, J = 11, 9, 3 Hz, 1 H), 7.27 (td, J = 9, 7 Hz, 1 H), 7.75 (dd, J = 8, 2 Hz, 1 H), 7.92 (d, J = 2 Hz, 1 H) | 540 |
| 44 | A | 1H NMR (400 MHz, DMSO-d6) δ ppm 1.53-1.84 (m, 2 H), 2.20 (m, 5 H), 2.69-3.12 (m, 7 H), 3.17-3.41 (m hidden, 4 H), 3.50-3.72 (m, 2 H), 4.45 (dt, J = 47, 6 Hz, 2 H), 6.78 (dd, J = 8, 2 Hz, 1 H), 6.80-6.91 (m, 4 H), 6.96 (dd, J = 10, 3 Hz, 1 H), 7.02 (t, J = 7 Hz, 1 H), 7.73 (dd, J = 8, 2 Hz, 1 H), 7.90 (d, J = 2 Hz, 1 H) | 514 |
| 45 | A | 1H NMR (400 MHz, DMSO-d6) δ ppm 1.59-1.85 (m, 5 H), 1.96-2.28 (m, 10 H), 2.59 (t, J = 7 Hz, 2 H), 2.86-3.06 (m, 2 H), 3.79-3.92 (m, 2 H), 3.95-4.05 (m, 2 H), 4.46 (dt, J = 47, 6 Hz, 2 H), 6.18 (t, J = 2 Hz, 1 H), 6.62-6.69 (m, 2 H), 6.70-6.82 (m, 2 H), 6.82-7.06 (m, 2 H), 7.71 (dd, J = 8, 2 Hz, 1 H), 7.90 (d, J = 2 Hz, 1 H) | 528 |
| 46 | A | 1H NMR (400 MHz, DMSO-d6) δ ppm 1.68 (dquin, J = 25, 6 Hz, 2 H), 2.11-2.25 (m, 7 H), 2.60 (t, J = 7 Hz, 2 H), 2.82-3.01 (m, 2 H), 3.90-3.97 (m, 2 H), 4.02-4.09 (m, 2 H), 4.46 (dt, J = 47, 6 Hz, 2 H), 6.33 (quin, J = 2 Hz, 1 H), 6.85 (d, J = 8 Hz, 1 H), 6.91 (td, J = 9, 3 Hz, 1 H), 6.97-7.07 (m, 3 H), 7.10 (dd, J = 8, 6 Hz, 1 H), 7.14 (d, J = 2 Hz, 1 H), 7.75 (dd, J = 8, 2 Hz, 1 H), 7.92 (d, J = 2 Hz, 1 H) | 525 |
| 47 | B | 1H NMR (500 MHz, DMSO-d6) δ ppm 1.71 (dquin, J = 26, 6 Hz, 2 H), 2.11-2.26 (m, 4 H), 2.69 ( t, J = 6 Hz, 2 H), 2.89 ( t, J = 7 Hz, 2 H), 4.00 (br s, 2 H), 4.16 (br s, 2 H), 4.47 (dt, J = 47, 6 Hz, 2 H), 6.12 (t, J = 2 Hz, 1 H), 6.81 (d, J = 8 Hz, 2 H), 6.87 (d, J = 8 Hz, 1 H), 6.91 (d, J = 8 Hz, 2 H), 7.06-7.13 (m, 1 H), 7.20 (td, J = 6, 3 Hz, 1 H), 7.40 (dd, J = 7, 2 Hz, 1 H), 7.76 (dd, J = 8, 2 Hz, 1 H), 7.93 (d, J = 2 Hz, 1 H), 12.75 (br s, 1 H) | 520 |
| 48 | B | 1H NMR (500 MHz, DMSO-d6) δ ppm 1.71 (dquin, J = 26, 6 Hz, 2 H), 2.10-2.24 (m, 7 H), 2.67-2.74 (m, 2 H), 2.88 (br t, J = 7 Hz, 2 H), 4.02 (br s, 2 H), 4.19 (br s, 2 H), 4.47 (dt, J = 47, 6 Hz, 2 H), 6.11 (t, J = 2 Hz, 1 H), 6.80 (d, J = 8 Hz, 2 H), 6.84-6.90 (m, 3 H), 6.92 (d, J = 7 Hz, 1 H), 6.96 (td, J = 7, 2 Hz, 1 H), 7.10 (t, J = 7 Hz, 1 H), 7.75 (dd, J = 8, 2 Hz, 1 H), 7.91 (d, J = 2 Hz, 1 H), 12.75 (br s, 1 H) | 500 |
| 49 | B | 1H NMR (500 MHz, DMSO-d6) δ ppm 1.71 (dquin, J = 26, 6 Hz, 2 H), 2.11-2.21 (m, 2 H), 2.21-2.29 (m, 2 H), 2.71 (t, J = 7 Hz, 2 H), 2.90 | 554 |

TABLE 1b-continued

| Ex. or cmpds | Preparation Method | NMR | MASS: LC/MS (m/z, MH+): |
|---|---|---|---|
| | | (br t, J = 7 Hz, 2 H), 3.96-4.23 (m, 4 H), 4.47 (dt, J = 47, 6 Hz, 2 H), 6.13 (t, J = 2 Hz, 1 H), 6.82 (d, J = 8 Hz, 2 H), 6.87 (d, J = 8 Hz, 1 H), 6.91 (d, J = 9 Hz, 2 H), 7.42-7.52 (m, 2 H), 7.57 (d, J = 10 Hz, 1 H), 7.76 (dd, J = 8, 2 Hz, 1 H), 7.94 (d, J = 2 Hz, 1 H), 12.68 (br s, 1 H) | |
| 50 | B | 1H NMR (500 MHz, DMSO-d6) δ ppm 1.77 (dquin, J = 26, 7 Hz, 2 H), 2.11-2.30 (m, 4 H), 2.86-2.93 (m, 2 H), 2.96 ( t, J = 6 Hz, 2 H), 4.19-4.32 (m, 2 H), 4.35-4.44 (m, 2 H), 4.49 (dt, J = 47, 6 Hz, 2 H), 6.19 (br s, 1 H), 6.84 (d, J = 8 Hz, 2 H), 6.87 (d, J = 8 Hz, 1 H), 6.92 (d, J = 9 Hz, 2 H), 7.44 (d, J = 8 Hz, 1 H), 7.57 (dd, J = 8, 1 Hz, 1 H), 7.76 (dd, J = 8, 2 Hz, 1 H), 7.85 (d, J = 1 Hz, 1 H), 7.94 (d, J = 2 Hz, 1 H), 12.75 (br s, 1 H) | 570 |
| 51 | B | 1H NMR (500 MHz, DMSO-d6) δ ppm 1.68 (dquin, J = 25, 6 Hz, 2 H), 2.10-2.18 (m, 4 H), 2.26 (s, 3 H), 2.60 (t, J = 7 Hz, 2 H), 2.88 (br t, J = 7 Hz, 2 H), 3.88 (br s, 2 H), 4.04 (br s, 2 H), 4.46 (dt, J = 47, 6 Hz, 2 H), 6.08 (t, J = 2 Hz, 1 H), 6.81 (d, J = 8 Hz, 2 H), 6.83 (d, J = 8 Hz, 2 H), 6.86 (d, J = 8 Hz, 1 H), 6.90 (d, J = 8 Hz, 2 H), 7.75 (dd, J = 8, 2 Hz, 1 H), 7.92 (d, J = 2 Hz, 1 H) | 518 |
| 52 | A | 1H NMR (500 MHz, DMSO-d6) δ ppm 1.68 (dquin, J = 25, 6 Hz, 2 H), 2.16-2.31 (m, 4 H), 2.59 (t, J = 7 Hz, 2 H), 2.90 (t, J = 7 Hz, 2 H), 3.85-3.92 (m, 2 H), 4.04-4.10 (m, 2 H), 4.46 (dt, J = 47, 6 Hz, 2 H), 6.12 (t, J = 2 Hz, 1 H), 6.67 (d, J = 9 Hz, 2 H), 6.90 (d, J = 8 Hz, 1 H), 6.97 (td, J = 8, 2 Hz, 1 H), 7.14 (ddd, J = 11, 9, 3 Hz, 1 H), 7.20 (td, J = 9, 7 Hz, 1 H), 7.75 (dd, J = 8, 2 Hz, 1 H), 7.91 (d, J = 2 Hz, 1 H), 12.48-13.45 (m, 1 H) | 540 |
| 53 | A | 1H NMR (500 MHz, DMSO-d6) δ ppm 1.68 (dquin, J = 25, 6 Hz, 2 H), 2.11-2.24 (m, 4 H), 2.59 (t, J = 7 Hz, 2 H), 2.87 (t, J = 7 Hz, 2 H), 3.86-3.91 (m, 2 H), 3.97-4.03 (m, 2 H), 4.46 (dt, J = 47, 6 Hz, 2 H), 6.19 (t, J = 2 Hz, 1 H), 6.60 (dd, J = 12, 2 Hz, 1 H), 6.63 (dd, J = 8, 2 Hz, 1 H), 6.88 (d, J = 8 Hz, 1 H), 6.93 (t, J = 8 Hz, 1 H), 7.00 (td, J = 8, 3 Hz, 1 H), 7.15 (ddd, J = 11, 9, 3 Hz, 1 H), 7.30 (td, J = 9, 7 Hz, 1 H), 7.75 (dd, J = 8, 2 Hz, 1 H), 7.91 (d, J = 2 Hz, 1 H) | 522 |
| 54 | B | 1H NMR (400 MHz, DMSO-d6) δ ppm 1.70 (dquin, J = 25, 6 Hz, 2 H), 2.10-2.24 (m, 4 H), 2.65 (br t, J = 7 Hz, 2 H), 2.87 (br t, J = 7 Hz, 2 H), 3.94 (br s, 2 H), 4.12 (br s, 2 H), 4.47 (dt, J = 47, 6 Hz, 2 H), 6.10 (t, J = 2 Hz, 1 H), 6.80 (d, J = 9 Hz, 2 H), 6.86 (d, J = 8 Hz, 1 H), 6.90 (d, J = 8 Hz, 2 H), 6.96 (td, J = 8, 2 Hz, 1 H), 7.11 (td, J = 10, 3 Hz, 1 H), 7.26 (td, J = 9, 7 Hz, 1 H), 7.75 (dd, J = 8, 2 Hz, 1 H), 7.92 (d, J = 2 Hz, 1 H) | 504 |
| 55 | B | 1H NMR (400 MHz, DMSO-d6) δ ppm 1.68 (dquin, J = 25, 6 Hz, 2 H), 2.10-2.27 (m, 4 H), 2.59 (t, J = 7 Hz, 2 H), 2.88 (br t, J = 7 Hz, 2 H), 3.88 (br s, 2 H), 4.03 (s, 2 H), 4.46 (dt, J = 47, 6 Hz, 2 H), 6.08 (t, J = 2 Hz, 1 H), 6.81 (d, J = 8 Hz, 2 H), 6.87 (d, J = 8 Hz, 1 H), 6.88-6.93 (m, 2 H), 7.07 (ddd, J = 7, 4, 4 Hz, 2 H), 7.18-7.30 (m, 1 H), 7.75 (dd, J = 8, 2 Hz, 1 H), 7.92 (d, J = 2 Hz, 1 H), 12.82 (br s, 1 H) | 504 |
| 56 | B | 1H NMR (400 MHz, DMSO-d6) δ ppm 1.68 (dquin, J = 25, 6 Hz, 2 H), 2.21 (br dd, J = 21, 6 Hz, 4 H), 2.61 (t, J = 7 Hz, 2 H), 2.90 (br t, J = 7 Hz, 2 H), 3.90 (br s, 2 H), 4.04 (br s, 2 H), 4.46 (dt, J = 47, 6 Hz, 2 H), 6.09 (t, J = 2 Hz, 1 H), 6.79 (d, J = 8 Hz, 2 H), 6.86-6.93 (m, 3 H), 7.28 (t, J = 8 Hz, 1 H), 7.59 (td, J = 7, 4 Hz, 2 H), 7.76 (dd, J = 8, 2 Hz, 1 H), 7.93 (d, J = 2 Hz, 1 H) | 554 |
| 57 | B | 1H NMR (400 MHz, DMSO-d6) δ ppm 1.68 (dquin, J = 25, 6 Hz, 2 H), 2.16 (br dd, J = 17, 6 Hz, 4 H), 2.25 (s, 3 H), 2.60 (t, J = 7 Hz, 2 H), 2.86 (br t, J = 6 Hz, 2 H), 3.90 (br s, 2 H), 4.05 (br s, 2 H), 4.46 (dt, J = 47, 6 Hz, 2 H), 6.08 (t, J = 2 Hz, 1 H), 6.76-6.82 (m, 2 H), 6.83-6.95 (m, 5 H), 7.06 (t, J = 8 Hz, 1 H), 7.74 (dd, J = 8, 2 | 500 |

TABLE 1b-continued

| Ex. or cmpds | Preparation Method | NMR | MASS: LC/MS (m/z, MH+): |
|---|---|---|---|
| | | Hz, 1 H), 7.91 (d, J = 2 Hz, 1 H), 12.81 (br s, 1 H) | |
| 58 | B | 1H NMR (400 MHz, DMSO-d6) δ ppm 1.68 (dquin, J = 25, 6 Hz, 2 H), 2.08-2.25 (m, 4 H), 2.60 (t, J = 7 Hz, 2 H), 2.87 (br t, J = 7 Hz, 2 H), 3.89 (br s, 2 H), 4.05 (br s, 2 H), 4.47 (dt, J = 47, 6 Hz, 2 H), 6.09 (t, J = 2 Hz, 1 H), 6.80 (d, J = 8 Hz, 2 H), 6.86 (d, J = 8 Hz, 1 H), 6.91 (d, J = 8 Hz, 2 H), 7.16 (dd, J = 8, 2 Hz, 1 H), 7.25 (t, J = 9 Hz, 1 H), 7.31 (dd, J = 10, 2 Hz, 1 H), 7.75 (dd, J = 8, 2 Hz, 1 H), 7.92 (d, J = 2 Hz, 1 H), 12.86 (br s, 1 H) | 520 |
| 59 | A | 1H NMR (400 MHz, DMSO-d6) δ ppm 1.66 (dquin, J = 25, 7 Hz, 2 H), 2.06-2.27 (m, 4 H), 2.54 (t, J = 7 Hz, 2 H), 2.80 (t, J = 7 Hz, 2 H), 3.69-3.80 (m, 2 H), 3.80-3.88 (m, 2 H), 4.45 (dt, J = 47, 6 Hz, 2 H), 6.05 (t, J = 2 Hz, 1 H), 6.37-6.54 (m, 2 H), 6.75 (d, J = 8 Hz, 1 H), 7.02 (td, J = 8, 3 Hz, 1 H), 7.16 (td, J = 10, 3 Hz, 1 H), 7.32 (td, J = 9, 7 Hz, 1 H), 7.68 (dd, J = 8, 1 Hz, 1 H), 7.82 (d, J = 1 Hz, 1 H) | 540 |
| 60 | E | 1H NMR (400 MHz, DMSO-d6) δ ppm 1.45 (br d, J = 11 Hz, 2 H), 1.61-1.77 (m, 4 H), 1.90 (br d, J = 7 Hz, 2 H), 2.07-2.19 (m, 2 H), 2.56(m, 1 H), 2.62 (t, J = 7 Hz, 2 H), 2.72 (t, J = 7 Hz, 2 H), 3.15 (t, J = 11 Hz, 2 H), 3.85 ( dd, J = 11, 4 Hz, 2 H), 3.92 (br s, 2 H), 4.12 (br s, 2 H), 4.49 (dt, J = 47, 6 Hz, 2 H), 6.20 (t, J = 2 Hz, 1 H), 6.73 (d, J = 8 Hz, 1 H), 7.03 (d, J = 8 Hz, 2 H), 7.11 (d, J = 8 Hz, 2 H), 7.65 (dd, J = 8, 2 Hz, 1 H), 7.82 (d, J = 2 Hz, 1 H) | 476 |
| 61 | A | 1H NMR (400 MHz, DMSO-d6) δ ppm 1.73-1.98 (m, 5 H), 2.02-2.40 (m, 7 H), 2.85-3.09 (m, 4 H), 4.53 (dt, J = 47, 6 Hz, 2 H), 4.61-4.77 (m, 2 H), 4.79-5.01 (m, 2 H), 6.38 (br s, 1 H), 6.55-7.19 (m, 6 H), 7.74 (dd, J = 8, 2 Hz, 1 H), 7.93 (d, J = 2 Hz, 1 H) | 532 |
| 62 | A | 1H NMR (400 MHz, DMSO-d6) δ ppm 1.79-2.10 (m, 5 H), 2.25 (m, 7 H), 2.79-3.11 (m, 2 H), 3.25 (m hidden, 2 H), 4.54 (dt, J = 47, 6 Hz, 2 H), 4.65-4.90 (m, 2 H), 4.91-5.17 (m, 2 H), 6.29 (br s, 1 H), 6.57-6.87 (m, 4 H), 6.90-7.06 (m, 2 H), 7.74 (dd, J = 8, 2 Hz, 1 H), 7.92 (br s, 1 H), 10.85 (br s, 1 H), 12.82 (br s, 1 H) | 532 |
| 63 | A | 1H NMR (500 MHz, DMSO-d6) δ ppm 1.71 (dquin, J = 25, 6 Hz, 2 H), 1.79 (br s, 3 H), 2.14-2.32 (m, 4 H), 2.68 (t, J = 5 Hz, 2 H), 2.89-3.11 (m, 2 H), 4.00 (br s, 2 H), 4.13 (br d, J = 1 Hz, 2 H), 4.47 (dt, J = 47, 6 Hz, 2 H), 6.23 (br s, 1 H), 6.78 (d, J = 8 Hz, 3 H), 7.17 (dd, J = 42, 8 Hz, 1 H), 7.28-7.42 (m, 1 H), 7.44-7.66 (m, 1 H), 7.74 (dd, J = 8, 2 Hz, 1 H), 7.94 (d, J = 2 Hz, 1 H), 12.36 (br s, 1 H) | 568 |
| 64 | A | 1H NMR (500 MHz, DMSO-d6) δ ppm 1.68 (dquin, J = 25, 7 Hz, 2 H), 2.07 (s, 3 H), 2.11-2.25 (m, 4 H), 2.58-2.63 (m, 2 H), 2.89-2.98 (m, 2 H), 3.91 (br s, 2 H), 4.00 (br s, 2 H), 4.46 (dt, J = 47, 6 Hz, 2 H), 6.24 (t, J = 2 Hz, 1 H), 6.61-6.69 (m, 2 H), 6.77 (d, J = 8 Hz, 1 H), 6.87 (d, J = 8 Hz, 1 H), 7.20 (d, J = 8 Hz, 1 H), 7.27 (dd, J = 7, 3 Hz, 1 H), 7.59 (d, J = 2 Hz, 1 H), 7.75 (dd, J = 8, 2 Hz, 1 H), 7.91 (d, J = 2 Hz, 1 H), 12.81 (br s, 1 H) | 550 |
| 65 | A | 1H NMR (500 MHz, DMSO-d6) δ ppm 1.74-1.91 (m, 2 H), 2.16-2.31 (m, 7 H), 2.83-3.07 (m, 4 H), 4.24-4.76 (m, 4 H), 4.49 (dt, J = 47, 6 Hz, 2 H), 6.30 (br s, 1 H), 6.81 (td, J = 10, 6 Hz, 2 H), 6.88 (td, J = 9, 3 Hz, 1 H), 6.92 (d, J = 8 Hz, 1 H), 7.01 (dd, J = 10, 3 Hz, 1 H), 7.08 (m, 1 H), 7.76 (dd, J = 8, 2 Hz, 1 H), 7.92 (d, J = 2 Hz, 1 H), 10.38 (br s, 1 H), 12.87 (br s, 1 H) | 536 |
| 66 | A | 1H NMR (500 MHz, DMSO-d6) δ ppm 1.68 (dquin, J = 25, 7 Hz, 2 H), 1.94-2.14 (m, 3 H), 2.17-2.30 (m, 3 H), 2.40 (m, 1 H), 2.59 (t, J = 7 Hz, 2 H), 2.92-3.02 (m, 2 H), 3.87 (br s, 2 H), 4.06 (br s, 2 H), 4.47 (dt, J = 47, 6 Hz, 2 H), 6.05 | 568 |

TABLE 1b-continued

| Ex. or cmpds | Preparation Method | NMR | MASS: LC/MS (m/z, MH+): |
|---|---|---|---|
| | | (s, 1 H), 6.57 (m, 1 H), 6.69 (m, 1 H), 6.81 (m, 1 H), 7.09-7.33 (m, 2 H), 7.55 (d, J = 2 Hz, 1 H), 7.73 (dd, J = 8, 2 Hz, 1 H), 7.91 (d, J = 1 Hz, 1 H), 12.49-13.14 (m, 2 H) | |
| 67 | A | 1H NMR (400 MHz, DMSO-d6) δ ppm 1.71 (dquin, J = 25, 7 Hz, 2 H), 2.01 (d, J = 2 Hz, 3 H), 2.11-2.28 (m, 7 H), 2.66-2.72 (m, 2 H), 2.85-3.03 (m, 2 H), 3.93-4.02 (m, 2 H), 4.04-4.14 (m, 2 H), 4.47 (dt, J = 47, 6 Hz, 2 H), 6.29 (t, J = 2 Hz, 1 H), 6.61 (d, J = 8 Hz, 1 H), 6.72 (t, J = 10 Hz, 1 H), 6.80-6.91 (m, 2 H), 6.97 (d, J = 9 Hz, 1 H), 7.06 (m, 1 H), 7.73 (dd, J = 8, 2 Hz, 1 H), 7.90 (d, J = 2 Hz, 1 H) | 532 |
| 68 | A | 1H NMR (500 MHz, DMSO-d6) δ ppm 1.71 (dquin, J = 25, 7 Hz, 2 H), 2.18-2.30 (m, 7 H), 2.66 (t, J = 6 Hz, 2 H), 2.85-3.03 (m, 2 H), 3.90-4.05 (m, 2 H), 4.10-4.26 (m, 2 H), 4.47 (dt, J = 47, 6 Hz, 2 H), 6.13 (t, J = 2 Hz, 1 H), 6.67 (d, J = 11 Hz, 2 H), 6.84 (td, J = 9, 3 Hz, 1 H), 6.91 (d, J = 8 Hz, 1 H), 6.96-7.04 (m, 2 H), 7.76 (dd, J = 8, 2 Hz, 1 H), 7.92 (d, J = 2 Hz, 1 H), 12.75 (br s, 1 H) | 536 |
| 69 | A | 1H NMR (500 MHz, DMSO-d6) δ ppm 1.73 (dquin, J = 26, 6 Hz, 2 H), 2.07-2.26 (m, 7 H), 2.69-2.82 (m, 2 H), 2.84-3.01 (m, 2 H), 4.00-4.16 (m, 2 H), 4.16-4.33 (m, 2 H), 4.48 (dt, J = 47, 6 Hz, 2 H), 6.24 (br s, 1 H), 6.54 (dd, J = 12, 2 Hz, 1 H), 6.59 (dd, J = 8, 2 Hz, 1 H), 6.86-6.95 (m, 3 H), 7.02 (dd, J = 10, 3 Hz, 1 H), 7.09 (dd, J = 8, 6 Hz, 1 H), 7.76 (dd, J = 8, 2 Hz, 1 H), 7.92 (d, J = 2 Hz, 1 H), 12.68 (br s, 1 H) | 518 |
| 70 | B | 1H NMR (500 MHz, DMSO-d6) δ ppm 1.67 (dquin, J = 25, 7 Hz, 2 H), 2.11-2.21 (m, 4 H), 2.32 (s, 3 H), 2.58 (t, J = 7 Hz, 2 H), 2.87 (t, J = 5 Hz, 1 H), 2.94-3.03 (m, 1 H), 3.87 (br s, 2 H), 4.02 (br s, 2 H), 4.46 (dt, J = 47, 6 Hz, 2 H), 6.05 (t, J = 2 Hz, 1 H), 6.76-6.81 (m, 2 H), 6.83-6.89 (m, 3 H), 7.08 (d, J = 8 Hz, 1 H), 7.25 (d, J = 8 Hz, 1 H), 7.52 (s, 1 H), 7.74 (dd, J = 8, 2 Hz, 1 H), 7.90 (d, J = 2 Hz, 1 H) | 550 |
| 71 | A | 1H NMR (400 MHz, DMSO-d6) δ ppm 1.81-2.00 (m, 2 H), 2.12 (s, 3 H), 2.14-2.27 (m, 4 H), 2.85-3.03 (m, 2 H), 3.24-3.28 (m hidden, 2 H), 4.52 (dt, J = 47, 6 Hz, 2 H), 4.61-4.72 (m, 2 H), 4.73-4.89 (m, 2 H), 6.40 (t, J = 2 Hz, 1 H), 6.52 (dd, J = 12, 1 Hz, 1 H), 6.60 (d, J = 1 Hz, 1 H), 6.89 (d, J = 8 Hz, 1 H), 7.24-7.28 (m, 1 H), 7.33 (dd, J = 8, 3 Hz, 1 H), 7.63 (d, J = 2 Hz, 1 H), 7.77 (dd, J = 8, 2 Hz, 1 H), 7.93 (d, J = 2 Hz, 1 H), 10.34 (br s, 1 H), 12.92 (br s, 1 H) | 568 |
| 72 | B | 1H NMR (400 MHz, DMSO-d6) δ ppm 1.68 (dquin, J = 25, 6 Hz, 2 H), 2.13-2.22 (m, 4 H), 2.25 (s, 3 H), 2.60 (br t, J = 7 Hz, 2 H), 2.87 (m, 1 H), 2.96 (m, 1 H), 3.89 (br s, 2 H), 4.05 (br s, 2 H), 4.46 (dt, J = 47, 6 Hz, 2 H), 6.07 (t, J = 2 Hz, 1 H), 6.74 (d, J = 8 Hz, 2 H), 6.83-6.91 (m, 3 H), 7.00 (dd, J = 9, 2 Hz, 1 H), 7.06 (t, J = 8 Hz, 1 H), 7.26 (d, J = 7 Hz, 1 H), 7.75 (dd, J = 8, 2 Hz, 1 H), 7.92 (d, J = 2 Hz, 1 H) | 516 |
| 73 | A | 1H NMR (500 MHz, DMSO-d6) δ ppm 1.68 (dquin, J = 25, 6 Hz, 2 H), 2.16-2.35 (m, 4 H), 2.59 (t, J = 7 Hz, 2 H), 2.86-3.02 (m, 2 H), 3.83-3.94 (m, 2 H), 4.04-4.12 (m, 2 H), 4.46 (dt, J = 47, 6 Hz, 2 H), 6.11 (t, J = 2 Hz, 1 H), 6.67 (d, J = 10 Hz, 2 H), 6.89 (d, J = 8 Hz, 1 H), 7.19 (d, J = 8 Hz, 1 H), 7.30 (dd, J = 8, 2 Hz, 1 H), 7.56 (d, J = 2 Hz, 1 H), 7.75 (dd, J = 8, 2 Hz, 1 H), 7.91 (d, J = 2 Hz, 1 H) | 572 |
| 74 | A | 1H NMR (400 MHz, DMSO-d6) δ ppm 1.79-1.97 (m, 2 H), 2.05 (d, J = 2 Hz, 3 H), 2.13-2.30 (m, 4 H), 2.89-3.03 (m, 2 H), 3.15-3.21 (m, 2 H), 4.52 (dt, J = 47, 6 Hz, 2 H), 4.58-4.87 (m, 4 H), 6.52 (br s, 1 H), 6.69 (d, J = 8 Hz, 1 H), 6.82 (t, J = 8 Hz, 1 H), 6.86 (d, J = 8 Hz, 1 H), 7.05-7.24 (m, 1 H), 7.29 (d, J = 7 Hz, 1 H), 7.59 ( s, 1 | 568 |

TABLE 1b-continued

| Ex. or cmpds | Preparation Method | NMR | MASS: LC/MS (m/z, MH+): |
|---|---|---|---|
| | | H), 7.75 (dd, J = 8, 2 Hz, 1 H), 7.92 (d, J = 2 Hz, 1 H), 10.52 (br s, 1 H), 12.82 (br s, 1 H) | |
| 75 | B | 1H NMR (500 MHz, DMSO-d6) δ ppm 1.58-1.75 (m, 2 H), 2.05-2.26 (m, 4 H), 2.58 (t, J = 7 Hz, 2 H), 2.91 (t, J = 7 Hz, 2 H), 3.73 (s, 3 H), 3.86 (br s, 2 H), 4.02 (br s, 2 H), 4.46 (dt, J = 47, 6 Hz, 2 H), 6.06 (t, J = 2 Hz, 1 H), 6.76 (dd, J = 9, 2 Hz, 1 H), 6.80 (d, J = 8 Hz, 2 H), 6.83 (br d, J = 8 Hz, 1 H), 6.87 (d, J = 10 Hz, 2 H), 6.99 (d, J = 3 Hz, 1 H), 7.07 (d, J = 8 Hz, 1 H), 7.72 (br d, J = 8 Hz, 1 H), 7.89 (s, 1 H) | 532 |
| 76 | B | 1H NMR (500 MHz, DMSO-d6) δ ppm 1.67 (dquin, J = 25, 6 Hz, 2 H), 2.08-2.26 (m, 4 H), 2.33 (s, 3 H), 2.59 (t, J = 7 Hz, 2 H), 2.86-3.00 (m, 2 H), 3.87 (br s, 2 H), 4.01-4.05 (m, 2 H), 4.46 (dt, J = 47, 6 Hz, 2 H), 6.05 (t, J = 2 Hz, 1 H), 6.77-6.82 (m, 2 H), 6.84-6.88 (m, 3 H), 6.97 (dd, J = 8, 1 Hz, 1 H), 7.04 (t, J = 7 Hz, 1 H), 7.18 (d, J = 7 Hz, 1 H), 7.74 (dd, J = 8, 2 Hz, 1 H), 7.91 (d, J = 2 Hz, 1 H) | 516 |
| 77 | B | 1H NMR (500 MHz, DMSO-d6) δ ppm 1.67 (dquin, J = 25, 6 Hz, 2 H), 2.08-2.17 (m, 7 H), 2.21 (s, 3 H), 2.58 (t, J = 7 Hz, 2 H), 2.80-2.98 (m, 2 H), 3.82-3.90 (m, 2 H), 3.97-4.08 (m, 2 H), 4.46 (dt, J = 47, 6 Hz, 2 H), 6.05 (t, J = 2 Hz, 1 H), 6.74 (d, J = 8 Hz, 2 H), 6.84 (dd, J = 8, 6 Hz, 4 H), 6.92 (dd, J = 4, 3 Hz, 2 H), 7.73 (dd, J = 8, 2 Hz, 1 H), 7.90 (d, J = 2 Hz, 1 H) | 496 |
| 78 | B | 1H NMR (500 MHz, DMSO-d6) δ ppm 1.67 (dquin, J = 25, 7 Hz, 2 H), 2.11-2.27 (m, 4 H), 2.58 (t, J = 7 Hz, 2 H), 2.94 (br t, J = 6 Hz, 2 H), 3.86 (br s, 2 H), 4.02 (br s, 2 H), 4.46 (dt, J = 47, 6 Hz, 2 H), 6.06 (t, J = 2 Hz, 1 H), 6.80 (d, J = 8 Hz, 2 H), 6.86 (d, J = 8 Hz, 1 H), 6.88 (d, J = 8 Hz, 2 H), 7.06 (m, 1 H), 7.18-7.28 (m, 2 H), 7.75 (dd, J = 8, 2 Hz, 1 H), 7.92 (s, 1 H) | 520 |
| 79 | B | 1H NMR (500 MHz, DMSO-d6) δ ppm 1.68 (dquin, J = 25, 7 Hz, 2 H), 2.12-2.26 (m, 4 H), 2.59 (t, J = 7 Hz, 2 H), 2.94 (t, J = 7 Hz, 2 H), 3.88 (br s, 2 H), 4.04 (br s, 2 H), 4.46 (dt, J = 47, 6 Hz, 2 H), 6.07 (t, J = 2 Hz, 1 H), 6.79 (d, J = 8 Hz, 2 H), 6.86 (d, J = 8 Hz, 1 H), 6.89 (d, J = 8 Hz, 2 H), 7.07 (td, J = 8, 3 Hz, 1 H), 7.23 (dd, J = 9, 6 Hz, 1 H), 7.40 (dd, J = 9, 3 Hz, 1 H), 7.74 (dd, J = 8, 2 Hz, 1 H), 7.91 (d, J = 2 Hz, 1 H) | 520 |
| 80 | A | 1H NMR (500 MHz, DMSO-d6) δ ppm 1.85-2.02 (m, 2 H), 2.14-2.33 (m, 4 H), 2.97 (m, J = 7 Hz, 2 H), 3.23 (m hidden, 2 H), 4.53 (dt, J = 47, 6 Hz, 2 H), 4.74-4.88 (m, 2 H), 4.91-5.05 (m, 2 H), 6.50 (t, J = 2 Hz, 1 H), 6.76-6.88 (m, 2 H), 6.91 (d, J = 8 Hz, 1 H), 7.21-7.38 (m, 2 H), 7.60 (s, 1 H), 7.77 (dd, J = 8, 2 Hz, 1 H), 7.94 (d, J = 2 Hz, 1 H), 10.63 (br s, 1 H) | 572 |
| 81 | B | 1H NMR (500 MHz, DMSO-d6) δ ppm 1.68 (dquin, J = 25, 7 Hz, 2 H), 2.13 (d, J = 3 Hz, 3 H), 2.14-2.22 (m, 4 H), 2.60 (t, J = 7 Hz, 2 H), 2.83-2.98 (m, 2 H), 3.88 (br s, 2 H), 4.04 (br s, 2 H), 4.46 (dt, J = 47, 6 Hz, 2 H), 6.08 (t, J = 2 Hz, 1 H), 6.75 (d, J = 8 Hz, 2 H), 6.86 (d, J = 8 Hz, 1 H), 6.89 (d, J = 8 Hz, 2 H), 6.92 (d, J = 8 Hz, 1 H), 7.26 (t, J = 8 Hz, 1 H), 7.75 (dd, J = 8, 2 Hz, 1 H), 7.92 (d, J = 2 Hz, 1 H) | 534 |
| 82 | B | 1H NMR (500 MHz, DMSO-d6) δ ppm 1.68 (dquin, J = 25, 7 Hz, 2 H), 2.05-2.19 (m, 4 H), 2.22 (s, 3 H), 2.26 (s, 3 H), 2.59 (t, J = 7 Hz, 2 H), 2.80-3.00 (m, 2 H), 3.87 (br s, 2 H), 4.04 (br s, 2 H), 4.46 (dt, J = 47, 6 Hz, 2 H), 6.06 (t, J = 2 Hz, 1 H), 6.74 (d, J = 8 Hz, 2 H), 6.83 (d, J = 8 Hz, 1 H), 6.85-6.90 (m, 3 H), 7.08 (d, J = 8 Hz, 1 H), 7.74 (dd, J = 8, 2 Hz, 1 H), 7.90 (d, J = 2 Hz, 1 H) | 530 |
| 83 | B | 1H NMR (500 MHz, DMSO-d6) δ ppm 1.68 (dquin, J = 25, 7 Hz, 2 H), 2.08 (t, J = 7 Hz, 2 H), 2.16 (s, 6 H), 2.17-2.23 (m, 2 H), 2.59 (t, J = 7 Hz, 2 H), 2.95 (t, J = 7 Hz, 2 H), 3.87 (br s, 2 H), 4.03 (br s, 2 H), 4.46 (dt, J = 47, 6 Hz, 2 H), 6.06 | 530 |

TABLE 1b-continued

| Ex. or cmpds | Preparation Method | NMR | MASS: LC/MS (m/z, MH+): |
|---|---|---|---|
| | | (t, J = 2 Hz, 1 H), 6.71 (d, J = 8 Hz, 2 H), 6.83 (d, J = 8 Hz, 1 H), 6.86 (d, J = 8 Hz, 2 H), 7.06 (s, 2 H), 7.73 (dd, J = 8, 2 Hz, 1 H), 7.92 (d, J = 2 Hz, 1 H) | |
| 84 | B | 1H NMR (500 MHz, DMSO-d6) δ ppm 1.67 (dquin, J = 25, 6 Hz, 2 H), 2.11-2.19 (m, 4 H), 2.21 (s, 3 H), 2.59 (t, J = 7 Hz, 2 H), 2.82-3.02 (m, 2 H), 3.79-3.91 (m, 2 H), 4.02 (br s, 2 H), 4.46 (dt, J = 47, 6 Hz, 2 H), 6.06 (t, J = 2 Hz, 1 H), 6.73 (d, J = 9 Hz, 2 H), 6.82-6.98 (m, 3 H), 7.26 (d, J = 8 Hz, 1 H), 7.52 (dd, J = 8, 1 Hz, 1 H), 7.62 (d, J = 2 Hz, 1 H), 7.75 (dd, J = 8, 2 Hz, 1 H), 7.92 (d, J = 2 Hz, 1 H) | 507 |
| 85 | B | 1H NMR (500 MHz, DMSO-d6) δ ppm 1.68 (dquin, J = 25, 6 Hz, 2 H), 2.08 (d, J = 2 Hz, 3 H), 2.13-2.22 (m, 4 H), 2.59 (t, J = 7 Hz, 2 H), 2.87 (m, 1 H), 2.94 (m, 1 H), 3.88 (br s, 2 H), 4.03 (br s, 2 H), 4.46 (dt, J = 47, 6 Hz, 2 H), 6.06 (t, J = 2 Hz, 1 H), 6.74 (d, J = 8 Hz, 2 H), 6.84-6.88 (m, 3 H), 6.90 (d, J = 8 Hz, 1 H), 6.97 (t, J = 9 Hz, 1 H), 7.08 (q, J = 7 Hz, 1 H), 7.75 (dd, J = 8, 2 Hz, 1 H), 7.92 (d, J = 2 Hz, 1 H) | 500 |
| 86 | B | 1H NMR (500 MHz, DMSO-d6) δ ppm 1.09-1.13 (m, 3 H), 1.67 (dquin, J = 25, 7 Hz, 2 H), 2.10-2.22 (m, 4 H), 2.44 (m, 1 H), 2.59 (t, J = 7 Hz, 2 H), 2.65 (m, 1 H), 2.86 (m, 1 H), 2.95 (br dd, J = 13, 7 Hz, 1 H), 3.87 (br s, 2 H), 4.02 (br s, 2 H), 4.46 (dt, J = 47, 6 Hz, 2 H), 6.04 (t, J = 2 Hz, 1 H), 6.73 (d, J = 8 Hz, 2 H), 6.82 (d, J = 8 Hz, 2 H), 6.86 (d, J = 8 Hz, 1 H), 7.00-7.06 (m, 2 H), 7.15 (dt, J = 10, 5 Hz, 1 H), 7.19 (d, J = 8 Hz, 1 H), 7.74 (dd, J = 8, 2 Hz, 1 H), 7.91 (d, J = 2 Hz, 1 H) | 496 |
| 87 | B | 1H NMR (500 MHz, DMSO-d6) δ ppm 1.68 (dquin, J = 25, 7 Hz, 2 H), 2.07-2.21 (m, 10 H), 2.59 (t, J = 7 Hz, 2 H), 2.86 (dt, J = 13, 5 Hz, 1 H), 2.95(m, 1 H), 3.88 (br s, 2 H), 4.03 (br s, 2 H), 4.46 (dt, J = 47, 6 Hz, 2 H), 6.06 (t, J = 2 Hz, 1 H), 6.73 (d, J = 8 Hz, 2 H), 6.78-6.89 (m, 5 H), 7.74 (dd, J = 8, 2 Hz, 1 H), 7.90 (d, J = 2 Hz, 1 H) | 514 |
| 88 | B | 1H NMR (500 MHz, DMSO-d6) δ ppm 1.68 (dquin, J = 25, 6 Hz, 2 H), 2.14-2.30 (m, 4 H), 2.38 (s, 3 H), 2.59 (t, J = 7 Hz, 2 H), 2.92 (m, 1 H), 3.09 (m, 1 H), 3.88 (br s, 2 H), 4.04 (br s, 2 H), 4.46 (dt, J = 47, 6 Hz, 2 H), 6.08 (t, J = 2 Hz, 1 H), 6.79 (d, J = 8 Hz, 2 H), 6.85-6.89 (m, 3 H), 7.27 (t, J = 8 Hz, 2 H), 7.48 (t, J = 8 Hz, 1 H), 7.76 (dd, J = 8, 2 Hz, 1 H), 7.93 (d, J = 2 Hz, 1 H) | 507 |
| 89 | B | 1H NMR (500 MHz, DMSO-d6) δ ppm 1.68 (dquin, J = 25, 6 Hz, 2 H), 2.13-2.20 (m, 7 H), 2.60 (t, J = 7 Hz, 2 H), 2.87 (m, 1 H), 2.93 (m, 1 H), 3.88 (br s, 2 H), 4.04 (br s, 2 H), 4.46 (dt, J = 47, 6 Hz, 2 H), 6.07 (t, J = 2 Hz, 1 H), 6.74 (d, J = 8 Hz, 2 H), 6.84-6.88 (m, 3 H), 7.06 (d, J = 9 Hz, 1 H), 7.11 (dd, J = 9, 3 Hz, 1 H), 7.21 (d, J = 2 Hz, 1 H), 7.74 (dd, J = 8, 2 Hz, 1 H), 7.91 (d, J = 2 Hz, 1 H) | 516 |
| 90 | B | 1H NMR (500 MHz, DMSO-d6) δ ppm 1.67 (dquin, J = 25, 6 Hz, 2 H), 2.03-2.22 (m, 10 H), 2.58 (t, J = 7 Hz, 2 H), 2.95 (br t, J = 7 Hz, 2 H), 3.86 (br s, 2 H), 4.02 (br s, 2 H), 4.46 (dt, J = 47, 6 Hz, 2 H), 6.06 (t, J = 2 Hz, 1 H), 6.70 (d, J = 8 Hz, 2 H), 6.80-6.87 (m, 5 H), 7.73 (dd, J = 8, 2 Hz, 1 H), 7.92 (d, J = 2 Hz, 1 H) | 514 |
| 91 | B | 1H NMR (500 MHz, DMSO-d6) δ ppm 1.68 (dquin, J = 25, 6 Hz, 2 H), 2.13-2.20 (m, 4 H), 2.37 (s, 3 H), 2.60 (t, J = 7 Hz, 2 H), 2.88 (m, 1 H), 2.97 (m, 1 H), 3.89 (br s, 2 H), 4.04 (br s, 2 H), 4.46 (dt, J = 47, 6 Hz, 2 H), 6.07 (t, J = 2 Hz, 1 H), 6.73 (d, J = 8 Hz, 2 H), 6.85-6.89 (m, 3 H), 7.24 (t, J = 8 Hz, 1 H), 7.38 (d, J = 8 Hz, 1 H), 7.62 (d, J = 8 Hz, 1 H), 7.75 (dd, J = 8, 2 Hz, 1 H), 7.93 (d, J = 2 Hz, 1 H) | 507 |
| 92 | A | 1H NMR (500 MHz, DMSO-d6) δ ppm 1.81-2.03 (m, 2 H), 2.12-2.33 (m, 4 H), 2.87-3.04 (m, 2 H), 3.24-3.29 (m hidden, 2 H), 4.53 (dt, | 572 |

TABLE 1b-continued

| Ex. or cmpds | Preparation Method | NMR | MASS: LC/MS (m/z, MH+): |
|---|---|---|---|
| | | J = 47, 6 Hz, 2 H), 4.67-5.10 (m, 4 H), 6.44 (br s, 1 H), 6.89 (td, J = 10, 6 Hz, 2 H), 6.93 (d, J = 8 Hz, 1 H), 7.24-7.39 (m, 2 H), 7.60 (s, 1 H), 7.77 (dd, J = 8, 2 Hz, 1 H), 7.93 (d, J = 2 Hz, 1 H), 10.97 (br s, 1 H), 12.90 (br s, 1 H) | |
| 93 | A | 1H NMR (500 MHz, DMSO-d6) δ ppm 1.82-2.02 (m, 5 H), 2.07-2.33 (m, 4 H), 2.81-3.12 (m, 2 H), 3.28(m hidden, 2 H), 4.54 (dt, J = 47, 6 Hz, 2 H), 4.66-4.86 (m, 2 H), 4.88-5.10 (m, 2 H), 6.30 (br s, 1 H), 6.76 (d, J = 8 Hz, 1 H), 6.79-6.83 (m, 1 H), 6.88 (br s, 1 H), 6.95-7.05 (m, 1 H), 7.11 (br d, J = 8 Hz, 1 H), 7.18 (br d, J = 8 Hz, 1 H), 7.61 (br s, 1 H), 7.73 (dd, J = 8, 2 Hz, 1 H), 7.93 (d, J = 2 Hz, 1 H), 10.63 (br s, 1 H), 12.87 (br s, 1 H) | 550 |
| 94 | B | 1H NMR (500 MHz, DMSO-d6) δ ppm 1.67 (dquin, J = 25, 6 Hz, 2 H), 2.08-2.18 (m, 7 H), 2.20 (s, 3 H), 2.59 (t, J = 7 Hz, 2 H), 2.84-2.98 (m, 2 H), 3.87 (br s, 2 H), 4.02 (br s, 2 H), 4.46 (dt, J = 47, 6 Hz, 2 H), 6.05 (t, J = 2 Hz, 1 H), 6.73 (d, J = 8 Hz, 2 H), 6.79-6.84 (m, 3 H), 6.86 (d, J = 8 Hz, 1 H), 6.90 (t, J = 7 Hz, 1 H), 6.97 (d, J = 7 Hz, 1 H), 7.74 (dd, J = 8, 2 Hz, 1 H), 7.91 (d, J = 2 Hz, 1 H) | 496 |
| 95 | B | 1H NMR (500 MHz, DMSO-d6) δ ppm 1.68 (dquin, J = 25, 6 Hz, 2 H), 2.16-2.22 (m, 4 H), 2.59 (t, J = 7 Hz, 2 H), 2.86 (m, 1 H), 3.01 (m, 1 H), 3.88 (br s, 2 H), 4.03 (br s, 2 H), 4.46 (dt, J = 47, 6 Hz, 2 H), 6.06 (t, J = 2 Hz, 1 H), 6.77 (d, J = 8 Hz, 2 H), 6.85-6.90 (m, 3 H), 7.27 (dd, J = 9, 7 Hz, 1 H), 7.35 (td, J = 8, 3 Hz, 1 H), 7.63 (dd, J = 9, 3 Hz, 1 H), 7.75 (dd, J = 8, 2 Hz, 1 H), 7.91 (d, J = 2 Hz, 1 H) | 554 |
| 96 | B | 1H NMR (500 MHz, DMSO-d6) δ ppm 1.10 (t, J = 8 Hz, 3 H), 1.67 (dquin, J = 25, 7 Hz, 2 H), 2.12-2.21 (m, 4 H), 2.44 (m, 1 H), 2.59 (t, J = 7 Hz, 2 H), 2.63 (m, 1 H), 2.81-2.98 (m, 2 H), 3.87 (br d, J = 2 Hz, 2 H), 4.02 (m, 2 H), 4.46 (dt, J = 47, 6 Hz, 2 H), 6.06 (quin, J = 2 Hz, 1 H), 6.72 (d, J = 8 Hz, 2 H), 6.82-6.91 (m, 4 H), 7.02 (dd, J = 11, 3 Hz, 1 H), 7.05 (dd, J = 8, 6 Hz, 1 H), 7.74 (dd, J = 8, 2 Hz, 1 H), 7.91 (d, J = 2 Hz, 1 H) | 514 |
| 97 | B | 1H NMR (500 MHz, DMSO-d6) δ ppm 1.60-1.73 (m, 2 H), 2.06-2.13 (m, 2 H), 2.16 (s, 6 H), 2.17-2.24 (m, 2 H), 2.58 (t, J = 7 Hz, 2 H), 2.96 (br t, J = 7 Hz, 2 H), 3.86 (br d, J = 2 Hz, 2 H), 4.00 (br d, J = 2 Hz, 2 H), 4.46 (dt, J = 47, 6 Hz, 2 H), 6.04 (t, J = 2 Hz, 1 H), 6.70 (d, J = 8 Hz, 2 H), 6.82 (d, J = 8 Hz, 2 H), 6.84 (d, J = 8 Hz, 1 H), 6.93-7.04 (m, 3 H), 7.73 (dd, J = 8, 2 Hz, 1 H), 7.92 (d, J = 2 Hz, 1 H), 12.64 (br s, 1 H) | 496 |
| 98 | B | 1H NMR (500 MHz, DMSO-d6) δ ppm 1.69-1.79 (m, 2 H), 2.20-2.26 (m, 7 H), 2.66 (t, J = 7 Hz, 2 H), 2.88-3.04 (m, 2 H), 3.94 (br s, 2 H), 4.10 (br s, 2 H), 4.52 (dt, J = 47, 6 Hz, 2 H), 6.13 (t, J = 2 Hz, 1 H), 6.79 (d, J = 8 Hz, 2 H), 6.88-6.93 (m, 3 H), 6.95 (dd, J = 9, 3 Hz, 1 H), 7.04 (dd, J = 10, 3 Hz, 1 H), 7.13 (dd, J = 8, 6 Hz, 1 H), 7.80 (dd, J = 8, 2 Hz, 1 H), 7.97 (d, J = 2 Hz, 1 H) | 500 |
| 99 | B | 1H NMR (500 MHz, DMSO-d6) δ ppm 1.74 (dquin, J = 25, 7 Hz, 2 H), 2.23 (m, 7 H), 2.65 (t, J = 7 Hz, 2 H), 2.86-3.05 (m, 2 H), 3.93 (br s, 2 H), 4.08 (br d, J = 2 Hz, 2 H), 4.52 (dt, J = 47, 6 Hz, 2 H), 6.11 (t, J = 2 Hz, 1 H), 6.79 (d, J = 9 Hz, 2 H), 6.89 (d, J = 9 Hz, 2 H), 6.92 (d, J = 8 Hz, 1 H), 7.06-7.21 (m, 4 H), 7.80 (dd, J = 8, 2 Hz, 1 H), 7.97 (d, J = 2 Hz, 1 H) | 482 |
| 100 | F | 1H NMR (500 MHz, DMSO-d6) δ ppm 0.81 (d, J = 7 Hz, 6 H), 1.65-1.79 (m, 2 H), 1.84 (dt, J = 13, 7 Hz, 1 H), 1.93 t, J = 7 Hz, 2 H), 2.11 (d, J = 7 Hz, 2 H), 2.17 (quin, J = 7 Hz, 2 H), 2.70 ( t, J = 6 Hz, 2 H), 2.78 (t, J = 7 Hz, 2 H), 4.02 (s, 2 H), 4.23 (s, 2 H), 4.49 (dt, J = 47, 6 Hz, 2 H), 6.22 (br s, 1 H), 6.76 (d, J = 8 Hz, 1 H), 7.03 (d, J = 8 Hz, 2 H), 7.11 (, J = 8 Hz, 2 H), 7.65 (dd, J = 8, 2 Hz, 1 H), 7.83 (s, 1 H) | 448 |

TABLE 1b-continued

| Ex. or cmpds | Preparation Method | NMR | MASS: LC/MS (m/z, MH+): |
|---|---|---|---|
| 101 | A | 1H NMR (500 MHz, DMSO-d6) δ ppm 1.82-1.97 (m, 2 H), 2.13-2.33 (m, 4 H), 2.88-3.05 (m, 2 H), 3.13-3.23 (m, 2 H), 4.53 (dt, J = 47, 6 Hz, 2 H), 4.60-4.75 (m, 2 H), 4.79-4.97 (m, 2 H), 6.32 (t, J = 2 Hz, 1 H), 6.77-6.93 (m, 3 H), 6.99 (br t, J = 8 Hz, 1 H), 7.23 (m, 1 H), 7.31 (m, 1 H), 7.58 (br s, 1 H), 7.76 (dd, J = 8, 2 Hz, 1 H), 7.93 (d, J = 2 Hz, 1 H), 10.12-11.46 (m, 2 H) | 554 |
| 102 | G | 1H NMR (400 MHz, DMSO-d6) δ ppm 1.70-2.01 (m, 5 H), 2.07-2.27 (m, 4 H), 2.94 ( t, J = 5 Hz, 3 H), 4.53 (dt, J = 47, 6 Hz, 3 H), 4.67-4.96 (m, 4 H), 6.85 (d, J = 7 Hz, 1 H), 6.87 (d, J = 7 Hz, 2 H), 7.07 (d, J = 9 Hz, 2 H), 7.19-7.25 (m, 1 H), 7.27-7.32 (m, 1 H), 7.61 (d, J = 2 Hz, 1 H), 7.76 (dd, J = 8, 2 Hz, 1 H), 7.93 (d, J = 2 Hz, 1 H), 10.45 (br s, 1 H), 12.88 (br s, 1 H) | 550 |
| 103 | A | 1H NMR (500 MHz, DMSO-d6) δ ppm 1.81-1.97 (m, 2 H), 2.12-2.28 (m, 4 H), 2.91-2.99 (m, 2 H), 3.16-3.24 (m, 2 H), 4.52 (dt, J = 47, 6 Hz, 2 H), 4.59-4.69 (m, 2 H), 4.71-4.85 (m, 2 H), 6.41 (t, J = 2 Hz, 1 H), 6.66 (dd, J = 12, 2 Hz, 1 H), 6.70 (dd, J = 8, 2 Hz, 1 H), 6.89 (d, J = 8 Hz, 1 H), 7.00 (t, J = 8 Hz, 1 H), 7.28 (d, J = 8 Hz, 1 H), 7.32 (dd, J = 9, 2 Hz, 1 H), 7.62 (d, J = 2 Hz, 1 H), 7.77 (dd, J = 8, 2 Hz, 1 H), 7.94 (d, J = 2 Hz, 1 H), 10.96 (br s, 1 H), 12.80 (br s, 1 H) | 554 |
| 104 | A | 1H NMR (400 MHz, DMSO-d6) δ ppm 1.80-1.96 (m, 2 H), 2.01 (s, 6 H), 2.12-2.23 (m, 4 H), 2.87-2.98 (m, 2 H), 3.22 (s, 2 H), 4.19-4.36 (m, 2 H), 4.51 (dt, J = 47, 6 Hz, 2 H), 4.62-4.76 (m, 2 H), 6.39 (br s, 1 H), 6.56 (s, 2 H), 6.87 (d, J = 8 Hz, 1 H), 7.19 (d, J = 8 Hz, 1 H), 7.28 (dd, J = 8, 2 Hz, 1 H), 7.61 (d, J = 2 Hz, 1 H), 7.76 (dd, J = 8, 2 Hz, 1 H), 7.92 (d, J = 2 Hz, 1 H), 10.61 (br s, 1 H), 12.87 (br s, 1 H) | 564 |
| 105 | A | 1H NMR (400 MHz, DMSO-d6) δ ppm 1.79-1.99 (m, 2 H), 2.10-2.27 (m, 4 H), 2.89-3.00 (m, 2 H), 3.24 (m hidden, 2 H), 4.52 (dt, J = 47, 6 Hz, 2 H), 4.60-4.78 (m, 4 H), 6.36 (t, J = 2 Hz, 1 H), 6.60 (d, J = 9 Hz, 2 H), 6.93 (d, J = 8 Hz, 1 H), 7.31 (m, 1 H), 7.36 (m, 1 H), 7.65 (d, J = 2 Hz, 1 H), 7.78 (dd, J = 8, 2 Hz, 1 H), 7.94 (d, J = 2 Hz, 1 H), 10.63 (br s, 1 H), 12.92 (br s, 1 H) | 572 |
| 106 | D | 1H NMR (400 MHz, DMSO-d6) δ ppm 1.70 (dquin, J = 25, 6 Hz, 2 H), 2.46 (m hidden, 1 H), 2.60 (t, J = 7 Hz, 2 H), 2.68 (m, 1 H), 2.93-3.05 (m, 2 H), 3.89 (m, 2 H), 4.07 (m, 2 H), 4.48 (dt, J = 47, 6 Hz, 2 H), 6.12 (quin, J = 2 Hz, 1 H), 6.61 (d, J = 8 Hz, 1 H), 6.95-7.06 (m, 4 H), 7.12 (d, J = 8 Hz, 1 H), 7.21 (dd, J = 8, 2 Hz, 1 H), 7.53 (d, J = 2 Hz, 1 H), 7.61 (d, J = 8 Hz, 1 H), 7.78 (s, 1 H) | 522 |
| 107 | B | 1H NMR (400 MHz, DMSO-d6) δ ppm 2.04-2.39 (m, 6 H), 2.72 (t, J = 7 Hz, 2 H), 2.84 (m, 1 H), 3.01(m, 1 H), 3.85-3.95 (m, 2 H), 4.04-4.10 (m, 2 H), 6.08 (t, J = 2 Hz, 1 H), 6.80 (d, J = 9 Hz, 2 H), 6.87 (d, J = 8 Hz, 1 H), 6.91 (d, J = 9 Hz, 2 H), 7.14 (d, J = 8 Hz, 1 H), 7.42 (t, J = 8 Hz, 1 H), 7.55 (d, J = 8 Hz, 1 H), 7.75 (dd, J = 8, 2 Hz, 1 H), 7.91 (d, J = 2 Hz, 1 H) | 606 |
| 108 | B | 1H NMR (400 MHz, DMSO-d6) δ ppm 2.11-2.23 (m, 2 H), 2.24-2.39 (m, 4 H), 2.72 (t, J = 7 Hz, 2 H), 2.87 (m, 1 H), 3.01 (m, 1 H), 3.91 (m, 2 H), 4.06 (m, 2 H), 6.07 (t, J = 2 Hz, 1 H), 6.78 (d, J = 7 Hz, 2 H), 6.84-6.91 (m, 3 H), 7.28 (dd, J = 8, 6 Hz, 1 H), 7.36 (td, J = 9, 3 Hz, 1 H), 7.64 (dd, J = 9, 3 Hz, 1 H), 7.75 (dd, J = 8, 2 Hz, 1 H), 7.91 (d, J = 2 Hz, 1 H) | 590 |
| 109 | B | produit salifie: 1H NMR (400 MHz, DMSO-d6) δ ppm 2.18-2.33 (m, 4 H), 2.72-2.84 (m, 2 H), 2.93-3.08 (m, 2 H), 3.62 (t, J = 8 Hz, 2 H), 4.80-5.05 (m, 2 H), 5.16 (m, 2 H), 6.43 (t, J = 2 Hz, 1 H), 6.86-6.97 (m, 3 H), 6.99-7.07 (m, 2 | 572 |

TABLE 1b-continued

| Ex. or cmpds | Preparation Method | NMR | MASS: LC/MS (m/z, MH+): |
|---|---|---|---|
| | | H), 7.30 (d, J = 8 Hz, 1 H), 7.35 (dd, J = 8, 3 Hz, 1 H), 7.66 (d, J = 2 Hz, 1 H), 7.82 (dd, J = 8, 2 Hz, 1 H), 8.00 (d, J = 2 Hz, 1 H), 10.33 (br s, 1 H), 13.00 (br s, 1 H) | |
| 110 | B | 1H NMR (400 MHz, DMSO-d6) δ ppm 2.00-2.36 (m, 6 H), 2.40-2.48 (m, 3 H), 2.71 (t, J = 7 Hz, 2 H), 2.83 (m, 1 H), 3.00 (m, 1 H), 3.83-3.96 (m, 2 H), 4.01-4.11 (m, 2 H), 6.06 (t, J = 2 Hz, 1 H), 6.78-6.82 (m, 2 H), 6.82-6.89 (m, 3 H), 6.96(m, 1 H), 7.23-7.29 (m, 2 H), 7.75 (dd, J = 8, 2 Hz, 1 H), 7.90 (d, J = 2 Hz, 1 H) | 586 |
| 111 | B | 1H NMR (400 MHz, DMSO-d6) δ ppm 2.08-2.20 (m, 5 H), 2.22-2.39 (m, 4 H), 2.72 (t, J = 8 Hz, 2 H), 2.90 (m, 2 H), 3.91 (br s, 2 H), 4.07 (br s, 2 H), 6.08 (t, J = 1 Hz, 1 H), 6.76 (d, J = 9 Hz, 2 H), 6.82-6.94 (m, 4 H), 7.26 (t, J = 8 Hz, 1 H), 7.74 (dd, J = 8, 2 Hz, 1 H), 7.91 (d, J = 2 Hz, 1 H) | 570 |
| 112 | B | 1H NMR (400 MHz, DMSO-d6) δ ppm 2.08-2.19 (m, 5 H), 2.21-2.38 (m, 4 H), 2.72 (t, J = 9 Hz, 2 H), 2.90 (m, 2 H), 3.91 (br s, 2 H), 4.06 (br s, 2 H), 6.08 (t, J = 2 Hz, 1 H), 6.74 (d, J = 8 Hz, 2 H), 6.82-6.93 (m, 4 H), 7.11 (m, 1 H), 7.75 (dd, J = 8, 2 Hz, 1 H), 7.92 (d, J = 2 Hz, 1 H) | 554 |
| 113 | B | 1H NMR (400 MHz, DMSO-d6) δ ppm 1.65-1.86 (m, 2 H), 2.15-2.23 (m, 4 H), 2.27 (s, 3 H), 2.77-2.87 (m, 2 H), 2.87-3.00 (m, 2 H), 4.16 (br s, 2 H), 4.32 (br s, 2 H), 4.48 (dt, J = 47, 6 Hz, 2 H), 6.15 (br s, 1 H), 6.77 (d, J = 9 Hz, 2 H), 6.88 (dd, J = 8, 5 Hz, 3 H), 7.27 (d, J = 8 Hz, 1 H), 7.41 (d, J = 8 Hz, 1 H), 7.51 (s, 1 H), 7.76 (dd, J = 8, 2 Hz, 1 H), 7.93 (d, J = 2 Hz, 1 H) | 550 |
| 114 | D | 1H NMR (400 MHz, DMSO-d6) δ ppm 1.61-1.97 (m, 2 H), 2.38-2.47 (m hidden, 2 H), 2.55 (m, 1 H), 2.72 (m, 1 H), 3.01-3.23 (m, 2 H), 4.52 (dt, J = 47, 6 Hz, 2 H), 4.54-4.58 (m, 2 H), 4.65-4.91 (m, 2 H), 6.28 (br s, 1 H), 6.83 (d, J = 8 Hz, 1 H), 6.89 (d, J = 8 Hz, 2 H), 6.99 (d, J = 8 Hz, 2 H), 7.11 (d, J = 8 Hz, 1 H), 7.27 (dd, J = 8, 2 Hz, 1 H), 7.59-7.67 (m, 3 H), 10.43 (br s, 1 H), 13.04 (br s, 1 H) | 538 |
| 115 | D | 1H NMR (400 MHz, DMSO-d6) δ ppm 1.84-2.04 (m, 2 H), 2.43 (m, 1 H), 2.63 (m, 1 H), 3.34-3.44 (m, 4 H), 4.54 (dt, J = 47, 6 Hz, 2 H), 4.68-5.24 (m, 4 H), 6.36 (m, 1 H), 6.84 (d, J = 8 Hz, 2 H), 7.00 (d, J = 8 Hz, 2 H), 7.14 (d, J = 8 Hz, 1 H), 7.30 (dd, J = 8, 2 Hz, 1 H), 7.38 (d, J = 2 Hz, 1 H), 7.69 (d, J = 2 Hz, 1 H), 7.78 (m, 1 H), 7.84 (dd, J = 8, 2 Hz, 1 H), 10.60 (br s, 1 H), 13.13 (br s, 1 H) | 554 |
| 116 | B | 1H NMR (400 MHz, DMSO-d6) δ ppm 1.75-1.94 (m, 2 H), 2.00-2.28 (m, 4 H), 2.47 (s, 3 H), 2.62 (t, J = 7 Hz, 2 H), 2.83 (m, 1 H), 2.99 (m, 1 H), 3.88 (m, 2 H), 4.05 (m, 2 H), 6.08 (tt, J = 57, 5 Hz, 1 H), 6.06 (t, J = 2 Hz, 1 H), 6.80 (d, J = 8 Hz, 2 H), 6.85 (d, J = 8 Hz, 1 H), 6.88 (d, J = 9 Hz, 2 H), 6.96 (dd, J = 6, 2 Hz, 1 H), 7.17-7.36 (m, 2 H), 7.74 (dd, J = 8, 2 Hz, 1 H), 7.90 (d, J = 2 Hz, 1 H), 12.54 (br s, 1 H) | 568 |
| 117 | B | 1H NMR (400 MHz, DMSO-d6) δ ppm 1.85 (td, J = 18, 5 Hz, 2 H), 2.11-2.27 (m, 4 H), 2.93 (t, J = 6 Hz, 2 H), 3.89 (m, 2 H), 4.05 (m, 2 H), 6.08 (tt, J = 57, 5 Hz, 1 H), 6.06 (m, 1 H), 6.80 (d, J = 8 Hz, 2 H), 6.85 (d, J = 8 Hz, 1 H), 6.90 (d, J = 9 Hz, 2 H), 7.21 (d, J = 9 Hz, 1 H), 7.27 (dd, J = 8, 2 Hz, 1 H), 7.59 (d, J = 2 Hz, 1 H), 7.74 (dd, J = 8, 2 Hz, 1 H), 7.91 (d, J = 2 Hz, 1 H), 12.89 (br s, 1 H) | 556 |
| 118 | B | 1H NMR (400 MHz, DMSO-d6) δ ppm 1.67 (dquin, J = 25, 6 Hz, 2 H), 2.00-2.29 (m, 4 H), 2.47 (q, J = 2 Hz, 3 H), 2.58 (t, J = 7 Hz, 2 H), 2.83 (m, 1 H), 2.99 (m, 1 H), 3.86 (m, 2 H), 4.02 (m, 2 H), 4.46 (dt, J = 47, 6 Hz, 2 H), 6.05 (t, J = 2 Hz, 1 H), 6.80 (d, J = 8 Hz, 2 H), 6.85 (d, J = 8 Hz, 1 H), 6.88 (d, J = 8 Hz, 2 H), 6.96 (dd, J = 7, 2 Hz, | 550 |

TABLE 1b-continued

| Ex. or cmpds | Preparation Method | NMR | MASS: LC/MS (m/z, MH+): |
|---|---|---|---|
| | | 1 H), 7.19-7.30 (m, 2 H), 7.74 (dd, J = 8, 2 Hz, 1 H), 7.90 (d, J = 2 Hz, 1 H), 13.39 (br s, 1 H) | |
| 119 | B | 1H NMR (400 MHz, DMSO-d6) δ ppm 1.57-1.77 (m, 2 H), 2.11-2.19 (m, 4 H), 2.22 (s, 3 H), 2.59 (t, J = 7 Hz, 2 H), 2.87 (m, 1 H), 2.99 (m, 1 H), 3.88 (br s, 2 H), 4.03 (br s, 2 H), 4.46 (dt, J = 47, 6 Hz, 2 H), 6.05 (s, 1 H), 6.75-6.82 (m, 2 H), 6.83-6.90 (m, 3 H), 7.04 (s, 1 H), 7.22 (br d, J = 8 Hz, 1 H), 7.58 (d, J = 8 Hz, 1 H), 7.74 (dd, J = 8, 2 Hz, 1 H), 7.91 (d, J = 2 Hz, 1 H), 12.80 (br s, 1 H) | 550 |
| 120 | D | 1H NMR (400 MHz, DMSO-d6) δ ppm 1.67 (dquin, J = 25, 6 Hz, 2 H), 2.08-2.25 (m, 4 H), 2.58 (t, J = 7 Hz, 2 H), 2.80-2.95 (m, 2 H), 3.86 (m, 2 H), 4.01 (m, 2 H), 4.46 (dt, J = 47, 6 Hz, 2 H), 6.05 (t, J = 2 Hz, 1 H), 6.73-6.89 (m, 5 H), 7.14-7.26 (m, 5 H), 7.34 (dd, J = 7, 1 Hz, 1 H), 7.41 (dt, J = 8, 1 Hz, 1 H) | 458 |
| 121 | B | 1H NMR (400 MHz, DMSO-d6) δ ppm 1.57-1.78 (m, 2 H), 2.12-2.31 (m, 4 H), 2.60 (t, J = 7 Hz, 2 H), 2.91 (br t, J = 6 Hz, 2 H), 3.89 (br s, 2 H), 4.03 (br s, 2 H), 4.47 (dt, J = 47, 6 Hz, 2 H), 6.09 (m, 1 H), 6.81 (d, J = 8 Hz, 2 H), 6.85-6.95 (m, 3 H), 7.33 (t, J = 9 Hz, 1 H), 7.51-7.69 (m, 2 H), 7.76 (dd, J = 8, 2 Hz, 1 H), 7.93 (d, J = 2 Hz, 1 H) | 554 |
| 122 | B | 1H NMR (400 MHz, DMSO-d6) δ ppm 1.67 (dt, J = 25, 6 Hz, 2 H), 2.10-2.26 (m, 4 H), 2.93 (t, J = 6 Hz, 2 H), 3.88 (br s, 2 H), 4.04 (br s, 2 H), 4.46 (dt, J = 47, 6 Hz, 2 H), 6.08 (t, J = 2 Hz, 1 H), 6.80 (d, J = 8 Hz, 2 H), 6.86 (d, J = 8 Hz, 1 H), 6.90 (d, J = 8 Hz, 2 H), 7.21 (d, J = 9 Hz, 1 H), 7.27 (dd, J = 9, 2 Hz, 1 H), 7.58 (d, J = 2 Hz, 1 H), 7.75 (dd, J = 8, 2 Hz, 1 H), 7.92 (d, J = 2 Hz, 1 H) | 538 |
| 123 | B | 1H NMR (400 MHz, DMSO-d6) δ ppm 1.68 (dquin, J = 25, 6 Hz, 2 H), 2.14-2.28 (m, 4 H), 2.59 (t, J = 7 Hz, 2 H), 2.93 (m, 1 H), 3.04 (m, 1 H), 3.87 (br s, 2 H), 4.03 (br s, 2 H), 4.46 (dt, J = 47, 6 Hz, 2 H), 6.09 (q, J = 3 Hz, 1 H), 6.83 (d, J = 9 Hz, 2 H), 6.87 (d, J = 8 Hz, 1 H), 6.92 (d, J = 8 Hz, 2 H), 7.53 (dd, J = 9, 3 Hz, 1 H), 7.66 (dd, J = 9, 3 Hz, 1 H), 7.75 (dd, J = 8, 2 Hz, 1 H), 7.93 (d, J = 2 Hz, 1 H), 12.68 (br s, 1 H) | 588 |
| 124 | B | 1H NMR (400 MHz, DMSO-d6) δ ppm 1.68 (dquin, J = 25, 6 Hz, 2 H), 2.14-2.28 (m, 4 H), 2.59 (t, J = 7 Hz, 2 H), 2.88 (t, J = 6 Hz, 2 H), 3.88 (br s, 2 H), 4.03 (br s, 2 H), 4.47 (dt, J = 47, 6 Hz, 2 H), 6.10 (t, J = 2 Hz, 1 H), 6.79 (d, J = 8 Hz, 2 H), 6.88 (d, J = 8 Hz, 1 H), 6.92 (d, J = 8 Hz, 2 H), 7.28 (t, J = 10 Hz, 1 H), 7.65 (m, 1 H), 7.75 (dd, J = 8, 2 Hz, 1 H), 7.92 (d, J = 2 Hz, 1 H), 12.94 (br s, 1 H) | 572 |
| 125 | C | 1H NMR (400 MHz, DMSO-d6) δ ppm 1.86 (dddt, J = 21, 14, 7, 4 Hz, 2 H), 2.11-2.32 (m, 4 H), 2.63 (t, J = 7 Hz, 2 H), 2.86-2.96 (m, 2 H), 3.89 (br s, 2 H), 4.04 (br s, 2 H), 6.08 (tt, J = 57, 5 Hz, 1 H), 6.07 (t, J = 2 Hz, 1 H), 6.66 (d, J = 9 Hz, 2 H), 6.84 (d, J = 8 Hz, 1 H), 6.87 (d, J = 9 Hz, 2 H), 7.75 (dd, J = 8, 2 Hz, 1 H), 7.93 (d, J = 2 Hz, 1 H), 8.31 (d, J = 2 Hz, 1 H), 8.91 (d, J = 2 Hz, 1 H), 13.15 (br s, 1 H) | 589 |
| 126 | B | 1H NMR (500 MHz, DMSO-d6) δ ppm 1.76-1.93 (m, 2 H), 2.09-2.21 (m, 4 H), 2.24 (s, 3 H), 2.62 (t, J = 7 Hz, 2 H), 2.83-3.00 (m, 2 H), 3.89 (br s, 2 H), 4.04 (br s, 2 H), 6.08 (tt, J = 57, 5 Hz, 1 H), 6.06 (m, 1 H), 6.74 (d, J = 8 Hz, 2 H), 6.87 (dd, J = 8, 2 Hz, 3 H), 7.00 (dd, J = 8, 1 Hz, 1 H), 7.05 (t, J = 8 Hz, 1 H), 7.25 (dd, J = 8, 1 Hz, 1 H), 7.75 (dd, J = 8, 2 Hz, 1 H), 7.92 (d, J = 2 Hz, 1 H), 12.84 (br s, 1 H) | 534 |
| 127 | B | 1H NMR (400 MHz, DMSO-d6) δ ppm 1.86 (ttd, J = 18, 7, 5 Hz, 2 H), 2.13 (d, J = 3 Hz, 3 H), 2.14-2.23 (m, 4 H), 2.63 (t, J = 7 Hz, 2 H), 2.81-2.99 (m, 2 H), 3.89 (br s, 2 H), 4.05 (br s, 2 H), 6.08 (tt, J = 57, 5 Hz, 1 H), 6.07 (m, 1 H), 6.75 (d, J = 8 Hz, 2 H), 6.86 (d, J = 8 Hz, 1 H), 6.89 (d, | 552 |

TABLE 1b-continued

| Ex. or cmpds | Preparation Method | NMR | MASS: LC/MS (m/z, MH+): |
|---|---|---|---|
| | | J = 8 Hz, 2 H), 6.92 (dd, J = 8, 1 Hz, 1 H), 7.26 (t, J = 8 Hz, 1 H), 7.74 (dd, J = 8, 2 Hz, 1 H), 7.92 (d, J = 2 Hz, 1 H), 12.79 (br s, 1 H) | |
| 128 | B | 1H NMR (400 MHz, DMSO-d6) δ ppm 1.86 (ttd, J = 18, 7, 5 Hz, 2 H), 2.12-2.23 (m, 4 H), 2.62 (t, J = 7 Hz, 2 H), 2.81-3.04 (m, 2 H), 3.88 (br s, 2 H), 4.05 (br s, 2 H), 6.08 (tt, J = 57, 5 Hz, 1 H), 6.05 (m, 1 H), 6.78 (d, J = 9 Hz, 2 H), 6.86 (d, J = 8 Hz, 1 H), 6.89 (d, J = 9 Hz, 2 H), 7.25 (d, J = 8 Hz, 1 H), 7.55 (dd, J = 8, 2 Hz, 1 H), 7.75 (dd, J = 8, 2 Hz, 1 H), 7.81 (d, J = 2 Hz, 1 H), 7.91 (d, J = 2 Hz, 1 H), 12.70 (br s, 1 H) | 588 |
| 129 | B | 1H NMR (400 MHz, DMSO-d6) δ ppm 1.77-1.95 (m, 2 H), 2.12-2.29 (m, 4 H), 2.63 (t, J = 7 Hz, 2 H), 2.90 (br t, J = 7 Hz, 2 H), 3.89 (br s, 2 H), 4.04 (br s, 2 H), 6.08 (tt, J = 57, 5 Hz, 1 H), 6.06 (m, 1 H), 6.79 (d, J = 9 Hz, 2 H), 6.89 (dd, J = 8, 3 Hz, 3 H), 7.28 (t, J = 8 Hz, 1 H), 7.53-7.68 (m, 2 H), 7.76 (dd, J = 8, 2 Hz, 1 H), 7.93 (d, J = 2 Hz, 1 H), 12.84 (br s, 1 H) | 572 |
| 130 | B | 1H NMR (400 MHz, DMSO-d6) δ ppm 1.75-1.98 (m, 2 H), 2.01-2.25 (m, 10 H), 2.63 (t, J = 7 Hz, 2 H), 2.79-3.01 (m, 2 H), 3.82-3.95 (m, 2 H), 3.99-4.15 (m, 2 H), 6.08 (tt, J = 57, 5 Hz, 1 H), 6.06 (m, 1 H), 6.73 (d, J = 9 Hz, 2 H), 6.77-6.88 (m, 5 H), 7.74 (dd, J = 8, 2 Hz, 1 H), 7.90 (d, J = 2 Hz, 1 H) | 532 |
| 131 | B | 1H NMR (500 MHz, DMSO-d6) δ ppm 1.79-1.92 (m, 2 H), 2.09-2.26 (m, 4 H), 2.33 (s, 3 H), 2.62 (t, J = 7 Hz, 2 H), 2.87-2.99 (m, 2 H), 3.88 (br d, J = 2 Hz, 2 H), 4.04 (br s, 2 H), 6.08 (tt, J = 57, 5 Hz, 1 H), 6.06 (t, J = 2 Hz, 1 H), 6.80 (d, J = 8 Hz, 2 H), 6.84-6.89 (m, 3 H), 6.97 (dd, J = 8, 1 Hz, 1 H), 7.04 (t, J = 7 Hz, 1 H), 7.18 (m, 1 H), 7.75 (dd, J = 8, 2 Hz, 1 H), 7.91 (d, J = 2 Hz, 1 H), 12.86 (br s, 1 H) | 534 |
| 132 | B | 1H NMR (400 MHz, DMSO-d6) δ ppm 1.86 (ttd, J = 18, 7, 5 Hz, 2 H), 2.07-2.23 (m, 7 H), 2.62 (t, J = 7 Hz, 2 H), 2.79-2.98 (m, 2 H), 3.89 (br s, 2 H), 4.04 (br s, 2 H), 6.08 (tt, J = 57, 5 Hz, 1 H), 6.07 (t, J = 2 Hz, 1 H), 6.74 (d, J = 9 Hz, 2 H), 6.86 (dd, J = 8, 3 Hz, 3 H), 7.06 (d, J = 8 Hz, 1 H), 7.11 (dd, J = 8, 2 Hz, 1 H), 7.21 (d, J = 2 Hz, 1 H), 7.74 (dd, J = 8, 2 Hz, 1 H), 7.91 (d, J = 2 Hz, 1 H), 12.79 (br s, 1 H) | 534 |
| 133 | B | 1H NMR (400 MHz, DMSO-d6) δ ppm 1.77-1.95 (m, 2 H), 2.11-2.28 (m, 4 H), 2.62 (t, J = 7 Hz, 2 H), 2.89-3.03 (m, 2 H), 3.88 (br s, 2 H), 4.04 (br s, 2 H), 6.08 (tt, J = 57, 5 Hz, 1 H), 6.07 (t, J = 2 Hz, 1 H), 6.80 (d, J = 8 Hz, 2 H), 6.84-6.92 (m, 3 H), 7.38 (t, J = 8 Hz, 1 H), 7.50 (dd, J = 8, 1 Hz, 1 H), 7.70 (dd, J = 8, 2 Hz, 1 H), 7.76 (dd, J = 8, 2 Hz, 1 H), 7.93 (d, J = 2 Hz, 1 H), 12.80 (br s, 1 H) | 588 |
| 134 | B | 1H NMR (500 MHz, DMSO-d6) δ ppm 1.77-1.92 (m, 2 H), 2.12-2.24 (m, 4 H), 2.34 (d, J = 1 Hz, 3 H), 2.62 (t, J = 7 Hz, 2 H), 2.84-3.03 (m, 2 H), 3.88 (br s, 2 H), 3.99-4.06 (m, 2 H), 6.08 (tt, J = 57, 5 Hz, 1 H), 6.06 (t, J = 2 Hz, 1 H), 6.73 (d, J = 8 Hz, 2 H), 6.85 (d, J = 8 Hz, 2 H), 6.89 (d, J = 8 Hz, 1 H), 7.24 (t, J = 8 Hz, 1 H), 7.33 (d, J = 7 Hz, 1 H), 7.52 (dd, J = 8, 1 Hz, 1 H), 7.76 (dd, J = 8, 2 Hz, 1 H), 7.93 (d, J = 2 Hz, 1 H), 12.85 (br s, 1 H) | 568 |
| 135 | B | 1H NMR (400 MHz, DMSO-d6) δ ppm 1.71 (dquin, J = 26, 6 Hz, 2 H), 2.11-2.28 (m, 4 H), 2.66-2.72 (m, 2 H), 2.88 (t, J = 7 Hz, 2 H), 4.00 (br s, 2 H), 4.17 (br s, 2 H), 4.47 (dt, J = 47, 6 Hz, 2 H), 6.13 (t, J = 2 Hz, 1 H), 6.82 (d, J = 9 Hz, 2 H), 6.87 (d, J = 8 Hz, 1 H), 6.93 (d, J = 9 Hz, 2 H), 7.04-7.15 (m, 1 H), 7.22 (m, 1 H), 7.76 (dd, J = 8, 2 Hz, 1 H), 7.93 (d, J = 2 Hz, 1 H), 12.56 (br s, 1 H) | 522 |
| 136 | B | 1H NMR (400 MHz, DMSO-d6) δ ppm 1.79 (dquin, J = 26, 6 Hz, 2 H), 2.14-2.23 (m, 4 H), 2.25 (s, 3 H), 2.83-3.04 (m, 4 H), 4.24-4.36 | 550 |

TABLE 1b-continued

| Ex. or cmpds | Preparation Method | NMR | MASS: LC/MS (m/z, MH+): |
|---|---|---|---|
| | | (m, 2 H), 4.49 (dt, J = 47, 6 Hz, 2 H), 4.45-4.52 (m, 2 H), 6.19 (s, 1 H), 6.76 (d, J = 8 Hz, 2 H), 6.87 (d, J = 6 Hz, 1 H), 6.88-6.95 (m, 2 H), 7.31-7.38 (m, 2 H), 7.44 (dd, J = 9, 2 Hz, 1 H), 7.76 (dd, J = 8, 2 Hz, 1 H), 7.94 (d, J = 2 Hz, 1 H), 9.33-13.85 (m, 1 H) | |
| 137 | B | 1H NMR (400 MHz, DMSO-d6) δ ppm 1.73-1.91 (m, 2 H), 2.06-2.27 (m, 4 H), 2.91 (t, J = 6 Hz, 2 H), 2.96-3.10 (m, 2 H), 3.79 (s, 3 H), 4.35-4.42 (m, 2 H), 4.50 (dt, J = 47, 6 Hz, 2 H), 4.57-4.63 (m, 2 H), 6.23 (br s, 1 H), 6.80 (d, J = 8 Hz, 2 H), 6.85 (d, J = 8 Hz, 1 H), 6.90 (d, J = 8 Hz, 2 H), 7.14 (d, J = 9 Hz, 1 H), 7.21 (d, J = 2 Hz, 1 H), 7.53 (dd, J = 9, 2 Hz, 1 H), 7.74 (dd, J = 8, 2 Hz, 1 H), 7.91 (d, J = 2 Hz, 1 H), 9.98-13.83 (m, 1 H) | 566 |
| 138 | A | 1H NMR (400 MHz, DMSO-d6) δ ppm 1.69 (dquin, J = 25, 6 Hz, 2 H), 2.11-2.31 (m, 4 H), 2.34 (s, 3 H), 2.61 (t, J = 7 Hz, 2 H), 2.75-3.03 (m, 2 H), 3.90 (br d, J = 2 Hz, 2 H), 4.08 (br d, J = 2 Hz, 2 H), 4.48 (dt, J = 47, 6 Hz, 2 H), 6.22 (br s, 1 H), 6.70 (br d, J = 8 Hz, 1 H), 6.77 (td, J = 9, 2 Hz, 1 H), 6.92 (t, J = 6 Hz, 1 H), 7.03 (br d, J = 10 Hz, 1 H), 7.10 (d, J = 7 Hz, 1 H), 7.17 (br d, J = 8 Hz, 1 H), 7.32 (s, 1 H), 7.56-7.78 (m, 1 H), 7.89 (d, J = 2 Hz, 1 H), 12.83 (br s, 1 H) | 568 |
| 139 | A | 1H NMR (400 MHz, DMSO-d6) δ ppm 1.69 (dquin, J = 25, 6 Hz, 2 H), 2.13-2.30 (m, 4 H), 2.32 (s, 3 H), 2.60 (t, J = 7 Hz, 2 H), 2.80-3.17 (m, 2 H), 3.89 (m, 2 H), 4.09 (m, 2 H), 4.47 (dt, J = 47, 6 Hz, 2 H), 6.15 (br s, 1 H), 6.75 (m, 1 H), 6.79-7.28 (m, 3 H), 7.08-7.13 (m, 2 H), 7.40 (s, 1 H), 7.73 (dd, J = 8, 2 Hz, 1 H), 7.91 (d, J = 2 Hz, 1 H), 12.31-13.66 (m, 1 H) | 525 |
| 140 | B | 1H NMR (400 MHz, DMSO-d6) δ ppm 1.70-1.87 (m, 2 H), 2.14-2.31 (m, 4 H), 2.85-3.04 (m, 4 H), 4.17-4.34 (m, 2 H), 4.38-4.48 (m, 2 H), 4.49 (dt, J = 47, 6 Hz, 2 H), 6.19 (br s, 1 H), 6.83 (d, J = 8 Hz, 2 H), 6.87 (d, J = 8 Hz, 1 H), 6.91 (d, J = 8 Hz, 2 H), 7.53 (d, J = 2 Hz, 1 H), 7.58 (dd, J = 8, 3 Hz, 1 H), 7.66 (d, J = 8 Hz, 1 H), 7.76 (dd, J = 8, 2 Hz, 1 H), 7.94 (d, J = 2 Hz, 1 H), 12.65 (br s, 1 H) | 570 |
| 141 | C | 1H NMR (400 MHz, DMSO-d6) δ ppm 0.65-0.74 (m, 2 H), 0.92-1.02 (m, 2 H), 1.64-1.82 (m, 2 H), 1.98 (m, 1 H), 2.07-2.22 (m, 4 H), 2.70-3.03 (m, 4 H), 4.08 (br s, 2 H), 4.16-4.33 (m, 2 H), 4.47 (dt, J = 47, 6 Hz, 2 H), 6.11 (br s, 1 H), 6.79 (d, J = 8 Hz, 2 H), 6.84 (d, J = 8 Hz, 1 H), 6.86-6.91 (m, 2 H), 7.05 (d, J = 8 Hz, 1 H), 7.10 (dd, J = 8, 3 Hz, 1 H), 7.42 (d, J = 2 Hz, 1 H), 7.74 (dd, J = 8, 2 Hz, 1 H), 7.90 (d, J = 2 Hz, 1 H), 12.58 (br s, 1 H) | 576 |
| 142 | A | 1H NMR (400 MHz, DMSO-d6) δ ppm 1.56-1.77 (m, 2 H), 2.09-2.28 (m, 4 H), 2.58 (t, J = 7 Hz, 2 H), 2.84 (t, J = 6 Hz, 2 H), 3.87 (br s, 2 H), 4.04 (br s, 2 H), 4.46 (dt, J = 47, 6 Hz, 2 H), 6.10 (br s, 1 H), 6.67-6.80 (m, 3 H), 6.82-7.00 (m, 2 H), 7.10 (td, J = 10, 3 Hz, 1 H), 7.16-7.28 (m, 1 H), 7.66-7.76 (m, 1 H), 7.80-8.01 (m, 1 H) | 522 |
| 143 | B | 1H NMR (500 MHz, DMSO-d6) δ ppm 1.68 (dquin, J = 25, 6 Hz, 2 H), 2.16 (quin, J = 7 Hz, 2 H), 2.32 (t, J = 7 Hz, 2 H), 2.59 (t, J = 7 Hz, 2 H), 2.88 (t, J = 7 Hz, 2 H), 3.88 (d, J = 3 Hz, 2 H), 4.02 (d, J = 3 Hz, 2 H), 4.47 (dt, J = 47, 6 Hz, 2 H), 6.11 (quin, J = 2 Hz, 1 H), 6.83 (d, J = 8 Hz, 2 H), 6.85 (d, J = 8 Hz, 1 H), 6.94 (d, J = 8 Hz, 2 H), 7.37-7.46 (m, 1 H), 7.57 (s, 1 H), 7.61 (s, 1 H), 7.74 (dd, J = 8, 2 Hz, 1 H), 7.91 (d, J = 2 Hz, 1 H), 13.03 (br s, 1 H) | 570 |
| 144 | B | 1H NMR (400 MHz, DMSO-d6) δ ppm 1.69 (dquin, J = 25, 7 Hz, 2 H), 2.14 (quin, J = 7 Hz, 2 H), 2.30 (t, J = 7 Hz, 2 H), 2.36 (d, J = 2 Hz, 3 H), 2.61 (t, J = 7 Hz, 2 H), 2.86 (t, J = 7 Hz, 2 H), 3.91 (br s, 2 H), 4.05 (br s, 2 H), 4.47 (dt, J = 47, 6 Hz, 2 H), 6.11 (t, J = 2 Hz, 1 H), 6.81 (d, J = 8 Hz, 2 | 550 |

TABLE 1b-continued

| Ex. or cmpds | Preparation Method | NMR | MASS: LC/MS (m/z, MH+): |
|---|---|---|---|
| | | H), 6.85 (d, J = 8 Hz, 1 H), 6.91 (d, J = 8 Hz, 2 H), 7.27 (d, J = 8 Hz, 1 H), 7.33-7.41 (m, 2 H), 7.74 (dd, J = 8, 2 Hz, 1 H), 7.90 (d, J = 2 Hz, 1 H), 12.06-13.66 (m, 1 H) | |
| 145 | B | 1H NMR (400 MHz, DMSO-d6) δ ppm 1.69 (dquin, J = 25, 6 Hz, 2 H), 2.15 (quin, J = 7 Hz, 2 H), 2.25-2.32 (m, 5 H), 2.64 (t, J = 7 Hz, 2 H), 2.87 (t, J = 7 Hz, 2 H), 3.93 (br s, 2 H), 4.08 (br s, 2 H), 4.47 (dt, J = 47, 6 Hz, 2 H), 6.12 (m, 1 H), 6.81 (d, J = 8 Hz, 2 H), 6.86 (d, J = 8 Hz, 1 H), 6.91 (d, J = 9 Hz, 2 H), 7.18 (s, 1 H), 7.33 (br d, J = 16 Hz, 2 H), 7.74 (dd, J = 8, 2 Hz, 1 H), 7.91 (d, J = 2 Hz, 1 H), 12.71 (br s, 1 H) | 550 |
| 146 | B | 1H NMR (400 MHz, DMSO-d6) δ ppm 1.69 (dquin, J = 25, 7 Hz, 2 H), 2.17 (quin, J = 7 Hz, 2 H), 2.36 (t, J = 7 Hz, 2 H), 2.62 (t, J = 7 Hz, 2 H), 2.89 (t, J = 7 Hz, 2 H), 3.91 (br s, 2 H), 4.05 (br s, 2 H), 4.47 (dt, J = 47, 6 Hz, 2 H), 6.13 (quin, J = 2 Hz, 1 H), 6.83 (d, J = 8 Hz, 2 H), 6.88 (d, J = 8 Hz, 1 H), 6.94 (d, J = 8 Hz, 2 H), 7.69 (s, 1 H), 7.73 (d, J = 9 Hz, 1 H), 7.76 (dd, J = 8, 3 Hz, 1 H), 7.89 (d, J = 8 Hz, 1 H), 7.93 (d, J = 2 Hz, 1 H), 11.11-13.48 (m, 1 H) | 604 |
| 147 | C | 1H NMR (500 MHz, DMSO-d6) δ ppm 1.68 (dquin, J = 25, 7 Hz, 2 H), 2.13-2.27 (m, 4 H), 2.61 (t, J = 7 Hz, 2 H), 2.89-3.04 (m, 2 H), 3.90 (br s, 2 H), 4.06 (br s, 2 H), 4.46 (dt, J = 47, 6 Hz, 2 H), 6.07 (t, J = 2 Hz, 1 H), 6.80 (d, J = 8 Hz, 2 H), 6.88 (d, J = 8 Hz, 3 H), 7.38 (t, J = 8 Hz, 1 H), 7.50 (dd, J = 8, 2 Hz, 1 H), 7.70 (dd, J = 8, 2 Hz, 1 H), 7.76 (dd, J = 8, 2 Hz, 1 H), 7.93 (d, J = 2 Hz, 1 H), 12.17-13.31 (m, 1 H) | 570 |
| 148 | B | 1H NMR (500 MHz, DMSO-d6) δ ppm 1.71 (dquin, J = 25, 6 Hz, 2 H), 2.14 (quin, J = 7 Hz, 2 H), 2.29 (t, J = 8 Hz, 2 H), 2.69 (br s, 2 H), 2.85 (t, J = 7 Hz, 2 H), 3.84 (s, 3 H), 3.89-4.05 (m, 2 H), 4.15 (s, 2 H), 4.47 (dt, J = 47, 6 Hz, 2 H), 6.14 ( s, 1 H), 6.78-6.87 (m, 3 H), 6.93 (d, J = 8 Hz, 2 H), 7.10 (d, J = 9 Hz, 1 H), 7.32 (s, 1 H), 7.44 (d, J = 9 Hz, 1 H), 7.73 (dd, J = 8, 2 Hz, 1 H), 7.90 (s, 1 H), 12.76 (br s, 1 H) | 566 |
| 149 | B | 1H NMR (400 MHz, DMSO-d6) δ ppm 1.30 (t, J = 7 Hz, 3 H), 1.68 (dquin, J = 25, 7 Hz, 2 H), 2.14 (quin, J = 7 Hz, 2 H), 2.29 (t, J = 7 Hz, 2 H), 2.60 (t, J = 7 Hz, 2 H), 2.84 (t, J = 7 Hz, 2 H), 3.89 (br s, 2 H), 4.03 (br s, 2 H), 4.11 (q, J = 7 Hz, 2 H), 4.47 (dt, J = 47, 6 Hz, 2 H), 6.10 (quin, J = 2 Hz, 1 H), 6.81 (d, J = 8 Hz, 2 H), 6.84 (d, J = 8 Hz, 1 H), 6.92 (d, J = 8 Hz, 2 H), 7.08 (d, J = 9 Hz, 1 H), 7.32 (d, J = 2 Hz, 1 H), 7.40 (dd, J = 9, 2 Hz, 1 H), 7.73 (dd, J = 8, 2 Hz, 1 H), 7.89 (d, J = 2 Hz, 1 H), 11.35-14.00 (m, 1 H) | 580 |
| 150 | B | 1H NMR (400 MHz, DMSO-d6) δ ppm 1.68 (dquin, J = 25, 7 Hz, 2 H), 2.07-2.21 (m, 2 H), 2.27-2.32 (m, 2 H), 2.59 (t, J = 7 Hz, 2 H), 2.87 (t, J = 7 Hz, 2 H), 3.70 (s, 3 H), 3.88 (br d, J = 2 Hz, 2 H), 4.02 (br d, J = 2 Hz, 2 H), 4.47 (dt, J = 47, 6 Hz, 2 H), 6.11 (quin, J = 2 Hz, 1 H), 6.83 (d, J = 8 Hz, 2 H), 6.86 (d, J = 8 Hz, 1 H), 6.92 (d, J = 8 Hz, 2 H), 6.97-7.06 (m, 3 H), 7.74 (dd, J = 8, 2 Hz, 1 H), 7.91 (d, J = 2 Hz, 1 H), 11.26-13.86 (m, 1 H) | 566 |
| 151 | B | 1H NMR (400 MHz, DMSO-d6) δ ppm 1.61-1.73 (m, 2 H), 2.19-2.28 (m, 4 H), 2.59 (t, J = 6 Hz, 2 H), 2.88 (m, 1 H), 3.16 (m, 1 H), 3.87 (br s, 2 H), 4.01 (br s, 2 H), 4.46 (dt, J = 47, 6 Hz, 2 H), 6.06 (br s, 1 H), 6.78 (d, J = 9 Hz, 2 H), 6.87 (d, J = 6 Hz, 2 H), 6.89 (d, J = 5 Hz, 1 H), 7.53 (s, 1 H), 7.76 (dd, J = 8, 2 Hz, 1 H), 7.80 (d, J = 8 Hz, 1 H), 7.93 (d, J = 2 Hz, 1 H), 7.97 (d, J = 8 Hz, 1 H), 12.84 (br s, 1 H) | 604 |
| 152 | A | 1H NMR (400 MHz, DMSO-d6) δ ppm 1.68 (dquin, J = 25, 6 Hz, 2 H), 2.16-2.23 (m, 4 H), 2.24 (s, 3 H), 2.59 (t, J = 7 Hz, 2 H), 2.85-3.05 (m, 2 H), 3.90 (br s, 2 H), 4.00 (br s, 2 H), 4.46 (dt, J = 47, 6 Hz, 2 H), 6.20 (quin, J = 2 Hz, 1 H), | 536 |

TABLE 1b-continued

| Ex. or cmpds | Preparation Method | NMR | MASS: LC/MS (m/z, MH+): |
|---|---|---|---|
| | | 6.65-6.78 (m, 2 H), 6.86 (td, J = 9, 3 Hz, 1 H), 6.90 (d, J = 8 Hz, 1 H), 7.00 (dd, J = 10, 3 Hz, 1 H), 7.04 (dd, J = 8, 6 Hz, 1 H), 7.75 (dd, J = 8, 2 Hz, 1 H), 7.92 (d, J = 2 Hz, 1 H), 11.35-13.71 (m, 1 H) | |
| 153 | B | 1H NMR (500 MHz, DMSO-d6) δ ppm 1.68 (dquin, J = 25, 7 Hz, 2 H), 2.13-2.25 (m, 4 H), 2.62 (t, J = 7 Hz, 2 H), 2.85 (m, 1 H), 3.05 (m, 1 H), 3.91 (br s, 2 H), 4.07 (br s, 2 H), 4.46 (dt, J = 47, 6 Hz, 2 H), 6.08 (quin, J = 2 Hz, 1 H), 6.81 (d, J = 8 Hz, 2 H), 6.86 (d, J = 8 Hz, 1 H), 6.90 (d, J = 8 Hz, 2 H), 7.12 (dd, J = 9, 3 Hz, 1 H), 7.27 (td, J = 8, 3 Hz, 1 H), 7.75 (dd, J = 8, 2 Hz, 1 H), 7.80 (dd, J = 9, 6 Hz, 1 H), 7.91 (d, J = 2 Hz, 1 H) | 554 |
| 154 | B | 1H NMR (400 MHz, DMSO-d6) δ ppm 1.68 (dquin, J = 25, 7 Hz, 2 H), 2.16 (quin, J = 7 Hz, 2 H), 2.28-2.32 (m, 2 H), 2.60 (t, J = 7 Hz, 2 H), 2.87 (t, J = 7 Hz, 2 H), 3.89 (br s, 2 H), 4.04 (br s, 2 H), 4.47 (dt, J = 47, 6 Hz, 2 H), 6.11 (quin, J = 2 Hz, 1 H), 6.82 (d, J = 9 Hz, 2 H), 6.86 (d, J = 8 Hz, 1 H), 6.93 (d, J = 8 Hz, 2 H), 7.35 (dd, J = 11, 9 Hz, 1 H), 7.48 (dd, J = 7, 2 Hz, 1 H), 7.54 (ddd, J = 8, 5, 2 Hz, 1 H), 7.74 (dd, J = 8, 2 Hz, 1 H), 7.91 (d, J = 2 Hz, 1 H) | 554 |
| 155 | B | 1H NMR (400 MHz, DMSO-d6) δ ppm 1.68 (dquin, J = 25, 6 Hz, 2 H), 2.17 (quin, J = 7 Hz, 2 H), 2.27-2.36 (m, 2 H), 2.60 (t, J = 7 Hz, 2 H), 2.88 (t, J = 7 Hz, 2 H), 3.89 (br s, 2 H), 4.04 (br s, 2 H), 4.47 (dt, J = 47, 6 Hz, 2 H), 6.11 (quin, J = 2 Hz, 1 H), 6.83 (d, J = 8 Hz, 2 H), 6.87 (d, J = 8 Hz, 1 H), 6.93 (d, J = 8 Hz, 2 H), 7.28 (s, 1 H), 7.39 (d, J = 10 Hz, 1 H), 7.44 (dt, J = 9, 2 Hz, 1 H), 7.75 (dd, J = 8, 2 Hz, 1 H), 7.92 (d, J = 2 Hz, 1 H), 10.82-14.08 (m, 1 H) | 554 |
| 156 | B | 1H NMR (500 MHz, DMSO-d6) δ ppm 1.68 (dquin, J = 25, 6 Hz, 2 H), 2.11-2.23 (m, 4 H), 2.60 (t, J = 7 Hz, 2 H), 2.87 (t, J = 7 Hz, 2 H), 3.77 (s, 3 H), 3.87-3.91 (m, 2 H), 4.04-4.08 (m, 2 H), 4.47 (dt, J = 47, 6 Hz, 2 H), 6.10 (quin, J = 2 Hz, 1 H), 6.71 (d, J = 5 Hz, 1 H), 6.83-6.88 (m, 3 H), 6.93 (d, J = 8 Hz, 2 H), 7.75 (dd, J = 8, 2 Hz, 1 H), 7.92 (d, J = 2 Hz, 1 H), 7.99 (d, J = 1 Hz, 1 H) | 517 |
| 157 | A | 1H NMR (400 MHz, DMSO-d6) δ ppm 1.67 (dquin, J = 25, 6 Hz, 2 H), 2.11-2.25 (m, 7 H), 2.59 (t, J = 7 Hz, 2 H), 2.81-3.01 (m, 2 H), 3.88 (br s, 2 H), 4.00 (br s, 2 H), 4.46 (dt, J = 47, 6 Hz, 2 H), 6.27 (quin, J = 2 Hz, 1 H), 6.83-6.95 (m, 2 H), 6.95-7.13 (m, 5 H), 7.76 (dd, J = 8, 2 Hz, 1 H), 7.93 (d, J = 2 Hz, 1 H) | 568 |
| 158 | I | 1H NMR (400 MHz, DMSO-d6) δ ppm 1.69 (dsxt, J = 25, 5 Hz, 2 H), 2.11-2.38 (m, 4 H), 2.62 (t, J = 7 Hz, 2 H), 2.88-3.00 (m, 2 H), 3.88-3.99 (m, 2 H), 4.07-4.15 (m, 2 H), 4.47 (dt, J = 47, 6 Hz, 2 H), 6.19 (m, 1 H), 6.87 (d, J = 8 Hz, 1 H), 7.13 (d, J = 8 Hz, 1 H), 7.19 (dd, J = 11, 2 Hz, 1 H), 7.25 (dd, J = 8, 2 Hz, 1 H), 7.55 (d, J = 2 Hz, 1 H), 7.74 (dd, J = 8, 2 Hz, 1 H), 7.93 (d, J = 2 Hz, 1 H), 8.05 (s, 1 H), 12.59 (br s, 1 H) | 555 |
| 159 | H | 1H NMR (400 MHz, DMSO-d6) δ ppm 1.86-2.05 (m, 2 H), 2.10-2.30 (m, 4 H), 2.85-3.00 (m, 2 H), 3.23-3.32 (m hidden, 2 H), 4.54 (dt, J = 47, 6 Hz, 2 H), 4.78 (m, 1 H), 4.90-5.24 (m, 3 H), 6.41 (br t, J = 2 Hz, 1 H), 6.84 (d, J = 8 Hz, 1 H), 6.90 (d, J = 8 Hz, 1 H), 7.20 (t, J = 10 Hz, 1 H), 7.29 (d, J = 8 Hz, 1 H), 7.37 (dd, J = 8, 2 Hz, 1 H), 7.61 (br s, 1 H), 7.75 (dd, J = 8, 2 Hz, 1 H), 7.93 (d, J = 2 Hz, 1 H), 8.25 (d, J = 2 Hz, 1 H), 10.82 (br s, 1 H), 12.89 (br s, 1 H) | 537 |
| 160 | C | 1H NMR (500 MHz, DMSO-d6) δ ppm 1.73 (m, 1 H), 1.80-1.92 (m, 2 H), 1.96 (ddd, J = 8, 6, 2 Hz, 1 H), 2.10-2.21 (m, 4 H), 2.41 (m, 1 H), 2.60-2.96 (m, 7 H), 3.84-3.94 (m, 2 H), 4.01-4.08 (m, 2 H), 6.09 (tt, J = 58, 5 Hz, 1 H), 6.10 (m, 1 H), 6.78 (d, J = 8 Hz, 2 H), 6.82-6.92 (m, | 544 |

TABLE 1b-continued

| Ex. or cmpds | Preparation Method | NMR | MASS: LC/MS (m/z, MH+): |
|---|---|---|---|
| | | 4 H), 7.07 (dd, J = 8, 5 Hz, 1 H), 7.75 (dd, J = 8, 2 Hz, 1 H), 7.93 (d, J = 2 Hz, 1 H) | |
| 161 | C | 1H NMR (400 MHz, DMSO-d6) δ ppm 1.76-1.94 (m, 2 H), 1.96-2.07 (m, 2 H), 2.08-2.24 (m, 4 H), 2.63 (t, J = 7 Hz, 2 H), 2.75-2.93 (m, 6 H), 3.87-3.92 (m, 2 H), 4.00-4.08 (m, 2 H), 6.08 (tt, J = 58, 5 Hz, 1 H), 6.11 (m, 1 H), 6.72-7.01 (m, 7 H), 7.74 (dd, J = 8, 2 Hz, 1 H), 7.90 (d, J = 2 Hz, 1 H) | 544 |
| 162 | C | 1H NMR (400 MHz, DMSO-d6) δ ppm 1.74-1.99 (m, 4 H), 2.06-2.23 (m, 4 H), 2.35-2.46 (m hidden, 2 H), 2.63 (t, J = 7 Hz, 2 H), 2.74 (t, J = 7 Hz, 2 H), 2.87 (t, J = 6 Hz, 2 H), 3.83-3.95 (m, 2 H), 4.00-4.11 (m, 2 H), 6.08 (tt, J = 58, 5 Hz, 1 H), 6.11 (m, 1 H), 6.72-6.94 (m, 7 H), 7.74 (dd, J = 8, 2 Hz, 1 H), 7.91 (d, J = 2 Hz, 1 H) | 544 |
| 163 | C | 1H NMR (400 MHz, DMSO-d6) δ ppm 1.69-1.96 (m, 4 H), 2.06-2.24 (m, 4 H), 2.41-2.47 (m hidden, 2 H), 2.62 (t, J = 7 Hz, 2 H), 2.75 (t, J = 7 Hz, 2 H), 2.87 (t, J = 7 Hz, 2 H), 3.78-3.93 (m, 2 H), 3.99-4.09 (m, 2 H), 6.08 (tt, J = 58, 5 Hz, 1 H), 6.05 (m, 1 H), 6.74 (d, J = 8 Hz, 2 H), 6.84 (dd, J = 10, 8 Hz, 3 H), 6.96 (dd, J = 6, 2 Hz, 1 H), 7.00-7.09 (m, 2 H), 7.74 (dd, J = 8, 2 Hz, 1 H), 7.91 (d, J = 2 Hz, 1 H) | 526 |
| 164 | C | 1H NMR (400 MHz, DMSO-d6) δ ppm 1.75-1.94 (m, 2 H), 2.07-2.43 (m, 8 H), 2.62 (t, J = 7 Hz, 2 H), 2.88 (t, J = 6 Hz, 2 H), 3.83-3.92 (m, 2 H), 3.97-4.09 (m, 2 H), 6.08 (tt, J = 58, 5 Hz, 1 H), 6.08 (m, 1 H), 6.74 (d, J = 8 Hz, 2 H), 6.81-6.93 (m, 3 H), 7.25-7.46 (m, 3 H), 7.75 (dd, J = 8, 2 Hz, 1 H), 7.92 (d, J = 2 Hz, 1 H) | 562 |
| 165 | C | 1H NMR (400 MHz, DMSO-d6) δ ppm 1.70-2.29 (m, 10 H), 2.63 (t, J = 7 Hz, 2 H), 2.77 (t, J = 7 Hz, 2 H), 2.86 (t, J = 6 Hz, 2 H), 3.85-3.94 (m, 2 H), 3.97-4.10 (m, 2 H), 6.08 (tt, J = 58, 5 Hz, 1 H), 6.11 (m, 1 H), 6.74 (d, J = 9 Hz, 2 H), 6.79-6.93 (m, 4 H), 7.01 (dd, J = 8, 5 Hz, 1 H), 7.74 (dd, J = 8, 2 Hz, 1 H), 7.91 (d, J = 2 Hz, 1 H) | 544 |
| 166 | J | 1H NMR (400 MHz, DMSO-d6) δ ppm 0.65-0.80 (m, 3 H), 1.68 (dquin, J = 25, 6 Hz, 2 H), 1.92-2.47 (m, 3 H), 2.60 (t, J = 6 Hz, 2 H), 2.78-3.11 (m, 2 H), 3.82-3.93 (m, 2 H), 4.00-4.08 (m, 2 H), 4.46 (dt, J = 48, 5 Hz, 2 H), 6.05 (m, 1 H), 6.83-7.63 (m, 8 H), 7.74 (td, J = 8, 2 Hz, 1 H), 7.91 (s, 1 H) | 550 |
| 167 | B | 1H NMR (400 MHz, DMSO-d6) δ ppm 1.60-1.78 (m, 4 H), 1.83-1.91 (m, 2 H), 2.59-2.67 (m, 4 H), 3.57 (s, 2 H), 3.90-3.96 (m, 2 H), 4.10-4.17 (m, 2 H), 4.48 (dt, J = 47, 6 Hz, 2 H), 6.20 (quin, J = 2 Hz, 1 H), 6.84 (d, J = 8 Hz, 1 H), 7.14 (s, 4 H), 7.21 (td, J = 5, 2 Hz, 3 H), 7.27-7.36 (m, 2 H), 7.69 (dd, J = 8, 2 Hz, 1 H), 7.80 (d, J = 2 Hz, 1 H) | 482 |
| 168 | B | 1H NMR (400 MHz, DMSO-d6) δ ppm 1.71 (dquin, J = 25, 7 Hz, 2 H), 2.00 (t, J = 8 Hz, 2 H), 2.18 (quin, J = 7 Hz, 2 H), 2.43-2.47 (m, 2 H), 2.58-2.67 (m, 4 H), 2.79 (dd, J = 9, 7 Hz, 2 H), 3.90-3.96 (m, 2 H), 4.07-4.18 (m, 2 H), 4.49 (dt, J = 47, 6 Hz, 2 H), 6.20 (t, J = 2 Hz, 1 H), 6.76 (d, J = 8 Hz, 1 H), 6.97 (d, J = 8 Hz, 2 H), 7.03-7.11 (m, 4 H), 7.13-7.28 (m, 3 H), 7.66 (dd, J = 8, 2 Hz, 1 H), 7.82 (d, J = 2 Hz, 1 H) | 496 |
| 169 | B | 1H NMR (400 MHz, DMSO-d6) δ ppm 1.38-1.53 (m, 2 H), 1.54-1.93 (m, 7 H), 1.95-2.07 (m, 2 H), 2.08-2.23 (m, 2 H), 2.29-2.40 (m, 2 H), 2.58-2.76 (m, 4 H), 3.87-3.98 (m, 2 H), 4.09-4.18 (m, 2 H), 4.49 (dt, J = 47, 6 Hz, 2 H), 6.20 (t, J = 2 Hz, 1 H), 6.74 (d, J = 8 Hz, 1 H), 7.02 (d, J = 8 Hz, 2 H), 7.08-7.19 (m, 2 H), 7.65 (dd, J = 8, 2 Hz, 1 H), 7.81 (d, J = 2 Hz, 1 H) | 460 |
| 170 | D | 1H NMR (400 MHz, DMSO-d6) δ ppm 1.58-1.77 (m, 2 H), 2.02-2.14 (m, 2 H), 2.14-2.26 (m, 2 H), 2.58 (t, J = 7 Hz, 2 H), 2.69-2.86 (m, 2 H), 3.82-3.91 (m, 2 H), 3.99-4.06 (m, 2 H), 4.46 (dt, J = 47, 6 Hz, 2 H), 6.06 (t, J = 2 Hz, 1 H), | 508 |

TABLE 1b-continued

| Ex. or cmpds | Preparation Method | NMR | MASS: LC/MS (m/z, MH+): |
|---|---|---|---|
| | | 6.52-6.61 (m, 2 H), 6.72 (d, J = 2 Hz, 1 H), 6.76-6.81 (m, 2 H), 6.83-6.91 (m, 2 H), 7.15 (m, 1 H), 7.22 (m, 1 H), 7.54 (d, J = 2 Hz, 1 H), 9.46 (s, 1 H) | |
| 171 | D | 1H NMR (400 MHz, DMSO-d6) δ ppm 0.69 (s, 3 H), 0.90 (s, 3 H), 1.04-1.98 (m, 13 H), 2.11 (dt, J = 14, 7 Hz, 2 H), 2.63 (t, J = 7 Hz, 2 H), 2.71 (t, J = 7 Hz, 2 H), 3.87-3.97 (m, 2 H), 4.06-4.18 (m, 2 H), 4.48 (dt, J = 47, 6 Hz, 2 H), 6.20 (t, J = 2 Hz, 1 H), 6.75 (d, J = 8 Hz, 1 H), 6.97-7.04 (m, 2 H), 7.06-7.15 (m, 2 H), 7.65 (dd, J = 8, 2 Hz, 1 H), 7.82 (d, J = 2 Hz, 1 H) | 502 |
| 172 | D | 1H NMR (400 MHz, DMSO-d6) δ ppm 0.69 (s, 3 H), 0.90 (s, 3 H), 1.12 (m, 1 H), 1.19-1.35 (m, 5 H), 1.45-1.58 (m, 2 H), 1.62-1.83 (m, 3 H), 1.94 (m, 1 H), 2.05-2.17 (m, 2 H), 2.62 (t, J = 7 Hz, 3 H), 2.71 (t, J = 7 Hz, 2 H), 3.88-3.96 (m, 2 H), 4.06-4.15 (m, 2 H), 4.48 (dt, J = 47, 6 Hz, 2 H), 6.20 (t, J = 2 Hz, 1 H), 6.75 (d, J = 8 Hz, 1 H), 7.01 (d, J = 8 Hz, 2 H), 7.09 (d, J = 8 Hz, 2 H), 7.65 (dd, J = 8, 2 Hz, 1 H), 7.81 (d, J = 2 Hz, 1 H) | 502 |
| 173 | B | 1H NMR (400 MHz, DMSO-d6) δ ppm 1.21-1.36 (m, 2 H), 1.56-1.79 (m, 4 H), 1.86 (m, 1 H), 2.09-2.24 (m, 3 H), 2.62 (t, J = 7 Hz, 2 H), 2.68-2.77 (m, 2 H), 3.88-3.93 (m, 2 H), 4.01-4.11 (m, 2 H), 4.49 (dt, J = 47, 6 Hz, 2 H), 6.14 (t, J = 2 Hz, 1 H), 6.73 (d, J = 8 Hz, 1 H), 6.91-7.00 (m, 4 H), 7.01-7.08 (m, 2 H), 7.14 (m, 1 H), 7.21-7.28 (m, 2 H), 7.67 (dd, J = 8, 2 Hz, 1 H), 7.84 (d, J = 2 Hz, 1 H) | 508 |
| 174 | B | 1H NMR (400 MHz, DMSO-d6) δ ppm 0.92-1.06 (m, 2 H), 1.08-1.27 (m, 4 H), 1.42 (t, J = 5 Hz, 1 H), 1.49 (t, J = 7 Hz, 2 H), 1.52-1.61 (m, 2 H), 1.71 (dquin, J = 25, 6 Hz, 2 H), 1.78-1.90 (m, 2 H), 2.05 (quin, J = 7 Hz, 2 H), 2.58-2.73 (m, 4 H), 3.89-3.98 (m, 2 H), 4.10-4.21 (m, 2 H), 4.49 (dt, J = 47, 6 Hz, 2 H), 6.21 (t, J = 2 Hz, 1 H), 6.72 (d, J = 8 Hz, 1 H), 7.01-7.18 (m, 4 H), 7.66 (dd, J = 8, 2 Hz, 1 H), 7.81 (d, J = 2 Hz, 1 H) | 486 |
| 175 | D | 1H NMR (500 MHz, DMSO-d6) δ ppm 0.17 (dd, J = 8, 5 Hz, 1 H), 0.37 (t, J = 5 Hz, 1 H), 1.08 (dt, J = 8, 4 Hz, 1 H), 1.17 (m, 1 H), 1.50-1.78 (m, 5 H), 1.81-2.02 (m, 3 H), 2.04-2.25 (m, 3 H), 2.57-2.74 (m, 4 H), 3.90-3.97 (m, 2 H), 4.10-4.15 (m, 2 H), 4.49 (dt, J = 47, 6 Hz, 2 H), 6.19 (t, J = 2 Hz, 1 H), 6.74 (d, J = 8 Hz, 1 H), 6.99 (d, J = 8 Hz, 2 H), 7.07 (d, J = 8 Hz, 2 H), 7.66 (dd, J = 8, 2 Hz, 1 H), 7.81 (d, J = 2 Hz, 1 H) | 472 |
| 176 | B | 1H NMR (500 MHz, DMSO-d6) δ ppm 0.77-0.90 (m, 2 H), 1.41 (m, 1 H), 1.46-1.57 (m, 2 H), 1.71 (dquin, J = 25, 7 Hz, 2 H), 1.93-2.21 (m, 8 H), 2.60-2.73 (m, 4 H), 3.88-3.98 (m, 2 H), 4.07-4.18 (m, 2 H), 4.49 (dt, J = 47, 6 Hz, 2 H), 6.20 (t, J = 2 Hz, 1 H), 6.78 (d, J = 8 Hz, 1 H), 7.14 (s, 4 H), 7.68 (dd, J = 8, 2 Hz, 1 H), 7.82 (d, J = 2 Hz, 1 H) | 472 |
| 177 | B | 1H NMR (500 MHz, DMSO-d6) δ ppm 1.47-1.79 (m, 6 H), 2.13 (s, 4 H), 2.53-2.72 (m, 6 H), 2.82-2.98 (m, 2 H), 3.84-3.90 (m, 2 H), 3.98-4.04 (m, 2 H), 4.46 (dt, J = 47, 6 Hz, 2 H), 6.05 (t, J = 2 Hz, 1 H), 6.73 (d, J = 8 Hz, 2 H), 6.79-6.99 (m, 6 H), 7.73 (dd, J = 8, 2 Hz, 1 H), 7.90 (d, J = 2 Hz, 1 H) | 522 |
| 178 | D | 1H NMR (500 MHz, DMSO-d6) δ ppm 0.83 (m, 1 H), 1.04 (m, 1 H), 1.22 (d, J = 13 Hz, 1 H), 1.31-1.41 (m, 4 H), 1.49 (m, 1 H), 1.61-1.94 (m, 6 H), 2.05-2.23 (m, 4 H), 2.59-2.82 (m, 5 H), 3.87-3.97 (m, 2 H), 4.12 (br s, 2 H), 4.49 (dt, J = 47, 6 Hz, 2 H), 6.20 (m, 1 H), 6.72 (m, 1 H), 6.97-7.07 (m, 2 H), 7.08-7.17 (m, 2 H), 7.63 (m, 1 H), 7.81 (d, J = 2 Hz, 1 H) | 500 |
| 179 | J | 1H NMR (400 MHz, DMSO-d6) δ ppm 0.73 (d, J = 7 Hz, 3 H), 1.24 (s, 1 H), 1.59-1.77 (m, 2 H), 1.96 (m, 1 H), 2.23 (m, 1 H), 2.41 (m, 1 H), 2.60 (t, J = 7 Hz, 2 H), 2.74-2.92 (m, 1 H), 3.02 (m, 1 | 516 |

TABLE 1b-continued

| Ex. or cmpds | Preparation Method | NMR | MASS: LC/MS (m/z, MH+): |
|---|---|---|---|
| | | H), 3.88 (br s, 2 H), 4.04 (br s, 2 H), 4.46 (dt, J = 47, 6 Hz, 1 H), 6.05 (t, J = 2 Hz, 1 H), 6.82-6.91 (m, 1 H), 6.86 (d, J = 1 Hz, 4 H), 7.13-7.21 (m, 2 H), 7.24-7.29 (m, 2 H), 7.74 (dd, J = 8, 2 Hz, 1 H), 7.90 (d, J = 2 Hz, 1 H), 12.78 (s, 1 H) | |
| 180 | B | 1H NMR (400 MHz, DMSO-d6) δ ppm 1.68 (dquin, J = 25, 7 Hz, 2 H), 2.08-2.21 (m, 2 H), 2.27 (t, J = 7 Hz, 2 H), 2.60 (t, J = 7 Hz, 2 H), 2.85 (t, J = 7 Hz, 2 H), 3.85-3.93 (m, 2 H), 4.01-4.08 (m, 2 H), 4.47 (dt, J = 47, 6 Hz, 2 H), 6.10 (t, J = 2 Hz, 1 H), 6.78-6.86 (m, 3 H), 6.86-6.96 (m, 2 H), 7.13 (m, 1 H), 7.17-7.26 (m, 3 H), 7.73 (dd, J = 8, 2 Hz, 1 H), 7.90 (d, J = 2 Hz, 1 H) | 502 |
| 181 | B | 1H NMR (400 MHz, DMSO-d6) δ ppm 1.60-1.77 (m, 2 H), 2.06-2.20 (m, 2 H), 2.23-2.30 (m, 2 H), 2.60 (t, J = 7 Hz, 2 H), 2.84 (t, J = 7 Hz, 2 H), 3.89 (br s, 2 H), 4.05 (br s, 2 H), 4.47 (dt, J = 47, 6 Hz, 2 H), 6.10 (t, J = 2 Hz, 1 H), 6.77-6.86 (m, 3 H), 6.91 (d, J = 8 Hz, 2 H), 7.16-7.28 (m, 4 H), 7.73 (dd, J = 8, 2 Hz, 1 H), 7.89 (d, J = 2 Hz, 1 H) | 502 |
| 182 | B | 1H NMR (400 MHz, DMSO-d6) δ ppm 1.78-2.02 (m, 2 H), 2.12-2.23 (m, 2 H), 2.29-2.37 (m, 2 H), 2.89 (t, J = 7 Hz, 2 H), 3.25-3.31 (m hidden, 2 H), 4.53 (dt, J = 47, 6 Hz, 2 H), 4.76 (s, 2 H), 4.90-5.02 (m, 2 H), 6.36 (t, J = 2 Hz, 1 H), 6.81-6.90 (m, 3 H), 6.97 (d, J = 8 Hz, 2 H), 7.39-7.56 (m, 4 H), 7.75 (dd, J = 8, 2 Hz, 1 H), 7.93 (d, J = 2 Hz, 1 H) | 536 |
| 183 | B | 1H NMR (400 MHz, DMSO-d6) δ ppm 1.80-2.02 (m, 2 H), 2.08-2.28 (m, 4 H), 2.84-3.06 (m, 2 H), 3.14-3.23 (m hidden, 2 H), 4.52 (dt, J = 47, 6 Hz, 2 H), 4.68-4.79 (m, 2 H), 4.90-5.01 (m, 2 H), 6.32 (m, 1 H), 6.76-6.98 (m, 5 H), 7.23 (m, 1 H), 7.38-7.53 (m, 2 H), 7.69-7.81 (m, 2 H), 7.93 (d, J = 2 Hz, 1 H) | 536 |
| 184 | J | 1H NMR (400 MHz, DMSO-d6) δ ppm 0.73 (d, J = 7 Hz, 3 H), 1.67 (dquin, J = 25, 7 Hz, 2 H), 1.96 (m, 1 H), 2.23 (m, 1 H), 2.42 (m, 1 H), 2.59 (t, J = 7 Hz, 2 H), 2.82 (ddd, J = 10, 7, 3 Hz, 1 H), 3.01 (m, 1 H), 3.87 (s, 2 H), 4.02 (s, 2 H), 4.46 (dt, J = 47, 6 Hz, 2 H), 6.05 (t, J = 2 Hz, 1 H), 6.78-6.98 (m, 5 H), 7.17 (d, J = 9 Hz, 2 H), 7.26 (d, J = 8 Hz, 2 H), 7.73 (dd, J = 8, 2 Hz, 1 H), 7.90 (d, J = 2 Hz, 1 H), 12.68 (br s, 1 H) | 516 |
| 185 | B | 1H NMR (400 MHz, DMSO-d6) δ ppm 1.71-1.94 (m, 2 H), 2.08-2.23 (m, 2 H), 2.25-2.41 (m, 2 H), 2.81-2.97 (m, 2 H), 2.98-3.26 (m partially hidden, 4 H), 4.23-4.75 (m, 4 H), 6.18-8.43 (m, 12 H) | 536 |
| 186 | K | 1H NMR (400 MHz, DMSO-d6) δ ppm 0.63 (s, 3 H), 0.88 (s, 3 H), 1.02-1.40 (m, 6 H), 1.45-1.58 (m, 2 H), 1.65-1.78 (m, 2 H), 1.82-2.05 (m, 2 H), 2.10-2.20 (m, 2 H), 2.32 (m, 1 H), 2.64 (t, J = 7 Hz, 2 H), 2.73 (t, J = 7 Hz, 2 H), 3.96 (s, 2 H), 4.16 (s, 2 H), 4.49 (dt, J = 47, 6 Hz, 2 H), 6.30 (br s, 1 H), 6.85 (d, J = 8 Hz, 1 H), 7.38 (dd, J = 11, 2 Hz, 1 H), 7.67 (dd, J = 8, 2 Hz, 1 H), 7.83 (d, J = 2 Hz, 1 H), 8.28 (t, J = 2 Hz, 1 H), 11.92-13.55 (m, 1 H) | 521 |
| 187 | B | 1H NMR (500 MHz, DMSO-d6) δ ppm 0.60 (m, 1 H), 0.70 (m, 1 H), 0.75-0.97 (m, 2 H), 1.26-1.38 (m, 2 H), 1.42-1.55 (m, 3 H), 1.58-1.83 (m, 6 H), 1.89-2.11 (m, 4 H), 2.54-2.76 (m, 4 H), 3.94 (br s, 2 H), 4.13 (br s, 2 H), 4.49 (dt, J = 48, 6 Hz, 2 H), 6.20 (quin, J = 2 Hz, 1 H), 6.74 (d, J = 8 Hz, 1 H), 7.11 (s, 4 H), 7.66 (dd, J = 8, 2 Hz, 1 H), 7.81 (d, J = 2 Hz, 1 H) | 550 |
| 188 | K | 1H NMR (400 MHz, DMSO-d6) δ ppm 0.64-1.52 (m, 10 H), 1.52-2.13 (m, 7 H), 2.13-2.25 (m, 2 H), 2.63 (t, J = 1 Hz, 2 H), 2.74 (br t, J = 7 Hz, 2 H), 3.96 (br s, 2 H), 4.17 (br s, 2 H), 4.49 (dt, J = 48, 6 Hz, 2 H), 6.30 (br s, 1 H), 6.82 (d, | 507 |

TABLE 1b-continued

| Ex. or cmpds | Preparation Method | NMR | MASS: LC/MS (m/z, MH+): |
|---|---|---|---|
| | | J = 8 Hz, 1 H), 7.37 (dd, J = 11, 2 Hz, 1 H), 7.67 (dd, J = 8, 2 Hz, 1 H), 7.83 (d, J = 2 Hz, 1 H), 8.28 (s, 1 H) | |

The examples which follow describe the preparation of some compounds of formula (I) described herein. The numbers of the compounds exemplified below match those given in the Tables 1a and 1b above. All reactions are performed under inert atmosphere, unless otherwise stated.

In the following examples, when the source of the starting products is not specified, it should be understood that said products are known compounds.

INTERMEDIATES

Intermediate 1: 3-(4-Bromobenzylidene)-1-(3-fluoropropyl)azetidine

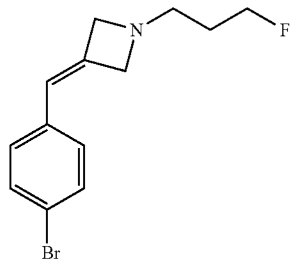 [SMILES: FCCCN1CC(=Cc2ccc(Br)cc2)C1]

Step 1: Tert-butyl 3-(4-bromobenzylidene)azetidine-1-carboxylate

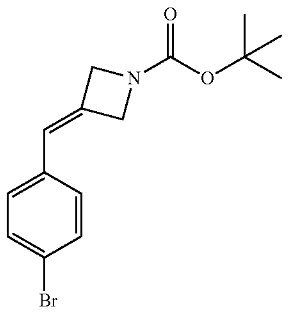 [SMILES: CC(C)(C)OC(=O)N1CC(=Cc2ccc(Br)cc2)C1]

Method 1

To a solution of (4-bromobenzyl)triphenylphosphonium bromide (79.2 g, 155 mmol) in DMF (400 mL) was added NaH (6.18 g, 155 mmol, 60% purity in weight) at 0° C. The mixture was stirred at 0° C. for 15 min To this reaction mixture, a solution of tert-butyl 3-oxoazetidine-1-carboxylate (24.1 g, 141 mmol) in DMF (160 mL) was added. The mixture was stirred at 20° C. for 9 hours. The reaction mixture was quenched by addition of saturated aqueous solution of $NH_4Cl$ (100 mL) at 0° C. The reaction mixture was filtered and the filtrate was concentrated under reduced pressure to give 60.0 g (crude) of tert-butyl 3-(4-bromobenzylidene)azetidine-1-carboxylate as a yellow solid.

LC/MS (m/z, MH+): 324

Method 2

A mixture of tert-butyl 3-methyleneazetidine-1-carboxylate (12.5 g, 73.9 mmol), 1-bromo-4-iodobenzene (23 g, 81.3 mmol), potassium carbonate (20.4 g, 148 mmol), tetrabutylammonium bromide (23.8 g, 73.9 mmol) and palladium(II) acetate (1.66 g, 7.39 mmol) in DMF (125 mL) was heated to 60° C. for 16 hours. After cooling to room temperature, EtOAc (500 ml) and water (500 mL) were added. After decantation, the organic phase was washed twice with water (500 ml), dried over $MgSO_4$, filtered, concentrated under reduced pressure and purified by flash chromatography, eluting with DCM to give 20.7 g (86%) of tert-butyl 3-(4-bromobenzylidene)azetidine-1-carboxylate as a beige solid.

LC/MS (m/z, MH+): 324

Step 2: 3-(4-Bromobenzylidene)azetidine, trifluoroacetic acid

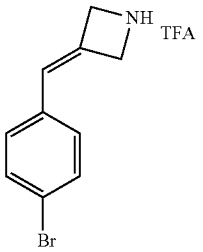 [SMILES: Brc1ccc(C=C2CNC2)cc1]

A mixture of tert-butyl 3-(4-bromobenzylidene)azetidine-1-carboxylate (60 g, 185 mmol) and TFA (192 mL, 2.59 mol) in DCM (300 mL) was stirred at room temperature for 15 hours. The reaction mixture was concentrated under reduced pressure to give a residue. The crude product was triturated with EtOAc (50 mL) and filtered to give 28 g (45%) of 3-(4-bromobenzylidene)azetidine, trifluoroacetic acid.

LC/MS (m/z, MH+): 224

Step 3: 3-(4-Bromobenzylidene)-1-(3-fluoropropyl)azetidine

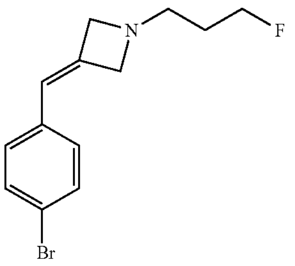 [SMILES: FCCCN1CC(=Cc2ccc(Br)cc2)C1]

A mixture of 1-fluoro-3-iodopropane (11.5 g, 61.2 mmol), 3-[(4-bromophenyl)methylene]-azetidine, trifluoroacetic acid (23.0 g, 68.0 mmol), KOH (5.72 g, 102 mmol) in DMF (100 ml) was stirred at room temperature for 10 hours. The reaction mixture was quenched by addition of water (200 mL), and then extracted with EtOAc (500 mL). After decantation, the organic phase was dried over $MgSO_4$, filtered, concentrated under reduced pressure, and the residue obtained was purified by flash chromatography, eluting with a gradient of DCM/MeOH: from 100/00 to 95/05 to give 8.9 g (47% yield) of 3-(4-bromobenzylidene)-1-(3-fluoropropyl)azetidine.

LC/MS (m/z, MH+): 284

Intermediate 2: 1-(3-Fluoropropyl)-3-(4-(4,4,5,5-tetramethyl-1,3,2-dioxaborolan-2-yl)benzylidene) azetidine

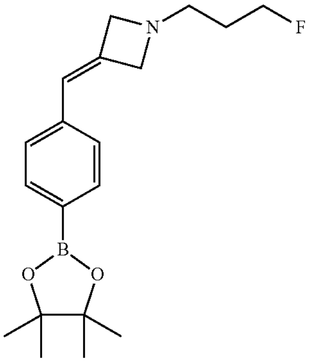 [SMILES: CC1(C)OB(c2ccc(C=C3CN(CCCF)C3)cc2)OC1(C)C]

A mixture of 3-(4-bromobenzylidene)-1-(3-fluoropropyl) azetidine (2 g, 7.04 mmol), bis(pinacolato)diboron (2.5 g, 9.85 mmol), KOAc (1.73 g, 17.6 mmol) and Pd(dppf)$Cl_2$ (257 mg, 0.35 mmol) in dioxane (40 mL) was degassed and purged with argon and then the mixture was refluxed for 2.5 hours. After cooling to room temperature, AcOEt (50 mL), $Et_2O$ (20 mL), water (30 mL) and brine (30 mL) were added under stirring. After decantation, the organic phase was washed twice with 30 mL of brine then concentrated under reduced pressure. The residue obtained was purified by flash chromatography eluting with a gradient of cyclohexane/AcOEt from 100/0 to 0/100 then a gradient of DCM/MeOH from 99/01 to to give 1.2 g (51% yield) of 1-(3-fluoropropyl)-3-(4-(4,4,5,5-tetramethyl-1,3,2-dioxaborolan-2-yl)benzylidene)azetidine.

LC/MS (m/z, MH+): 332

Intermediate 3: Methyl 9-(4,4,5,5-tetramethyl-1,3,2-dioxaborolan-2-yl)-6,7-dihydro-5H-benzo[7]annulene-3-carboxylate

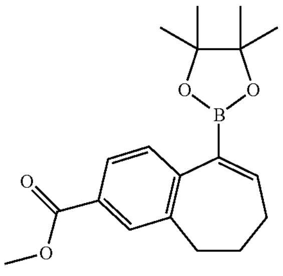

A mixture of methyl 9-(((trifluoromethyl)sulfonyl)oxy)-6,7-dihydro-5H-benzo[7]annulene-3-carboxylate (15 g, 42.82 mmol) (prepared according to WO2017140669), in toluene (150 ml), $Pd(PPh_3)_2Cl_2$ (1.53 g, 2.14 mmol), $PPh_3$ (673.87 mg, 2.57 mmol), bis(pinacolato)diboron (144.08 g, 52.67 mmol) and PhOK (8.04 g, 60.80 mmol) was heated to 75° C. for 1.5 h. The yellow suspension becomes orange then brown. After cooling to room temperature, DCM (150 mL) and water (150 mL) were added, and decantation was done by hydrophobic column. The organic phase was concentrated under reduced pressure. The residue obtained was purified by flash chromatography, eluting with a gradient of heptane/DCM: from 85/15 to 20/80 to give 10.1 g (72%) of methyl 9-(4,4,5,5-tetramethyl-1,3,2-dioxaborolan-2-yl)-6,7-dihydro-5H-benzo[7]annulene-3-carboxylate as a white solid.

LC/MS (m/z, MH+): 329

Intermediate 4: Methyl 8-(2,4-dichlorophenyl)-9-(4,4,5,5-tetramethyl-1,3,2-dioxaborolan-2-yl)-6,7-dihydro-5H-benzo[7]annulene-3-carboxylate

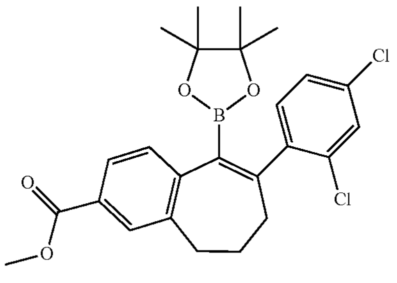 [SMILES: COC(=O)c1ccc2c(c1)CCCC(c1ccc(Cl)cc1Cl)=C2B1OC(C)(C)C(C)(C)O1]

Intermediate 4 was prepared following a similar procedure to that of Intermediate 3 from methyl 8-(2,4-dichlorophenyl)-9-(((trifluoromethyl)sulfonyl)oxy)-6,7-dihydro-5H-benzo[7]annulene-3-carboxylate (prepared according to WO2020/049153) to give 3.9 g (82%) of methyl 8-(2,4-dichlorophenyl)-9-(4,4,5,5-tetramethyl-1,3,2-dioxaborolan-2-yl)-6,7-dihydro-5H-benzo[7]annulene-3-carboxylate as a white solid.

LC/MS (m/z, MH+): 473

Intermediate 5: Methyl 8-(2,4-difluorophenyl)-9-(4,4,5,5-tetramethyl-1,3,2-dioxaborolan-2-yl)-6,7-dihydro-5H-benzo[7]annulene-3-carboxylate

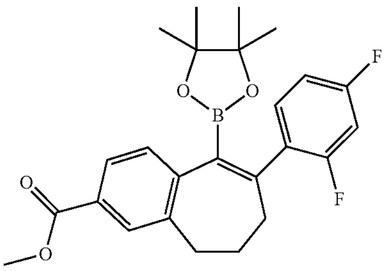 [SMILES: COC(=O)c1ccc2c(c1)CCCC(c1ccc(F)cc1F)=C2B1OC(C)(C)C(C)(C)O1]

Step 1: Methyl 6-(2,4-difluorophenyl)-5-oxo-6,7,8,9-tetrahydro-5H-benzo[7]annulene-2-carboxylate

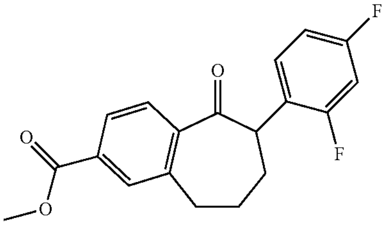 [SMILES: COC(=O)c1ccc2c(c1)CCCC(c1ccc(F)cc1F)C2=O]

Argon is bubbled for 10 minutes in a mixture of 1-bromo-2,4-difluoro-benzene (6.63 g, 34.37 mmol), methyl 5-oxo-6,7,8,9-tetrahydro-5H-benzo[7]annulene-2-carboxylate (5 g, 22.91 mmol), $K_2CO_3$ (12.67 g, 91.66 mmol) in toluene (40 mL). After addition of 4,5-bis(diphenylphosphino)-9,9-dimethylxanthene (1.32 g, 2.29 mmol) and tris(dibenzylideneacetone)dipalladium(0) (1.05 g, 1.15 mmol), the reaction mixture was heated to reflux for 72 hours. After cooling to room temperature, water (40 mL) and DCM (40 mL) were added. After decantation, the aqueous phase was washed three times with 40 ml of DCM. The combined organic phases were dried over $MgSO_4$, filtered and concentrated under reduced pressure. The residue obtained was purified by flash chromatography, eluting with a gradient of Heptane/EtOAc from 100/00 to 90/10 to give 2.55 g (34%) of methyl 6-(2,4-difluorophenyl)-5-oxo-6,7,8,9-tetrahydro-5H-benzo[7]annulene-2-carboxylate.

LC/MS (m/z, MH+): 331

Step 2: Methyl 8-(2,4-difluorophenyl)-9-(((trifluoromethyl)sulfonyl)oxy)-6,7-dihydro-5H-benzo[7]annulene-3-carboxylate

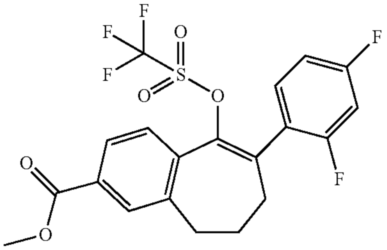 [SMILES: COC(=O)c1ccc2c(c1)CCCC(c1ccc(F)cc1F)=C2OS(=O)(=O)C(F)(F)F]

To a suspension of sodium hydride (545 mg, 13.62 mmol, 60% purity in weight) in MeTHF (22 mL) cooled at 5° C. was added DBU (277 mg, 0.27 mL, 1.82 mmol) followed by a solution of methyl 6-(2,4-difluorophenyl)-5-oxo-6,7,8,9-tetrahydrobenzo[7]annulene-2-carboxylate (3 g, 9.08 mmol) and N,N-bis(trifluoromethylsulfonyl)aniline (4.2 g, 11.81 mmol) in THF. The cooling bath was removed to allow the temperature to warm up to room temperature. A mixture of acetic acid (0.4 mL) and water (32 mL) was dropwise added, followed by water (100 mL) and EtOAc (150 mL). After decantation, the organic phase was dried over $MgSO_4$, filtered and concentrated under reduced pressure The residue obtained was purified by flash chromatography, eluting with DCM/heptane 50/50 to give 2.77 g (66%) of methyl 8-(2,4-difluorophenyl)-9-(((trifluoromethyl)sulfonyl)oxy)-6,7-dihydro-5H-benzo[7]annulene-3-carboxylate.

LC/MS (m/z, MH+): 463

Step 3: Methyl 8-(2,4-difluorophenyl)-9-(4,4,5,5-tetramethyl-1,3,2-dioxaborolan-2-yl)-6,7-dihydro-5H-benzo[7]annulene-3-carboxylate

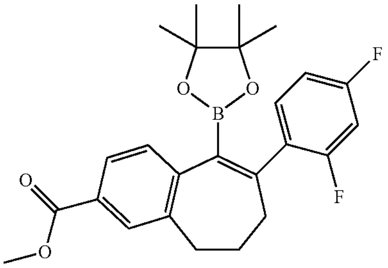 [SMILES: COC(=O)c1ccc2c(c1)CCCC(c1ccc(F)cc1F)=C2B1OC(C)(C)C(C)(C)O1]

Step 3 of Intermediate 5 was prepared following a similar procedure to that of Intermediate 3 from 8-(2,4-difluorophenyl)-9-(((trifluoromethyl)sulfonyl)oxy)-6,7-dihydro-5H-benzo[7]annulene-3-carboxylate to give 1.89 g (72%) of methyl 8-(2,4-difluorophenyl)-9-(4,4,5,5-tetramethyl-1,3,2-dioxaborolan-2-yl)-6,7-dihydro-5H-benzo[7]annulene-3-carboxylate.

LC/MS (m/z, MH+): 441

Intermediate 6: Methyl 8-(2-methyl-4-fluorophenyl)-9-(4,4,5,5-tetramethyl-1,3,2-dioxaborolan-2-yl)-6,7-dihydro-5H-benzo[7]annulene-3-carboxylate

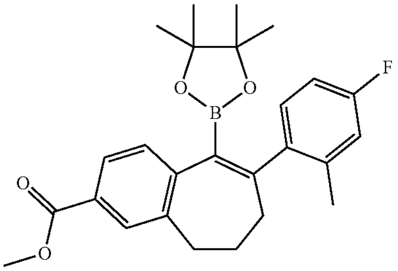 [SMILES: COC(=O)c1ccc2c(c1)CCCC(c1ccc(F)cc1C)=C2B1OC(C)(C)C(C)(C)O1]

Step 1: Methyl 6-(2-methyl-4-fluorophenyl)-5-oxo-6,7,8,9-tetrahydro-5H-benzo[7]annulene-2-carboxylate

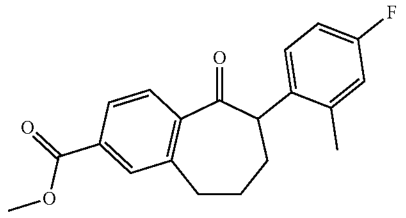 [SMILES: COC(=O)c1ccc2c(c1)CCCC(c1ccc(F)cc1C)C2=O]

Step 1 of Intermediate 6 was prepared following a similar procedure to that of step 1 of Intermediate 5 from 1-bromo-2-methyl-4-fluoro-benzene to give 700 mg (47%) of methyl 6-(2-methyl-4-fluorophenyl)-5-oxo-6,7,8,9-tetrahydro-5H-benzo[7]annulene-2-carboxylate.

LC/MS (m/z, MH+): 327

Step 2: Methyl 8-(2-methyl-4-fluorophenyl)-9-(((trifluoromethyl)sulfonyl)oxy)-6,7-dihydro-5H-benzo[7]annulene-3-carboxylate

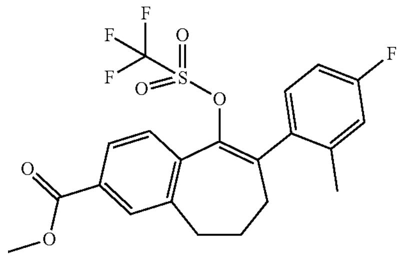 [SMILES: COC(=O)c1ccc2c(c1)CCCC(c1ccc(F)cc1C)=C2OS(=O)(=O)C(F)(F)F]

Step 2 of Intermediate 6 was prepared following a similar procedure to that of step 2 of Intermediate 5 from methyl 6-(2-methyl-4-fluorophenyl)-5-oxo-6,7,8,9-tetrahydrobenzo[7]annulene-2-carboxylate to give 7.86 g (82%) of methyl 8-(2-methyl-4-fluorophenyl)-9-(((trifluoromethyl)sulfonyl)oxy)-6,7-dihydro-5H-benzo[7]annulene-3-carboxylate.

LC/MS (m/z, MH+): 459

Step 3: Methyl 8-(2-methyl-4-fluorophenyl)-9-(4,4,5,5-tetramethyl-1,3,2-dioxaborolan-2-yl)-6,7-dihydro-5H-benzo[7]annulene-3-carboxylate

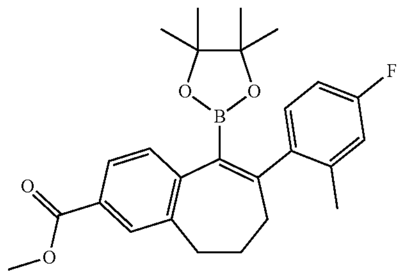 [SMILES: COC(=O)c1ccc2c(c1)CCCC(c1ccc(F)cc1C)=C2B1OC(C)(C)C(C)(C)O1]

Step 3 of Intermediate 6 was prepared following a similar procedure to that of Intermediate 3 from methyl 8-(2-methyl-4-fluorophenyl)-9-(((trifluoromethyl)sulfonyl)oxy)-6,7-dihydro-5H-benzo[7]annulene-3-carboxylate to give 3.93 g (43%) of methyl 8-(2-methyl-4-fluorophenyl)-9-(4,4,5,5-tetramethyl-1,3,2-dioxaborolan-2-yl)-6,7-dihydro-5H-benzo[7]annulene-3-carboxylate.

LC/MS (m/z, MH+): 437

Intermediate 7: Methyl 8-bromo-9-(4-((1-(3-fluoropropyl)azetidin-3-ylidene)methyl)phenyl)-6,7-dihydro-5H-benzo[7]annulene-3-carboxylate

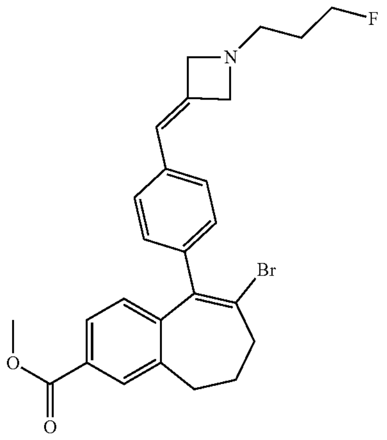 [SMILES: COC(=O)c1ccc2c(c1)CCCC(Br)=C2c1ccc(C=C2CN(CCCF)C2)cc1]

Method 1

Step 1: Methyl 9-(4-aminophenyl)-6,7-dihydro-5H-benzo[7]annulene-3-carboxylate

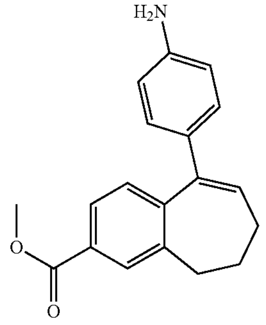 [SMILES: COC(=O)c1ccc2c(c1)CCCC=C2c1ccc(N)cc1]

A mixture of methyl 9-(((trifluoromethyl)sulfonyl)oxy)-6,7-dihydro-5H-benzo[7]annulene-3-carboxylate (20 g, 57.09 mmol) (prepared according to WO2017140669), 4-(4,4,5,5-tetramethyl-1,3,2-dioxaborolan-2-yl)aniline (13.13 g, 59.95 mmol), $Cs_2CO_3$ (37.21 g, 114.2 mmol), and Pd(dppf)$Cl_2$, complex with DCM (1.25 g, 1.71 mmol) in dioxane (160 mL) and water (40 mL) was heated to 95° C. for 1 hour. Water (200 mL) and EtOAc (500 mL) were added. After decantation, the organic phase was dried over $MgSO_4$, filtered, concentrated under reduced pressure and the residue obtained was purified by flash chromatography eluting with cyclohexane/EtOAc: 85/15 to give 14.5 g (87%) of methyl 9-(4-aminophenyl)-6,7-dihydro-5H-benzo[7]annulene-3-carboxylate.

LC/MS (m/z, MH+): 294

Step 2: Methyl 9-(4-iodophenyl)-6,7-dihydro-5H-benzo[7]annulene-3-carboxylate

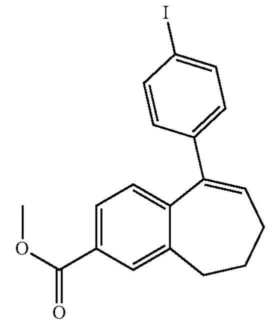 [SMILES: COC(=O)c1ccc2c(c1)CCCC=C2c1ccc(I)cc1]

To a mixture of methyl 9-(4-aminophenyl)-6,7-dihydro-5H-benzo[7]annulene-3-carboxylate (14.5 g, 49.4 mmol) in MeCN (270 mL) and 4N HCl (300 mL, 1200 mmol) cooled at 0° C., was slowly added a solution of sodium nitrite (3.58 g, 51.9 mmol) in water (20 mL). After stirring of the reaction mixture for 1 hour at 0° C., a solution of sodium iodide (14.8 g, 98.9 mmol) in water (40 mL) was added. The cooling bath was removed allowing the temperature to warm up to room temperature. After stirring for 4 hours at room temperature, $Et_2O$ (500 mL) and a 2N solution of $NaHSO_3$ (200 mL) were added. After decantation, the organic phase was washed twice with water (100 mL), then with brine (100 mL), dried over $MgSO_4$, filtered, concentrated under reduced pressure and the residue obtained was purified by flash chromatography eluting with cyclohexane/EtOAc: 95/05 to give 14.8 g (74%) of methyl 9-(4-iodophenyl)-6,7-dihydro-5H-benzo[7]annulene-3-carboxylate.

LC/MS (m/z, MH+): 405

Step 3: Methyl 8-bromo-9-(4-iodophenyl)-6,7-dihydro-5H-benzo[7]annulene-3-carboxylate

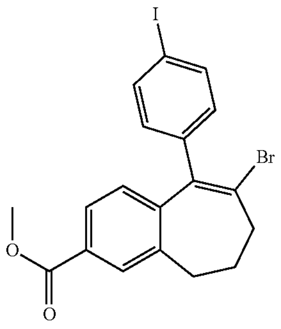 [SMILES: COC(=O)c1ccc2c(c1)CCCC(Br)=C2c1ccc(I)cc1]

To a mixture of methyl 9-(4-iodophenyl)-6,7-dihydro-5H-benzo[7]annulene-3-carboxylate (14.8 g, 36.6 mmol) in DCM (500 mL) was added pyridinium tribromide (12.9 g, 40.3 mmol). The reaction mixture was stirred for 18 hours at room temperature then diluted with $Et_2O$ (500 mL) and pentane (500 mL) and washed with a 0.2N solution of $NaHSO_3$ (100 mL) and twice with water (200 mL). After decantation, the organic phase was dried over $MgSO_4$, filtered, concentrated under reduced pressure to give 17.7 g (100%) of methyl 8-bromo-9-(4-iodophenyl)-6,7-dihydro-5H-benzo[7]annulene-3-carboxylate.

LC/MS (m/z, MH+): 484

Step 4: Tert-butyl 3-(4-(8-bromo-3-(methoxycarbonyl)-6,7-dihydro-5H-benzo[7]annulen-9-yl)benzylidene)azetidine-1-carboxylate

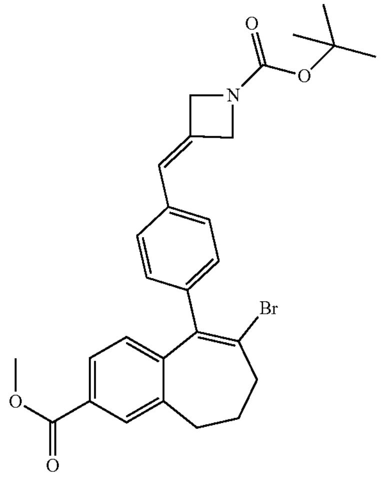 [SMILES: COC(=O)c1ccc2c(c1)CCCC(Br)=C2c1ccc(C=C2CN(C(=O)OC(C)(C)C)C2)cc1]

A solution of tert-butyl 3-methyleneazetidine-1-carboxylate (7.44 g, 44 mmol) and methyl 8-bromo-9-(4-iodophenyl)-6,7-dihydro-5H-benzo[7]annulene-3-carboxylate (17.7 g, 36.6 mmol) in DMF (200 mL) was degassed and purged with Ar for 5 min To this solution under stirring was added $K_2CO_3$ (10.1 g, 73.3 mmol), tetrabutylammonium bromide (11.8 g, 36.6 mmol) and palladium(II) acetate (0.83 g, 3.66 mmol). The mixture was heated to 50° C. for hours then cooled to room temperature. $Et_2O$ (300 mL) and water (300 mL) were added. After decantation, the aqueous phase was extracted with another 300 mL of $Et_2O$ and the combined organic phases were washed twice with water (200 mL), dried over $MgSO_4$, filtered, concentrated under reduced pressure and purified by flash chromatography, eluting with a gradient of cyclohexane/EtOAc (95/05 to 80/20) to give 14.7 g (76.5%) tert-butyl 3-(4-(8-bromo-3-(methoxycarbonyl)-6,7-dihydro-5H-benzo[7]annulen-9-yl)benzylidene) azetidine-1-carboxylate.

LC/MS (m/z, MH+): 525

Step 5: Methyl 9-(4-(azetidin-3-ylidenemethyl)phenyl)-8-bromo-6,7-dihydro-5H-benzo[7]annulene-3-carboxylate, trifluoroacetic acid

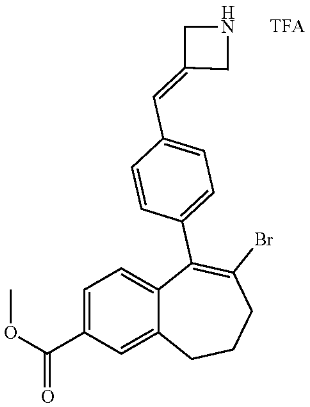 [SMILES: COC(=O)c1ccc2c(c1)CCCC(Br)=C2c1ccc(C=C2CNC2)cc1]

Step 5 of Intermediate 7 was prepared following a similar procedure to that of Step 2 of Intermediate 1 from tert-butyl 3-(4-(8-bromo-3-(methoxycarbonyl)-6,7-dihydro-5H-benzo[7]annulen-9-yl)benzylidene)azetidine-1-carboxylate to give 9.66 g (94%) of methyl 9-(4-(azetidin-3-ylidenemethyl)phenyl)-8-bromo-6,7-dihydro-5H-benzo[7]annulene-3-carboxylate, trifluoroacetic acid.

LC/MS (m/z, MH+): 425

Step 6: Methyl 8-bromo-9-(4-((1-(3-fluoropropyl)azetidin-3-ylidene)methyl)phenyl)-6,7-dihydro-5H-benzo[7]annulene-3-carboxylate

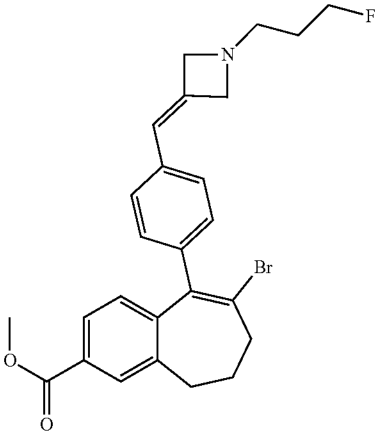 [SMILES: COC(=O)c1ccc2c(c1)CCCC(Br)=C2c1ccc(C=C2CN(CCCF)C2)cc1]

A mixture of 1-fluoro-3-iodopropane (2.88 g, 15.3 mmol) and methyl 9-(4-(azetidin-3-ylidenemethyl)phenyl)-8-bromo-6,7-dihydro-5H-benzo[7]annulene-3-carboxylate, trifluoroacetic acid (8.24 g, 15.3 mmol) in a mixture of NaOH 1N (46 mL, 46 mmol) and DCM (70 mL) was stirred at room temperature for 48 hours. DCM (200 mL) and water (100 mL) were added. After decantation, the organic phase was dried over $MgSO_4$, filtered and concentrated under reduced pressure to give a residue. The residue obtained was purified by flash chromatography, eluting with a gradient of cyclohexane/EtOAc: from 100/00 to to give 4.41 g (59% yield) of methyl 8-bromo-9-(4-((1-(3-fluoropropyl)azetidin-3-ylidene)methyl)phenyl)-6,7-dihydro-5H-benzo[7]annulene-3-carboxylate.

LC/MS (m/z, MH+): 485

Method 2

Step 1: Tert-butyl 3-(4-bromobenzoyl)azetidine-1-carboxylate

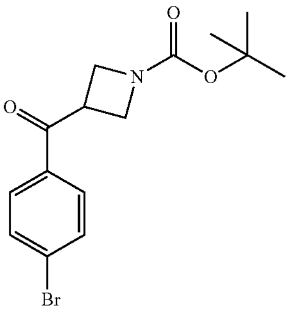 [SMILES: CC(C)(C)OC(=O)N1CC(C(=O)c2ccc(Br)cc2)C1]

To a solution of 1,4-dibromobenzene (290 g, 1.23 mol, 157 mL) in THF (1050 mL) was added n-BuLi (2.5 M, 491 mL) at −70° C. The mixture was stirred for 30 minutes before addition of tert-butyl 3-(methoxy(methyl)carbamoyl)azetidine-1-carboxylate (200 g, 819 mmol) in THF (420 mL) at −70° C. The reaction mixture was stirred for 1.5 hours. The solution was warmed up to −25° C. and slowly quenched by aqueous solution of saturated $NH_4Cl$ (2000 mL). The mixture was extracted twice with MTBE (800 mL), dried over $Na_2SO_4$, filtered, and concentrated under reduced pressure. The obtained residue was purified by flash chromatography eluting with a gradient of petroleum ether/EtOAc from 10/1 to 0/1 to give 180 g (65%) of tert-butyl 3-(4-bromobenzoyl)azetidine-1-carboxylate as a white solid.

LC/MS (m/z, MH+): 340

Step 2: Tert-butyl 3-(4-(3-(methoxycarbonyl)-6,7-dihydro-5H-benzo[7]annulen-9-yl)benzoyl)azetidine-1-carboxylate

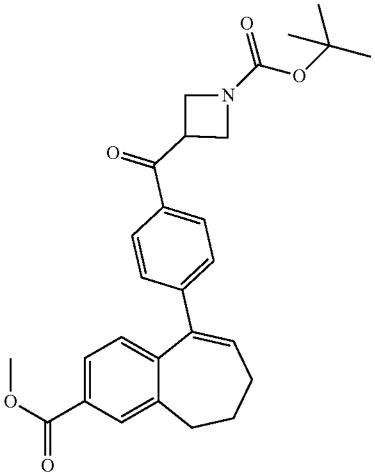 [SMILES: COC(=O)c1ccc2c(c1)CCCC=C2c1ccc(C(=O)C2CN(C(=O)OC(C)(C)C)C2)cc1]

Step 2 of Intermediate 7 (Method 2) was prepared following a similar procedure to that of step 1 of Intermediate 7 (Method 1) from methyl 9-(4,4,5,5-tetramethyl-1,3,2-dioxaborolan-2-yl)-6,7-dihydro-5H-benzo[7]annulene-3-carboxylate (Intermediate 3) and tert-butyl 3-(4-bromobenzoyl) azetidine-1-carboxylate to give 8.5 g (99%) of tert-butyl 3-(4-(3-(methoxycarbonyl)-6,7-dihydro-5H-benzo[7]annulen-9-yl)benzoyl)azetidine-1-carboxylate LC/MS (m/z, MH+): 462

Step 3: Tert-butyl 3-(4-(8-bromo-3-(methoxycarbonyl)-6,7-dihydro-5H-benzo[7]annulen-9-yl)benzoyl) azetidine-1-carboxylate

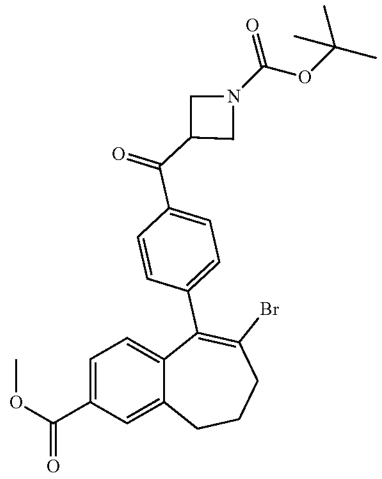 [SMILES: COC(=O)c1ccc2c(c1)CCCC(Br)=C2c1ccc(C(=O)C2CN(C(=O)OC(C)(C)C)C2)cc1]

Step 3 of Intermediate 7 (Method 2) was prepared following a similar procedure to that of step 3 of Intermediate 7 (Method 1) from tert-butyl 3-(4-(3-(methoxycarbonyl)-6,7-dihydro-1-carboxylate to give 6.1 g (88%) of tert-butyl 3-(4-(8-bromo-3-(methoxycarbonyl)-6,7-dihydro-5H-benzo[7]annulen-9-yl)benzoyl)azetidine-1-carboxylate.

LC/MS (m/z, MH+): 540

Step 4: Methyl 9-(4-(azetidine-3-carbonyl)phenyl)-8-bromo-6,7-dihydro-5H-benzo[7]annulene-3-carboxylate, trifluoroacetic acid

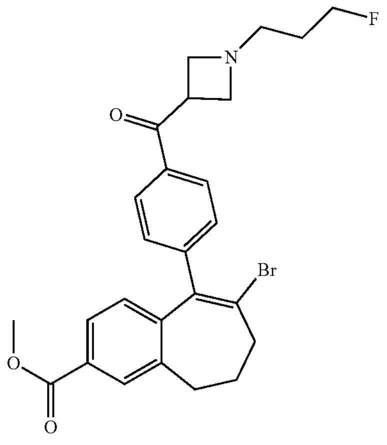 [SMILES: COC(=O)c1ccc2c(c1)CCCC(Br)=C2c1ccc(C(=O)C2CN(CCCF)C2)cc1]

Step 4 of Intermediate 7 (Method 2) was prepared following a similar procedure to that of step 2 of Intermediate 1 from tert-butyl 3-(4-(8-bromo-3-(methoxycarbonyl)-6,7-dihydro-5H-benzo[7]annulen-9-yl)benzoyl)azetidine-1-carboxylate to give 5 g (100%) of methyl 9-(4-(azetidine-3-carbonyl)phenyl)-8-bromo-6,7-dihydro-5H-benzo[7]annulene-3-carboxylate, trifluoroacetic acid.

LC/MS (m/z, MH+): 440

Step 5: Methyl 8-bromo-9-(4-(1-(3-fluoropropyl) azetidine-3-carbonyl)phenyl)-6,7-dihydro-5H-benzo[7]annulene-3-carboxylate

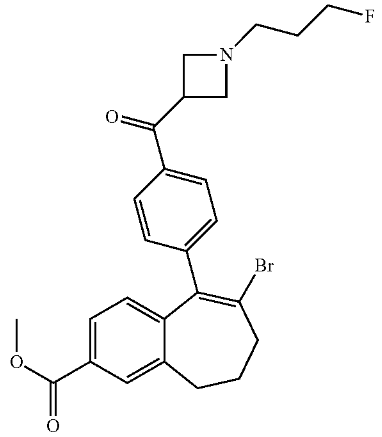 [SMILES: COC(=O)c1ccc2c(c1)CCCC(Br)=C2c1ccc(C(=O)C2CN(CCCF)C2)cc1]

A mixture of 1-fluoro-3-iodopropane (4.27 g, 22.7 mmol), methyl 9-(4-(azetidine-3-carbonyl)phenyl)-8-bromo-6,7-dihydro-5H-benzo[7]annulene-3-carboxylate, trifluoroacetic acid (5 g, 9.24 mmol), $K_2CO_3$ (4.71 g, 34 mmol) in MeCN (200 mL) was heated to 70° C. for 1 hour. The reaction mixture was quenched by addition of water (200 mL), and then extracted with EtOAc (500 mL). After decantation, the organic phase was dried over $MgSO_4$, filtered, concentrated under reduced pressure, and the residue obtained was purified by flash chromatography, eluting with a gradient of cyclohexane/EtOAc: from 100/00 to 00/100 to give 3 g (53%) of methyl 8-bromo-9-(4-(1-(3-fluoropropyl)azetidine-3-carbonyl)phenyl)-6,7-dihydro-5H-benzo[7]annulene-3-carboxylate.

LC/MS (m/z, MH+): 500

Step 6: Methyl 8-bromo-9-(4-((1-(3-fluoropropyl)azetidin-3-yl)(hydroxy)methyl)phenyl)-6,7-dihydro-5H-benzo[7]annulene-3-carboxylate

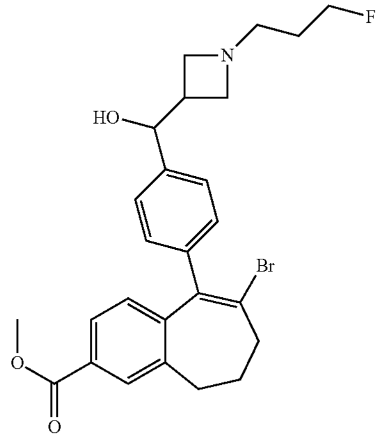 [SMILES: COC(=O)c1ccc2c(c1)CCCC(Br)=C2c1ccc(C(O)C2CN(CCCF)C2)cc1]

To a mixture of methyl 8-bromo-9-(4-(1-(3-fluoropropyl)azetidine-3-carbonyl)phenyl)-6,7-dihydro-5H-benzo[7]annulene-3-carboxylate (3 g, 6 mmol) in methanol (5 mL) cooled at 0° C. was added $NaBH_4$ (340 mg, 9 mmol). The reaction mixture was stirred at 0° C. for 30 minutes. 10% Citric acid aqueous solution (20 mL) and DCM (250 mL) were added. After decantation, the organic phase was dried over $MgSO_4$, filtered, concentrated under reduced pressure, and the residue obtained was purified by flash chromatography, eluting with a gradient of DCM/MeOH: from 100/00 to 05/95 to give 3 g (99%) of methyl 8-bromo-9-(4-((1-(3-fluoropropyl)azetidin-3-yl)(hydroxy)methyl)phenyl)-6,7-dihydro-5H-benzo[7]annulene-3-carboxylate.

LC/MS (m/z, MH+): 502

Step 7: Methyl 8-bromo-9-(4-((1-(3-fluoropropyl)azetidin-3-ylidene)methyl)phenyl)-6,7-dihydro-5H-benzo[7]annulene-3-carboxylate

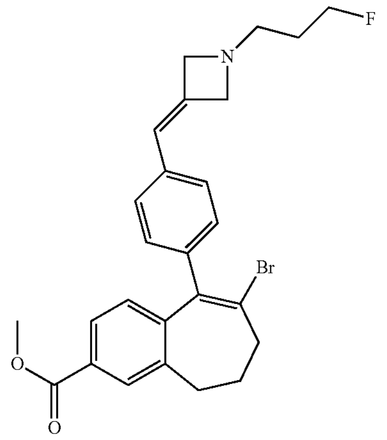 [SMILES: COC(=O)c1ccc2c(c1)CCCC(Br)=C2c1ccc(C=C2CN(CCCF)C2)cc1]

To a mixture of methyl 8-bromo-9-(4-((1-(3-fluoropropyl)azetidin-3-yl)(hydroxy)methyl)phenyl)-6,7-dihydro-5H-benzo[7]annulene-3-carboxylate (3 g, 5.97 mmol) in DCM (200 mL) were added pyridine (945 mg, 11.94 mmol, 0.96 mL) and trifluoromethylsulfonyl trifluoromethanesulfonate (3.37 g, 11.94 mmol, 2 mL). The reaction mixture was stirred at room temperature for 18 hours. DCM (400 mL) and a saturated aqueous solution of hydrogenocarbonate (300 mL) were added. After decantation, the organic phase was dried over $MgSO_4$, filtered and concentrated under reduced pressure to give a residue. The residue obtained was purified by flash chromatography, eluting with a gradient of DCM/MeOH: from 100/00 to 05/95 to give 1.9 g (66%) of methyl 8-bromo-9-(4-((1-(3-fluoropropyl)azetidin-3-ylidene)methyl)phenyl)-6,7-dihydro-5H-benzo[7]annulene-3-carboxylate.

LC/MS (m/z, MH+): 484

Alternative Method for Preparation of Step 6 of Intermediate 7 (Method 2)

Step 1: 3-Azetidinyl(4-bromophenyl)-methanone, trifluoroacetic acid

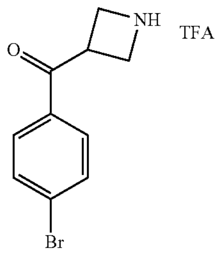 [SMILES: O=C(c1ccc(Br)cc1)C1CNC1]

Step 1 was prepared following a similar procedure to that of Step 2 of Intermediate 1 from tert-butyl 3-(4-bromobenzoyl)azetidine-1-carboxylate to give 41.6 g (100%) of 3-azetidinyl(4-bromophenyl)-methanone, trifluoroacetic acid.

LC/MS (m/z, MH+): 240

Step 2: (4-Bromophenyl)(3-fluoropropyl)azetidin-3-ylmethanone

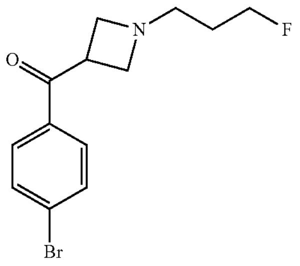 [SMILES: O=C(c1ccc(Br)cc1)C1CN(CCCF)C1]

Step 2 was prepared following a similar procedure to that of step 3 of intermediate 1 from 3-azetidinyl(4-bromophenyl)-methanone, trifluoroacetic acid to give 20 g (54%) of (4-bromophenyl)(3-fluoropropyl)azetidin-3-ylmethanone.

LC/MS (m/z, MH+): 300

Step 3: (4-Bromophenyl)(1-(3-fluoropropyl)azetidin-3-yl)methanol

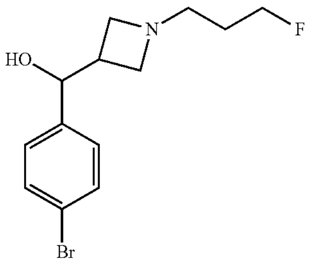 [SMILES: OC(c1ccc(Br)cc1)C1CN(CCCF)C1]

To a solution of (4-bromophenyl)(3-fluoropropyl)azetidin-3-ylmethanone (20.0 g, 66.6 mmol) in MeOH (100 mL) was added $NaBH_4$ (5.04 g, 133 mmol) at 0° C. The mixture was stirred at 15° C. for 1 hour. The reaction mixture was slowly quenched by water (100 mL) and concentrated under reduced pressure to remove MeOH. The aqueous phase was extracted three times with EtOAc (80 mL). After decantation, the organic phase was dried over $Na_2SO_4$, filtered, concentrated under reduced pressure, and the residue obtained was purified by flash chromatography eluting with a gradient of DCM: MeOH from 98/02 to 90/10 to give 16 g (77%) of (4-bromophenyl)(1-(3-fluoropropyl)azetidin-3-yl)methanol as a mixture of two isomers.

LC/MS (m/z, MH+): 302

Step 4: Methyl 9-(4-((1-(3-fluoropropyl)azetidin-3-yl)(hydroxy)methyl)phenyl)-6,7-dihydro-5H-benzo[7]annulene-3-carboxylate

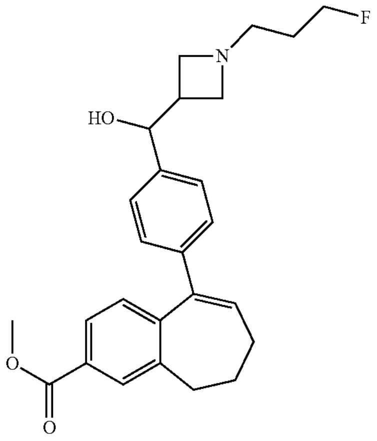 [SMILES: COC(=O)c1ccc2c(c1)CCCC=C2c1ccc(C(O)C2CN(CCCF)C2)cc1]

Step 4 was prepared following a similar procedure to that of step 1 of Intermediate 7 (Method 1) from methyl 9-(4,4,5,5-tetramethyl-1,3,2-dioxaborolan-2-yl)-6,7-dihydro-5H-benzo[7]annulene-3-carboxylate (Intermediate 3) and (4-bromophenyl)(1-(3-fluoropropyl)azetidin-3-yl)methanol to give 1.39 g (79%) of methyl 9-(4-((1-(3-fluoropropyl)azetidin-3-yl)(hydroxy)methyl)phenyl)-6,7-dihydro-5H-benzo[7]annulene-3-carboxylate.

LC/MS (m/z, MH+): 424

Step 5: Methyl 8-bromo-9-(4-((1-(3-fluoropropyl)azetidin-3-yl)(hydroxy)methyl)phenyl)-6,7-dihydro-5H-benzo[7]annulene-3-carboxylate

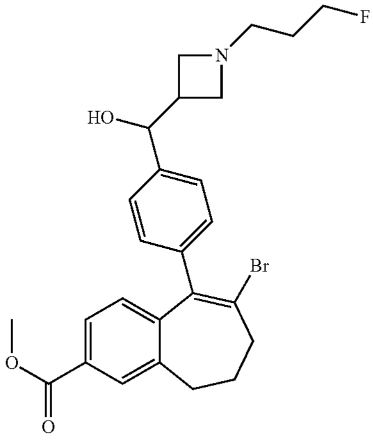 [SMILES: COC(=O)c1ccc2c(c1)CCCC(Br)=C2c1ccc(C(O)C2CN(CCCF)C2)cc1]

Step 5 was prepared following a similar procedure to that of step 3 of Intermediate 7 (Method 1) from methyl 9-(4-((1-(3-fluoropropyl)azetidin-3-yl)(hydroxy)methyl)phenyl)-6,7-dihydro-5H-benzo[7]annulene-3-carboxylate to give 1.59 g (100%) of methyl 8-bromo-9-(4-((1-(3-fluoropropyl)azetidin-3-yl)(hydroxy)methyl)phenyl)-6,7-dihydro-5H-benzo[7]annulene-3-carboxylate.

LC/MS (m/z, MH+): 502

Intermediate 8: Methyl 9-(4-((1-(3-fluoropropyl)azetidin-3-ylidene)methyl)phenyl)-8-(4,4,5,5-tetramethyl-1,3,2-dioxaborolan-2-yl)-6,7-dihydro-5H-benzo[7]annulene-3-carboxylate

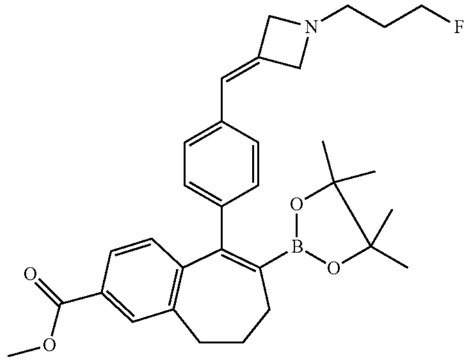 [SMILES: COC(=O)c1ccc2c(c1)CCCC(B1OC(C)(C)C(C)(C)O1)=C2c1ccc(C=C2CN(CCCF)C2)cc1]

A mixture of methyl 8-bromo-9-(4-((1-(3-fluoropropyl)azetidin-3-ylidene)methyl)phenyl)-6,7-dihydro-5H-benzo[7]annulene-3-carboxylate (Intermediate 7) (605 mg, 1.25 mmol) in toluene (30 mL), $Pd(PPh_3)_2Cl_2$ (35 mg, 50 μmol), $PPh_3$ (26 mg, 100 μmol), bis(pinacolato)diboron (793 mg, 3.12 mmol), $K_2CO_3$ (38 mg, 0.27 mmol) and PhOK (413 mg, 3.12 mmol) was degassed and purged with Ar for 5 min. then heated to 75° C. for 6 hours. After cooling to room temperature, $Et_2O$ (100 mL) and a 5% solution of $Na_2CO_3$ (50 mL) were added. After decantation, the organic phase was washed with water (50 mL), dried over $MgSO_4$, filtered, concentrated under reduced pressure, and the residue obtained was purified by flash chromatography, eluting with a gradient of cyclohexane/EtOAc: from 100/00 to to give 500 mg (75%) of methyl 9-(4-((1-(3-fluoropropyl)azetidin-3-ylidene)methyl)phenyl)-8-(4,4,5,5-tetramethyl-1,3,2-dioxaborolan-2-yl)-6,7-dihydro-5H-benzo[7]annulene-3-carboxylate.

LC/MS (m/z, MH+): 532

Intermediate 9: Methyl 8-bromo-9-(4-((1-(3,3-difluoropropyl)azetidin-3-ylidene)methyl)phenyl)-6,7-dihydro-5H-benzo[7]annulene-3-carboxylate

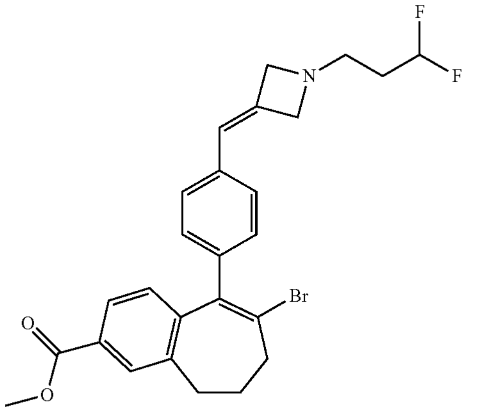 [SMILES: COC(=O)c1ccc2c(c1)CCCC(Br)=C2c1ccc(C=C2CN(CCC(F)F)C2)cc1]

Step 1: 3,3-Difluoropropyl trifluoromethanesulfonate

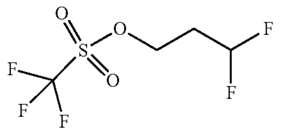 [SMILES: O=S(=O)(OCCC(F)F)C(F)(F)F]

To a solution of 3,3-difluoropropan-1-ol (1 g, 10.41 mmol) and 2,6-lutidine (2.66 mL, 22.9 mmol) in DCM (20 mL) cooled at 0° C. was dropwise added trifluoromethanesulfonic anhydride (1.93 mL, 11.45 mmol). The mixture was stirred at 0° C. for 30 minutes. $Et_2O$ and water were added. The aqueous phase was separated and extracted three times with ether. The combined organic phases were washed twice with a 10% aqueous solution of citric acid then water and dried over $Na_2SO_4$, filtered and concentrated under reduced pressure to give 2.06 g (86%) of 3,3-difluoropropyl trifluoromethanesulfonate which was used in the next step without further purification.

Step 2: Methyl 8-bromo-9-(4-((1-(3,3-difluoropropyl)azetidin-3-ylidene)methyl)phenyl)-6,7-dihydro-5H-benzo[7]annulene-3-carboxylate

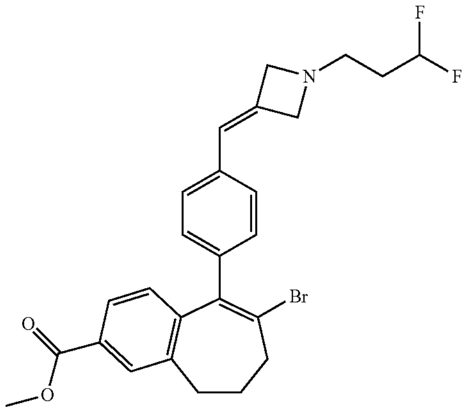 [SMILES: COC(=O)c1ccc2c(c1)CCCC(Br)=C2c1ccc(C=C2CN(CCC(F)F)C2)cc1]

To a suspension of methyl 9-(4-(azetidin-3-ylidenemethyl)phenyl)-8-bromo-6,7-dihydro-trifluoro acetic acid (Intermediate 7, Method 1, Step 5) (3 g, 5.57 mmol), 3,3-difluoropropyl trifluoromethanesulfonate (1.27 g, 5.57 mmol) in DCM (70 mL) was added NaOH 1N (22.29 mL, 22.29 mmol). The mixture was stirred at room temperature for 18 hours. Water (100 mL) was added. The aqueous phase was separated and extracted with a mixture of 150 mL of $Et_2O$ and 150 mL of EtOAc. The combined organic phases were washed with 100 mL of water, dried over $Na_2SO_4$, filtered, concentrated under reduced pressure. The residue obtained was purified by flash chromatography, eluting with a gradient of DCM/MeOH: from 100/0 to 80/20 to give 1.02 g (36%) of methyl 8-bromo-9-(4-((1-(3,3-difluoropropyl)azetidin-3-ylidene)methyl)phenyl)-6,7-dihydro-5H-benzo[7]annulene-3-carboxylate.

LC/MS (m/z, MH+): 502

Intermediate 10: Methyl 9-(4-((1-(3,3-difluoropropyl)azetidin-3-ylidene)methyl)phenyl)-8-(4,4,5,5-tetramethyl-1,3,2-dioxaborolan-2-yl)-6,7-dihydro-5H-benzo[7]annulene-3-carboxylate

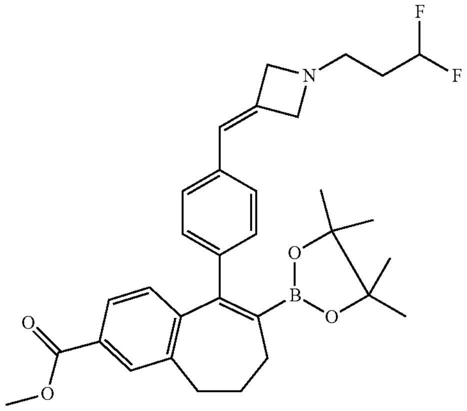 [SMILES: COC(=O)c1ccc2c(c1)CCCC(B1OC(C)(C)C(C)(C)O1)=C2c1ccc(C=C2CN(CCC(F)F)C2)cc1]

Intermediate 10 was prepared following a similar procedure to that of Intermediate 8 from methyl 8-bromo-9-(4-

((1-(3,3-difluoropropyl)azetidin-3-ylidene)methyl)phenyl)-6,7-dihydro-5H-benzo[7]annulene-3-carboxylate to give 118 mg (50%) of methyl 9-(4-((1-(3,3-difluoropropyl)azetidin-3-ylidene)methyl)phenyl)-8-(4,4,5,5-tetramethyl-1,3,2-dioxaborolan-2-yl)-6,7-dihydro-5H-benzo[7]annulene-3-carboxylate.

LC/MS (m/z, MH+): 550

Intermediate 11: 3-(4-Bromo-2,3-difluorobenzylidene)-1-(3-fluoropropyl)azetidine

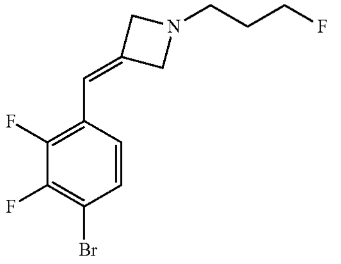

A mixture of 1-fluoro-3-iodopropane (501 mg, 2.66 mmol), 3-(4-bromo-2,3-difluorobenzylidene)azetidine, trifluoroacetic acid (950 mg, 2.54 mmol) commercially available, powder NaOH (304.7 mg, 7.6 mmol) in acetonitrile (30 mL) was stirred at room temperature for 18 hours. The reaction mixture was quenched by addition of $NH_4Cl$ saturated aqueous solution (50 mL) and extracted with EtOAc (50 mL). After decantation, the organic phase was dried over $MgSO_4$, filtered, concentrated under reduced pressure, and the residue obtained was purified by flash chromatography, eluting with a gradient of DCM/EtOAc: from 100/00 to 00/100 to give 0.65 g (34%) of 3-(4-bromo-2,3-difluorobenzylidene)-1-(3-fluoropropyl)azetidine.

LC/MS (m/z, MH+): 320

Intermediate 12: 3-(4-Bromo-2,6-difluorobenzylidene)-1-(3-fluoropropyl)azetidine

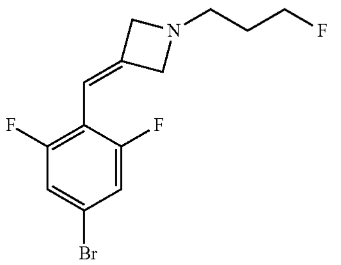 [SMILES: FCCCN1CC(=Cc2c(F)cc(Br)cc2F)C1]

Step 1: (4-Bromo-2,6-difluorophenyl)methanol

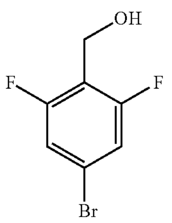 [SMILES: OCc1c(F)cc(Br)cc1F]

To a solution of 4-bromo-2,6-difluorobenzaldehyde (2 g, 9.05 mmol) in DCM (40 mL) and MeOH (10 mL) at 0° C. was portionwise added $NaBH_4$ (377 mg, 9.95 mmol). The reaction mixture was stirred at 0° C. for 1 hour then slowly quenched at 0° C. with a 1N aqueous solution of HCl. After stirring at 0° C. for 30 min, water was added, and the mixture was transferred in a separating funnel and extracted three times with EtOAc. The combined organic phases were washed with brine, dried over $Na_2SO_4$, filtered, concentrated to dryness, triturated with pentane and filtered to give 1.83 g (91%) of (4-bromo-2,6-difluorophenyl)methanol.

LC/MS (m/z, MH+): 223

Step 2: 5-Bromo-2-(bromomethyl)-1,3-difluorobenzene

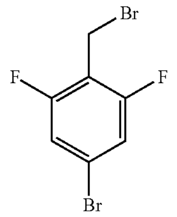 [SMILES: Fc1cc(Br)cc(F)c1CBr]

To a solution of (4-bromo-2,6-difluorophenyl)methanol (2.67 g, 11.99 mmol) in $Et_2O$ (60 mL) at 0° C. was dropwise added tribromophosphane (0.57 mL, 6 mmol). The reaction mixture was stirred for 12 hours at RT then slowly poured onto a saturated aqueous solution of $NaHCO_3$ under stirring. After stirring for 30 min, the mixture was transferred in a separating funnel and extracted three times with EtOAc. The combined organic phases were washed with brine, dried over $Na_2SO_4$, filtered and concentrated to dryness to give 3.04 g (88%) of 5-bromo-2-(bromomethyl)-1,3-difluorobenzene as a colorless oil which was used in the next step without further purification.

LC/MS (m/z, MH+): 285

Step 3: Diethyl (4-bromo-2,6-difluorobenzyl)phosphonate

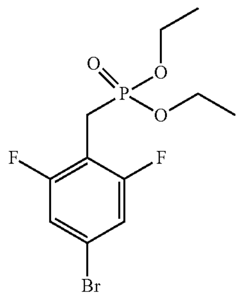 [SMILES: CCOP(=O)(Cc1c(F)cc(Br)cc1F)OCC]

A mixture of 5-bromo-2-(bromomethyl)-1,3-difluorobenzene (2.5 g, 8.74 mmol) and triethyl phosphite (2.25 mL, 13.12 mmol) was heated to 130° C. for 4 hours in a sealed tube. The resulting mixture was purified by flash chromatography eluting with a gradient of cyclohexane/EtOAc from 100/0 to 80/20 to give 2.95 g (98%) of diethyl (4-bromo-2,6-difluorobenzyl)phosphonate as a colorless oil.

LC/MS (m/z, MH+): 343

Step 4: Tert-butyl 3-(4-bromo-2,6-difluorobenzylidene)azetidine-1-carboxylate

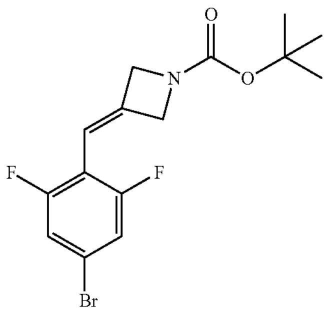 [SMILES: CC(C)(C)OC(=O)N1CC(=Cc2c(F)cc(Br)cc2F)C1]

To a solution of diisopropylamine (1.35 mL, 9.62 mmol) in THF (15 mL) at −78° C. under argon atmosphere was dropwise added a 2.5M solution of n-butyllithium in hexanes (3.5 mL, 8.74 mmol). The reaction mixture was stirred for 5 minutes then a solution of diethyl (4-bromo-2,6-difluorobenzyl)phosphonate (3 g, 8.74 mmol) in THF (15 mL) was added. After stirring for 45 minutes, a solution of tert-butyl 3-oxoazetidine-1-carboxylate (1.65 g, 9.62 mmol) in THF (30 mL) was added. The reaction mixture was stirred allowing the temperature to warm up to RT until completion. It was then transferred in a separating funnel containing an aqueous saturated solution of $NH_4Cl$, extracted three times with EtOAc. The combined organic phases were dried over $Na_2SO_4$, filtered, and concentrated to dryness. The resulting residue was then purified by flash chromatography eluting with a gradient of cyclohexane/EtOAc from 100/0 to 50/50 to give 1.67 g (53%) of tert-butyl 3-(4-bromo-2,6-difluorobenzylidene)azetidine-1-carboxylate as a colorless viscous oil.

LC/MS (m/z, MH+): 360

Step 5: 3-(4-Bromo-2,6-difluorobenzylidene)azetidine, trifluoroacetic acid

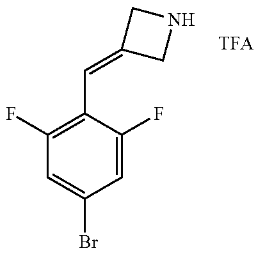 [SMILES: Fc1cc(Br)cc(F)c1C=C1CNC1]

Step 5 of Intermediate 12 was prepared following a similar procedure to that of step 2 of Intermediate 1 from tert-butyl 3-(4-bromo-2,6-difluorobenzylidene)azetidine-1-carboxylate to give 1.65 g (98%) of 3-(4-bromo-2,6-difluorobenzylidene)azetidine, trifluoroacetic acid as a white solid.

LC/MS (m/z, MH+): 260

Step 6: 3-(4-Bromo-2,6-difluorobenzylidene)-1-(3-fluoropropyl)azetidine

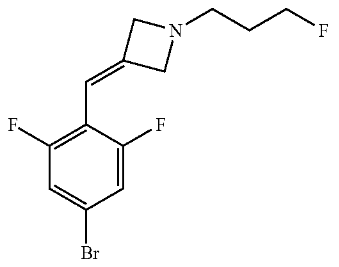

Step 6 of Intermediate 12 was prepared following a similar procedure to that of Intermediate 11 from 3-(4-bromo-2,6-difluorobenzylidene)azetidine trifluoroacetic acid to give 79 mg (18%) of 3-(4-bromo-2,6-difluorobenzylidene)-1-(3-fluoropropyl)azetidine. LC/MS (m/z, MH+): 320

Intermediate 13: 3-(4-Bromo-2,6-dimethylbenzylidene)-1-(3-fluoropropyl)azetidine

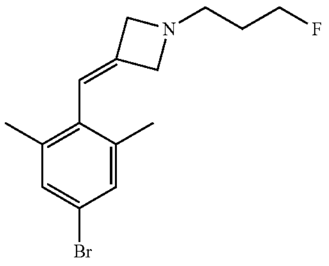 [SMILES: Cc1cc(Br)cc(C)c1C=C1CN(CCCF)C1]

Step 1: (4-Bromo-2,6-dimethylphenyl)methanol

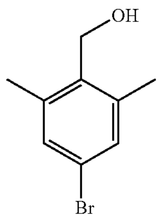

Step 1 of Intermediate 13 was prepared following a similar procedure to that of step 1 of Intermediate 12 from 4-bromo-2,6-dimethylbenzaldehyde to give 1.86 g (92%) of (4-bromo-2,6-dimethylphenyl)methanol.

LC/MS (m/z, MH+): 215

Step 2:
5-Bromo-2-(bromomethyl)-1,3-dimethylbenzene

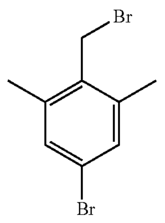

Step 2 of Intermediate 13 was prepared following a similar procedure to that of step 2 of Intermediate 12 from (4-bromo-2,6-dimethylphenyl)methanol to give 1.27 g (98%) of 5-bromo-2-(bromomethyl)-1,3-dimethylbenzene.

LC/MS (m/z, MH+): 277

Step 3: Diethyl (4-bromo-2,6-dimethylbenzyl)phosphonate

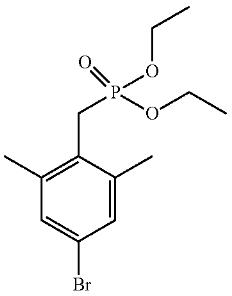 [SMILES: CCOP(=O)(Cc1c(C)cc(Br)cc1C)OCC]

Step 3 of Intermediate 13 was prepared following a similar procedure to that of step 3 of Intermediate 12 from 5-bromo-2-(bromomethyl)-1,3-dimethylbenzene to give 1.16 g (86%) of diethyl (4-bromo-2,6-dimethylbenzyl)phosphonate.

LC/MS (m/z, MH+): 335

Step 4: Tert-butyl 3-(4-bromo-2,6-dimethylbenzylidene)azetidine-1-carboxylate

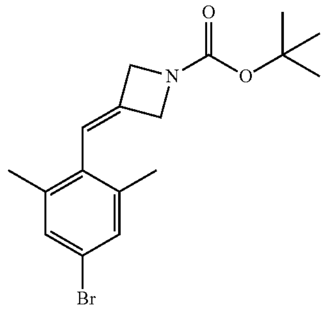 [SMILES: Cc1cc(Br)cc(C)c1C=C1CN(C(=O)OC(C)(C)C)C1]

Step 4 of Intermediate 13 was prepared following a similar procedure to that of step 4 of Intermediate 12 from diethyl (4-bromo-2,6-dimethylbenzyl)phosphonate to give 0.86 g (27%) of tert-butyl 3-(4-bromo-2,6-dimethylbenzylidene)azetidine-1-carboxylate.

LC/MS (m/z, MH+): 352

Step 5:
3-(4-Bromo-2,6-dimethylbenzylidene)azetidine, trifluoroacetic acid

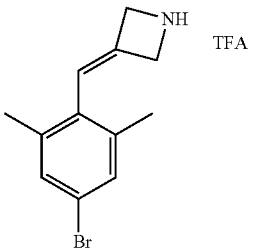

Step 5 of Intermediate 13 was prepared following a similar procedure to that of step 2 of Intermediate 1 from tert-butyl 3-(4-bromo-2,6-dimethylbenzylidene)azetidine-1-carboxylate to give 0.77 g (86%) of 3-(4-bromo-2,6-dimethylbenzylidene)azetidine, trifluoroacetic acid.

LC/MS (m/z, MH+): 252

Step 6: 3-(4-Bromo-2,6-dimethylbenzylidene)-1-(3-fluoropropyl)azetidine

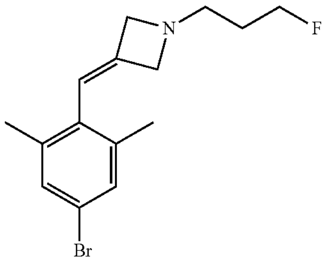 [SMILES: Cc1cc(Br)cc(C)c1C=C1CN(CCCF)C1]

Step 6 of Intermediate 13 was prepared following a similar procedure to that of Intermediate 11 from 3-(4-bromo-2,6-dimethylbenzylidene)azetidine trifluoroacetic acid to give 0.7 g (50%) of 3-(4-bromo-2,6-dimethylbenzylidene)-1-(3-fluoropropyl)azetidine.

LC/MS (m/z, MH+): 312

Intermediate 14: 3-(4-Bromo-2,5-difluorobenzylidene)-1-(3-fluoropropyl)azetidine

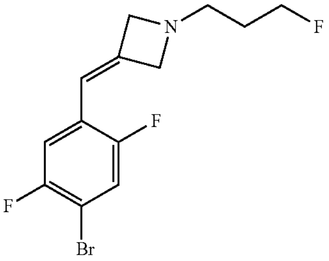 [SMILES: FCCCN1CC(=Cc2cc(F)c(Br)cc2F)C1]

Step 1: Diethyl (4-bromo-2,5-difluorobenzyl)phosphonate

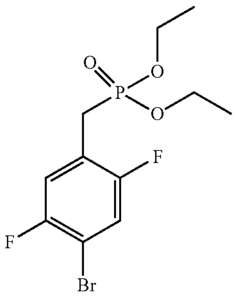 [SMILES: CCOP(=O)(Cc1cc(F)c(Br)cc1F)OCC]

Step 1 of Intermediate 14 was prepared following a similar procedure to that of Step 3 of Intermediate 12 from commercially available 1-bromo-4-(bromomethyl)-2,5-difluorobenzene to give 6.48 g (87%) of diethyl (4-bromo-2,5-difluorobenzyl)phosphonate.

LC/MS (m/z, MH+): 343

Step 2: Tert-butyl 3-(4-bromo-2,5-difluorobenzylidene)azetidine-1-carboxylate

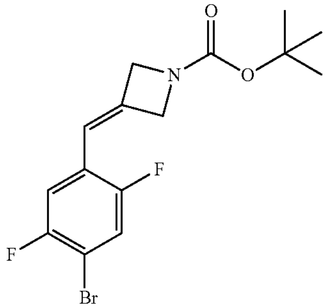 [SMILES: CC(C)(C)OC(=O)N1CC(=Cc2cc(F)c(Br)cc2F)C1]

Step 2 of Intermediate 14 was prepared following a similar procedure to that of step 4 of Intermediate 12 from diethyl (4-bromo-2,5-difluorobenzyl)phosphonate to give 1.16 g (73%) of tert-butyl 3-(4-bromo-2,5-difluorobenzylidene)azetidine-1-carboxylate.

LC/MS (m/z, MH+): 360

Step 3: 3-(4-Bromo-2,5-difluorobenzylidene)azetidine, trifluoroacetic acid

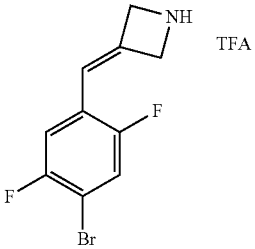 [SMILES: Fc1cc(C=C2CNC2)c(F)cc1Br]

Step 3 of Intermediate 14 was prepared following a similar procedure to that of step 2 of Intermediate 1 from tert-butyl 3-(4-bromo-2,5-difluorobenzylidene)azetidine-1-carboxylate to give 1.07 g (89%) of 3-(4-bromo-2,5-difluorobenzylidene)azetidine, trifluoroacetic acid.

LC/MS (m/z, MH+): 260

Step 4: 3-(4-Bromo-2,5-difluorobenzylidene)-1-(3-fluoropropyl)azetidine

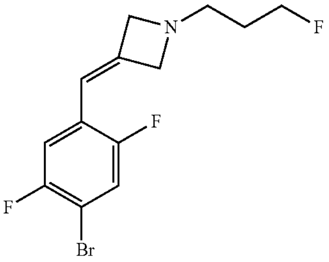 [SMILES: FCCCN1CC(=Cc2cc(F)c(Br)cc2F)C1]

Step 4 of Intermediate 14 was prepared following a similar procedure to that of Intermediate 11 from 3-(4-bromo-2,5-difluorobenzylidene)azetidine, trifluoroacetic acid to give 0.7 g (76%) of 3-(4-bromo-2,5-difluorobenzylidene)-1-(3-fluoropropyl)azetidine.

LC/MS (m/z, MH+): 320

Intermediate 15: 3-[(4-Bromo-3-fluoro-phenyl)methylene]-1-(3-fluoropropyl)azetidine

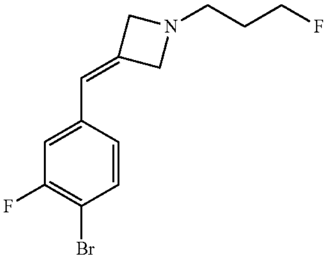 [SMILES: FCCCN1CC(=Cc2ccc(Br)c(F)c2)C1]

Step 1: (4-Bromo-3-fluoro-phenyl)methanol

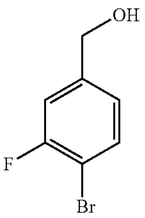

Step 1 of Intermediate 15 was prepared following a similar procedure to that of step 1 of Intermediate 12 from 4-bromo-3-fluoro-benzaldehyde to give 5 g (99%) of (4-bromo-3-fluoro-phenyl)methanol.

LC/MS (m/z, MH+): 205

Step 2: 1-Bromo-4-(bromomethyl)-2-fluoro-benzene

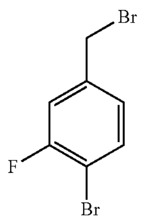

Step 2 of Intermediate 15 was prepared following a similar procedure to that of step 2 of Intermediate 12 from (4-bromo-3-fluoro-phenyl)methanol to give 5.1 g (77%) of 1-bromo-4-(bromomethyl)-2-fluoro-benzene.

LC/MS (m/z, MH+): 267

Step 3: 1-Bromo-4-(diethoxyphosphorylmethyl)-2-fluoro-benzene

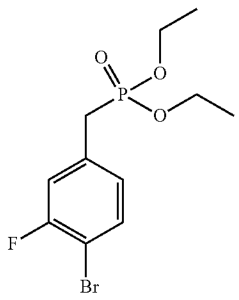 [SMILES: CCOP(=O)(Cc1ccc(Br)c(F)c1)OCC]

Step 3 of Intermediate 15 was prepared following a similar procedure to that of step 3 of Intermediate 12 from 1-bromo-4-(bromomethyl)-2-fluoro-benzene to give 3 g (99%) of 1-bromo-4-(diethoxyphosphorylmethyl)-2-fluoro-benzene.

LC/MS (m/z, MH+): 325

Step 4: Tert-butyl 3-[(4-bromo-3-fluoro-phenyl) methylene]azetidine-1-carboxylate

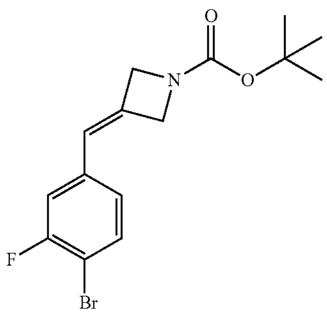 [SMILES: CC(C)(C)OC(=O)N1CC(=Cc2ccc(Br)c(F)c2)C1]

Step 4 of Intermediate 15 was prepared following a similar procedure to that of step 4 of Intermediate 12 from 1-bromo-4-(diethoxyphosphorylmethyl)-2-fluoro-benzene to give 3.75 g (85%) of tert-butyl 3-[(4-bromo-3-fluoro-phenyl)methylene]azetidine-1-carboxylate.

LC/MS (m/z, MH+): 342

Step 5: 3-[(4-Bromo-3-fluoro-phenyl)methylene] azetidine, trifluoroacetic acid

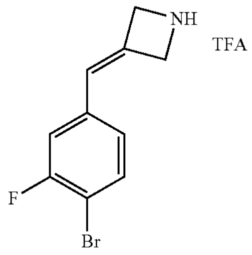 [SMILES: Fc1cc(C=C2CNC2)ccc1Br]

Step 5 of Intermediate 15 was prepared following a similar procedure to that of step 2 of Intermediate 1 from tert-butyl 3-[(4-bromo-3-fluoro-phenyl)methylene]azetidine-1-carboxylate to give 2.66 g of 3-[(4-bromo-3-fluoro-phenyl)methylene]azetidine, trifluoroacetic acid.

LC/MS (m/z, MH+): 242

Step 6: 3-[(4-Bromo-3-fluoro-phenyl)methylene]-1-(3-fluoropropyl)azetidine

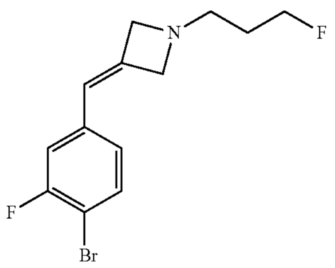

Step 6 of Intermediate 15 was prepared following a similar procedure to that of Intermediate 11 from 3-[(4-bromo-3-fluoro-phenyl)methylene]azetidine, trifluoroacetic acid to give 2.1 g (95%) of 3-[(4-bromo-3-fluoro-phenyl) methylene]-1-(3-fluoropropyl)azetidine.

LC/MS (m/z, MH+): 302

Intermediate 16: 3-[(4-Bromo-2-fluoro-5-methyl-phenyl)methylene]-1-(3-fluoropropyl)azetidine

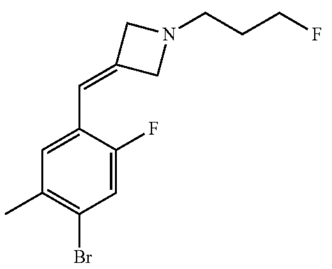 [SMILES: Cc1cc(C=C2CN(CCCF)C2)c(F)cc1Br]

Step 1: (4-Bromo-2-fluoro-5-methyl-phenyl)methanol

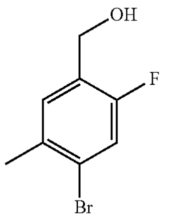

Step 1 of Intermediate 16 was prepared following a similar procedure to that of step 1 of Intermediate 12 from 4-bromo-2-fluoro-5-methyl-benzaldehyde to give 2 g (99%) of (4-bromo-2-fluoro-5-methyl-phenyl)methanol.

LC/MS (m/z, MH+): 219

Step 2: 1-Bromo-4-(bromomethyl)-5-fluoro-2-methyl-benzene

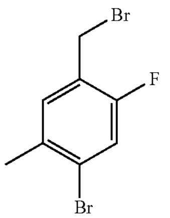

Step 2 of Intermediate 16 was prepared following a similar procedure to that of step 2 of Intermediate 12 from (4-bromo-2-fluoro-5-methyl-phenyl)methanol to give 2.7 g (91%) of 1-bromo-4-(bromomethyl)-5-fluoro-2-methyl-benzene.

LC/MS (m/z, MH+): 281

Step 3: 1-Bromo-4-(diethoxyphosphorylmethyl)-5-fluoro-2-methyl-benzene

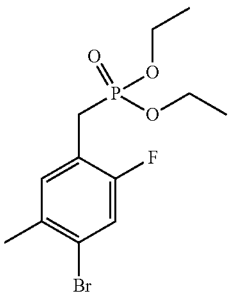 [SMILES: CCOP(=O)(Cc1cc(C)c(Br)cc1F)OCC]

Step 3 of Intermediate 16 was prepared following a similar procedure to that of step 3 of Intermediate 12 from 1-bromo-4-(bromomethyl)-5-fluoro-2-methyl-benzene to give 3.2 g (100%) of 1-bromo-4-(diethoxyphosphorylmethyl)-5-fluoro-2-methyl-benzene.

LC/MS (m/z, MH+): 339

Step 4: Tert-butyl 3-[(4-bromo-2-fluoro-5-methyl-phenyl)methylene]azetidine-1-carboxylate

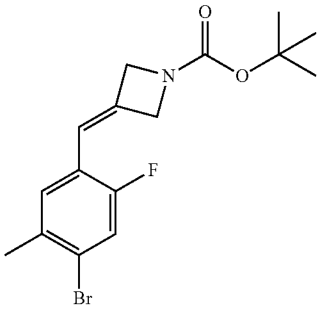 [SMILES: Cc1cc(C=C2CN(C(=O)OC(C)(C)C)C2)c(F)cc1Br]

Step 4 of Intermediate 16 was prepared following a similar procedure to that of step 4 of Intermediate 12 from 1-bromo-4-(diethoxyphosphorylmethyl)-5-fluoro-2-methyl-benzene to give 2.75 g (80%) of tert-butyl 3-[(4-bromo-2-fluoro-5-methyl-phenyl)methylene]azetidine-1-carboxylate.

LC/MS (m/z, MH+): 356

Step 5: 3-[(4-Bromo-2-fluoro-5-methyl-phenyl) methylene]azetidine, trifluoroacetic acid

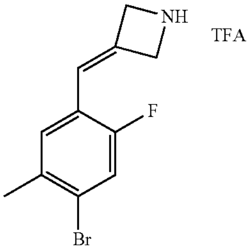

Step 5 of Intermediate 16 was prepared following a similar procedure to that of step 2 of Intermediate 1 from tert-butyl 3-[(4-bromo-2-fluoro-5-methyl-phenyl)methylene]azetidine-1-carboxylate to give 3.6 g of 3-[(4-bromo-2-fluoro-5-methyl-phenyl)methylene]azetidine, trifluoroacetic acid.

LC/MS (m/z, MH+): 256

Step 6: 3-[(4-Bromo-2-fluoro-5-methyl-phenyl) methylene]-1-(3-fluoropropyl)azetidine

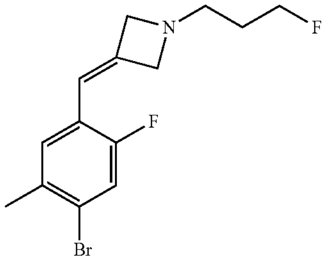 [SMILES: Cc1cc(C=C2CN(CCCF)C2)c(F)cc1Br]

Step 6 of Intermediate 16 was prepared following a similar procedure to that of Intermediate 11 from 3-[(4- bromo-2-fluoro-5-methyl-phenyl)methylene]azetidine, trifluoroacetic acid to give 145 mg (48%) of 3-[(4-bromo-2-fluoro-5-methyl-phenyl)methylene]-1-(3-fluoropropyl)azetidine.

LC/MS (m/z, MH+): 316

Intermediate 17: 3-[(4-Bromo-2-fluoro-3-methyl-phenyl)methylene]-1-(3-fluoropropyl)azetidine

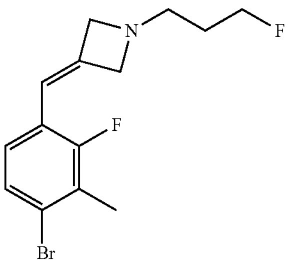 [SMILES: Cc1c(Br)ccc(C=C2CN(CCCF)C2)c1F]

Step 1: (4-Bromo-2-fluoro-3-methyl-phenyl)methanol

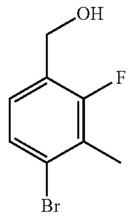

Step 1 of Intermediate 17 was prepared following a similar procedure to that of step 1 of Intermediate 12 from 4-bromo-2-fluoro-3-methyl-benzaldehyde to give 5.1 g (100%) of (4-bromo-2-fluoro-5-methyl-phenyl)methanol.

LC/MS (m/z, MH+): 219

Step 2: 1-Bromo-4-(bromomethyl)-3-fluoro-2-methyl-benzene

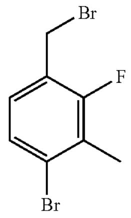

Step 2 of Intermediate 17 was prepared following a similar procedure to that of step 2 of Intermediate 12 from (4-bromo-2-fluoro-3-methyl-phenyl)methanol to give 2.33 g (91%) of 1-bromo-4-(bromomethyl)-3-fluoro-2-methyl-benzene.

LC/MS (m/z, MH+): 281

Step 3: 1-Bromo-4-(diethoxyphosphorylmethyl)-3-fluoro-2-methyl-benzene

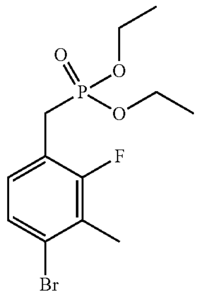 [SMILES: CCOP(=O)(Cc1ccc(Br)c(C)c1F)OCC]

Step 3 of Intermediate 17 was prepared following a similar procedure to that of step 3 of Intermediate 12 from 1-bromo-4-(bromomethyl)-3-fluoro-2-methyl-benzene to give 2.8 g (100%) of 1-bromo-4-(diethoxyphosphorylmethyl)-3-fluoro-2-methyl-benzene.

LC/MS (m/z, MH+): 339

Step 4: Tert-butyl 3-[(4-bromo-3-fluoro-2-methyl-phenyl)methylene]azetidine-1-carboxylate

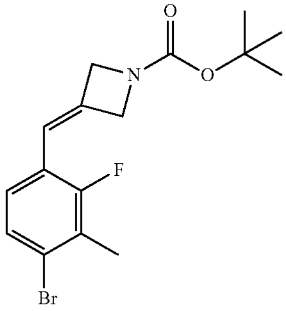 [SMILES: Cc1c(Br)ccc(C=C2CN(C(=O)OC(C)(C)C)C2)c1F]

Step 4 of Intermediate 17 was prepared following a similar procedure to that of step 4 of Intermediate 12 from 1-bromo-4-(diethoxyphosphorylmethyl)-3-fluoro-2-methyl-benzene to give 2.3 g (77%) of tert-butyl 3-[(4-bromo-2-fluoro-3-methyl-phenyl)methylene]azetidine-1-carboxylate.

LC/MS (m/z, MH+): 356

Step 5: 3-[(4-Bromo-2-fluoro-3-methyl-phenyl)methylene]azetidine, trifluoroacetic acid

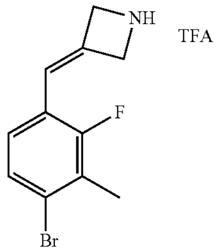

Step 5 of Intermediate 17 was prepared following a similar procedure to that of step 2 of Intermediate 1 from tert-butyl 3-[(4-bromo-2-fluoro-3-methyl-phenyl)methylene]azetidine-1-carboxylate to give 2.86 g of 3-[(4-bromo-2-fluoro-3-methyl-phenyl)methylene]azetidine, trifluoroacetic acid.

LC/MS (m/z, MH+): 256

Step 6: 3-[(4-Bromo-2-fluoro-3-methyl-phenyl) methylene]-1-(3-fluoropropyl)azetidine

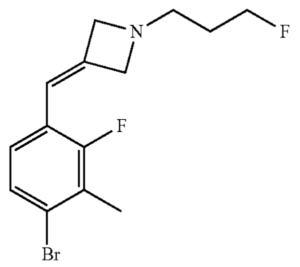 [SMILES: Cc1c(Br)ccc(C=C2CN(CCCF)C2)c1F]

Step 6 of Intermediate 17 was prepared following a similar procedure to that of Intermediate 11 from 3-[(4-bromo-2-fluoro-3-methyl-phenyl)methylene]azetidine, trifluoroacetic acid to give 203 mg (68%) of 3-[(4-bromo-2-fluoro-3-methyl-phenyl)methylene]-1-(3-fluoropropyl) azetidine.

LC/MS (m/z, MH+): 316

Intermediate 18: 3-(4-Bromo-2,6-difluorobenzylidene)-1-(3-fluoropropyl)azetidine

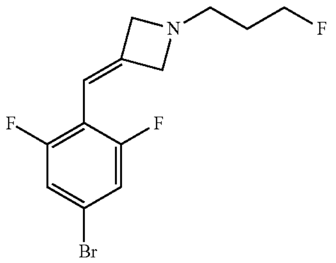 [SMILES: FCCCN1CC(=Cc2c(F)cc(Br)cc2F)C1]

Step 1: 5-Bromo-2-(bromomethyl)-1,3-difluorobenzene

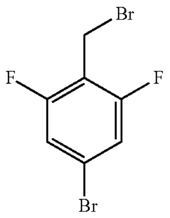 [SMILES: Fc1cc(Br)cc(F)c1CBr]

Step 1 of Intermediate 18 was prepared following a similar procedure to that of step 2 of Intermediate 12 from commercially available (4-bromo-2,6-difluoro-phenyl) methanol to give 6 g (94%) of 5-bromo-2-(bromomethyl)-1,3-difluorobenzene.

LC/MS (m/z, MH+): 285

Step 2: Diethyl (4-bromo-2,6-difluorobenzyl)phosphonate

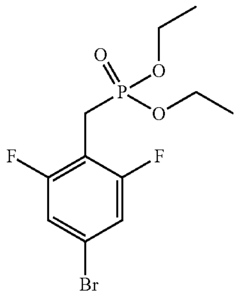 [SMILES: CCOP(=O)(Cc1c(F)cc(Br)cc1F)OCC]

Step 2 of Intermediate 18 was prepared following a similar procedure to that of step 3 of Intermediate 12 from 5-bromo-2-(bromomethyl)-1,3-difluorobenzene to give 6.5 g (88%) of diethyl (4-bromo-2,6-difluorobenzyl)phosphonate as a a colorless oil.

LC/MS (m/z, MH+): 343

Step 3: Tert-butyl 3-(4-bromo-2,6-difluorobenzylidene)azetidine-1-carboxylate

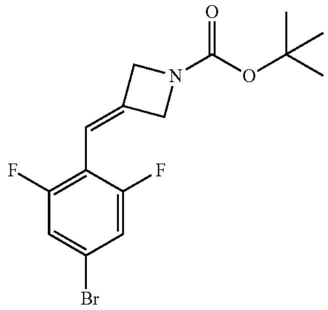 [SMILES: CC(C)(C)OC(=O)N1CC(=Cc2c(F)cc(Br)cc2F)C1]

Step 3 of Intermediate 18 was prepared following a similar procedure to that of step 4 of Intermediate 12 from diethyl (4-bromo-2,6-difluorobenzyl)phosphonate to give 7 g (86%) of tert-butyl 3-(4-bromo-2,6-difluorobenzylidene) azetidine-1-carboxylate as a colorless viscous oil.

LC/MS (m/z, MH+): 360

Step 4: 3-(4-Bromo-2,6-difluorobenzylidene)azetidine, trifluoroacetic acid

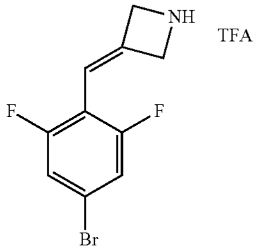 [SMILES: Fc1cc(Br)cc(F)c1C=C1CNC1]

Step 4 of Intermediate 18 was prepared following a similar procedure to that of step 2 of Intermediate 1 from tert-butyl 3-(4-bromo-2,6-difluorobenzylidene)azetidine-1-carboxylate to give 12 g of 3-(4-bromo-2,6-difluorobenzylidene)azetidine, trifluoroacetic acid as a white solid.

LC/MS (m/z, MH+): 260

Step 5: 3-(4-Bromo-2,6-difluorobenzylidene)-1-(3-fluoropropyl)azetidine

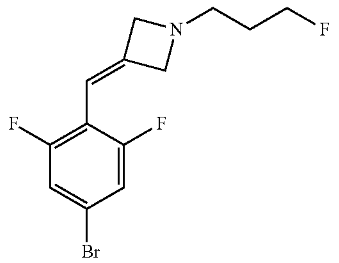 [SMILES: FCCCN1CC(=Cc2c(F)cc(Br)cc2F)C1]

Step 5 of Intermediate 18 was prepared following a similar procedure to that of Intermediate 11 from 3-(4-bromo-2,6-difluorobenzylidene)azetidine, trifluoroacetic acid to give 600 mg (52%) of 3-(4-bromo-2,6-difluorobenzylidene)-1-(3-fluoropropyl)azetidine.

LC/MS (m/z, MH+): 320

Intermediate 19: 3-[(4-Bromo-2-fluoro-6-methyl-phenyl)methylene]-1-(3-fluoropropyl)azetidine

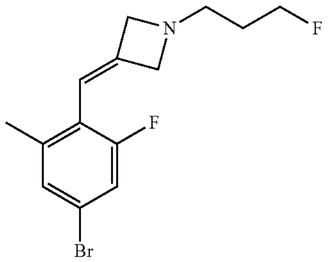

Step 1: (4-Bromo-2-fluoro-6-methyl-phenyl)methanol

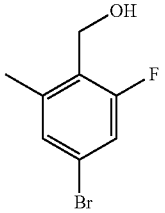

Step 1 of Intermediate 19 was prepared following a similar procedure to that of step 1 of Intermediate 12 from 4-bromo-2-fluoro-6-methyl-benzaldehyde to give 2.3 g (73%) of (4-bromo-2-fluoro-6-methyl-phenyl)methanol.

LC/MS (m/z, MH+): 219

Step 2: 1-Bromo-4-(bromomethyl)-3-fluoro-5-methyl-benzene

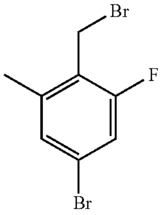

Step 2 of Intermediate 19 was prepared following a similar procedure to that of step 2 of Intermediate 12 from (4-bromo-2-fluoro-6-methyl-phenyl)methanol to give 5.8 g (100%) of 1-bromo-4-(bromomethyl)-3-fluoro-5-methyl-benzene.

LC/MS (m/z, MH+): 281

Step 3: 1-Bromo-4-(diethoxyphosphorylmethyl)-3-fluoro-5-methyl-benzene

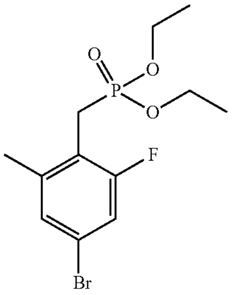 [SMILES: CCOP(=O)(Cc1c(C)cc(Br)cc1F)OCC]

Step 3 of Intermediate 19 was prepared following a similar procedure to that of step 3 of Intermediate 12 from 1-bromo-4-(bromomethyl)-3-fluoro-5-methyl-benzene to give 3 g (100%) of 1-bromo-4-(diethoxyphosphorylmethyl)-3-fluoro-5-methyl-benzene.

LC/MS (m/z, MH+): 339

Step 4: Tert-butyl 3-[(4-bromo-2-fluoro-6-methyl-phenyl)methylene]azetidine-1-carboxylate

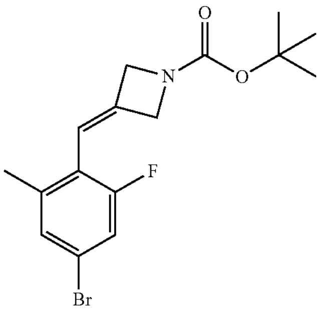 [SMILES: Cc1cc(Br)cc(F)c1C=C1CN(C(=O)OC(C)(C)C)C1]

Step 4 of Intermediate 19 was prepared following a similar procedure to that of step 4 of Intermediate 12 from 1-bromo-4-(diethoxyphosphorylmethyl)-3-fluoro-5-methylbenzene to give 3.5 g (78%) of tert-butyl 3-[(4-bromo-2-fluoro-6-methyl-phenyl)methylene]azetidine-1-carboxylate.

LC/MS (m/z, MH+): 356

Step 5: 3-[(4-Bromo-2-fluoro-6-methyl-phenyl)methylene]azetidine, trifluoroacetic acid

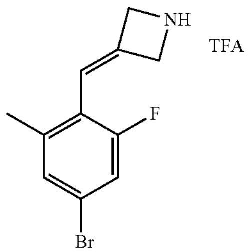

Step 5 of Intermediate 19 was prepared following a similar procedure to that of step 2 of Intermediate 1 from tert-butyl 3-[(4-bromo-2-fluoro-6-methyl-phenyl)methylene]azetidine-1-carboxylate to give 5.4 g of 3-[(4-bromo-2-fluoro-6-methyl-phenyl)methylene]azetidine, trifluoroacetic acid.

LC/MS (m/z, MH+): 256

Step 6: 3-[(4-Bromo-2-fluoro-6-methyl-phenyl)methylene]-1-(3-fluoropropyl)azetidine

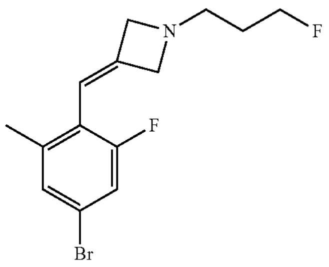 [SMILES: Cc1cc(Br)cc(F)c1C=C1CN(CCCF)C1]

Step 6 of Intermediate 19 was prepared following a similar procedure to that of Intermediate 11 from 3-[(4-bromo-2-fluoro-6-methyl-phenyl)methylene]azetidine, trifluoroacetic acid to give 203 mg (68%) of 3-[(4-bromo-2-fluoro-6-methyl-phenyl)methylene]-1-(3-fluoropropyl)azetidine.

LC/MS (m/z, MH+): 316

Intermediate 20: 3-[(4-Bromo-3-fluoro-5-methyl-phenyl)methylene]-1-(3-fluoropropyl)azetidine

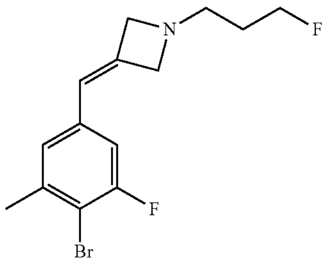 [SMILES: Cc1cc(C=C2CN(CCCF)C2)cc(F)c1Br]

Step 1: (4-Bromo-3-fluoro-5-methyl-phenyl)methanol

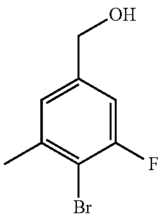

Step 1 of Intermediate 20 was prepared following a similar procedure to that of step 1 of Intermediate 12 from 4-bromo-3-fluoro-5-methyl-benzaldehyde to give 4.97 g (99%) of (4-bromo-3-fluoro-5-methyl-phenyl)methanol.

LC/MS (m/z, MH+): 219

Step 2: 2-Bromo-5-(bromomethyl)-1-fluoro-3-methyl-benzene

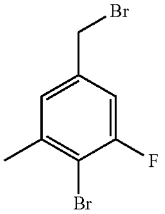

Step 2 of Intermediate 20 was prepared following a similar procedure to that of step 2 of Intermediate 12 from (4-bromo-3-fluoro-5-methyl-phenyl)methanol to give 5.3 g (83%) of 2-bromo-5-(bromomethyl)-1-fluoro-3-methyl-benzene.

LC/MS (m/z, MH+): 281

Step 3: 2-Bromo-5-(diethoxyphosphorylmethyl)-1-fluoro-3-methyl-benzene

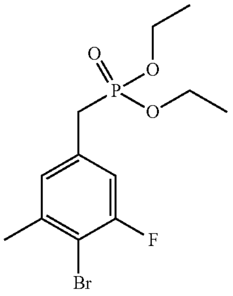 [SMILES: CCOP(=O)(Cc1cc(C)c(Br)c(F)c1)OCC]

Step 3 of Intermediate 20 was prepared following a similar procedure to that of step 3 of Intermediate 12 from 2-bromo-5-(bromomethyl)-1-fluoro-3-methyl-benzene to give 5.7 g (88%) of 2-bromo-5-(diethoxyphosphorylmethyl)-1-fluoro-3-methyl-benzene.

LC/MS (m/z, MH+): 339

Step 4: Tert-butyl 3-[(4-bromo-3-fluoro-5-methyl-phenyl)methylene]azetidine-1-carboxylate

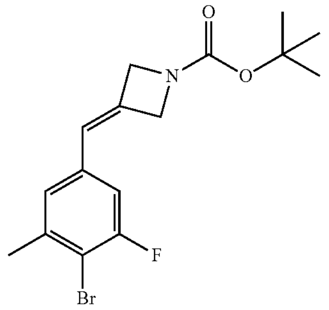 [SMILES: Cc1cc(C=C2CN(C(=O)OC(C)(C)C)C2)cc(F)c1Br]

Step 4 of Intermediate 20 was prepared following a similar procedure to that of step 4 of Intermediate 12 from 2-bromo-5-(diethoxyphosphorylmethyl)-1-fluoro-3-methyl-benzene to give 4.16 g (70%) of tert-butyl 3-[(4-bromo-3-fluoro-5-methyl-phenyl)methylene]azetidine-1-carboxylate.

LC/MS (m/z, MH+): 356

Step 5: 3-[(4-Bromo-3-fluoro-5-methyl-phenyl) methylene]azetidine, trifluoroacetic acid

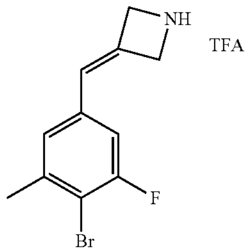

Step 5 of Intermediate 20 was prepared following a similar procedure to that of step 2 of Intermediate 1 from tert-butyl 3-[(4-bromo-3-fluoro-5-methyl-phenyl)methylene]azetidine-1-carboxylate to give 2.33 g of 3-[(4-bromo-3-fluoro-5-methyl-phenyl)methylene]azetidine, trifluoroacetic acid.

LC/MS (m/z, MH+): 256

Step 6: 3-[(4-Bromo-3-fluoro-5-methyl-phenyl) methylene]-1-(3-fluoropropyl)azetidine

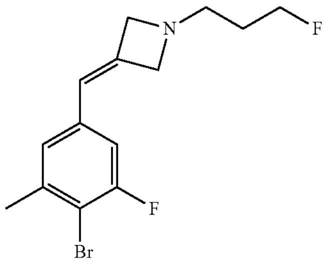 [SMILES: Cc1cc(C=C2CN(CCCF)C2)cc(F)c1Br]

Step 6 of Intermediate 20 was prepared following a similar procedure to that of Intermediate 11 from 3-[(4-bromo-3-fluoro-5-methyl-phenyl)methylene]azetidine, trifluoroacetic acid to give 850 mg (51%) of 3-[(4-bromo-3-fluoro-5-methyl-phenyl)methylene]-1-(3-fluoropropyl) azetidine.

LC/MS (m/z, MH+): 316

Intermediate 21: 3-[(4-Bromo-2-methyl-phenyl) methylene]-1-(3-fluoropropyl)azetidine

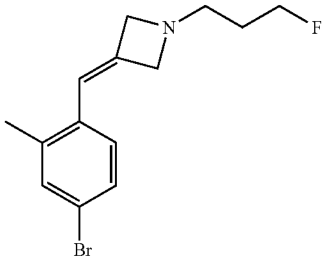 [SMILES: Cc1cc(Br)ccc1C=C1CN(CCCF)C1]

Step 1: 4-Bromo-1-(diethoxyphosphorylmethyl)-2-methyl-benzene

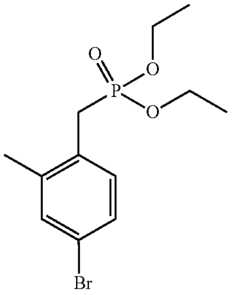 [SMILES: CCOP(=O)(Cc1ccc(Br)cc1C)OCC]

Step 1 of Intermediate 21 was prepared following a similar procedure to that of step 3 of Intermediate 12 from commercially available 4-bromo-1-(bromomethyl)-2-methylbenzene to give 1.46 g (60%) of 4-bromo-1-(diethoxyphosphorylmethyl)-2-methyl-benzene.

LC/MS (m/z, MH+): 321

Step 2: Tert-butyl 3-[(4-bromo-2-methyl-phenyl) methylene]azetidine-1-carboxylate

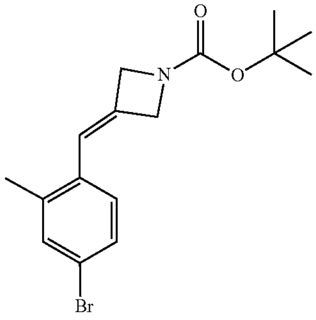 [SMILES: Cc1cc(Br)ccc1C=C1CN(C(=O)OC(C)(C)C)C1]

Step 2 of Intermediate 21 was prepared following a similar procedure to that of step 4 of Intermediate 12 from 4-bromo-1-(diethoxyphosphorylmethyl)-2-methyl-benzene to give 0.82 g (43%) of tert-butyl 3-[(4-bromo-2-methyl-phenyl)methylene]azetidine-1-carboxylate.

LC/MS (m/z, MH+): 338

Step 3: 3-[(4-Bromo-2-methyl-phenyl)methylene] azetidine, trifluoroacetic acid

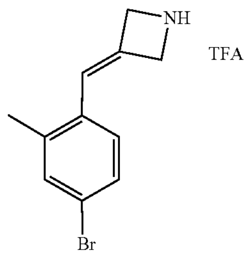

Step 3 of Intermediate 21 was prepared following a similar procedure to that of step 2 of Intermediate 1 from tert-butyl 3-[(4-bromo-2-methyl-phenyl)methylene]azetidine-1-carboxylate to give 0.65 g (78%) of 3-[(4-bromo-2-methyl-phenyl)methylene]azetidine, trifluoroacetic acid.

LC/MS (m/z, MH+): 238

Step 4: 3-[(4-Bromo-2-methyl-phenyl)methylene]-1-(3-fluoropropyl)azetidine

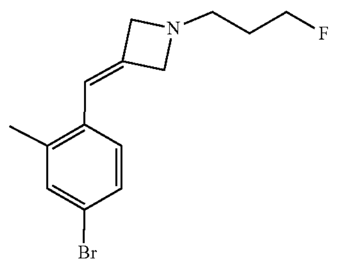 [SMILES: Cc1cc(Br)ccc1C=C1CN(CCCF)C1]

Step 4 of Intermediate 21 was prepared following a similar procedure to that of Intermediate 11 from 3-[(4-bromo-2-methyl-phenyl)methylene]azetidine, trifluoroacetic acid to give 160 mg (49%) of 3-[(4-bromo-2-methyl-phenyl)methylene]-1-(3-fluoropropyl)azetidine.

LC/MS (m/z, MH+): 298

Intermediate 22: 3-[(4-Bromo-2,5-dimethyl-phenyl) methylene]-1-(3-fluoropropyl)azetidine

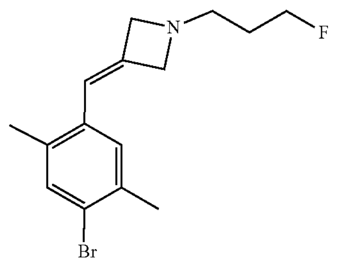 [SMILES: Cc1cc(C=C2CN(CCCF)C2)c(C)cc1Br]

Step 1: 1-Bromo-4-(bromomethyl)-2,5-dimethyl-benzene

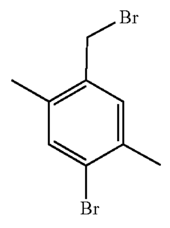

Step 1 of Intermediate 22 was prepared following a similar procedure to that of step 2 of Intermediate 12 from commercially available (4-bromo-2,5-dimethyl-phenyl) methanol to give 3.75 g (97%) of 1-bromo-4-(bromomethyl)-2,5-dimethyl-benzene.

LC/MS (m/z, MH+): 277

Step 2: 1-Bromo-4-(diethoxyphosphorylmethyl)-2, 5-dimethyl-benzene

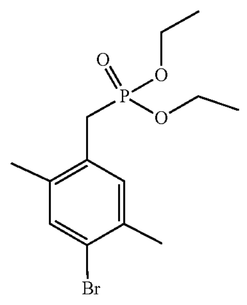 [SMILES: CCOP(=O)(Cc1cc(C)c(Br)cc1C)OCC]

Step 2 of Intermediate 22 was prepared following a similar procedure to that of step 3 of Intermediate 12 from 1-bromo-4-(bromomethyl)-2,5-dimethyl-benzene to give 3 g (67%) of 1-bromo-4-(diethoxyphosphorylmethyl)-2,5-dimethyl-benzene.

LC/MS (m/z, MH+): 335

Step 3: Tert-butyl 3-[(4-bromo-2,5-dimethyl-phenyl) methylene]azetidine-1-carboxylate

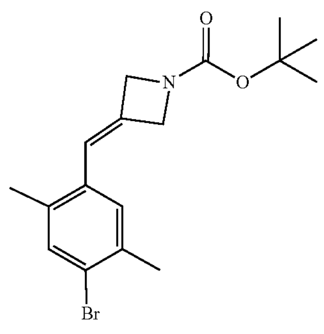 [SMILES: Cc1cc(C=C2CN(C(=O)OC(C)(C)C)C2)c(C)cc1Br]

Step 3 of Intermediate 22 was prepared following a similar procedure to that of step 4 of Intermediate 12 from 1-bromo-4-(diethoxyphosphorylmethyl)-2,5-dimethyl-benzene to give 0.90 g (28%) of tert-butyl 3-[(4-bromo-2,5-dimethyl-phenyl)methylene]azetidine-1-carboxylate.

LC/MS (m/z, MH+): 352

Step 4: 3-[(4-Bromo-2,5-dimethyl-phenyl)methylene]azetidine, trifluoroacetic acid

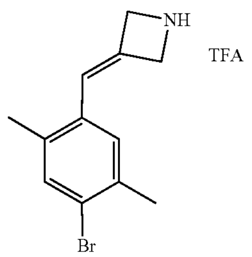

Step 4 of Intermediate 22 was prepared following a similar procedure to that of step 2 of Intermediate 1 from tert-butyl 3-[(4-bromo-2,5-dimethyl-phenyl)methylene]azetidine-1-carboxylate to give 0.81 g (86%) of 3-[(4-bromo-2,5-dimethyl-phenyl)methylene]azetidine, trifluoroacetic acid.

LC/MS (m/z, MH+): 252

Step 5: 3-[(4-Bromo-2,5-dimethyl-phenyl)methylene]-1-(3-fluoropropyl)azetidine

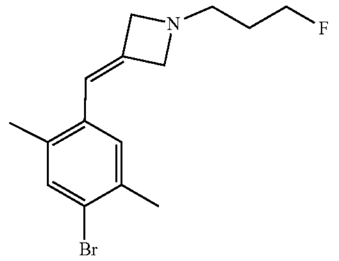 [SMILES: Cc1cc(C=C2CN(CCCF)C2)c(C)cc1Br]

Step 5 of Intermediate 22 was prepared following a similar procedure to that of Intermediate 11 from 3-[(4-bromo-2,5-dimethyl-phenyl)methylene]azetidine, trifluoroacetic acid to give 0.48 g (69%) of 3-[(4-bromo-2,5-dimethyl-phenyl)methylene]-1-(3-fluoropropyl)azetidine.

LC/MS (m/z, MH+): 312

Intermediate 23: 3-[(4-Bromo-3,5-difluoro-phenyl)methylene]-1-(3-fluoropropyl)azetidine

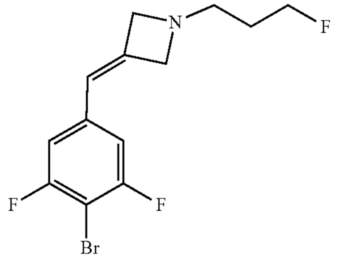 [SMILES: FCCCN1CC(=Cc2cc(F)c(Br)c(F)c2)C1]

Step 1: (4-Bromo-3,5-difluoro-phenyl)methanol

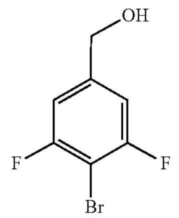 [SMILES: OCc1cc(F)c(Br)c(F)c1]

Step 1 of Intermediate 23 was prepared following a similar procedure to that of step 1 of Intermediate 12 from 4-bromo-3,5-difluoro-benzaldehyde to give 3 g (99%) of (4-bromo-3,5-difluoro-phenyl)methanol.

LC/MS (m/z, MH+): 223

Step 2: 2-Bromo-5-(bromomethyl)-1,3-difluoro-benzene

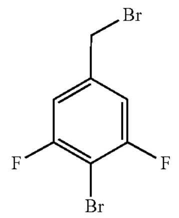 [SMILES: Fc1cc(CBr)cc(F)c1Br]

Step 2 of Intermediate 23 was prepared following a similar procedure to that of step 2 of Intermediate 12 from 4-bromo-3,5-difluoro-phenyl)methanol to give 3.7 g (96%) of 2-bromo-5-(bromomethyl)-1,3-difluoro-benzene.

LC/MS (m/z, MH+): 285

Step 3: 2-Bromo-5-(diethoxyphosphorylmethyl)-1,3-difluoro-benzene

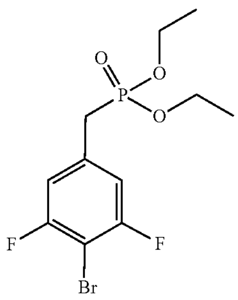 [SMILES: CCOP(=O)(Cc1cc(F)c(Br)c(F)c1)OCC]

Step 3 of Intermediate 23 was prepared following a similar procedure to that of Step 3 of Intermediate 12 from 2-bromo-5-(bromomethyl)-1,3-difluoro-benzene to give 4.27 g (96%) of 2-bromo-5-(diethoxyphosphorylmethyl)-1,3-difluoro-benzene.

LC/MS (m/z, MH+): 343

Step 4: Tert-butyl 3-[(4-bromo-3,5-difluoro-phenyl)methylene]azetidine-1-carboxylate

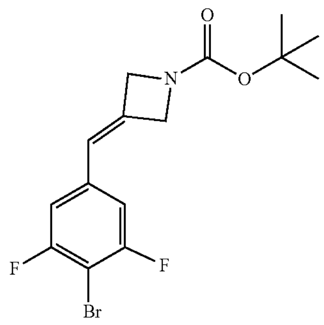 [SMILES: CC(C)(C)OC(=O)N1CC(=Cc2cc(F)c(Br)c(F)c2)C1]

Step 4 of Intermediate 23 was prepared following a similar procedure to that of step 4 of Intermediate 12 from 2-bromo-5-(diethoxyphosphorylmethyl)-1,3-difluoro-benzene to give 2.54 g (57%) of tert-butyl 3-[(4-bromo-3,5-difluoro-phenyl)methylene]azetidine-1-carboxylate.

LC/MS (m/z, MH+): 360

Step 5: 3-[(4-Bromo-3,5-difluoro-phenyl)methylene]azetidine, trifluoroacetic acid

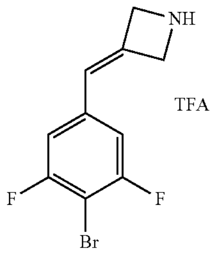 [SMILES: Fc1cc(C=C2CNC2)cc(F)c1Br]

Step 5 of Intermediate 23 was prepared following a similar procedure to that of step 2 of Intermediate 1 from tert-butyl 3-[(4-bromo-3,5-difluoro-phenyl)methylene]azetidine-1-carboxylate to give 2.45 g (93%) of 3-[(4-bromo-3,5-difluoro-phenyl)methylene]azetidine, trifluoroacetic acid.

LC/MS (m/z, MH+): 260

Step 6: 3-[(4-Bromo-3,5-difluoro-phenyl)methylene]-1-(3-fluoropropyl)azetidine

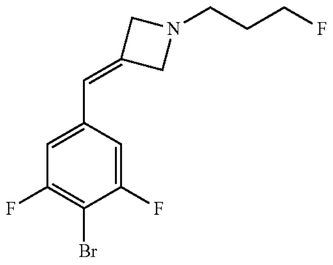 [SMILES: FCCCN1CC(=Cc2cc(F)c(Br)c(F)c2)C1]

Step 6 of Intermediate 23 was prepared following a similar procedure to that of Intermediate 11 from 3-[(4- bromo-3,5-difluoro-phenyl)methylene]azetidine, trifluoroacetic acid to give 191 mg (45%) of 3-[(4-bromo-3,5-difluoro-phenyl)methylene]-1-(3-fluoropropyl)azetidine.

LC/MS (m/z, MH+): 320

Intermediate 24: 3-[(4-Bromo-3-fluoro-2-methyl-phenyl)methylene]-1-(3-fluoropropyl)azetidine

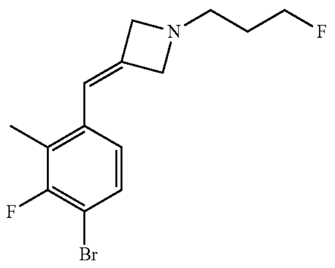 [SMILES: Cc1c(C=C2CN(CCCF)C2)ccc(Br)c1F]

Step 1: (4-Bromo-3-fluoro-2-methyl-phenyl)methanol

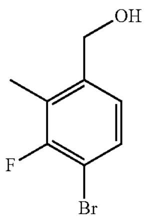

Step 1 of Intermediate 24 was prepared following a similar procedure to that of step 1 of Intermediate 12 from 4-bromo-3-fluoro-2-methyl-benzaldehyde to give 2.87 g (97%) of (4-bromo-3-fluoro-2-methyl-phenyl)methanol.

LC/MS (m/z, MH+): 219

Step 2: 1-Bromo-4-(bromomethyl)-2-fluoro-3-methyl-benzene

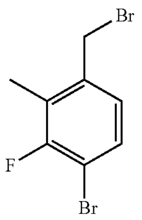

Step 2 of Intermediate 24 was prepared following a similar procedure to that of step 2 of Intermediate 12 from (4-bromo-3-fluoro-2-methyl-phenyl)methanol to give 3.63 g (98%) of 1-bromo-4-(bromomethyl)-2-fluoro-3-methyl-benzene.

LC/MS (m/z, MH+): 281

Step 3: 1-Bromo-4-(diethoxyphosphorylmethyl)-2-fluoro-3-methyl-benzene

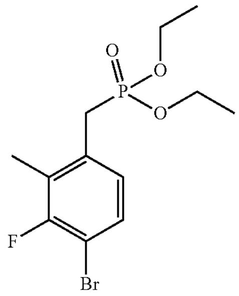 [SMILES: CCOP(=O)(Cc1ccc(Br)c(F)c1C)OCC]

Step 3 of Intermediate 24 was prepared following a similar procedure to that of step 3 of Intermediate 12 from 1-bromo-4-(bromomethyl)-2-fluoro-3-methyl-benzene to give 4.3 g (100%) of 1-bromo-4-(diethoxyphosphorylmethyl)-2-fluoro-3-methyl-benzene.

LC/MS (m/z, MH+): 339

Step 4: Tert-butyl 3-[(4-bromo-3-fluoro-2-methyl-phenyl)methylene]azetidine-1-carboxylate

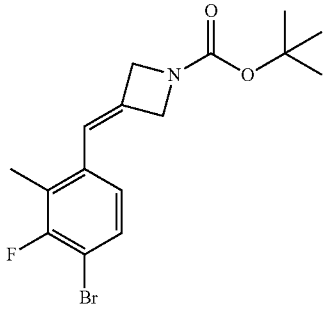 [SMILES: Cc1c(C=C2CN(C(=O)OC(C)(C)C)C2)ccc(Br)c1F]

Step 4 of Intermediate 24 was prepared following a similar procedure to that of step 4 of Intermediate 12 from 1-bromo-4-(diethoxyphosphorylmethyl)-2-fluoro-3-methyl-benzene to give 1.8 g (40%) of tert-butyl 3-[(4-bromo-3-fluoro-2-methyl-phenyl)methylene]azetidine-1-carboxylate.

LC/MS (m/z, MH+): 356

Step 5: 3-[(4-Bromo-3-fluoro-2-methyl-phenyl) methylene]azetidine, trifluoroacetic acid

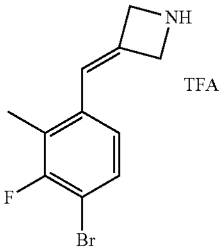

Step 5 of Intermediate 24 was prepared following a similar procedure to that of step 2 of Intermediate 1 from tert-butyl 3-[(4-bromo-3-fluoro-2-methyl-phenyl)methylene]azetidine-1-carboxylate to give 979 mg (66%) of 3-[(4-bromo-3-fluoro-2-methyl-phenyl)methylene]azetidine, trifluoroacetic acid.

LC/MS (m/z, MH+): 256

Step 6: 3-[(4-Bromo-3-fluoro-2-methyl-phenyl) methylene]-1-(3-fluoropropyl)azetidine

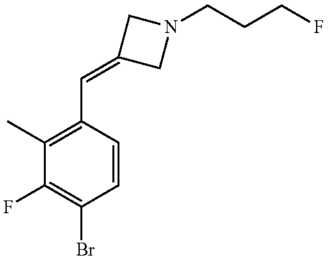 [SMILES: Cc1c(C=C2CN(CCCF)C2)ccc(Br)c1F]

Step 6 of Intermediate 24 was prepared following a similar procedure to that of Intermediate 11 from 3-[(4-bromo-3-fluoro-2-methyl-phenyl)methylene]azetidine, trifluoroacetic acid to give 219 mg (51%) of 3-[(4-bromo-3-fluoro-2-methyl-phenyl)methylene]-1-(3-fluoropropyl) azetidine.

LC/MS (m/z, MH+): 316

Intermediate 25: 3-[(4-Bromo-2-fluoro-phenyl) methylene]-1-(3-fluoropropyl)azetidine

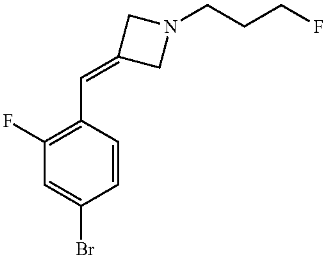 [SMILES: FCCCN1CC(=Cc2ccc(Br)cc2F)C1]

Intermediate 25 was prepared following a similar procedure to that of Intermediate 11 from commercially available 3-[(4-bromo-2-fluoro-phenyl)methylene]azetidine hydrochloride to give 730 mg (58%) of 3-[(4-bromo-2-fluoro-phenyl)methylene]-1-(3-fluoropropyl)azetidine.

LC/MS (m/z, MH+): 302

Intermediate 26: 3-[(4-Bromo-2,3-difluoro-phenyl) methylene]-1-(3-fluoropropyl)azetidine

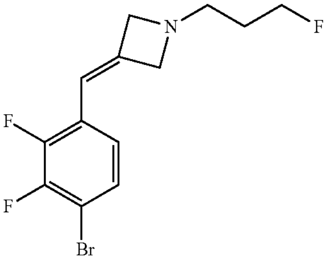 [SMILES: FCCCN1CC(=Cc2ccc(Br)c(F)c2F)C1]

Intermediate 26 was prepared following a similar procedure to that of Intermediate 11 from commercially available 3-[(4-bromo-2,3-difluoro-phenyl)methylene]azetidine hydrochloride to give 952 mg (77%) of 3-[(4-bromo-2,3-difluoro-phenyl)methylene]-1-(3-fluoropropyl)azetidine.

LC/MS (m/z, MH+): 320

Intermediate 27: 5-Bromo-2-[[1-(3-fluoropropyl)azetidin-3-ylidene]methyl]benzonitrile

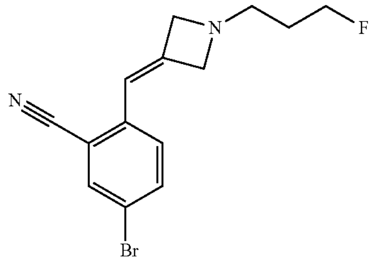 [SMILES: N#Cc1cc(Br)ccc1C=C1CN(CCCF)C1]

Step 1: 5-Bromo-2-(diethoxyphosphorylmethyl)benzonitrile

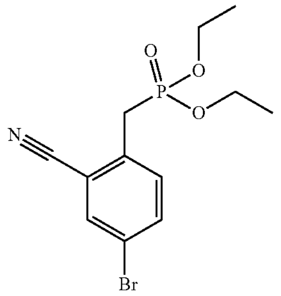 [SMILES: CCOP(=O)(Cc1ccc(Br)cc1C#N)OCC]

Step 1 of Intermediate 27 was prepared following a similar procedure to that of step 3 of Intermediate 12 from commercially available 5-bromo-2-(bromomethyl)benzonitrile to give 2.93 g (97%) of 5-bromo-2-(diethoxyphosphorylmethyl)benzonitrile.

LC/MS (m/z, MH+): 332

Step 2: Tert-butyl 3-[(4-bromo-2-cyano-phenyl)methylene]azetidine-1-carboxylate

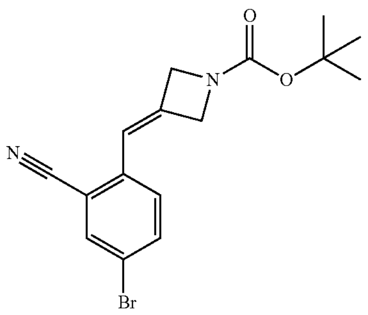 [SMILES: CC(C)(C)OC(=O)N1CC(=Cc2ccc(Br)cc2C#N)C1]

Step 2 of Intermediate 27 was prepared following a similar procedure to that of step 4 of Intermediate 12 from 5-bromo-2-(diethoxyphosphorylmethyl)benzonitrile to give 2.19 g (71%) of tert-butyl 3-[(4-bromo-2-cyano-phenyl)methylene]azetidine-1-carboxylate.

LC/MS (m/z, MH+): 349

Step 3: 2-(Azetidin-3-ylidenemethyl)-5-bromo-benzonitrile, trifluoroacetic acid

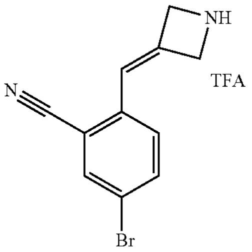 [SMILES: N#Cc1cc(Br)ccc1C=C1CNC1]

Step 3 of Intermediate 27 was prepared following a similar procedure to that of step 2 of Intermediate 1 from tert-butyl 3-[(4-bromo-2-cyano-phenyl)methylene]azetidine-1-carboxylate to give 2.18 g (96%) of 2-(azetidin-3-ylidenemethyl)-5-bromo-benzonitrile, trifluoroacetic acid.

LC/MS (m/z, MH+): 249

Step 4: 5-Bromo-2-[[1-(3-fluoropropyl)azetidin-3-ylidene]methyl]benzonitrile

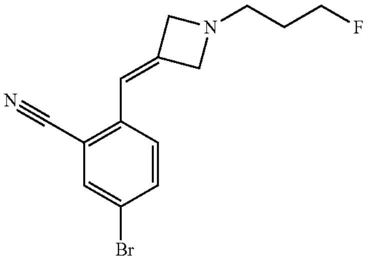 [SMILES: N#Cc1cc(Br)ccc1C=C1CN(CCCF)C1]

Step 4 of Intermediate 27 was prepared following a similar procedure to that of Intermediate 11 from 2-(azetidin-3-ylidenemethyl)-5-bromo-benzonitrile, trifluoroacetic acid to give 1.35 g (73%) of 5-bromo-2-[[1-(3-fluoropropyl)azetidin-3-ylidene]methyl]benzonitrile.

LC/MS (m/z, MH+): 309

Intermediate 28: 3-[[4-Bromo-2-(trifluoromethyl)phenyl]methylene]-1-(3-fluoropropyl)azetidine

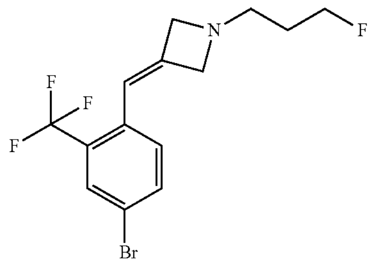 [SMILES: FCCCN1CC(=Cc2ccc(Br)cc2C(F)(F)F)C1]

Step 1: 4-Bromo-1-(bromomethyl)-2-(trifluoromethyl)benzene

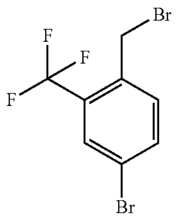

Step 1 of Intermediate 28 was prepared following a similar procedure to that of step 2 of Intermediate 12 from commercially available [4-bromo-2-(trifluoromethyl)phenyl]methanol to give 2.87 g (92%) of 4-bromo-1-(bromomethyl)-2-(trifluoromethyl)benzene.

LC/MS (m/z, MH+): 317

Step 2: 4-Bromo-1-(diethoxyphosphorylmethyl)-2-(trifluoromethyl)benzene

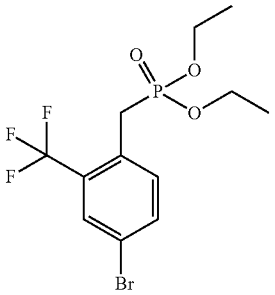 [SMILES: CCOP(=O)(Cc1ccc(Br)cc1C(F)(F)F)OCC]

Step 2 of Intermediate 28 was prepared following a similar procedure to that of step 3 of Intermediate 12 from 4-bromo-1-(bromomethyl)-2-(trifluoromethyl)benzene to give 3.13 g (93%) of 4-bromo-1-(diethoxyphosphorylmethyl)-2-(trifluoromethyl)benzene.

LC/MS (m/z, MH+): 375

Step 3: Tert-butyl 3-[[4-bromo-2-(trifluoromethyl)phenyl]methylene]azetidine-1-carboxylate

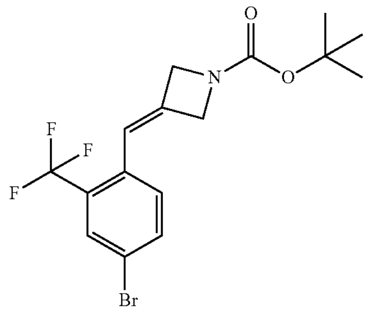 [SMILES: CC(C)(C)OC(=O)N1CC(=Cc2ccc(Br)cc2C(F)(F)F)C1]

Step 3 of Intermediate 28 was prepared following a similar procedure to that of step 4 of Intermediate 12 from 4-bromo-1-(diethoxyphosphorylmethyl)-2-(trifluoromethyl)benzene to give 2.42 g (74%) of tert-butyl 3-[[4-bromo-2-(trifluoromethyl)phenyl]methylene]azetidine-1-carboxylate.

LC/MS (m/z, MH+): 392

Step 4: 3-[[4-Bromo-2-(trifluoromethyl)phenyl]methylene]azetidine, trifluoroacetic acid

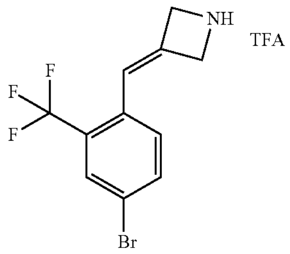 [SMILES: FC(F)(F)c1cc(Br)ccc1C=C1CNC1]

Step 4 of Intermediate 28 was prepared following a similar procedure to that of step 2 of Intermediate 1 from tert-butyl 3-[[4-bromo-2-(trifluoromethyl)phenyl]methylene]azetidine-1-carboxylate to give 3.07 g of 3-[[4-bromo-2-(trifluoromethyl)phenyl]methylene]azetidine, trifluoroacetic acid.

LC/MS (m/z, MH+): 291

Step 5: 3-[[4-Bromo-2-(trifluoromethyl)phenyl]methylene]-1-(3-fluoropropyl)azetidine

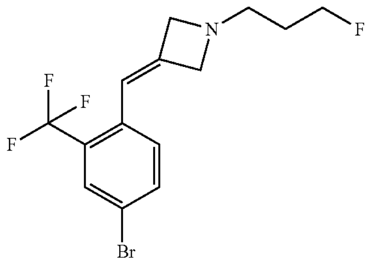 [SMILES: FCCCN1CC(=Cc2ccc(Br)cc2C(F)(F)F)C1]

Step 5 of Intermediate 28 was prepared following a similar procedure to that of Intermediate 11 from 3-[[4- bromo-2-(trifluoromethyl)phenyl]methylene]azetidine, trifluoroacetic acid to give 1.29 g (60%) of 3-[[4-bromo-2-(trifluoromethyl)phenyl]methylene]-1-(3-fluoropropyl) azetidine.

LC/MS (m/z, MH+): 352

Intermediate 29: 3-[(4-Bromo-2-methyl-phenyl) methylene]-1-(3-fluoropropyl)azetidine

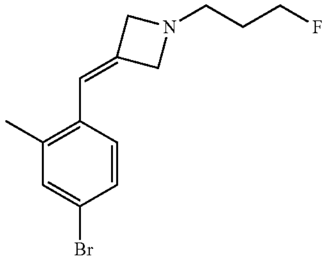 [SMILES: Cc1cc(Br)ccc1C=C1CN(CCCF)C1]

Step 1: 4-Bromo-1-(diethoxyphosphorylmethyl)-2-methyl-benzene

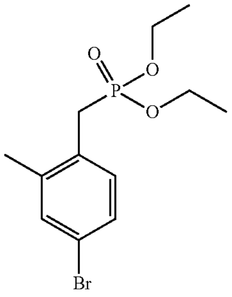 [SMILES: CCOP(=O)(Cc1ccc(Br)cc1C)OCC]

Step 1 of Intermediate 29 was prepared following a similar procedure to that of step 3 of Intermediate 12 from commercially available 4-bromo-1-(bromomethyl)-2-methylbenzene to give 1.46 g (60%) of 4-bromo-1-(diethoxyphosphorylmethyl)-2-methyl-benzene.

LC/MS (m/z, MH+): 321

Step 2: Tert-butyl 3-[(4-Bromo-2-methyl-phenyl) methylene]azetidine-1-carboxylate

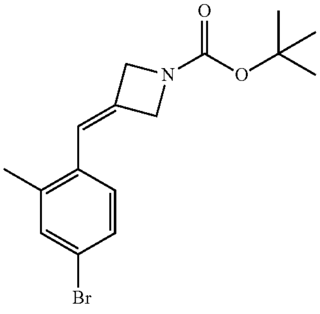 [SMILES: Cc1cc(Br)ccc1C=C1CN(C(=O)OC(C)(C)C)C1]

Step 2 of Intermediate 29 was prepared following a similar procedure to that of step 4 of Intermediate 12 from 4-bromo-1-(diethoxyphosphorylmethyl)-2-methyl-benzene to give 0.82 g (53%) of tert-butyl 3-[(4-bromo-2-methyl-phenyl)methylene]azetidine-1-carboxylate.

LC/MS (m/z, MH+): 338

Step 3: 3-[(4-Bromo-2-methyl-phenyl)methylene] azetidine, trifluoroacetic acid

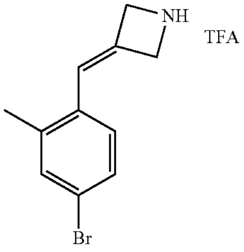

Step 3 of Intermediate 29 was prepared following a similar procedure to that of step 2 of Intermediate 1 from tert-butyl 3-[(4-bromo-2-methyl-phenyl)methylene]azetidine-1-carboxylate to give 0.65 g (78%) of 3-[(4-bromo-2-methyl-phenyl)methylene]azetidine, trifluoroacetic acid.

LC/MS (m/z, MH+): 238

Step 4: 3-[(4-Bromo-2-methyl-phenyl)methylene]-1-(3-fluoropropyl)azetidine

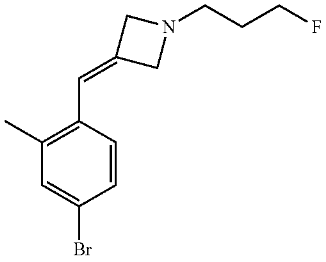 [SMILES: Cc1cc(Br)ccc1C=C1CN(CCCF)C1]

Step 4 of Intermediate 29 was prepared following a similar procedure to that of Intermediate 11 from 3-[(4-bromo-2-methyl-phenyl)methylene]azetidine, trifluoroacetic acid to give 170 mg (57%) of 3-[(4-bromo-2-methyl-phenyl)methylene]-1-(3-fluoropropyl)azetidine.

LC/MS (m/z, MH+): 298

Intermediate 30: 3-[[4-Bromo-3-(trifluoromethyl) phenyl]methylene]-1-(3-fluoropropyl)azetidine

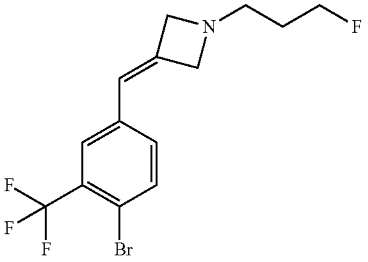 [SMILES: FCCCN1CC(=Cc2ccc(Br)c(C(F)(F)F)c2)C1]

Step 1: 1-Bromo-4-(bromomethyl)-2-(trifluoromethyl)benzene

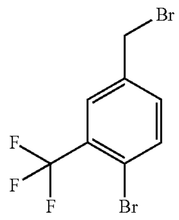

Step 1 of Intermediate 30 was prepared following a similar procedure to that of step 2 of Intermediate 12 from commercially available [4-bromo-2-(trifluoromethyl)phenyl]methanol to give 2.35 g (94%) of 1-bromo-4-(bromomethyl)-2-(trifluoromethyl)benzene.

LC/MS (m/z, MH+): 317

Step 2: 1-Bromo-4-(diethoxyphosphorylmethyl)-2-(trifluoromethyl)benzene

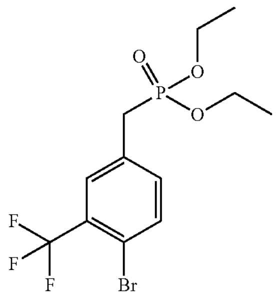 [SMILES: CCOP(=O)(Cc1ccc(Br)c(C(F)(F)F)c1)OCC]

Step 2 of Intermediate 30 was prepared following a similar procedure to that of step 3 of Intermediate 12 from 1-bromo-4-(bromomethyl)-2-(trifluoromethyl)benzene to give 2.86 g (100%) of 1-bromo-4-(diethoxyphosphorylmethyl)-2-(trifluoromethyl)benzene.

LC/MS (m/z, MH+): 375

Step 3: Tert-butyl 3-[[4-bromo-3-(trifluoromethyl)phenyl]methylene]azetidine-1-carboxylate

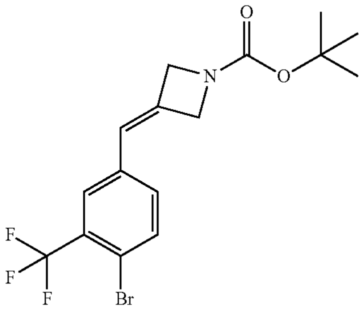 [SMILES: CC(C)(C)OC(=O)N1CC(=Cc2ccc(Br)c(C(F)(F)F)c2)C1]

Step 3 of Intermediate 30 was prepared following a similar procedure to that of step 4 of Intermediate 12 from 1-bromo-4-(diethoxyphosphorylmethyl)-2-(trifluoromethyl)benzene to give 2.24 g (75%) of tert-butyl 3-[[4-bromo-3-(trifluoromethyl)phenyl]methylene]azetidine-1-carboxylate.

LC/MS (m/z, MH+): 392

Step 4: 3-[[4-Bromo-3-(trifluoromethyl)phenyl]methylene]azetidine, trifluoroacetic acid

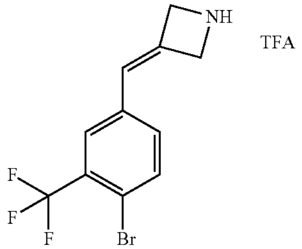 [SMILES: FC(F)(F)c1cc(C=C2CNC2)ccc1Br ; "TFA"]

Step 4 of Intermediate 30 was prepared following a similar procedure to that of step 2 of Intermediate 1 from tert-butyl 3-[[4-bromo-3-(trifluoromethyl)phenyl]methylene]azetidine-1-carboxylate to give 2.13 g (92%) of 3-[[4-bromo-3-(trifluoromethyl)phenyl]methylene]azetidine, trifluoroacetic acid.

LC/MS (m/z, MH+): 291

Step 5: 3-[[4-Bromo-3-(trifluoromethyl)phenyl]methylene]-1-(3-fluoropropyl)azetidine

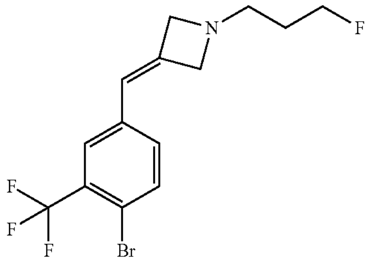 [SMILES: FCCCN1CC(=Cc2ccc(Br)c(C(F)(F)F)c2)C1]

Step 5 of Intermediate 30 was prepared following a similar procedure to that of Intermediate 11 from 3-[[4-bromo-3-(trifluoromethyl)phenyl]methylene]azetidine, trifluoroacetic acid to give 1.83 g (99%) of 3-[[4-bromo-3-(trifluoromethyl)phenyl]methylene]-1-(3-fluoropropyl)azetidine.

LC/MS (m/z, MH+): 352

Intermediate 31: 2-Bromo-5-[[1-(3-fluoropropyl)azetidin-3-ylidene]methyl]benzonitrile

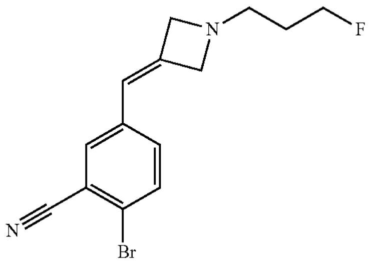 [SMILES: N#Cc1cc(C=C2CN(CCCF)C2)ccc1Br]

Step 1: 2-Bromo-5-(hydroxymethyl)benzonitrile

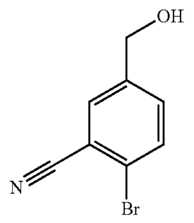 [SMILES: N#Cc1cc(CO)ccc1Br]

Step 1 of Intermediate 31 was prepared following a similar procedure to that of step 1 of Intermediate 12 from 2-bromo-5-formylbenzonitrile to give 2.06 g (100%) of 2-bromo-5-(hydroxymethyl)benzonitrile.

LC/MS (m/z, MH+): 212

Step 2: 2-Bromo-5-(bromomethyl)benzonitrile

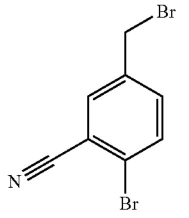 [SMILES: N#Cc1cc(CBr)ccc1Br]

Step 2 of Intermediate 31 was prepared following a similar procedure to that of step 2 of Intermediate 12 from 2-bromo-5-(hydroxymethyl)benzonitrile to give 2.3 g (97%) of 2-bromo-5-(bromomethyl)benzonitrile.

LC/MS (m/z, MH+): 274

Step 3: 2-Bromo-5-(diethoxyphosphorylmethyl)benzonitrile

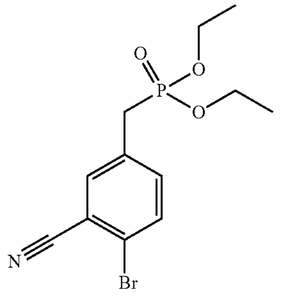 [SMILES: CCOP(=O)(Cc1ccc(Br)c(C#N)c1)OCC]

Step 3 of Intermediate 31 was prepared following a similar procedure to that of step 3 of Intermediate 12 from 2-bromo-5-(bromomethyl)benzonitrile to give 3.18 g (93%) of 2-bromo-5-(diethoxyphosphorylmethyl)benzonitrile.

LC/MS (m/z, MH+): 332

Step 4: Tert-butyl 3-[(4-bromo-3-cyano-phenyl) methylene]azetidine-1-carboxylate

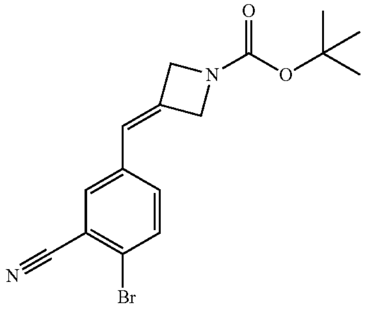 [SMILES: CC(C)(C)OC(=O)N1CC(=Cc2ccc(Br)c(C#N)c2)C1]

Step 4 of Intermediate 31 was prepared following a similar procedure to that of step 4 of Intermediate 12 from 2-bromo-5-(diethoxyphosphorylmethyl)benzonitrile to give 2.56 g (80%) of tert-butyl 3-[(4-bromo-3-cyano-phenyl) methylene]azetidine-1-carboxylate.

LC/MS (m/z, MH+): 349

Step 5: 5-(azetidin-3-ylidenemethyl)-2-bromo-benzonitrile, trifluoroacetic acid

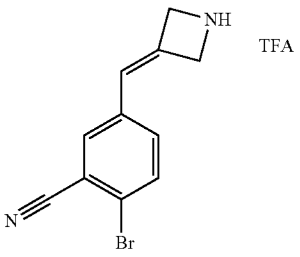 [SMILES: N#Cc1cc(C=C2CNC2)ccc1Br ; "TFA"]

Step 5 of Intermediate 31 was prepared following a similar procedure to that of step 2 of Intermediate 1 from tert-butyl 3-[(4-bromo-3-cyano-phenyl)methylene]azetidine-1-carboxylate to give 2.1 g (81%) of 5-(azetidin-3-ylidenemethyl)-2-bromo-benzonitrile, trifluoroacetic acid.

LC/MS (m/z, MH+): 249

Step 6: 2-Bromo-5-[[1-(3-fluoropropyl)azetidin-3-ylidene]methyl]benzonitrile

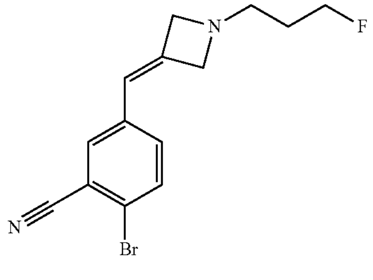 [SMILES: N#Cc1cc(C=C2CN(CCCF)C2)ccc1Br]

Step 6 of Intermediate 31 was prepared following a similar procedure to that of Intermediate 11 from 5-(azetidin-3-ylidenemethyl)-2-bromo-benzonitrile, trifluoroacetic acid to give 900 mg (96%) of 2-bromo-5-[[1-(3-fluoropropyl)azetidin-3-ylidene]methyl]benzonitrile.

LC/MS (m/z, MH+): 309

Intermediate 32: 8-(2-Chlorophenyl)-6,7-dihydro-5H-benzo[7]annulen-9-yl trifluoromethanesulfonate

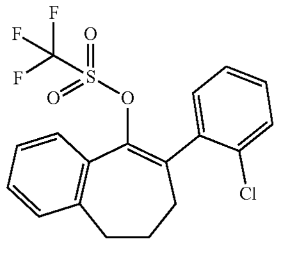 [SMILES: O=S(=O)(OC1=C(c2ccccc2Cl)CCCc2ccccc21)C(F)(F)F]

Step 1: 6-(2-Chlorophenyl)-6,7,8,9-tetrahydrobenzo[7]annulen-5-one

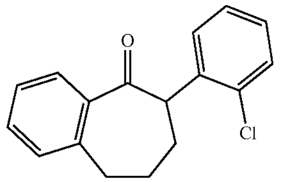 [SMILES: O=C1c2ccccc2CCCC1c1ccccc1Cl]

Step 1 of Intermediate 32 was prepared following a similar procedure to that of step 1 of Intermediate 5 from methyl 5-oxo-2,3,4,5-tetrahydrobenzo[b]oxepine-8-carboxylate to give 580 mg (16%) of 6-(2-chlorophenyl)-6,7,8,9-tetrahydrobenzo[7]annulen-5-one.

LC/MS (m/z, MH+): 271

Step 2: 8-(2-Chlorophenyl)-6,7-dihydro-5H-benzo[7]annulen-9-yl trifluoromethanesulfonate

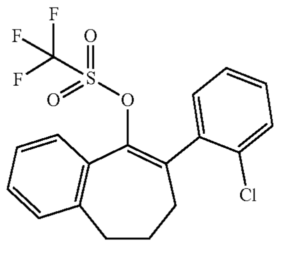 [SMILES: O=S(=O)(OC1=C(c2ccccc2Cl)CCCc2ccccc21)C(F)(F)F]

To a solution of 6-(2-chlorophenyl)-6,7,8,9-tetrahydrobenzo[7]annulen-5-one (580 mg, 2.14 mmol) in THF (15 ml) was added KHMDS (1 M, 2.57 ml, 2.57 mmol) at −50° C. under Ar atmosphere. The mixture was stirred for 30 min and 1,1,1-trifluoro-N-phenyl-N-(trifluoromethylsulfonyl)methanesulfonamide (765 mg, 2.14 mmol) was added to the resulting mixture. The reaction mixture was slowly warmed up to 20° C. and stirred for 90 minutes. The reaction mixture was quenched with saturated aqueous citric acid solution, then diluted with $H_2O$ and extracted twice with $Et_2O$. The combined organic layers were dried over anhydrous $Na_2SO_4$, filtered, and concentrated under reduced pressure. The residue was purified by flash chromatography with a 0-50% gradient of ethyl acetate in cyclohexane to give 608 mg (71%) of 8-(2-chlorophenyl)-6,7-dihydro-5H-benzo[7]annulen-9-yl trifluoromethanesulfonate.

LC/MS (m/z, MH+): 403

Intermediate 33: Methyl 4-(2,4-dichlorophenyl)-5-(((trifluoromethyl)sulfonyl)oxy)-2,3-dihydrobenzo[b]oxepine-8-carboxylate

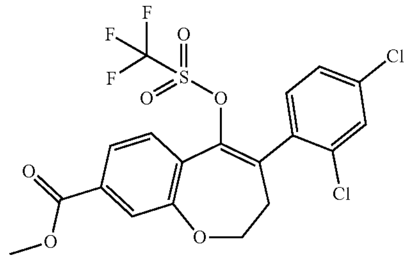 [SMILES: COC(=O)c1ccc2c(c1)OCCC(c1ccc(Cl)cc1Cl)=C2OS(=O)(=O)C(F)(F)F]

Step 1: 5-Oxo-2,3,4,5-tetrahydrobenzo[b]oxepine-8-yl trifluoromethanesulfonate

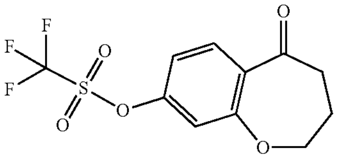 [SMILES: O=C1CCCOc2cc(OS(=O)(=O)C(F)(F)F)ccc21]

To a mixture of 8-hydroxy-3,4-dihydrobenzo[b]oxepine-5(2H)-one (4.2 g, 23.57 mmol) (prepared according to WO2018091153) and pyridine (2.82 g, 2.89 mL, 35.36 mmol) in DCM (120 mL) cooled at −20° C. was dropwise added trifluoromethanesulfonic anhydride (8.14 g, 6 mL, 28.28 mmol). The reaction mixture was stirred at 0° C. for 30 minutes. Water (50 mL) was added. The organic phase was separated and washed with an aqueous saturated solution of $NaHCO_3$ (50 mL). The organic phase was dried over $MgSO_4$, filtered, and concentrated under reduced pressure to give 7.30 g (100%) of 5-oxo-2,3,4,5-tetrahydrobenzo[b]oxepine-8-yl trifluoromethanesulfonate.

LC/MS (m/z, MH+): 311

Step 2: Methyl 5-oxo-2,3,4,5-tetrahydrobenzo[b]oxepine-8-carboxylate

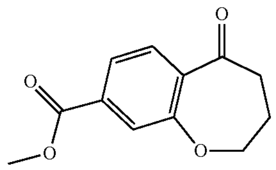 [SMILES: COC(=O)c1ccc2c(c1)OCCCC2=O]

To a solution of compound 5-oxo-2,3,4,5-tetrahydrobenzo[b]oxepine-8-yl trifluoromethanesulfonate (7.4 g, 23.85 mmol) in DMF (30 mL) and MeOH (15 mL) was added DIEA (3.15 g, 4.16 mL, 23.85 mmol) and Pd(dppf)$Cl_2$ complex with DCM (1.10 g, 1.43 mmol), the suspension was degassed and purged three times with CO. The mixture was stirred under CO (5 bars) at 75° C. for 2 hours. The reaction was filtered through celite. The filtrate was diluted with water (400 mL) and extracted three times with EtOAc (300 mL). The combined organic phases were dried over $Na_2SO_4$, filtered, concentrated under reduced pressure, and the residue obtained was purified by flash chromatography eluting with a gradient of heptane/ethyl acetate: from 85/15 to 80/20 to give 4.6 g (88%) methyl 5-oxo-2,3,4,5-tetrahydrobenzo[b]oxepine-8-carboxylate.

LC/MS (m/z, MH+): 221

Step 3: Methyl 4-(2,4-dichlorophenyl)-5-oxo-2,3,4,5-tetrahydrobenzo[b]oxepine-8-carboxylate

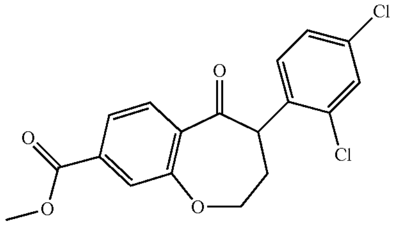 [SMILES: COC(=O)c1ccc2c(c1)OCCC(c1ccc(Cl)cc1Cl)C2=O]

Step 3 of Intermediate 33 was prepared following a similar procedure to that of step 1 of Intermediate 5 from methyl 5-oxo-2,3,4,5-tetrahydrobenzo[b]oxepine-8-carboxylate to give 1.13 g (67%) of methyl 4-(2,4-dichlorophenyl)-5-oxo-2,3,4,5-tetrahydrobenzo[b]oxepine-8-carboxylate.

LC/MS (m/z, MH+): 365

Step 4: Methyl 4-(2,4-dichlorophenyl)-5-(((trifluoromethyl)sulfonyl)oxy)-2,3-dihydrobenzo[b]oxepine-8-carboxylate

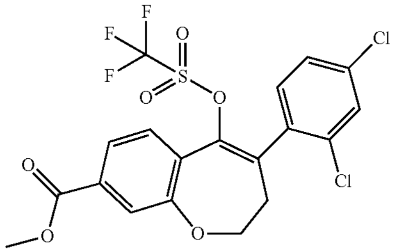 [SMILES: COC(=O)c1ccc2c(c1)OCCC(c1ccc(Cl)cc1Cl)=C2OS(=O)(=O)C(F)(F)F]

Step 4 of Intermediate 33 was prepared following a similar procedure to that of step 2 of Intermediate 5 from methyl 4-(2,4-dichlorophenyl)-5-oxo-2,3,4,5-tetrahydrobenzo[b]oxepine-8-carboxylate to give 0.48 g (31%) of methyl 4-(2,4-dichlorophenyl)-5-(((trifluoromethyl)sulfonyl)oxy)-2,3-dihydrobenzo[b]oxepine-8-carboxylate.

LC/MS (m/z, MH+): 496

Intermediate 34: Methyl 4-(2,4-dichlorophenyl)-5-(((trifluoromethyl)sulfonyl)oxy)-2,3-dihydrobenzo[b]thiepine-8-carboxylate

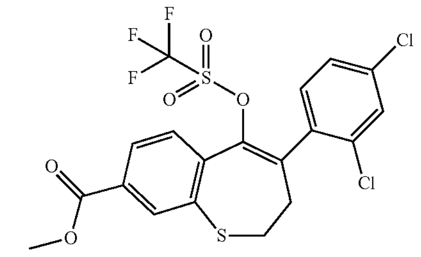 [SMILES: COC(=O)c1ccc2c(c1)SCCC(c1ccc(Cl)cc1Cl)=C2OS(=O)(=O)C(F)(F)F]

Step 1: 5-Oxo-2,3,4,5-tetrahydrobenzo[b]thiepine-8-yl trifluoromethanesulfonate

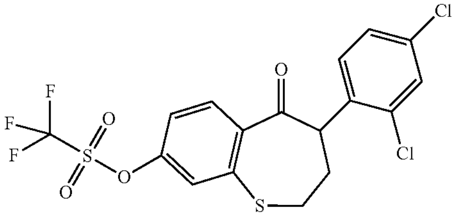 [SMILES: O=C1c2ccc(OS(=O)(=O)C(F)(F)F)cc2SCCC1c1ccc(Cl)cc1Cl]

Step 1 of Intermediate 34 was prepared following a similar procedure to that of step 1 of Intermediate 33 from 8-hydroxy-3,4-dihydrobenzo[b]thiepine-5(2H)-one (prepared according to WO2018091153) to give 6.3 g (48%) of 5-oxo-2,3,4,5-tetrahydrobenzo[b]thiepine-8-yl trifluoromethanesulfonate.

LC/MS (m/z, MH+): 327

Step 2: Methyl 5-oxo-2,3,4,5-tetrahydrobenzo[b]thiepine-8-carboxylate

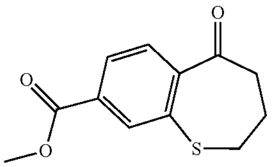 [SMILES: COC(=O)c1ccc2c(c1)SCCCC2=O]

Step 2 of Intermediate 34 was prepared following a similar procedure to that of step 2 Intermediate 33 from 5-oxo-2,3,4,5-tetrahydrobenzo[b]thiepine-8-yl trifluoromethanesulfonate to give 6.36 g (94%) of methyl 5-oxo-2,3,4,5-tetrahydrobenzo[b]thiepine-8-carboxylate.

LC/MS (m/z, MH+): 237

Step 3: Methyl 4-(2,4-dichlorophenyl)-5-oxo-2,3,4,5-tetrahydrobenzo[b]thiepine-8-carboxylate

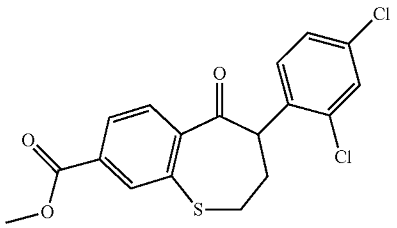 [SMILES: COC(=O)c1ccc2c(c1)SCCC(c1ccc(Cl)cc1Cl)C2=O]

Step 3 of Intermediate 34 was prepared following a similar procedure to that of step 1 of Intermediate 5 from methyl 5-oxo-2,3,4,5-tetrahydrobenzo[b]thiepine-8-carboxylate to give 0.9 g (60%) of methyl 4-(2,4-dichlorophenyl)-5-oxo-2,3,4,5-tetrahydrobenzo[b]thiepine-8-carboxylate.

LC/MS (m/z, MH+): 381

Step 4: Methyl 4-(2,4-dichlorophenyl)-5-(((trifluoromethyl)sulfonyl)oxy)-2,3-dihydrobenzo[b]thiepine-8-carboxylate

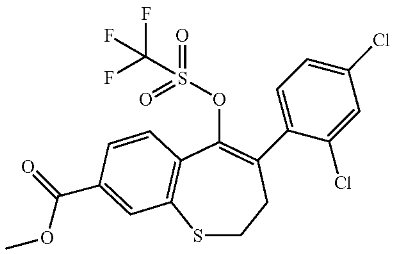 [SMILES: COC(=O)c1ccc2c(c1)SCCC(c1ccc(Cl)cc1Cl)=C2OS(=O)(=O)C(F)(F)F]

Step 4 of Intermediate 34 was prepared following a similar procedure to that of step 2 of Intermediate 5 from methyl 4-(2,4-dichlorophenyl)-5-oxo-2,3,4,5-tetrahydrobenzo[b]thiepine-8-carboxylate to give 1.31 g (44%) of methyl 4-(2,4-dichlorophenyl)-5-(((trifluoromethyl)sulfonyl)oxy)-2,3-dihydrobenzo[b]thiepine-8-carboxylate.

LC/MS (m/z, MH+): 512

Intermediate 35: Methyl 6-(2,4-dichlorophenyl)-5-(trifluoromethylsulfonyloxy)-7,8-dihydronaphthalene-2-carboxylate

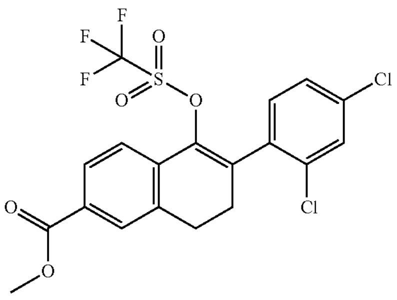 [SMILES: COC(=O)c1ccc2c(c1)CCC(c1ccc(Cl)cc1Cl)=C2OS(=O)(=O)C(F)(F)F]

Step 1: Methyl 2-(2,4-dichlorophenyl)-1-oxo-tetralin-6-carboxylate

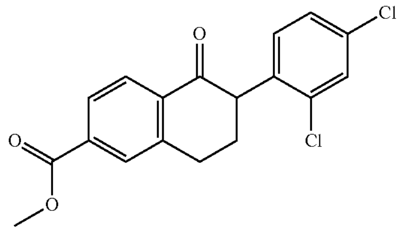 [SMILES: COC(=O)c1ccc2c(c1)CCC(c1ccc(Cl)cc1Cl)C2=O]

Step 1 of Intermediate 35 was prepared following a similar procedure to that of step 1 of Intermediate 5 from methyl 1-oxotetralin-6-carboxylate to give 459 mg (19%) of methyl 4-(2,4-dichlorophenyl)-5-oxo-2,3,4,5-tetrahydrobenzo[b]oxepine-8-carboxylate.

LC/MS (m/z, MH+): 349

Step 2: Methyl 6-(2,4-dichlorophenyl)-5-(trifluoromethylsulfonyloxy)-7,8-dihydronaphthalene-2-carboxylate

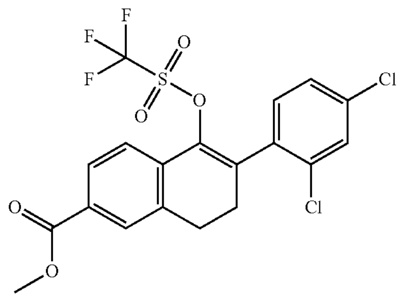 [SMILES: COC(=O)c1ccc2c(c1)CCC(c1ccc(Cl)cc1Cl)=C2OS(=O)(=O)C(F)(F)F]

Step 2 of Intermediate 35 was prepared following a similar procedure to that of step 2 of Intermediate 32 from methyl 2-(2,4-dichlorophenyl)-1-oxo-tetralin-6-carboxylate to give 0.48 g (31%) of methyl 6-(2,4-dichlorophenyl)-5-(trifluoromethylsulfonyloxy)-7,8-dihydronaphthalene-2-carboxylate.

LC/MS (m/z, MH+): 481

Intermediate 36: Methyl 8-bromo-9-(4-((1-(3,3,3-trifluoropropyl)azetidin-3-ylidene)methyl)phenyl)-6,7-dihydro-5H-benzo[7]annulene-3-carboxylate

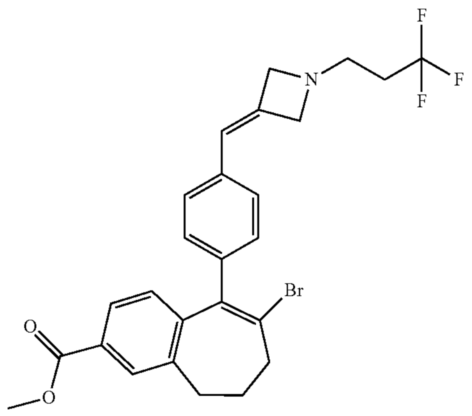 [SMILES: COC(=O)c1ccc2c(c1)CCCC(Br)=C2c1ccc(C=C2CN(CCC(F)(F)F)C2)cc1]

Intermediate 36 was prepared following a similar procedure to that of step 2 of Intermediate 9 from methyl 9-(4-(azetidin-3-ylidenemethyl)phenyl)-8-bromo-6,7-dihydro-5H-benzo[7]annulene-3-carboxylate, trifluoroacetic acid (Intermediate 7, Method 1, Step 5) and 1,1,1-trifluoro-3-iodo-propane to give 332 mg (27%) methyl 8-bromo-9-(4-((1-(3,3,3-trifluoropropyl)azetidin-3-ylidene)methyl)phenyl)-6,7-dihydro-5H-benzo[7]annulene-3-carboxylate.

LC/MS (m/z, MH+): 520

Intermediate 37: Methyl 8-bromo-9-(4-((1-(3-fluoropropyl-1,1-d2)azetidin-3-ylidene)methyl)phenyl)-6,7-dihydro-5H-benzo[7]annulene-3-carboxylate

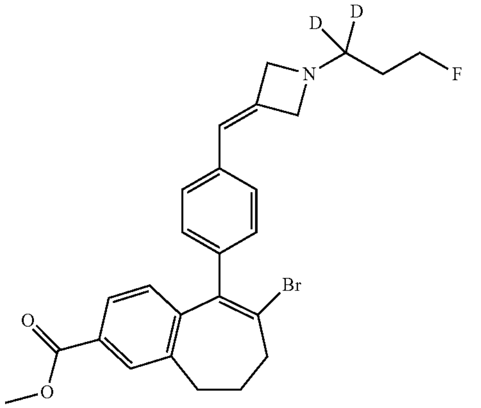 [SMILES: [2H]C([2H])(CCF)N1CC(=Cc2ccc(C3=C(Br)CCCc4cc(C(=O)OC)ccc43)cc2)C1]

Step 1: 1,1-Dideuterio-3-fluoro-propan-1-ol

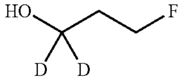

To a solution of lithium aluminum deuteride (911 mg, 21.7 mmol) in $Et_2O$ (50 ml) cooled at 0° C., was dropwise added a solution of 3-fluoropropanoic acid (1 g, 10.41 mmol) in $Et_2O$ (30 ml). The reaction mixture was slowly warmed up to 20° C. and stirred for 48 hours. The reaction mixture was poured to a mixture of ice, HCl 2N and $Et_2O$. the organic dried over $Na_2SO_4$, filtered and concentrated under reduced pressure to give 400 mg (38%) of 1,1-dideuterio-3-fluoro-propan-1-ol which was used in the next step without further purification.

Step 2: (1,1-Dideuterio-3-fluoro-propyl) trifluoromethanesulfonate

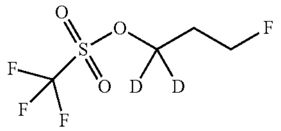 [SMILES: [2H]C([2H])(CCF)OS(=O)(=O)C(F)(F)F]

Step 2 of Intermediate 37 was prepared following a similar procedure to that of step 1 of Intermediate 9 from 1,1-dideuterio-3-fluoro-propan-1-ol to give 600 mg (37%) of (1,1-dideuterio-3-fluoro-propyl) trifluoromethanesulfonate which was used in the next step without further purification.

Step 3: Methyl 8-bromo-9-(4-((1-(3-fluoropropyl-1,1-d2)azetidin-3-ylidene)methyl)phenyl)-6,7-dihydro-5H-benzo[7]annulene-3-carboxylate

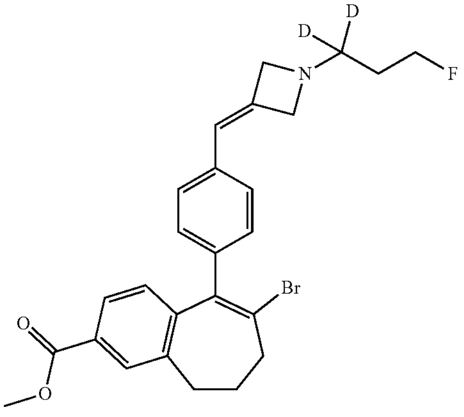 [SMILES: [2H]C([2H])(CCF)N1CC(=Cc2ccc(C3=C(Br)CCCc4cc(C(=O)OC)ccc43)cc2)C1]

Step 3 of Intermediate 37 was prepared following a similar procedure to that of step 2 of Intermediate 9 from methyl 9-(4-(azetidin-3-ylidenemethyl)phenyl)-8-bromo-6,7-dihydro-trifluoroacetic acid (Intermediate 7, Method 1, Step 5) and (1,1-dideuterio-3-fluoro-propyl) trifluoromethanesulfonate to give 270 mg (67%) of methyl 8-bromo-9-(4-((1-(3-fluoropropyl-1,1-d2)azetidin-3-ylidene)methyl)phenyl)-6,7-dihydro-5H-benzo[7]annulene-3-carboxylate.

LC/MS (m/z, MH+): 487

Intermediate 38: Methyl 8-bromo-9-(4-((1-(3,3-difluoropropyl-1,1-d2)azetidin-3-ylidene)methyl)phenyl)-6,7-dihydro-5H-benzo[7]annulene-3-carboxylate

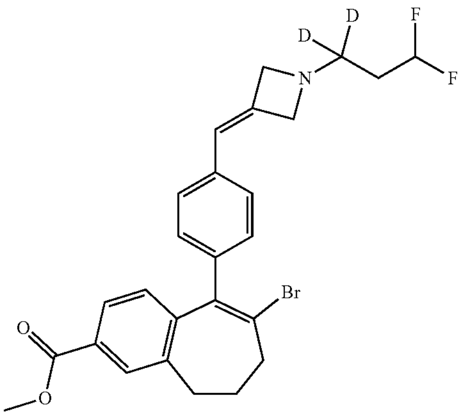 [SMILES: [2H]C([2H])(CC(F)F)N1CC(=Cc2ccc(C3=C(Br)CCCc4cc(C(=O)OC)ccc43)cc2)C1]

Step 1: 1,1-Dideuterio-3,3-difluoro-propan-1-ol

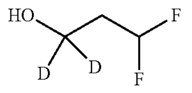

Step 1 of Intermediate 38 was prepared following a similar procedure to that of step 1 of Intermediate 37 from 3,3-difluoropropanoic acid to give 810 mg (47%) of 1,1-dideuterio-3,3-difluoro-propan-1-ol which was used in the next step without further purification.

Step 2: (1,1-Dideuterio-3,3-difluoro-propyl) trifluoromethanesulfonate

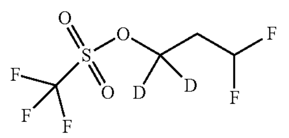 [SMILES: [2H]C([2H])(CC(F)F)OS(=O)(=O)C(F)(F)F]

Step 2 of Intermediate 38 was prepared following a similar procedure to that of step 1 of Intermediate 9 from 1,1-dideuterio-3,3-difluoro-propan-1-ol to give 1.1 g (79%) of (1,1-dideuterio-3,3-difluoro-propyl) trifluoromethanesulfonate which was used in the next step without further purification.

Step 3: Methyl 8-bromo-9-(4-((1-(3,3-difluoropropyl-1,1-d2)azetidin-3-ylidene)methyl)phenyl)-6,7-dihydro-5H-benzo[7]annulene-3-carboxylate

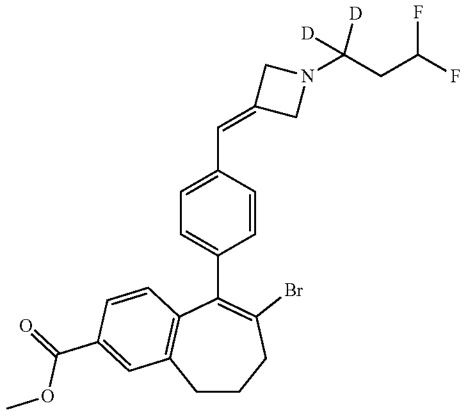 [SMILES: [2H]C([2H])(CC(F)F)N1CC(=Cc2ccc(C3=C(Br)CCCc4cc(C(=O)OC)ccc43)cc2)C1]

Step 3 of Intermediate 38 was prepared following a similar procedure to that of step 2 of Intermediate 9 from methyl 9-(4-(azetidin-3-ylidenemethyl)phenyl)-8-bromo-6,7-dihydro-5H-benzo[7]annulene-3-carboxylate, trifluoroacetic acid (Intermediate 7, Method 1, Step 5) and (1,1-dideuterio-3,3-difluoro-propyl) trifluoromethanesulfonate to give 243 mg (51%) of methyl 8-bromo-9-(4-((1-(3,3-difluoropropyl-1,1-d2)azetidin-3-ylidene)methyl)phenyl)-6,7-dihydro-5H-benzo[7]annulene-3-carboxylate.

LC/MS (m/z, MH+): 505

Intermediate 39: Methyl 8-(3,3-dimethylcyclohexyl)-9-(((trifluoromethyl)sulfonyl)oxy)-6,7-dihydro-5H-benzo[7]annulene-3-carboxylate

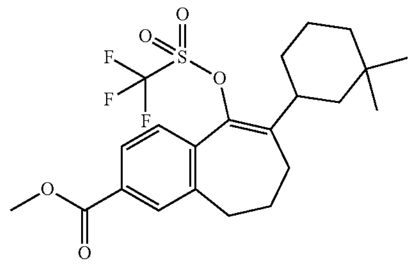

Step 1: Methyl 6-bromo-5-oxo-6,7,8,9-tetrahydro-5H-benzo[7]annulene-2-carboxylate

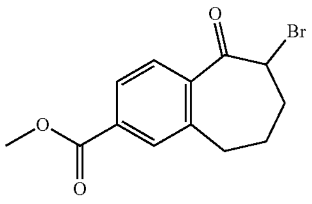 [SMILES: COC(=O)c1ccc2c(c1)CCCC(Br)C2=O]

To a mixture of methyl 5-oxo-6,7,8,9-tetrahydro-5H-benzo[7]annulene-2-carboxylate (9.42 g, 43.2 mmol) in DCM (400 mL) was portionwise added pyridinium tribromide (16.12 g, mmol). The reaction mixture was stirred overnight at room temperature. Water (500 ml) and ether (1 L) were added. The organic phase was separated and washed twice with water, dried over $MgSO_4$, filtered and concentrated under reduced pressure to give 14.4 g (90%) of methyl 6-bromo-5-oxo-6,7,8,9-tetrahydro-5H-benzo[7]annulene-2-carboxylate.

LC/MS (m/z, MH+): 297

Step 2: Methyl 9-acetoxy-8-bromo-6,7-dihydro-5H-benzo[7]annulene-3-carboxylate

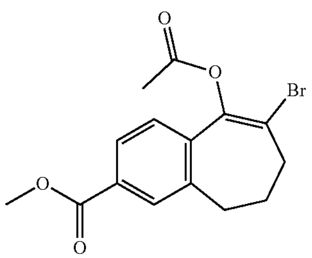 [SMILES: COC(=O)c1ccc2c(c1)CCCC(Br)=C2OC(C)=O]

To a solution of methyl 6-bromo-5-oxo-6,7,8,9-tetrahydro-5H-benzo[7]annulene-2-carboxylate (7.4 g, 25 mmol) in THF (80 mL) at −78° C. under Ar atmosphere was added LiHMDS (1 M, 27 mL). The mixture was stirred for 2 hours then treated with acetic anhydride (8.8 mL, 75 mmol) allowing the temperature to warmed up to 0° C. After pouring onto diisopropyl ether and water, the aqueous layer was separated and extracted with diisopropyl ether. The combined organic layers were washed with water, dried over $Na_2SO_4$, filtered, and concentrated under reduced pressure. The residue was purified by flash chromatography with a 0-50% gradient of ethyl acetate in cyclohexane to give 6.97 g (83%) of methyl 9-acetoxy-8-bromo-6,7-dihydro-5H-benzo[7]annulene-3-carboxylate.

LC/MS (m/z, MH+): 339

Step 3: Methyl 9-acetoxy-8-(3,3-dimethylcyclohex-1-en-1-yl)-6,7-dihydro-5H-benzo[7]annulene-3-carboxylate

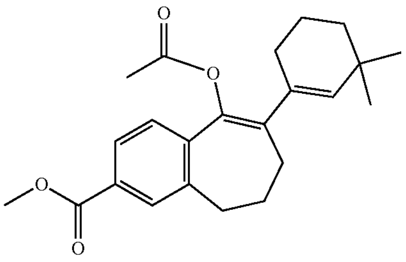

Step 3 of Intermediate 39 was prepared following a similar procedure to that of step 1 of Example 79 from methyl 9-acetoxy-8-bromo-6,7-dihydro-5H-benzo[7]annulene-3-carboxylate and 2-(3,3-dimethylcyclohexen-1-yl)-4,4,5,5-tetramethyl-1,3,2-dioxaborolane to give 2.9 g (89%) of methyl 9-acetoxy-8-(3,3-dimethylcyclohex-1-en-1-yl)-6,7-dihydro-[7]annulene-3-carboxylate.

LC/MS (m/z, MH+): 369

Step 4: Methyl 9-acetoxy-8-(3,3-dimethylcyclohexyl)-6,7-dihydro-5H-benzo[7]annulene-3-carboxylate

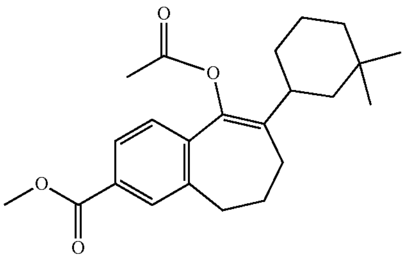

Step 4 of Intermediate 39 was prepared following a similar procedure to that of step 2 of Example 100 from methyl 9-acetoxy-8-(3,3-dimethylcyclohex-1-en-1-yl)-6,7-dihydro-5H-benzo[7]annulene-3-carboxylate to give 1.19 g (54%) of methyl 9-acetoxy-8-(3,3-dimethylcyclohexyl)-6,7-dihydro-5H-benzo[7]annulene-3-carboxylate.

LC/MS (m/z, MH+): 371

Step 5: Methyl 6-benzyl-5-oxo-6,7,8,9-tetrahydro-5H-benzo[7]annulene-2-carboxylate

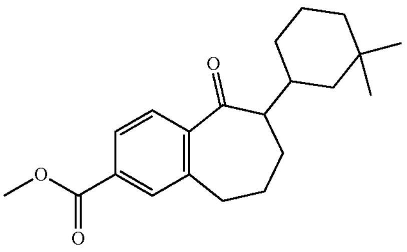

To a solution of methyl 9-acetoxy-8-bromo-6,7-dihydro-5H-benzo[7]annulene-3-carboxylate (285 mg, 0.81 mmol) in methanol (8 mL) and DCM (4 mL) was added a 12 N solution of HCl (0.44 mL, 5.29 mmol). The resulting reaction mixture was heated to reflux for 7 hours then stirred overnight at room temperature. After pouring onto diisopropyl ether and water, the aqueous layer was separated and extracted with diisopropyl ether. The combined organic layers were washed with water, a 5% aqueous solution of $Na_2CO_3$ and water then dried over $Na_2SO_4$, filtered, and concentrated under reduced pressure to give 220 mg (88%) of methyl 6-benzyl-5-oxo-6,7,8,9-tetrahydro-5H-benzo[7]annulene-2-carboxylate which was used in the next step without further purification.

LC/MS (m/z, MH+): 309

Step 6: Methyl 8-(3,3-dimethylcyclohexyl)-9-(((trifluoromethyl)sulfonyl)oxy)-6,7-dihydro-5H-benzo[7]annulene-3-carboxylate

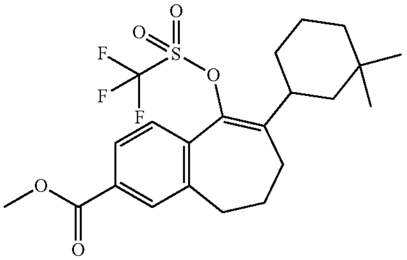

Step 6 of Intermediate 39 was prepared following a similar procedure to that of step 2 of Intermediate 32 from methyl 6-benzyl-5-oxo-6,7,8,9-tetrahydro-5H-benzo[7]annulene-2-carboxylate to give 760 mg (77%) of methyl 8-(3,3-dimethylcyclohexyl)-9-(((trifluoromethyl)sulfonyl)oxy)-6,7-dihydro-5H-benzo[7]annulene-3-carboxylate.

LC/MS (m/z, MH+): 461

Intermediate 40: Methyl 8-(bicyclo[3.1.0]hexan-1-yl)-9-(((trifluoromethyl)sulfonyl)oxy)-6,7-dihydro-5H-benzo[7]annulene-3-carboxylate

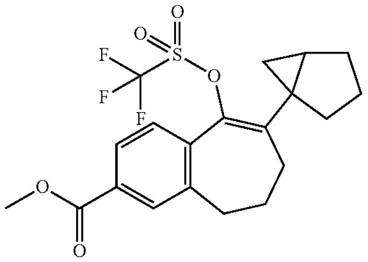 [SMILES: COC(=O)c1ccc2c(c1)CCCC(C13CCCC1C3)=C2OS(=O)(=O)C(F)(F)F]

Step 1: Methyl 9-acetoxy-8-(bicyclo[3.1.0]hexan-1-yl)-6,7-dihydro-5H-benzo[7]annulene-3-carboxylate

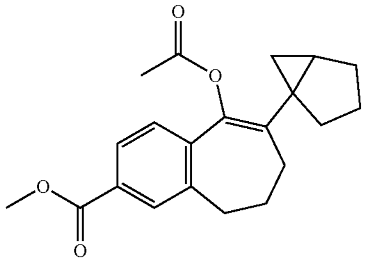 [SMILES: COC(=O)c1ccc2c(c1)CCCC(C13CCCC1C3)=C2OC(C)=O]

A mixture of methyl 9-acetoxy-8-bromo-6,7-dihydro-5H-benzo[7]annulene-3-carboxylate (0.4 g, 1.18 mmol), potassium bicyclo[3.1.0]hexan-1-yltrifluoroborate (266 mg, 1.41 mmol), $Cs_2CO_3$ (1.15 g, 3.54 mmol), and Pd(dppf)$Cl_2$, complex with DCM (91 mg, 120 μmol) in toluene (6 mL) and water (2 mL) was heated to 90° C. in a sealed tube for 6 hours. After cooling to room temperature, EtOAc (200 mL) and water (50 mL) were added. After separation, the organic layer was washed with water (50 mL), dried over $Na_2SO_4$, filtered and concentrated under reduced pressure. The residue was purified by flash chromatography with a 0-20% gradient of ethyl acetate in cyclohexane to give 0.45 g (40%) of methyl 9-acetoxy-8-(bicyclo[3.1.0]hexan-1-yl)-6,7-dihydro-5H-benzo[7]annulene-3-carboxylate.

LC/MS (m/z, MH+): 341

Step 2: Methyl 6-(bicyclo[3.1.0]hexan-1-yl)-5-oxo-6,7,8,9-tetrahydro-5H-benzo[7]annulene-2-carboxylate

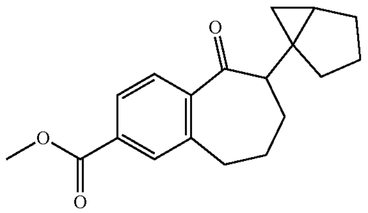 [SMILES: COC(=O)c1ccc2c(c1)CCCC(C13CCCC1C3)C2=O]

Step 2 of Intermediate 40 was prepared following a similar procedure to that of step 5 of Intermediate 39 from methyl 9-acetoxy-8-(bicyclo[3.1.0]hexan-1-yl)-6,7-dihydro-5H-benzo[7]annulene-3-carboxylate to give 0.3 g (100%) of methyl 6-(bicyclo[3.1.0]hexan-1-yl)-5-oxo-6,7,8,9-tetrahydro-5H-benzo[7]annulene-2-carboxylate.

LC/MS (m/z, MH+): 299

Step 3: Methyl 8-(bicyclo[3.1.0]hexan-1-yl)-9-(((trifluoromethyl)sulfonyl)oxy)-6,7-dihydro-5H-benzo[7]annulene-3-carboxylate

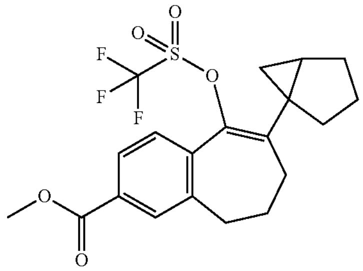 [SMILES: COC(=O)c1ccc2c(c1)CCCC(C13CCCC1C3)=C2OS(=O)(=O)C(F)(F)F]

Step 3 of Intermediate 40 was prepared following a similar procedure to that of step 2 of Intermediate 32 from methyl 6-(bicyclo[3.1.0]hexan-1-yl)-5-oxo-6,7,8,9-tetrahydro-5H-benzo[7]annulene-2-carboxylate to give 247 mg (56%) of methyl 8-(bicyclo[3.1.0]hexan-1-yl)-9-(((trifluoromethyl)sulfonyl)oxy)-6,7-dihydro-5H-benzo[7]annulene-3-carboxylate.

LC/MS (m/z, MH+): 431

Intermediate 41: Methyl 8-(bicyclo[3.2.1]octan-3-yl)-9-(((trifluoromethyl)sulfonyl)oxy)-6,7-dihydro-5H-benzo[7]annulene-3-carboxylate

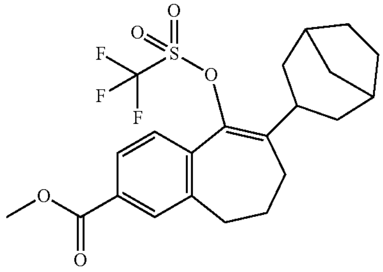 [SMILES: COC(=O)c1ccc2c(c1)CCCC(C1CC3CCC(C3)C1)=C2OS(=O)(=O)C(F)(F)F]

Step 1: Methyl 9-acetoxy-8-(bicyclo[3.2.1]oct-2-en-3-yl)-6,7-dihydro-5H-benzo[7]annulene-3-carboxylate

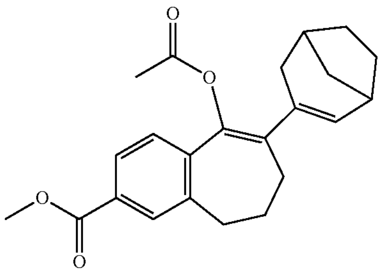 [SMILES: COC(=O)c1ccc2c(c1)CCCC(C1=CC3CCC(C1)C3)=C2OC(C)=O]

Step 1 of Intermediate 41 was prepared following a similar procedure to that of step 1 of Example 79 from methyl 9-acetoxy-8-bromo-6,7-dihydro-5H-benzo[7]annulene-3-carboxylate and 2-(3-bicyclo[3.2.1]oct-2-enyl)-4,4,5,5-tetramethyl-1,3,2-dioxaborolane to give 1.07 g (99%) of methyl 9-acetoxy-8-(bicyclo[3.2.1]oct-2-en-3-yl)-6,7-dihydro-5H-benzo[7]annulene-3-carboxylate.

LC/MS (m/z, MH+): 367

Step 2: Methyl 9-acetoxy-8-(bicyclo[3.2.1]octan-3-yl)-6,7-dihydro-5H-benzo[7]annulene-3-carboxylate

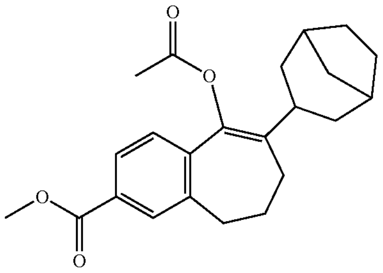 [SMILES: COC(=O)c1ccc2c(c1)CCCC(C1CC3CCC(C3)C1)=C2OC(C)=O]

Step 2 of Intermediate 41 was prepared following a similar procedure to that of step 2 of Example 100 from methyl 9-acetoxy-8-(bicyclo[3.2.1]oct-2-en-3-yl)-6,7-dihydro-5H-benzo[7]annulene-3-carboxylate to give 0.58 g (54%) of methyl 9-acetoxy-8-(bicyclo[3.2.1]octan-3-yl)-6,7-dihydro-5H-benzo[7]annulene-3-carboxylate.

LC/MS (m/z, MH+): 369

Step 3: Methyl 6-(bicyclo[3.2.1]octan-3-yl)-5-oxo-6,7,8,9-tetrahydro-5H-benzo[7]annulene-2-carboxylate

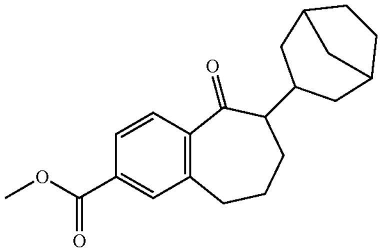 [SMILES: COC(=O)c1ccc2c(c1)CCCC(C1CC3CCC(C3)C1)C2=O]

Step 3 of Intermediate 41 was prepared following a similar procedure to that of step 5 of Intermediate 39 from methyl 9-acetoxy-8-(bicyclo[3.2.1]octan-3-yl)-6,7-dihydro-5H-benzo[7]annulene-3-carboxylate to give 0.51 mg (99%) of methyl 6-(bicyclo[3.2.1]octan-3-yl)-5-oxo-6,7,8,9-tetrahydro-5H-benzo[7]annulene-2-carboxylate.

LC/MS (m/z, MH+): 327

Step 4: Methyl 8-(bicyclo[3.2.1]octan-3-yl)-9-(((trifluoromethyl)sulfonyl)oxy)-6,7-dihydro-5H-benzo[7]annulene-3-carboxylate

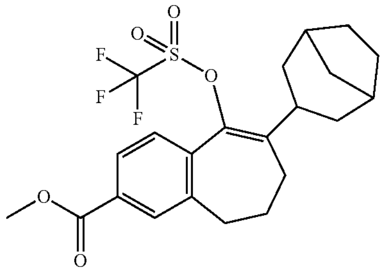 [SMILES: COC(=O)c1ccc2c(c1)CCCC(C1CC3CCC(C3)C1)=C2OS(=O)(=O)C(F)(F)F]

Step 4 of Intermediate 41 was prepared following a similar procedure to that of step 2 of Intermediate 32 from methyl 6-(bicyclo[3.2.1]octan-3-yl)-5-oxo-6,7,8,9-tetrahydro-5H-benzo[7]annulene-2-carboxylate to give 0.48 g (67%) of methyl 8-(bicyclo[3.2.1]octan-3-yl)-9-(((trifluoromethyl) sulfonyl)oxy)-6,7-dihydro-5H-benzo[7]annulene-3-carboxylate. LC/MS (m/z, MH+): 459

Intermediate 42: 8-(2,4-Dichlorophenyl)-9-(((trifluoromethyl)sulfonyl)oxy)-6,7-dihydro-pivalate

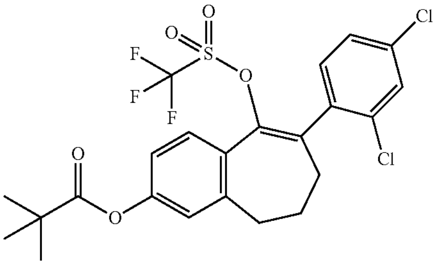 [SMILES: CC(C)(C)C(=O)Oc1ccc2c(c1)CCCC(c1ccc(Cl)cc1Cl)=C2OS(=O)(=O)C(F)(F)F]

Step 1: 6-(2,4-Dichlorophenyl)-5-oxo-6,7,8,9-tetrahydro-5H-benzo[7]annulen-2-yl pivalate

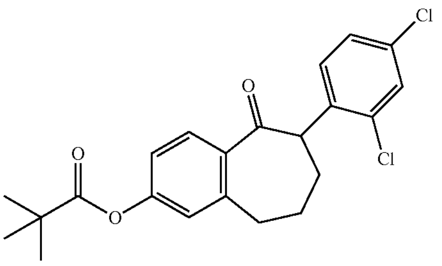 [SMILES: CC(C)(C)C(=O)Oc1ccc2c(c1)CCCC(c1ccc(Cl)cc1Cl)C2=O]

Step 1 of Intermediate 42 was prepared following a similar procedure to that of step 1 of Intermediate 5 from 5-oxo-6,7,8,9-tetrahydro-5H-benzo[7]annulen-2-yl pivalate (prepared according to WO2018091153) to give 795 mg (30%) of 6-(2,4-dichlorophenyl)-5-oxo-6,7,8,9-tetrahydro-5H-benzo[7]annulen-2-yl pivalate LC/MS (m/z, MH+): 405

Step 2: 8-(2,4-Dichlorophenyl)-9-(((trifluoromethyl) sulfonyl)oxy)-6,7-dihydro-5H-benzo[7]annulen-3-yl pivalate

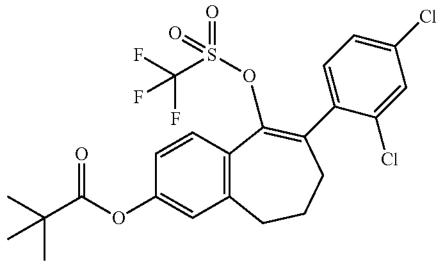 [SMILES: CC(C)(C)C(=O)Oc1ccc2c(c1)CCCC(c1ccc(Cl)cc1Cl)=C2OS(=O)(=O)C(F)(F)F]

Step 2 of Intermediate 42 was prepared following a similar procedure to that of step 2 of Intermediate 32 from 6-(2,4-dichlorophenyl)-5-oxo-6,7,8,9-tetrahydro-5H-benzo [7]annulen-2-yl pivalate to give 0.33 g (69%) of 8-(2,4-dichlorophenyl)-9-(((trifluoromethyl) sulfonyl)oxy)-6,7-dihydro-5H-benzo[7]annulen-3-yl pivalate.

LC/MS (m/z, MH+): 537

Intermediate 43: Tert-butyl 3-(4-(8-bromo-3-(methoxycarbonyl)-7-methyl-6,7-dihydro-Isomer 1 and Isomer 2

Isomer 1

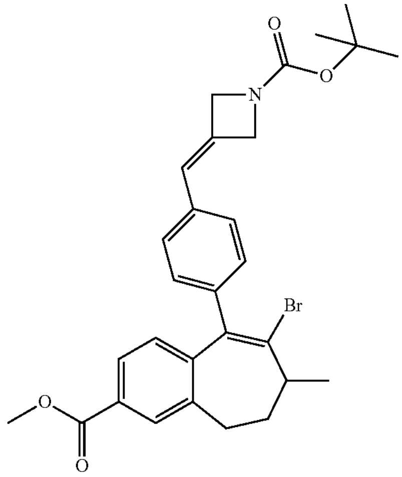

-continued

Isomer 2

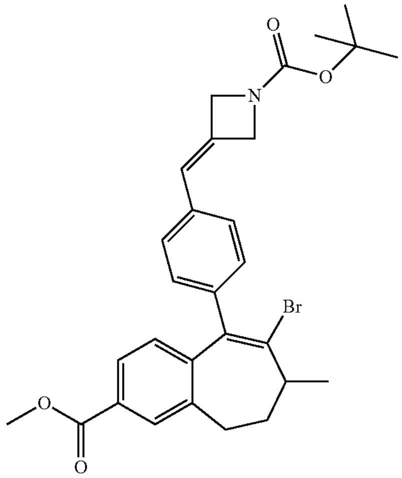

Step 1: Methyl 6-bromo-5-oxo-6,7,8,9-tetrahydro-5H-benzo[7]annulene-2-carboxylate

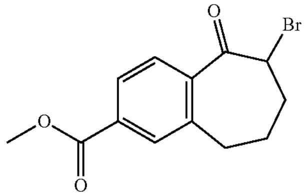 [SMILES: COC(=O)c1ccc2c(c1)CCCC(Br)C2=O]

To a mixture of methyl 5-oxo-6,7,8,9-tetrahydro-5H-benzo[7]annulene-2-carboxylate (9.42 g, 43.2 mmol) in DCM (400 mL) was portionwise added pyridinium tribromide (16.12 g, 45.4 mmol). The reaction mixture was stirred overnight at room temperature. Water (500 ml) and ether (1 L) were added. The organic phase was separated and washed twice with water, dried over $MgSO_4$, filtered and concentrated under reduced pressure to give 14.4 g (90%) of methyl 6-bromo-5-oxo-6,7,8,9-tetrahydro-5H-benzo[7]annulene-2-carboxylate.

LC/MS (m/z, MH+): 297

Step 2: Methyl 5-oxo-8,9-dihydro-5H-benzo[7]annulene-2-carboxylate

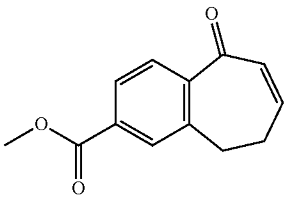 [SMILES: COC(=O)c1ccc2c(c1)CCC=CC2=O]

To a solution of methyl 6-bromo-5-oxo-6,7,8,9-tetrahydro-5H-benzo[7]annulene-2-carboxylate (10 g, 33.66 mmol) in acetonitrile (100 mL) was added DABCO (7.4 mL, 67.32 mmol). The reaction mixture was heated to 55° C. for 2.5 hours under Ar. Ether and 1N HCl were added. The organic phase was separated and washed twice with water, with brine, dried over $MgSO_4$, filtered and concentrated under reduced pressure. The resulting residue was then purified by flash chromatography eluting with a mixture of cyclohexane/EtOAc 85/15 to give 1.88 g (26%) of methyl 5-oxo-8,9-dihydro-5H-benzo[7]annulene-2-carboxylate.

LC/MS (m/z, MH+): 217

Step 3: Methyl 7-methyl-5-oxo-6,7,8,9-tetrahydro-5H-benzo[7]annulene-2-carboxylate, racemic mixture

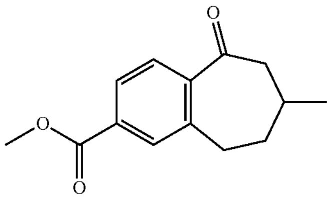

To a solution of methyl 5-oxo-8,9-dihydro-5H-benzo[7]annulene-2-carboxylate (1.88 g, 8.6 mmol) in THF (30 mL) under Ar at 0° C. was added a 0.328 M cuprate solution (35 mL, 11.5 mmol) prepared by addition of 15 mL of a 1.6 N solution of methyl lithium in ether to a suspension of 2.5 g of CuI (13 mmol) in 25 mL of ether under Ar at 0° C. The reaction mixture was stirred for 30 minutes at 0° C. Ether (200 mL) and 1N HCl (200 mL) were added. The organic phase was separated and the aqueous phase extracted with ether. The combined organic phases were washed with water, dried over $MgSO_4$, filtered and concentrated under reduced pressure. The resulting residue was then purified by flash chromatography eluting with a mixture of cyclohexane/EtOAc 95/5 to give 1.95 g (86%) of methyl 7-methyl-5-oxo-6,7,8,9-tetrahydro-5H-benzo[7]annulene-2-carboxylate as a racemic mixture.

LC/MS (m/z, MH+): 233

Step 4: Methyl 7-methyl-9-(((trifluoromethyl)sulfonyl)oxy)-6,7-dihydro-5H-benzo[7]annulene-3-carboxylate, racemic mixture

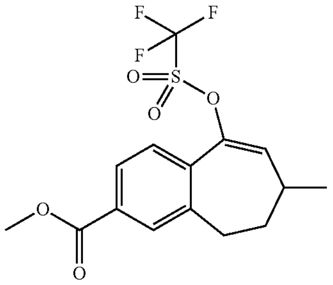

Step 4 of Intermediate 43 was prepared following a similar procedure to that of step 2 of Intermediate 32 from methyl 7-methyl-5-oxo-6,7,8,9-tetrahydro-5H-benzo[7]annulene-2-carboxylate to give 2.5 g (86%) of methyl 7-methyl-9-(((trifluoromethyl)sulfonyl)oxy)-6,7-dihydro-5H-benzo[7]annulene-3-carboxylate as a racemic mixture.

LC/MS (m/z, MH+): 365

Step 5: Methyl 9-(4-aminophenyl)-7-methyl-6,7-dihydro-5H-benzo[7]annulene-3-carboxylate, racemic mixture

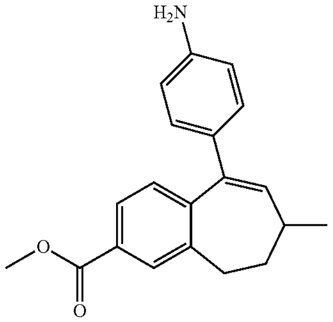

Step 5 of Intermediate 43 was prepared following a similar procedure to that of step 1 (Method 1) of Intermediate 7 from methyl 7-methyl-9-(((trifluoromethyl)sulfonyl)oxy)-6,7-dihydro-5H-benzo[7]annulene-3-carboxylate to give 0.87 g (100%) of methyl 9-(4-aminophenyl)-7-methyl-6,7-dihydro-5H-benzo[7]annulene-3-carboxylate as a racemic mixture.

LC/MS (m/z, MH+): 308

Step 6: Methyl 9-(4-iodophenyl)-7-methyl-6,7-dihydro-5H-benzo[7]annulene-3-carboxylate, racemic mixture

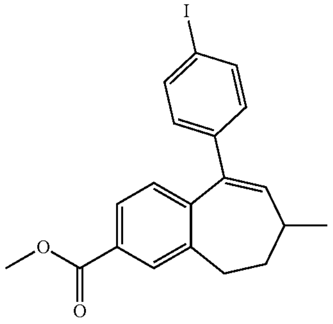

Step 6 of Intermediate 43 was prepared following a similar procedure to that of step 2 (Method 1) of Intermediate 7 from methyl 9-(4-aminophenyl)-7-methyl-6,7-dihydro-5H-benzo[7]annulene-3-carboxylate to give 0.96 g (80%) of methyl 9-(4-iodophenyl)-7-methyl-6,7-dihydro-5H-benzo[7]annulene-3-carboxylate as a racemic mixture.

LC/MS (m/z, MH+): 419

Step 7: Methyl 8-bromo-9-(4-iodophenyl)-7-methyl-6,7-dihydro-5H-benzo[7]annulene-3-carboxylate, racemic mixture

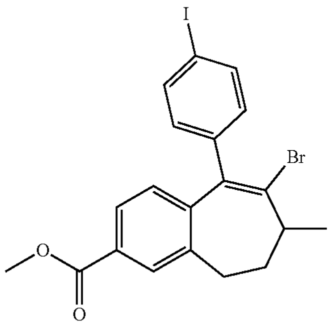

Step 7 of Intermediate 43 was prepared following a similar procedure to that of step 3 (Method 1) of Intermediate 7 from methyl 9-(4-iodophenyl)-7-methyl-6,7-dihydro-5H-benzo[7]annulene-3-carboxylate to give 1.09 g (95%) of methyl 8-bromo-9-(4-iodophenyl)-7-methyl-6,7-dihydro-5H-benzo[7]annulene-3-carboxylate as a racemic mixture. LC/MS (m/z, MH+): 497

Step 8: Tert-butyl 3-(4-(8-bromo-3-(methoxycarbonyl)-7-methyl-6,7-dihydro-5H-benzo[7]annulen-9-yl)benzylidene)azetidine-1-carboxylate, Isomer 1 and Isomer 2

Isomer 1

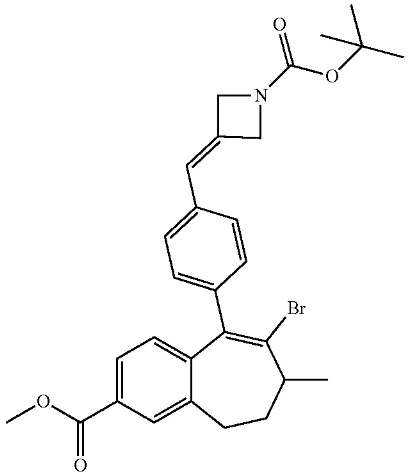

-continued

Isomer 2

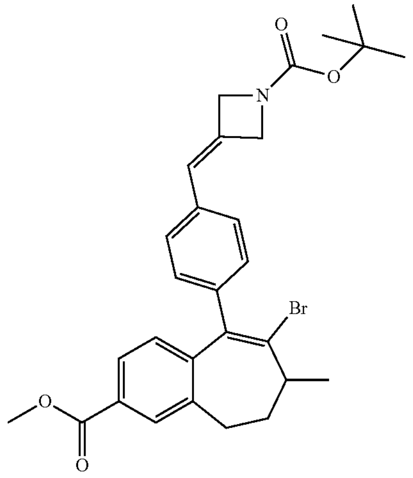

Step 8 of Intermediate 43 was prepared following a similar procedure to that of step 4 (Method 1) of Intermediate 7 from methyl 8-bromo-9-(4-iodophenyl)-7-methyl-6,7-dihydro-5H-benzo[7]annulene-3-carboxylate to give 0.73 g (62%) of tert-butyl 3-(4-(8-bromo-3-(methoxycarbonyl)-7-methyl-6,7-dihydro-5H-benzo[7]annulen-9-yl)benzylidene)azetidine-1-carboxylate as a racemic mixture of Isomer 1 and Isomer 2.

LC/MS (m/z, MH+): 538

The racemic mixture of (4-bromophenyl)(1-(3-fluoropropyl)azetidin-3-yl)methanol was separated by chiral chromatography (condition: flash CHIRALPAK AD 20 μm (350×76.5 mm); Heptane 7%/EtOH 30% to give 0.188 g of Isomer 1 and 0.201 g of Isomer 2.

EXAMPLES

Method A

Example 1: 8-(2,4-Dichlorophenyl)-9-(4-((1-(3-fluoropropyl)azetidin-3-ylidene)methyl)phenyl)-6,7-dihydro-5H-benzo[7]annulene-3-carboxylic acid

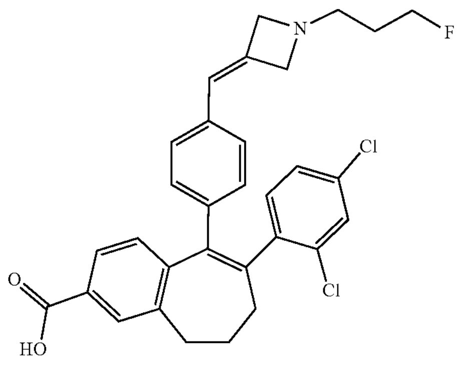 [SMILES: O=C(O)c1ccc2c(c1)CCCC(c1ccc(Cl)cc1Cl)=C2c1ccc(C=C2CN(CCCF)C2)cc1]

Step 1: Methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate

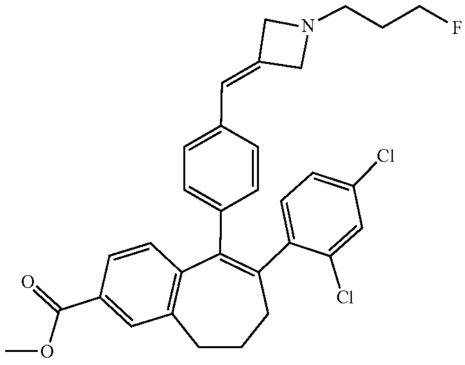 [SMILES: COC(=O)c1ccc2c(c1)CCCC(c1ccc(Cl)cc1Cl)=C2c1ccc(C=C2CN(CCCF)C2)cc1]

A mixture of methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 4) (100 mg, 211 μmol), 3-(4-bromobenzylidene)-1-(3-fluoropropyl)azetidine (Intermediate 1) (60 mg, 211 μmol), $Cs_2CO_3$ (178 mg, 534.5 μmol), and Pd(dppf)$Cl_2$, complex with DCM (11 mg, 13 μmol) in dioxane (1 mL) and water (0.4 mL) was heated to reflux 1 hour. Water (2 mL) and DCM (5 mL) were added. After hydrophobic column decantation, the organic phase was concentrated under reduced pressure and the residue was treated on SCX column. The residue obtained was purified by flash chromatography eluting with a gradient of MeOH in DCM (100/0 to 95/05, v/v) to give 101 mg (86%) of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate.

LC/MS (m/z, MH+): 550

Step 2: 8-(2,4-Dichlorophenyl)-9-(4-((1-(3-fluoropropyl)azetidin-3-ylidene)methyl)phenyl)-6,7-dihydro-5H-benzo[7]annulene-3-carboxylic acid

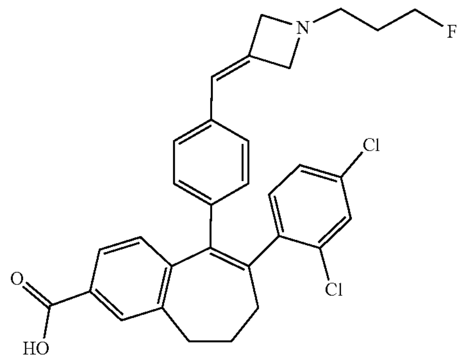 [SMILES: O=C(O)c1ccc2c(c1)CCCC(c1ccc(Cl)cc1Cl)=C2c1ccc(C=C2CN(CCCF)C2)cc1]

To a solution of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate (101 mg, 183.6 μmol) in MeOH (0.50 mL) and THF (1 mL) was added a solution of NaOH 1N (0.55 mL) and the reaction mixture was heated to reflux for 1 hour. After cooling, water (5 mL) and DCM (5 mL) were added and pH was adjusted to 2 with HCl 1N. After hydrophobic column decantation, the organic phase was concentrated under reduced pressure and the residue was purified by SFC (Flash DCPAK B 5 μm; 250×30 mm; supercritical $CO_2$ 70%/MeOH 30%/TEA 0.1% at 120 mL/min) to give 47.5 mg (45%) of 8-(2,4-dichlorophenyl)-9-(4-((1-(3-fluoropropyl)azetidin-3-ylidene)methyl)phenyl)-6,7-dihydro-5H-benzo[7]annulene-3-carboxylic acid.

Method B

Example 79: 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylic acid

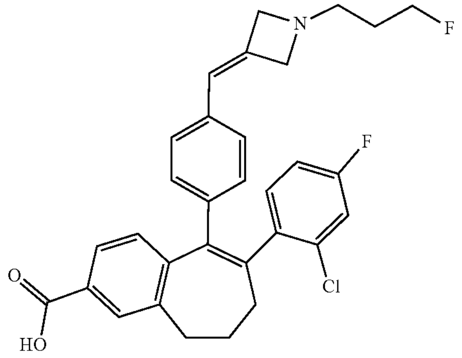 [SMILES: O=C(O)c1ccc2c(c1)CCCC(c1ccc(F)cc1Cl)=C2c1ccc(C=C2CN(CCCF)C2)cc1]

Step 1: Methyl 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylate

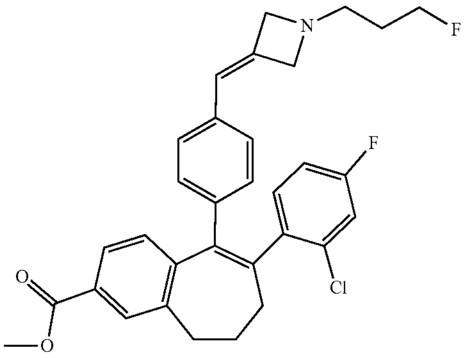 [SMILES: COC(=O)c1ccc2c(c1)CCCC(c1ccc(F)cc1Cl)=C2c1ccc(C=C2CN(CCCF)C2)cc1]

A mixture of methyl 8-bromo-9-(4-((1-(3-fluoropropyl)azetidin-3-ylidene)methyl)phenyl)-6,7-dihydro-5H-benzo[7]annulene-3-carboxylate (Intermediate 7) (100 mg, 206 μmol), (2-chloro-4-fluoro-phenyl)boronic acid (54 mg, 310 μmol), $Cs_2CO_3$ (141 mg, 433 μmol), and Pd(dppf)$Cl_2$, complex with DCM (15 mg, 21 μmol) in dioxane (4 mL) and water (1 mL) was heated to reflux for 30 minutes. After cooling to room temperature, addition of EtOAc (200 mL) and water (50 mL). After decantation, the organic phase was dried over $MgSO_4$, filtered and concentrated under reduced pressure to give 65 mg (59%) of methyl 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylate.

LC/MS (m/z, MH+): 534

Step 2: 8-(2,4-Dichlorophenyl)-9-(4-((1-(3-fluoropropyl)azetidin-3-ylidene)methyl)phenyl)-6,7-dihydro-5H-benzo[7]annulene-3-carboxylic acid

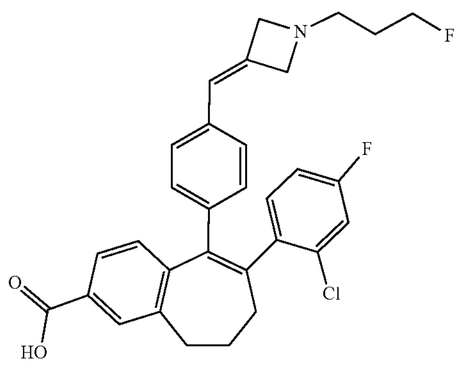 [SMILES: O=C(O)c1ccc2c(c1)CCCC(c1ccc(F)cc1Cl)=C2c1ccc(C=C2CN(CCCF)C2)cc1]

To a solution of methyl 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylate (65 mg, 121.7 μmol) in MeOH (5 mL) and water (1 mL) was added LiOH (15 mg, 608 μmol) and the reaction mixture was heated to 50° C. for 2 hours. After cooling, water (50 mL), EtOAc (100 mL) and $Et_2O$ (100 mL) were added and pH was adjusted to 7 with HCl 0.1N. After decantation, the organic phase was dried over $MgSO_4$, filtered, concentrated under reduced pressure and the residue obtained was purified by flash chromatography eluting with a gradient of MeOH in DCM (100/0 to 90/10, v/v) to give 43 mg (68%) of 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylic acid.

Method C

Example 8: 8-(Bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylic acid

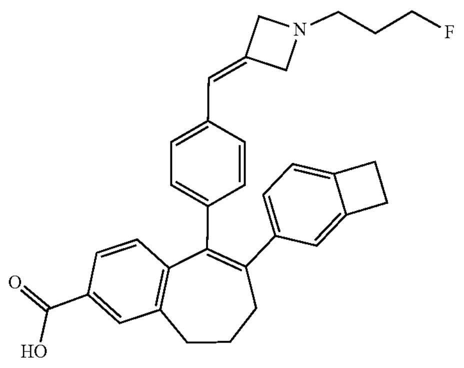 [SMILES: O=C(O)c1ccc2c(c1)CCCC(c1ccc3c(c1)CC3)=C2c1ccc(C=C2CN(CCCF)C2)cc1]

Step 1: Methyl 8-(bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylate

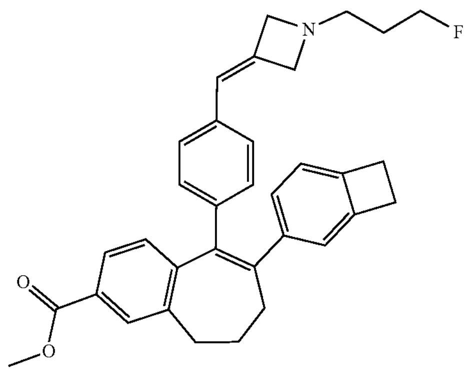 [SMILES: COC(=O)c1ccc2c(c1)CCCC(c1ccc3c(c1)CC3)=C2c1ccc(C=C2CN(CCCF)C2)cc1]

A mixture of methyl 9-(4-((1-(3-fluoropropyl)azetidin-3-ylidene)methyl)phenyl)-8-(4,4,5,5-tetramethyl-1,3,2-dioxaborolan-2-yl)-6,7-dihydro-5H-benzo[7]annulene-3-carboxylate (Intermediate 8) (200 mg, 376 μmol), 3-bromobicyclo[4.2.0]octa-1(6),2,4-triene (137 mg, 752 μmol), $Cs_2CO_3$ (245 mg, 752 μmol), and Pd(dppf)$Cl_2$, complex with DCM (14 mg, 19 μmol) in dioxane (8 mL) and water (2 mL) was heated to 95° C. for 3 hours. After cooling to room temperature, addition of EtOAc (200 mL) and water (50 mL). After decantation, the organic phase was dried over $MgSO_4$, filtered concentrated under reduced pressure and the residue obtained was purified by flash chromatography eluting with a gradient of cyclohexane/EtOAc (100/0 to 100/0, v/v) to give 55 mg (29%) of methyl 8-(bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylate.

LC/MS (m/z, MH+): 508

Step 2: 8-(Bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylic acid

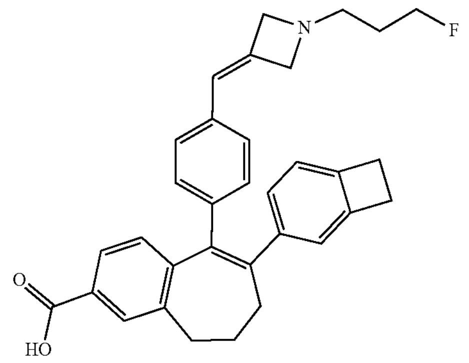 [SMILES: O=C(O)c1ccc2c(c1)CCCC(c1ccc3c(c1)CC3)=C2c1ccc(C=C2CN(CCCF)C2)cc1]

Step 2 of Example 8 was prepared following a similar procedure to that of step 2 of Example 79 from methyl 8-(bicyclo[4.2.0]octa-1,3,5-trien-3-yl)-9-(4-((1-(3-fluoropropyl)azetidin-3-ylidene)methyl)phenyl)-6,7-dihydro-5H- benzo[7]annulene-3-carboxylate to give 16 mg (30%) of 8-(bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylic acid.

Method D

Example 114: 4-(2,4-Dichlorophenyl)-5-(4-((1-(3-fluoropropyl)azetidin-3-ylidene)methyl)phenyl)-2,3-dihydrobenzo[b]oxepine-8-carboxylic acid hydrochloride

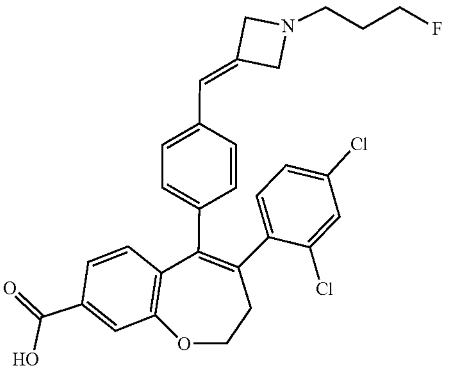 [SMILES: O=C(O)c1ccc2c(c1)OCCC(c1ccc(Cl)cc1Cl)=C2c1ccc(C=C2CN(CCCF)C2)cc1]

Step 1: Methyl 4-(2,4-dichlorophenyl)-5-(4-((1-(3-fluoropropyl)azetidin-3-ylidene)methyl)phenyl)-2,3-dihydrobenzo[b]oxepine-8-carboxylate

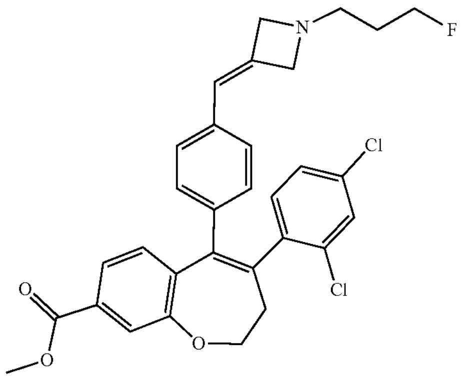 [SMILES: COC(=O)c1ccc2c(c1)OCCC(c1ccc(Cl)cc1Cl)=C2c1ccc(C=C2CN(CCCF)C2)cc1]

A mixture of methyl 4-(2,4-dichlorophenyl)-5-(((trifluoromethyl)sulfonyl)oxy)-2,3-dihydrobenzo[b]oxepine-8-carboxylate (Intermediate 30) (250 mg, 504 μmol), 1-(3-fluoropropyl)-3-[[4-(4,4,5,5-tetramethyl-1,3,2-dioxaborolan-2-yl)phenyl]methylene]azetidine (Intermediate 2) (158 mg, 478 μmol), $Cs_2CO_3$ (447 mg, 1.37 mmol), and Pd(dppf)$Cl_2$, complex with DCM (33 mg, 41 μmol) in dioxane (2 mL) and water (0.8 mL) was heated to 85° C. for 2 hours. After cooling to room temperature, addition of DCM (4 mL) and water (2 mL). After decantation in hydrophobic column, the organic phase was concentrated under reduced pressure and the residue was purified by flash chromatography eluting with EtOAc to give 69 mg (26%) of methyl 4-(2,4-dichlorophenyl)-8-carboxylate.

LC/MS (m/z, MH+): 552

Step 2: 4-(2,4-Dichlorophenyl)-5-(4-((1-(3-fluoropropyl)azetidin-3-ylidene)methyl)phenyl)-2,3-dihydrobenzo[b]oxepine-8-carboxylic acid

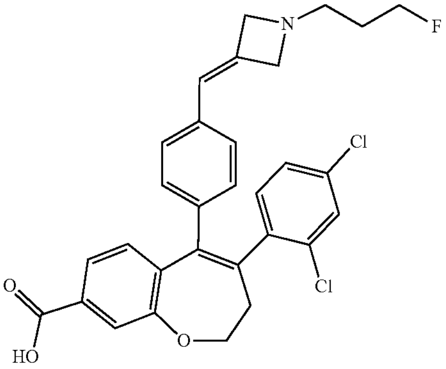 [SMILES: O=C(O)c1ccc2c(c1)OCCC(c1ccc(Cl)cc1Cl)=C2c1ccc(C=C2CN(CCCF)C2)cc1]

Step 2 of Example 115 was prepared following a similar procedure to that of step 2 of Example 79 from methyl 4-(2,4-dichlorophenyl)-5-(4-((1-(3-fluoropropyl)azetidin-3-ylidene)methyl)phenyl)-2,3-dihydrobenzo[b]oxepine-8-carboxylate to give 46 mg (65%) of 4-(2,4-dichlorophenyl)-5-(4-((1-(3-fluoropropyl)azetidin-3-ylidene)methyl)phenyl)-2,3-dihydrobenzo[b]oxepine-8-carboxylic acid hydrochloride.

Method E

Example 60: 9-(4-((1-(3-Fluoropropyl)azetidin-3-ylidene)methyl)phenyl)-8-(tetrahydro-2H-pyran-4-yl)-6,7-dihydro-5H-benzo[7]annulene-3-carboxylic acid

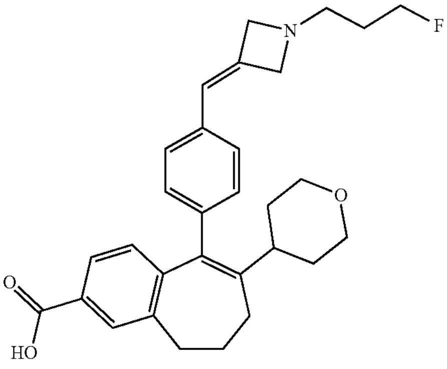 [SMILES: O=C(O)c1ccc2c(c1)CCCC(C1CCOCC1)=C2c1ccc(C=C2CN(CCCF)C2)cc1]

Step 1: Methyl 9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylate

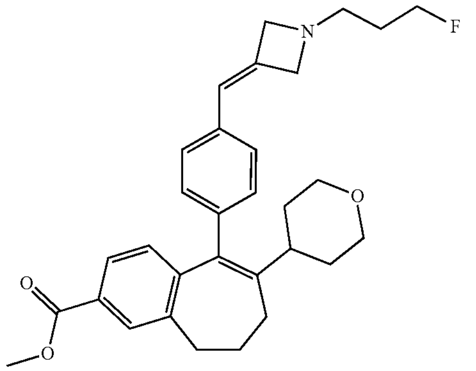 [SMILES: COC(=O)c1ccc2c(c1)CCCC(C1CCOCC1)=C2c1ccc(C=C2CN(CCCF)C2)cc1]

To a mixture of methyl 8-bromo-9-(4-((1-(3-fluoropropyl)azetidin-3-ylidene)methyl)phenyl)-6,7-dihydro-5H-benzo[7]annulene-3-carboxylate (Intermediate 7) (100 mg, 206 μmol), tri-o-tolylphosphine (10 mg, 33 μmol), $Pd_2(dba)_3$ (9.5 mg, 16.5 μmol) in DMF (4 mL) degassed and purged with argon for 5 min, was added a 0.5M solution of tetrahydropyran-4-ylzinc iodide (0.6 mL, 309.7 μmol). After 2 hours of stirring at room temperature, EtOAc (100 mL), $Et_2O$ (100 mL) and water (150 mL) were added. After decantation, the organic phase was dried over $MgSO_4$, filtered concentrated under reduced pressure and the residue obtained was purified by flash chromatography eluting with a gradient of cyclohexane/EtOEt (100/0 to 00/100, v/v) to give 60 mg (59%) of methyl 9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylate.

LC/MS (m/z, MH+): 490

Step 2: 9-(4-((1-(3-Fluoropropyl)azetidin-3-ylidene)methyl)phenyl)-8-(tetrahydro-2H-pyran-4-yl)-6,7-dihydro-5H-benzo[7]annulene-3-carboxylic acid

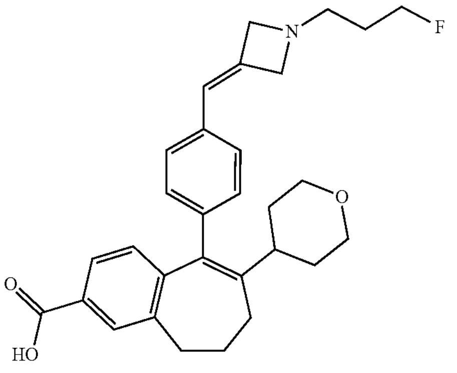 [SMILES: O=C(O)c1ccc2c(c1)CCCC(C1CCOCC1)=C2c1ccc(C=C2CN(CCCF)C2)cc1]

Step 2 of Example 60 was prepared following a similar procedure to that of step 2 of Example 79 from methyl 9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylate to give 10 mg (17%) of 9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylic acid.

Method F

Example 100: 9-(4-((1-(3-Fluoropropyl)azetidin-3-ylidene)methyl)phenyl)-8-isobutyl-6,7-dihydro-5H-benzo[7]annulene-3-carboxylic acid

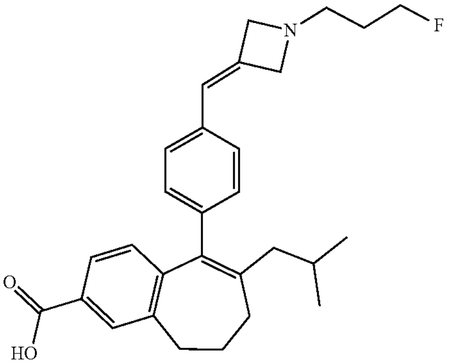 [SMILES: CC(C)CC1=C(c2ccc(C=C3CN(CCCF)C3)cc2)c2ccc(C(=O)O)cc2CCC1]

Step 1: Methyl 9-(4-(1-(3-fluoropropyl)azetidine-3-carbonyl)phenyl)-8-(2-methylprop-1-en-1-yl)-6,7-dihydro-5H-benzo[7]annulene-3-carboxylate

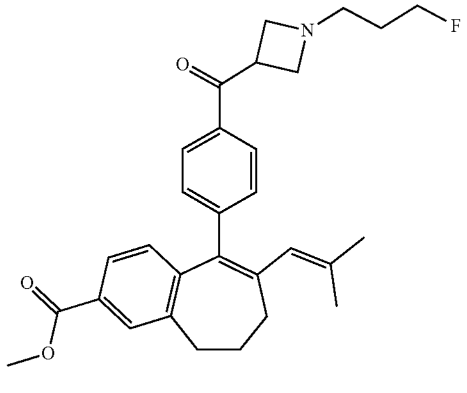 [SMILES: COC(=O)c1ccc2c(c1)CCCC(C=C(C)C)=C2c1ccc(C(=O)C2CN(CCCF)C2)cc1]

Step 1 of Example 100 was prepared following a similar procedure to that of step 1 of Example 79 from methyl 8-bromo-9-(4-(1-(3-fluoropropyl)azetidine-3-carbonyl)phenyl)-6,7-dihydro-5H-benzo[7]annulene-3-carboxylate (Step 5 (Method 2) Intermediate 7) and 4,4,5,5,-tetramethyl-2-(2-methylpropo-1-en-1-yl)-1,3,2-dioxaborolane to give 224 mg (62%) methyl 9-(4-(1-(3-fluoropropyl)azetidine-3-carbonyl)phenyl)-8-(2-methylprop-1-en-1-yl)-6,7-dihydro-5H-benzo[7]annulene-3-carboxylate.

LC/MS (m/z, MH+): 476

Step 2: Methyl 5-[4-[1-(3-fluoropropyl)azetidine-3-carbonyl]phenyl]-6-isobutyl-6,7,8,9-tetrahydro-5H-benzo[7]annulene-2-carboxylate

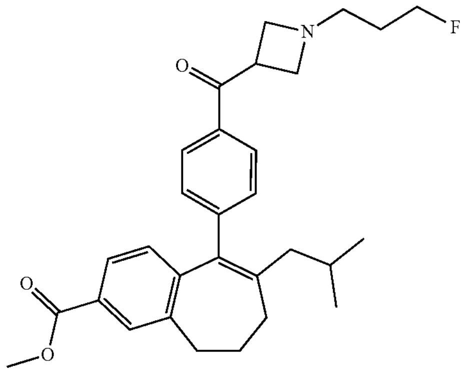 [SMILES: COC(=O)c1ccc2c(c1)CCCC(CC(C)C)=C2c1ccc(C(=O)C2CN(CCCF)C2)cc1]

A mixture of methyl 9-(4-(1-(3-fluoropropyl)azetidine-3-carbonyl)phenyl)-8-(2-methylprop-1-en-1-yl)-6,7-dihydro-5H-benzo[7]annulene-3-carboxylate (224 mg, 471 μmol), Pd/C 10% (90 mg, 85 μmol) in EtOH (30 mL) and EtOAc (15 mL) was hydrogenated at 50° C. and 5 bars of $H_2$ for 20 hours. The reaction mixture was filtered, and the filtrate was evaporated under reduced pressure. The residue was purified by flash chromatography eluting with a gradient of DCM/MeOH (100/0 to 95/05, v/v) to give 150 mg (66%) of methyl 8-(4,4-difluorocyclohexyl)-9-(4-((1-(3-fluoropropyl)azetidin-3-yl)methyl)phenyl)-6,7-dihydro-5H-benzo[7]annulene-3-carboxylate.

LC/MS (m/z, MH+): 478

Step 3: Methyl 5-[4-[[1-(3-fluoropropyl)azetidin-3-yl]-hydroxy-methyl]phenyl]-6-isobutyl-6,7,8,9-tetrahydro-5H-benzo[7]annulene-2-carboxylate

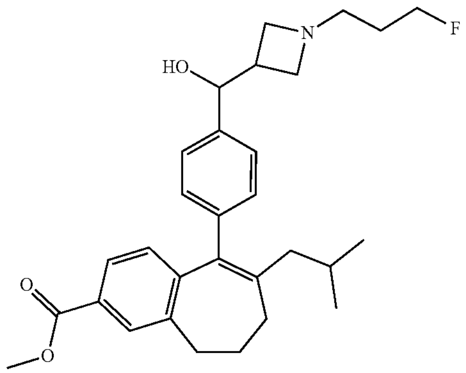 [SMILES: COC(=O)c1ccc2c(c1)CCCC(CC(C)C)=C2c1ccc(C(O)C2CN(CCCF)C2)cc1]

Step 3 of Example 100 was prepared following a similar procedure to that of step 6 (Method 2) of Intermediate 7 from methyl 5-[4-[1-(3-fluoropropyl)azetidine-3-carbonyl]phenyl]-6-isobutyl-6,7,8,9-tetrahydro-5H-benzo[7]annulene-2-carboxylate to give 75 mg (50%) of methyl 5-[4-[[1-(3-fluoropropyl)azetidin-3-yl]-hydroxy-methyl]phenyl]-6-isobutyl-6,7,8,9-tetrahydro-5H-benzo[7]annulene-2-carboxylate.

LC/MS (m/z, MH+): 480

Step 4: Methyl 9-(4-((1-(3-fluoropropyl)azetidin-3-ylidene)methyl)phenyl)-8-isobutyl-6,7-dihydro-5H-benzo[7]annulene-3-carboxylate

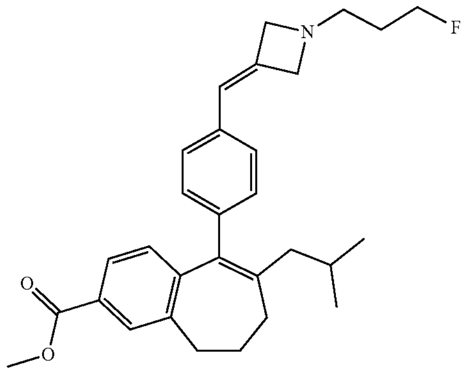 [SMILES: COC(=O)c1ccc2c(c1)CCCC(CC(C)C)=C2c1ccc(C=C2CN(CCCF)C2)cc1]

Step 4 of Example 100 was prepared following a similar procedure to that of step 7 (Method 2) of Intermediate 7 from methyl 5-[4-[[1-(3-fluoropropyl)azetidin-3-yl]-hydroxy-methyl]phenyl]-6-isobutyl-6,7,8,9-tetrahydro-5H-benzo[7]annulene-2-carboxylate to give 71 mg (66%) of methyl 9-(4-((1-(3-fluoropropyl)azetidin-3-ylidene)methyl)phenyl)-8-isobutyl-6,7-dihydro-5H-benzo[7]annulene-3-carboxylate.

LC/MS (m/z, MH+): 462

Step 5: 9-(4-((1-(3-Fluoropropyl)azetidin-3-ylidene)methyl)phenyl)-8-isobutyl-6,7-dihydro-5H-benzo[7]annulene-3-carboxylic acid

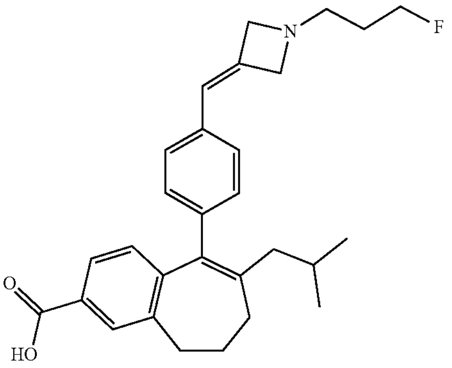 [SMILES: CC(C)CC1=C(c2ccc(C=C3CN(CCCF)C3)cc2)c2ccc(C(=O)O)cc2CCC1]

Step 5 of Example 100 was prepared following a similar procedure to that of step 2 of Example 79 from methyl 9-(4-((1-(3-fluoropropyl)azetidin-3-ylidene)methyl)phenyl)-8-isobutyl-6,7-dihydro-5H-benzo[7]annulene-3-carboxylate to give 44 mg (40%) of 9-(4-((1-(3-fluoropropyl)azetidin-3-ylidene)methyl)phenyl)-8-isobutyl-6,7-dihydro-5H-benzo[7]annulene-3-carboxylic acid Method G Example 102: 8-(2,4-Dichlorophenyl)-9-(4-(1-(1-(3-fluoropropyl)azetidin-3-ylidene)ethyl)phenyl)-6,7-dihydro-5H-benzo[7]annulene-3-carboxylic acid

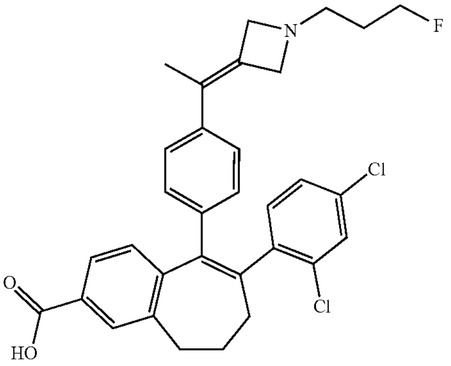 [SMILES: CC(=C1CN(CCCF)C1)c1ccc(C2=C(c3ccc(Cl)cc3Cl)CCCc3cc(C(=O)O)ccc32)cc1]

Step 1: Methyl 8-(2,4-dichlorophenyl)-9-(4-(1-(3-fluoropropyl)azetidine-3-carbonyl)phenyl)-6,7-dihydro-5H-benzo[7]annulene-3-carboxylate

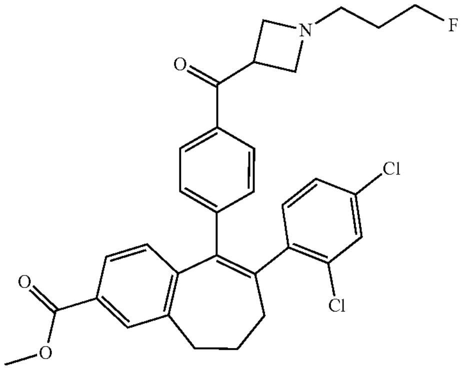 [SMILES: COC(=O)c1ccc2c(c1)CCCC(c1ccc(Cl)cc1Cl)=C2c1ccc(C(=O)C2CN(CCCF)C2)cc1]

Step 1 of Example 102 was prepared following a similar procedure to that of step 1 of Example 1 from (4-bromophenyl)(1-(3-fluoropropyl)azetidin-3-yl)methanone and methyl 8-(2,4-dichlorophenyl)-9-(4,4,5,5-tetramethyl-1,3,2-dioxaborolan-2-yl)-6,7-dihydro-5H-benzo[7]annulene-3-carboxylate to give 270 mg (34%) of methyl 8-(2,4-dichlorophenyl)-9-(4-(1-(3-fluoropropyl)azetidine-3-carbonyl)phenyl)-6,7-dihydro-5H-benzo[7]annulene-3-carboxylate.

LC/MS (m/z, MH+): 566

Step 2: Methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate

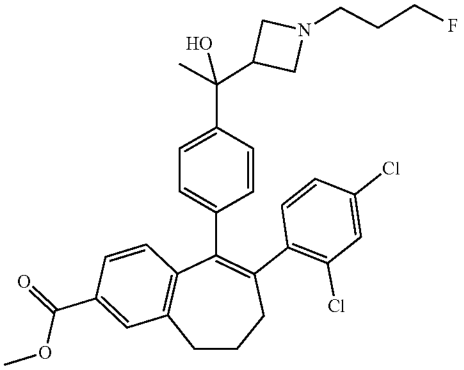 [SMILES: COC(=O)c1ccc2c(c1)CCCC(c1ccc(Cl)cc1Cl)=C2c1ccc(C(C)(O)C2CN(CCCF)C2)cc1]

To a mixture of methyl 8-(2,4-dichlorophenyl)-9-(4-(1-(3-fluoropropyl)azetidine-3-carbonyl)phenyl)-6,7-dihydro-5H-benzo[7]annulene-3-carboxylate (430 mg, 759 μmol) in THF (20 mL) cooled at −20° C. was added methylmagnesium bromide 3M in $Et_2O$ (759 μL, 2.28 mmol). After 45 minutes of stirring at −10° C., saturated $NH_4Cl$ aqueous solution (5 mL), EtOAc (50 mL) and water (20 mL) were added. After decantation, the organic phase was dried over $MgSO_4$, filtered concentrated under reduced pressure to give 442 mg (100%) of methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate.

LC/MS (m/z, MH+): 582

Step 3: Methyl 8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylate

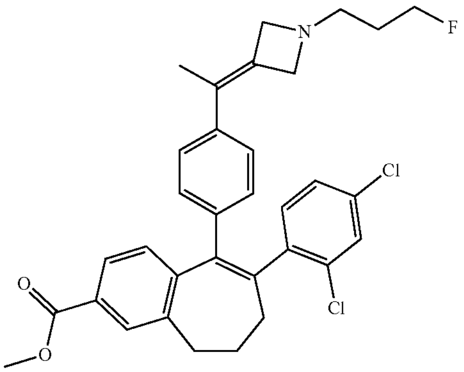 [SMILES: COC(=O)c1ccc2c(c1)CCCC(c1ccc(Cl)cc1Cl)=C2c1ccc(C(C)=C2CN(CCCF)C2)cc1]

A mixture of methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate (50 mg, 85.83 μmol) in water (0.5 mL) and sulfuric acid (1 mL, 18.76 mmol) was stirred at room temperature for 2 hours. Ice and EtOAc were added and the pH was adjusted to 9 by addition of saturated aqueous solution of $NaHCO_3$ and $Na_2CO_3$. After decantation, the organic phase was dried over $MgSO_4$, filtered concentrated under reduced pressure and the residue obtained was purified by flash chromatography eluting with a gradient of DCM/MeOH (100/0 to 95/05, v/v) to give 24 mg (49%) of methyl 8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylate.

LC/MS (m/z, MH+): 564

Step 4: 8-(2,4-Dichlorophenyl)-9-(4-(1-(1-(3-fluoropropyl)azetidin-3-ylidene)ethyl)phenyl)-6,7-dihydro-5H-benzo[7]annulene-3-carboxylic acid

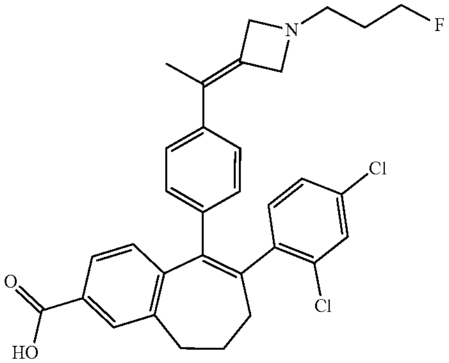 [SMILES: CC(=C1CN(CCCF)C1)c1ccc(C2=C(c3ccc(Cl)cc3Cl)CCCc3cc(C(=O)O)ccc32)cc1]

Step 4 of Example 102 was prepared following a similar procedure to that of step 2 of Example 79 from methyl 8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylate to give 6 mg (26%) of 8-(2,4-dichlorophenyl)-9-(4-(1-(1-(3-fluoropropyl)azetidin-3-ylidene)ethyl) phenyl)-6,7-dihydro-5H-benzo[7]annulene-3-carboxylic acid.

Method H

Example 159: 8-(2,4-Dichlorophenyl)-9-(5-((1-(3-fluoropropyl)azetidin-3-ylidene)methyl)pyridin-2-yl)-6,7-dihydro-5H-benzo[7]annulene-3-carboxylic acid

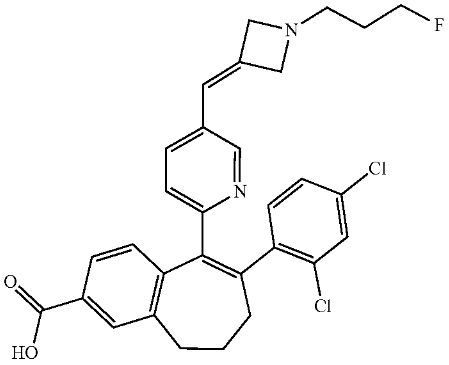 [SMILES: O=C(O)c1ccc2c(c1)CCCC(c1ccc(Cl)cc1Cl)=C2c1ccc(C=C2CN(CCCF)C2)cn1]

Step 1: Methyl 9-(5-bromopyridin-2-yl)-8-(2,4-dichlorophenyl)-6,7-dihydro-5H-benzo[7]annulene-3-carboxylate

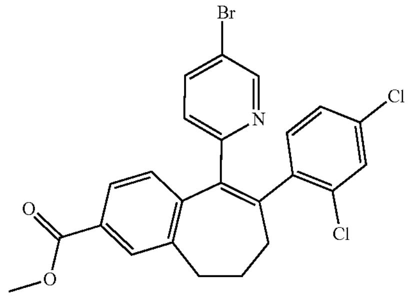 [SMILES: COC(=O)c1ccc2c(c1)CCCC(c1ccc(Cl)cc1Cl)=C2c1ccc(Br)cn1]

Step 1 of Example 159 was prepared following a similar procedure to that of step 1 (Method 1) of Intermediate 7 from methyl 9-(4,4,5,5-tetramethyl-1,3,2-dioxaborolan-2-yl)-6,7-dihydro-5H-benzo[7]annulene-3-carboxylate and 5-bromo-2-iodopyridine to give 108 mg (10%) of methyl 9-(5-bromopyridin-2-yl)-8-(2,4-dichlorophenyl)-6,7-dihydro-5H-benzo[7]annulene-3-carboxylate.

LC/MS (m/z, MH+): 502

Step 2: Tert-butyl 3-((6-(8-(2,4-dichlorophenyl)-3-(methoxycarbonyl)-6,7-dihydro-5H-benzo[7]annulen-9-yl)pyridin-3-yl)methylene)azetidine-1-carboxylate

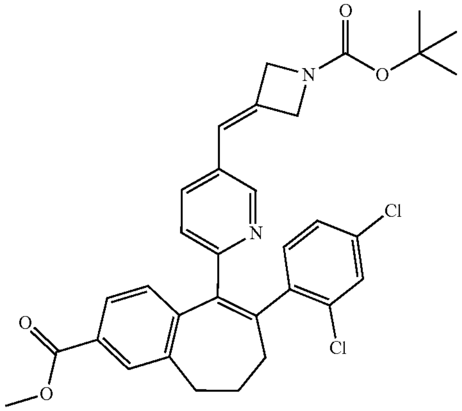 [SMILES: COC(=O)c1ccc2c(c1)CCCC(c1ccc(Cl)cc1Cl)=C2c1ccc(C=C2CN(C(=O)OC(C)(C)C)C2)cn1]

Step 2 of Example 159 was prepared following a similar procedure to that of step 1 (Method 2) of Intermediate 1 from methyl 9-(5-bromopyridin-2-yl)-8-(2,4-dichlorophenyl)-6,7-dihydro-5H-benzo[7]annulene-3-carboxylate to give 87 mg (68%) of tert-butyl 3-((6-(8-(2,4-dichlorophenyl)-3-(methoxycarbonyl)-6,7-dihydro-5H-benzo[7]annulen-9-yl)pyridin-3-yl)methylene)azetidine-1-carboxylate.

LC/MS (m/z, MH+): 590

Step 3: Methyl 9-(5-(azetidin-3-ylidenemethyl)pyridin-2-yl)-8-(2,4-dichlorophenyl)-6,7-dihydro-5H-benzo[7]annulene-3-carboxylate, trifluoroacetic acid

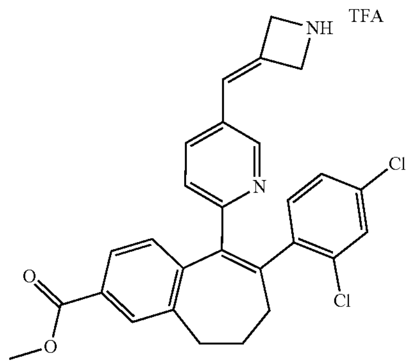 [SMILES: COC(=O)c1ccc2c(c1)CCCC(c1ccc(Cl)cc1Cl)=C2c1ccc(C=C2CNC2)cn1]

Step 3 of Example 159 was prepared following a similar procedure to that of step 2 of Intermediate 1 from tert-butyl 3-((6-(8-(2,4-dichlorophenyl)-3-(methoxycarbonyl)-6,7-dihydro-5H-benzo[7]annulen-9-yl)pyridin-3-yl)methylene) azetidine-1-carboxylate to give methyl 9-(5-(azetidin-3-ylidenemethyl)pyridin-2-yl)-8-(2,4-dichlorophenyl)-6,7-dihydro-trifluoroacetic acid which was used without further purification.

LC/MS (m/z, MH+): 491

Step 4: Methyl 8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylate

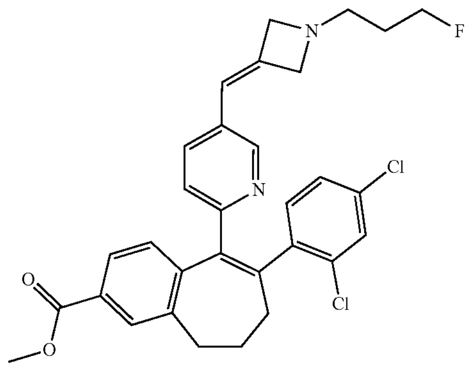 [SMILES: COC(=O)c1ccc2c(c1)CCCC(c1ccc(Cl)cc1Cl)=C2c1ccc(C=C2CN(CCCF)C2)cn1]

Step 4 of example 159 was prepared following a similar procedure to that of step 5 (Method 2) of Intermediate 7 from methyl 9-(5-(azetidin-3-ylidenemethyl)pyridin-2-yl)-8-(2,4-dichlorophenyl)-6,7-dihydro-5H-benzo[7]annulene-3-carboxylate, trifluoroacetic acid to give 40 mg (49% for steps 3 and 4) of methyl 8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylate.

LC/MS (m/z, MH+): 551

Step 5: 8-(2,4-Dichlorophenyl)-9-(5-((1-(3-fluoropropyl)azetidin-3-ylidene)methyl)pyridin-2-yl)-6,7-dihydro-5H-benzo[7]annulene-3-carboxylic acid, trifluoroacetic acid

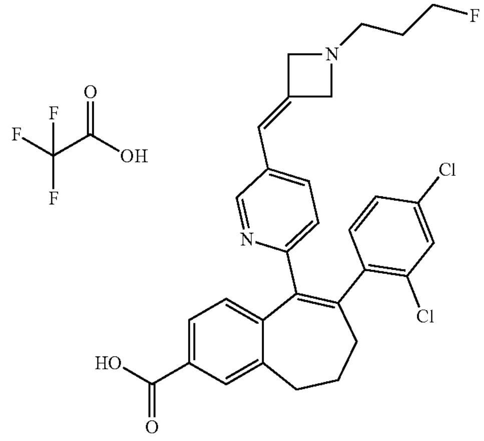 [SMILES: O=C(O)C(F)(F)F ; O=C(O)c1ccc2c(c1)CCCC(c1ccc(Cl)cc1Cl)=C2c1ccc(C=C2CN(CCCF)C2)cn1]

Step 4 of Example 159 was prepared following a similar procedure to that of step 2 of Example 79 from methyl 8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylate to give 34 mg (72%) of 8-(2,4-dichlorophenyl)-9-(5-((1-(3-fluoropropyl)azetidin-3-ylidene) methyl)pyridin-2-yl)-6,7-dihydro-5H-benzo[7]annulene-3-carboxylic acid, trifluoroacetic acid.

Method I

Example 158: 8-(2,4-Dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylic acid

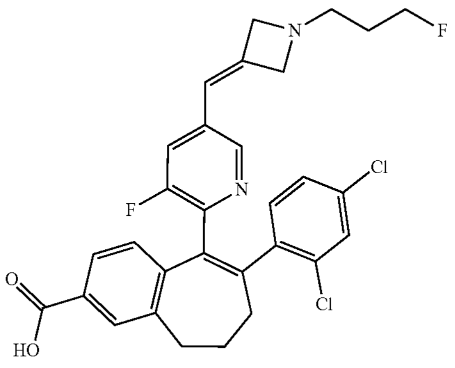 [SMILES: O=C(O)c1ccc2c(c1)CCCC(c1ccc(Cl)cc1Cl)=C2c1ncc(C=C2CN(CCCF)C2)cc1F]

Step 1: Tert-butyl 3-[(6-bromo-5-fluoro-3-pyridyl) methylene]azetidine-1-carboxylate

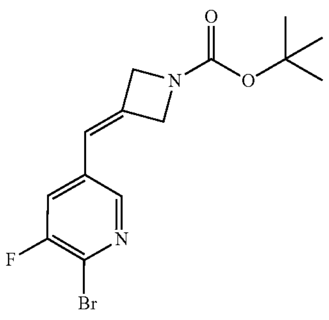

Step 1 of Example 158 was prepared following a similar procedure to that of step 1 (Method 2) of Intermediate 1 from 2-bromo-3-fluoro-5-iodo-pyridine to give 587 mg (61%) of tert-butyl 3-[(6-bromo-5-fluoro-3-pyridyl)methylene]azetidine-1-carboxylate.

LC/MS (m/z, MH+): 343

Step 2: 9-(5-((1-(Tert-butoxycarbonyl)azetidin-3-ylidene)methyl)-3-fluoropyridin-2-yl)-8-(2,4-dichlorophenyl)-6,7-dihydro-5H-benzo[7]annulene-3-carboxylic acid

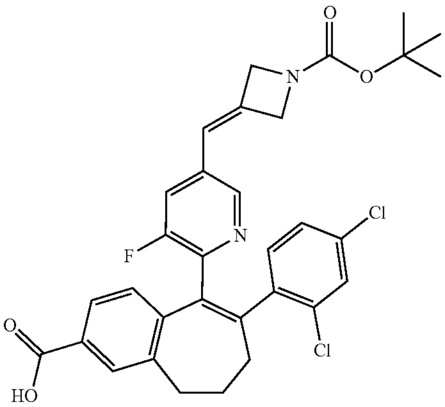 [SMILES: CC(C)(C)OC(=O)N1CC(=Cc2cnc(C3=C(c4ccc(Cl)cc4Cl)CCCc4cc(C(=O)O)ccc43)c(F)c2)C1]

Step 2 of Example 158 was prepared following a similar procedure to that of step 1 of Example 1 (Method A) from methyl 9-(4,4,5,5-tetramethyl-1,3,2-dioxaborolan-2-yl)-6,7-dihydro-5H-benzo[7]annulene-3-carboxylate and tert-butyl 3-[(6-bromo-5-fluoro-3-pyridyl)methylene]azetidine-1-carboxylate to give 585 mg (81%) of 9-(5-((1-(tert-butoxycarbonyl)azetidin-3-ylidene)methyl)-3-fluoropyridin-2-yl)-8-(2,4-dichlorophenyl)-6,7-dihydro-5H-benzo[7]annulene-3-carboxylic acid.

LC/MS (m/z, MH+): 595

Step 3: Tert-butyl 3-((6-(8-(2,4-dichlorophenyl)-3-(methoxycarbonyl)-6,7-dihydro-5H-benzo[7]annulen-9-yl)-5-fluoropyridin-3-yl)methylene)azetidine-1-carboxylate

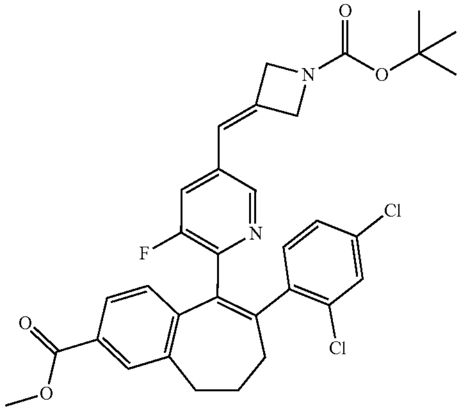 [SMILES: COC(=O)c1ccc2c(c1)CCCC(c1ccc(Cl)cc1Cl)=C2c1ncc(C=C2CN(C(=O)OC(C)(C)C)C2)cc1F]

A mixture of 9-(5-((1-(tert-butoxycarbonyl)azetidin-3-ylidene)methyl)-3-fluoropyridin-2-yl)-8-(2,4-dichlorophenyl)-6,7-dihydro-5H-benzo[7]annulene-3-carboxylic acid (585 mg, mmol), $K_2CO_3$ (271 mg, 1.96 mmol) and methyl iodide (209 mg, 1.47 mmol, 0.09 mL) in DMF (10 mL) was stirred at room temperature for 20 minutes. The reaction mixture was quenched by addition of water (50 mL) and then extracted with a mixture of EtOAc (30 mL) and $Et_2O$ (70 mL). After decantation, the organic phase was washed twice with water (50 mL), dried over $MgSO_4$, filtered, and concentrated under reduced pressure. The residue obtained was purified by flash chromatography, eluting with a gradient of cyclohexane/EtOAc: from 100/00 to 75/25 to give 327 mg (55%) of tert-butyl 3-((6-(8-(2,4-dichlorophenyl)-3-(methoxycarbonyl)-6,7-dihydro-5H-benzo[7]annulen-9-yl)-5-fluoropyridin-3-yl)methylene)azetidine-1-carboxylate.

LC/MS (m/z, MH+): 609

Step 4: Methyl 9-(5-(azetidin-3-ylidenemethyl)-3-fluoropyridin-2-yl)-8-(2,4-dichlorophenyl)-6,7-dihydro-5H-benzo[7]annulene-3-carboxylate, trifluoroacetic acid

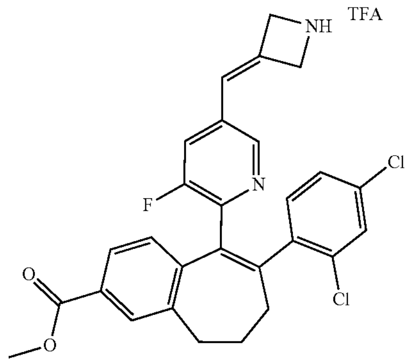 [SMILES: COC(=O)c1ccc2c(c1)CCCC(c1ccc(Cl)cc1Cl)=C2c1ncc(C=C2CNC2)cc1F]

Step 4 of Example 158 was prepared following a similar procedure to that of step 2 of Intermediate 1 from tert-butyl 3-((6-(8-(2,4-dichlorophenyl)-3-(methoxycarbonyl)-6,7-dihydro-5H-benzo[7]annulen-9-yl)-5-fluoropyridin-3-yl) methylene)azetidine-1-carboxylate to give 287 mg (98%) of methyl 9-(5-(azetidin-3-ylidenemethyl)-3-fluoropyridin-2-yl)-8-(2,4-dichlorophenyl)-6,7-dihydro-5H-benzo[7]annulene-3-carboxylate, trifluoroacetic acid.

LC/MS (m/z, MH+): 509

Step 5: Methyl 8-(2,4-dichlorophenyl)-9-(3-fluoro-5-((1-(3-fluoropropyl)azetidin-3-ylidene)methyl) pyridin-2-yl)-6,7-dihydro-5H-benzo[7]annulene-3-carboxylate

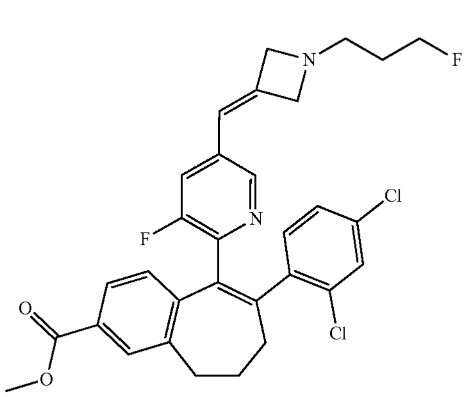 [SMILES: COC(=O)c1ccc2c(c1)CCCC(c1ccc(Cl)cc1Cl)=C2c1ncc(C=C2CN(CCCF)C2)cc1F]

Step 5 of Example 158 was prepared following a similar procedure to that of step 5 (Method 2) of Intermediate 7 from methyl 9-(5-(azetidin-3-ylidenemethyl)-3-fluoropyridin-2-yl)-8-(2,4-dichlorophenyl)-6,7-dihydro-5H-benzo[7] annulene-3-carboxylate, trifluoroacetic acid to give 90 mg (41%) of methyl 8-(2,4-dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylate.

LC/MS (m/z, MH+): 569

Step 6: 8-(2,4-Dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylic acid

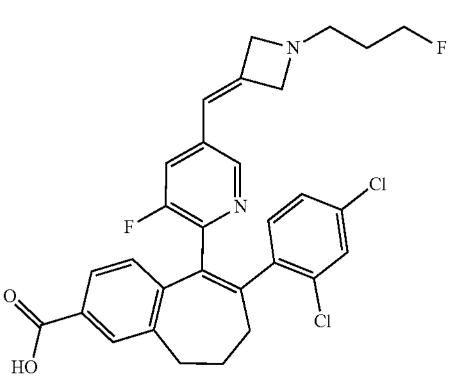 [SMILES: O=C(O)c1ccc2c(c1)CCCC(c1ccc(Cl)cc1Cl)=C2c1ncc(C=C2CN(CCCF)C2)cc1F]

Step 6 of Example 158 was prepared following a similar procedure to that of step 2 of Example 79 from methyl 8-(2,4-dichlorophenyl)-9-(3-fluoro-5-((1-(3-fluoropropyl) azetidin-3-ylidene)methyl)pyridin-2-yl)-6,7-dihydro-5H-benzo[7]annulene-3-carboxylate to give 7 mg (14%) of 8-(2,4-dichlorophenyl)-9-(3-fluoro-5-((1-(3-fluoropropyl) azetidin-3-ylidene)methyl)pyridin-2-yl)-6,7-dihydro-5H-benzo[7]annulene-3-carboxylic acid.

Method J

Example 166: 8-(2,4-Dichlorophenyl)-9-(4-((1-(3-fluoropropyl) azetidin-3-ylidene)methyl)phenyl)-7-methyl-6,7-dihydro-5H-benzo[7]annulene-3-carboxylic acid, racemic mixture

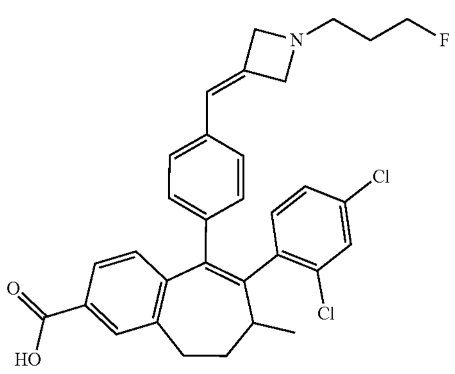 [SMILES: CC1CCc2cc(C(=O)O)ccc2C(c2ccc(C=C3CN(CCCF)C3)cc2)=C1c1ccc(Cl)cc1Cl]

Step 1: 9-(4-((1-(Tert-butoxycarbonyl)azetidin-3-ylidene)methyl)phenyl)-8-(2,4-dichlorophenyl)-7-methyl-6,7-dihydro-5H-benzo[7]annulene-3-carboxylic acid, racemic mixture

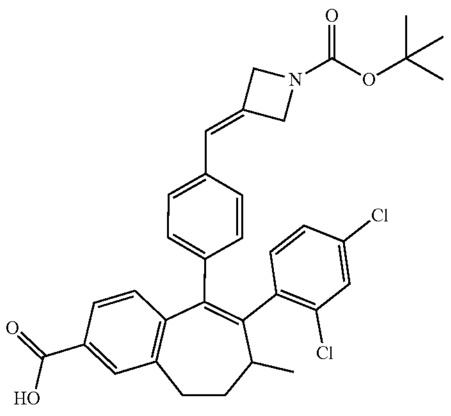 [SMILES: CC1CCc2cc(C(=O)O)ccc2C(c2ccc(C=C3CN(C(=O)OC(C)(C)C)C3)cc2)=C1c1ccc(Cl)cc1Cl]

Step 1 of Example 166 was prepared following a similar procedure to that of step 1 of Example 79 from tert-butyl 3-(4-(8-bromo-3-(methoxycarbonyl)-7-methyl-6,7-dihydro-5H-benzo[7]annulen-9-yl)benzylidene)azetidine-1-carboxylate (Intermediate 43) to give 217 mg (88%) of 9-(4-((1-(tert-butoxycarbonyl)azetidin-3-ylidene)methyl) phenyl)-8-(2,4-dichlorophenyl)-7-methyl-6,7-dihydro-5H-benzo[7]annulene-3-carboxylic acid as a racemic mixture.

LC/MS (m/z, MH+): 590

Step 2: Methyl 9-(4-(azetidin-3-ylidenemethyl)phenyl)-8-(2,4-dichlorophenyl)-7-methyl-6,7-dihydro-5H-benzo[7]annulene-3-carboxylate, trifluoroacetic acid (racemic mixture)

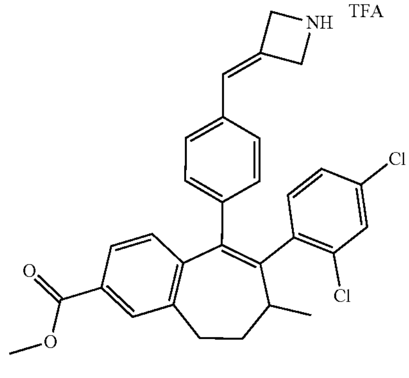 [SMILES: COC(=O)c1ccc2c(c1)CCC(C)C(c1ccc(Cl)cc1Cl)=C2c1ccc(C=C2CNC2)cc1]

Step 2 of Example 166 was prepared following a similar procedure to that of step 2 of Intermediate 1 from 9-(4-((1-(tert-butoxycarbonyl)azetidin-3-ylidene)methyl)phenyl)-8-(2,4-dichlorophenyl)-7-methyl-6,7-dihydro-5H-benzo[7]annulene-3-carboxylic acid to give 252 mg (100%) of methyl 9-(4-(azetidin-3-ylidenemethyl)phenyl)-8-(2,4-dichlorophenyl)-7-methyl-6,7-dihydro-5H-benzo[7]annulene-3-carboxylate, trifluoroacetic acid as a racemic mixture.

LC/MS (m/z, MH+): 504

Step 3: Methyl 8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylate, racemic mixture

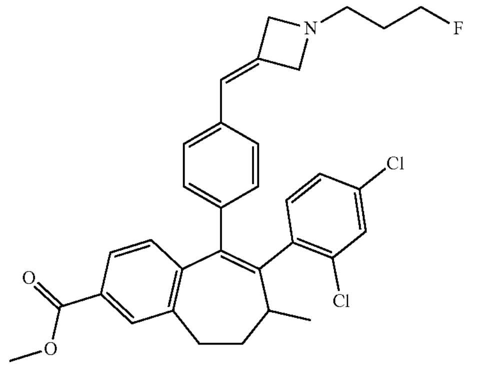 [SMILES: COC(=O)c1ccc2c(c1)CCC(C)C(c1ccc(Cl)cc1Cl)=C2c1ccc(C=C2CN(CCCF)C2)cc1]

Step 3 of Example 166 was prepared following a similar procedure to that of step 6 (Method 1) of Intermediate 7 from methyl 9-(4-(azetidin-3-ylidenemethyl)phenyl)-8-(2,4-dichlorophenyl)-7-methyl-6,7-dihydro-5H-benzo[7]annulene-3-carboxylate, trifluoroacetic acid to give 70 mg (30%) of methyl 8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylate as a racemic mixture.

LC/MS (m/z, MH+): 564

Step 4: 8-(2,4-Dichlorophenyl)-9-(4-((1-(3-fluoropropyl)azetidin-3-ylidene)methyl)phenyl)-7-methyl-6,7-dihydro-5H-benzo[7]annulene-3-carboxylic acid, racemic mixture

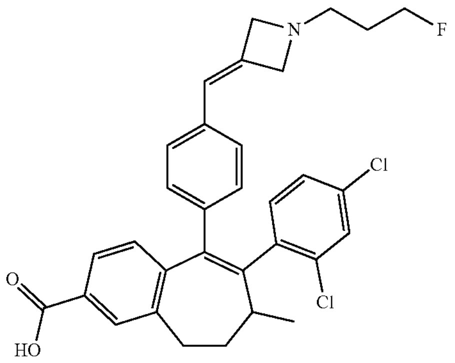 [SMILES: CC1CCc2cc(C(=O)O)ccc2C(c2ccc(C=C3CN(CCCF)C3)cc2)=C1c1ccc(Cl)cc1Cl]

Step 4 of Example 166 was prepared following a similar procedure to that of step 2 of Example 79 from methyl 8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylate to give 38 mg (55%) of 8-(2,4-dichlorophenyl)-9-(4-((1-(3-fluoropropyl) azetidin-3-ylidene)methyl)phenyl)-7-methyl-6,7-dihydro-5H-benzo[7]annulene-3-carboxylic acid as a racemic mixture.

Method K

Example 186: 8-(3,3-Dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid, racemic mixture

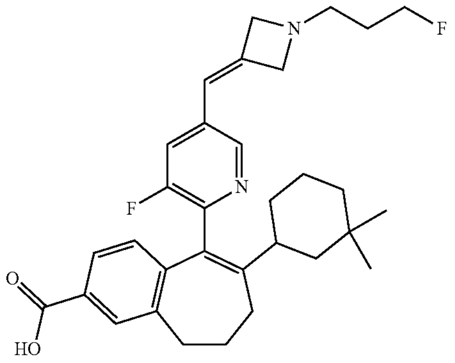 [SMILES: CC1(C)CCCC(C2=C(c3ncc(C=C4CN(CCCF)C4)cc3F)c3ccc(C(=O)O)cc3CCC2)C1]

Step 1: Tert-butyl 3-((5-fluoro-6-(tributylstannyl) pyridin-3-yl)methylene)azetidine-1-carboxylate

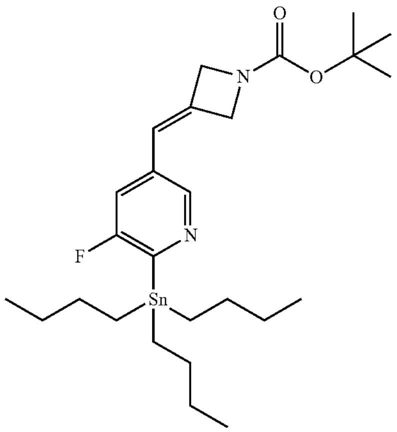 [SMILES: CCC[CH2][Sn]([CH2]CCC)([CH2]CCC)[c]1ncc(C=C2CN(C(=O)OC(C)(C)C)C2)cc1F]

A mixture of tert-butyl 3-[(6-bromo-5-fluoro-3-pyridyl) methylene]azetidine-1-carboxylate (4 g, 11.66 mmol), $Pd(PPh_3)_2Cl_2$ (0.82 g, 1.17 mmol), 1,1,1,2,2,2-hexabutyldistannane (17.64 mL, 34.97 mmol) in toluene (50 mL) was degassed and purged with Ar for 5 min then heated to 110° C. for 17 hours in a sealed tube. After cooling to room temperature, the reaction mixture was filtered and purified by flash chromatography, eluting with a gradient of cyclohexane/EtOAc: from 100/00 to 50/50 to give 2 g (31%) of tert-butyl 3-((5-fluoro-6-(tributylstannyl)pyridin-3-yl)methylene)azetidine-1-carboxylate.

LC/MS (m/z, MH+): 555

Step 2: Tert-butyl 3-((6-(8-(3,3-dimethylcyclohexyl)-3-(methoxycarbonyl)-6,7-dihydro-5H-benzo[7]annulen-9-yl)-5-fluoropyridin-3-yl)methylene) azetidine-1-carboxylate, racemic mixture

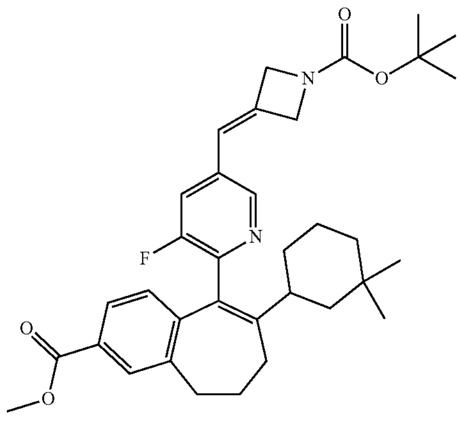 [SMILES: COC(=O)c1ccc2c(c1)CCCC(C1CCCC(C)(C)C1)=C2c1ncc(C=C2CN(C(=O)OC(C)(C)C)C2)cc1F]

A mixture of methyl 8-(3,3-dimethylcyclohexyl)-9-(((trifluoromethyl)sulfonyl)oxy)-6,7-dihydro-5H-benzo[7]annulene-3-carboxylate (Intermediate 39) (0.46 g, 1 mmol), $Pd(PPh_3)_4$ (231 mg, 200 μmol), tert-butyl 3-((5-fluoro-6-(tributylstannyl)pyridin-3-yl)methylene)azetidine-1-carboxylate (1.11 g, 2 mmol) in toluene (20 mL) was degassed and purged with Ar for 5 min then heated to 80° C. for 2.5 hours in a sealed tube. After cooling to room temperature, the reaction mixture was filtered and transferred in a new tube, then $Pd(PPh_3)_4$ (50 mg, 47 μmol) was added and the mixture degassed. The tube was sealed and heated to 80° C. for 3 hours. After cooling to room temperature, $Et_2O$ (50 mL), EtOAc (50 mL) and a 10% aqueous solution of KF (50 mL) were added and the mixture was filtered. After decantation, the organic phase was washed with dried over $MgSO_4$, filtered, concentrated under reduced pressure and the residue obtained was purified by flash chromatography, eluting with a gradient of cyclohexane/EtOAc: from 100/00 to 00/100 to give 67 mg (10%) of tert-butyl 3-((6-(8-(3,3-dimethylcyclohexyl)-3-(methoxycarbonyl)-6,7-dihydro-5H-benzo[7]annulen-9-yl)-5-fluoropyridin-3-yl)methylene) azetidine-1-carboxylate as a racemic mixture.

LC/MS (m/z, MH+): 575

Step 3: Methyl 9-(5-(azetidin-3-ylidenemethyl)-3-fluoropyridin-2-yl)-8-(3,3-dimethylcyclohexyl)-6,7-dihydro-5H-benzo[7]annulene-3-carboxylate, trifluoroacetic acid (racemic mixture)

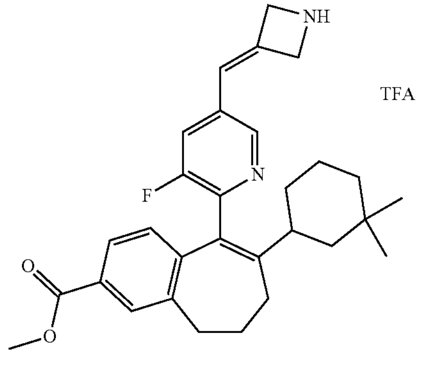

Step 3 of Example 186 was prepared following a similar procedure to that of step 2 of Intermediate 1 from 9-(4-((1-(tert-butoxycarbonyl)azetidin-3-ylidene)methyl)phenyl)-8-(2,4-dichlorophenyl)-7-methyl-6,7-dihydro-5H-benzo[7]annulene-3-carboxylic acid to give methyl 9-(5-(azetidin-3-ylidenemethyl)-3-fluoropyridin-2-yl)-8-(3,3-dimethylcyclohexyl)-6,7-dihydro-5H-benzo[7]annulene-3-carboxylate, trifluoroacetic acid as a racemic mixture.

LC/MS (m/z, MH+): 475

Step 4: Methyl 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylate, racemic mixture

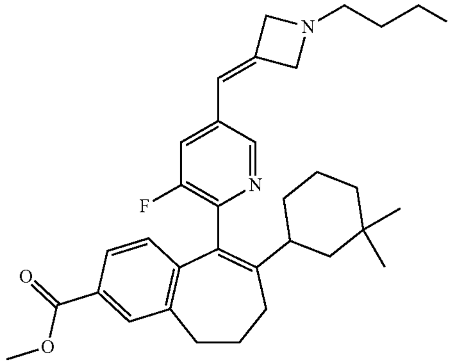

Step 4 of Example 186 was prepared following a similar procedure to that of step 6 (Method 1) of Intermediate 7 from methyl 9-(4-(azetidin-3-ylidenemethyl)phenyl)-8-(2,4-dichlorophenyl)-7-methyl-6,7-dihydro-5H-benzo[7]annulene-3-carboxylate, trifluoro acetic acid to give 35 mg (33%) of methyl 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylate as a racemic mixture.

LC/MS (m/z, MH+): 535

Step 5: 8-(3,3-Dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid, racemic mixture

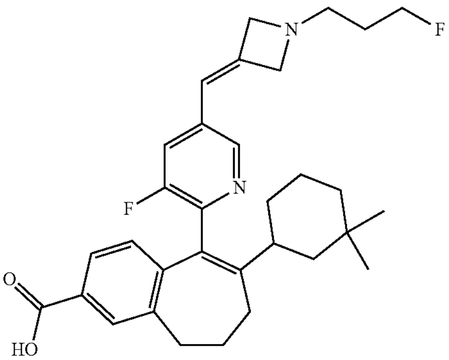 [SMILES: CC1(C)CCCC(C2=C(c3ncc(C=C4CN(CCCF)C4)cc3F)c3ccc(C(=O)O)cc3CCC2)C1]

Step 5 of Example 186 was prepared following a similar procedure to that of step 2 of Example 79 from methyl 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylate to give 25 mg (73%) of 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid as a racemic mixture.

The compounds according to Table 1a above were subjected to pharmacological tests for determining their degradation effects on estrogen receptors.

Test: Estrogen Receptor Degradation Activity

Said test involves measuring the in vitro degradation activity of the compounds of the Table 1a.

The measurements of the degradation activities were made using a breast cancer cell ERα in cell western assay as described hereunder.

MCF7 cells (ATCC) were seeded in 384 wells microplate (collagen coated) at a concentration of 10000 cells/30 μL per well in red phenol free MEM alpha medium (invitrogen) containing 5% charcoal dextran striped FBS. The following day, 9 points serial 1:5 dilution of each compound was added to the cells in 2.5 μL at final concentrations ranging from 0.3-0.0000018 μM (in table 2), or 0.1 μM for fulvestrant (using as positive control). At 4 hours post compound addition the cells were fixed by adding 25 μL of formalin (final concentration 5% formalin containing 0.1% triton) for 10 minutes at room temperature and then washed twice with PBS. Then, 50 μL of LI-COR blocking buffer containing 0.1% Triton was added to plate for 30 minutes at room temperature. LI-COR blocking buffer was removed and cells were incubated overnight at cold room with 50 μL anti-ER rabbit monoclonal antibody (Thermo scientific MA1-39540) diluted at 1:1000 in LI-COR blocking buffer containing 0.1% tween-20. Wells which were treated with blocking buffer but no antibody were used as background control. Wells were washed twice with PBS (0.1% tween-20) and incubated at 37° C. for 60 minutes in LI-COR (0.1% tween-20) containing goat anti-rabbit antibody Alexa 488 (1:1000) and Syto-64 a DNA dye (2 μM final concentration). Cells were then washed 3 times in PBS and scanned in ACUMEN explorer (TTP-Labtech). Integrated intensities in the green fluorescence and red fluorescence were measured to determine the levels of ERα and DNA respectively.

The degradation activity with respect to estrogen receptors in this test is given by the concentration which degrades 50% of the estrogen receptor (or $IC_{50}$) in nM.

The % of ERα levels decrease were determined as follows: % inhibition=100*(1−(sample−fulvestrant: DMSO−fulvestrant)).

The Table 2 below indicates the estrogen receptor degradation activity results for the compounds of Table 1a tested at 0.3 μM, and demonstrates that said compounds have a significant degradation activity on estrogen receptors.

TABLE 2

| Compound No. | Degradation $IC_{50}$ (nM) | % Degradation At 0.3 μM |
|---|---|---|
| 1 | 0.4 | 96 |
| 2 | 0.6 | 92 |
| 3 | 0.3 | 90 |
| 4 | 0.8 | 86 |
| 5 | 1 | 88 |
| 6 | 0.4 | 92 |
| 7 | 0.6 | 90 |
| 8 | 0.4 | 86 |
| 9 | 0.6 | 90 |
| 10 | 0.2 | 90 |
| 11 | 0.3 | 91 |
| 12 | 0.4 | 93 |
| 13 | 0.5 | 89 |
| 14 | 0.2 | 88 |
| 15 | 0.6 | 87 |
| 16 | 0.4 | 93 |
| 17 | 0.5 | 89 |
| 18 | 0.6 | 90 |
| 19 | 0.2 | 93 |
| 20 | 0.3 | 92 |
| 21 | 0.3 | 93 |
| 22 | 0.5 | 93 |

TABLE 2-continued

| Compound No. | Degradation $IC_{50}$ (nM) | % Degradation At 0.3 μM |
|---|---|---|
| 23 | 0.4 | 96 |
| 24 | 0.2 | 95 |
| 25 | 0.5 | 92 |
| 26 | 0.4 | 91 |
| 27 | 0.9 | 92 |
| 28 | 1.0 | 90 |
| 29 | 0.3 | 96 |
| 30 | 1.8 | 91 |
| 31 | 0.8 | 92 |
| 32 | 2.4 | 88 |
| 33 | 0.3 | 92 |
| 34 | 0.3 | 90 |
| 35 | 0.4 | 93 |
| 36 | 0.4 | 89 |
| 37 | 0.4 | 87 |
| 38 | 0.2 | 91 |
| 39 | 0.2 | 87 |
| 40 | 0.3 | 87 |
| 41 | 0.2 | 92 |
| 42 | 0.2 | 91 |
| 43 | 0.4 | 92 |
| 44 | 0.4 | 91 |
| 45 | 0.7 | 89 |
| 46 | 6.0 | 94 |
| 47 | 0.3 | 91 |
| 48 | 0.3 | 95 |
| 49 | 0.3 | 98 |
| 50 | 0.1 | 93 |
| 51 | 0.4 | 95 |
| 52 | 0.3 | 97 |
| 53 | 0.3 | 94 |
| 54 | 0.4 | 93 |
| 55 | 1.0 | 94 |
| 56 | 0.2 | 93 |
| 57 | 0.2 | 93 |
| 58 | 0.2 | 99 |
| 59 | 0.4 | 93 |
| 60 | 2.3 | 91 |
| 61 | 0.8 | 93 |
| 62 | 0.5 | 99 |
| 63 | 0.7 | 90 |
| 64 | 0.3 | 93 |
| 65 | 0.3 | 95 |
| 66 | 0.4 | 98 |
| 67 | 0.5 | 99 |
| 68 | 0.3 | 96 |
| 69 | 0.5 | 94 |
| 70 | 0.2 | 101 |
| 71 | 0.2 | 101 |
| 72 | 0.3 | 97 |
| 73 | 0.3 | 98 |
| 74 | 0.5 | 92 |
| 75 | 1.1 | 92 |
| 76 | 0.5 | 94 |
| 77 | 0.4 | 92 |
| 78 | 0.6 | 93 |
| 79 | 0.4 | 97 |
| 80 | 0.6 | 98 |
| 81 | 0.4 | 98 |
| 82 | 0.5 | 90 |
| 83 | 0.4 | 93 |
| 84 | 2.1 | 92 |
| 85 | 0.2 | 94 |
| 86 | 0.2 | 92 |
| 87 | 0.4 | 94 |
| 88 | 2.4 | 94 |
| 89 | 0.2 | 98 |
| 90 | 0.2 | 93 |
| 91 | 0.9 | 87 |
| 92 | 0.3 | 98 |
| 93 | 0.6 | 97 |
| 94 | 0.2 | 96 |
| 95 | 0.2 | 94 |
| 96 | 0.2 | 98 |
| 97 | 0.2 | 95 |
| 98 | 0.3 | 96 |
| 99 | 0.3 | 95 |

TABLE 2-continued

| Compound No. | Degradation $IC_{50}$ (nM) | % Degradation At 0.3 μM |
|---|---|---|
| 100 | 0.3 | 94 |
| 101 | 0.4 | 93 |
| 102 | 0.3 | 89 |
| 103 | 0.2 | 92 |
| 104 | 4.9 | 79 |
| 105 | 0.1 | 94 |
| 106 | 1 | 93 |
| 107 | 1.3 | 93 |
| 108 | 1.2 | 92 |
| 109 | 1.4 | 91 |
| 110 | 2.9 | 93 |
| 111 | 1 | 90 |
| 112 | 27.8 | 100 |
| 113 | 0.3 | 90 |
| 114 | 0.4 | 91 |
| 115 | 120 | 100 |
| 116 | 0.7 | 90 |
| 117 | 0.9 | 90 |
| 118 | 0.4 | 93 |
| 119 | 0.9 | 94 |
| 120 | 2.68 | 98 |
| 121 | 0.7 | 94 |
| 122 | 0.4 | 94 |
| 123 | 0.7 | 94 |
| 124 | 1.2 | 93 |
| 125 | 0.7 | 91 |
| 126 | 0.5 | 93 |
| 127 | 0.6 | 93 |
| 128 | 1.1 | 93 |
| 129 | 1.0 | 94 |
| 130 | 1.6 | 96 |
| 131 | 1.1 | 95 |
| 132 | 0.8 | 95 |
| 133 | 1.0 | 92 |
| 134 | 1.1 | 93 |
| 135 | 0.5 | 96 |
| 136 | 0.8 | 92 |
| 137 | 3.7 | 92 |
| 138 | 1.8 | 95 |
| 139 | 3.1 | 97 |
| 140 | 0.5 | 92 |
| 141 | 0.4 | 88 |
| 142 | 0.3 | 96 |
| 143 | 3.7 | 81 |
| 144 | 0.4 | 90 |
| 145 | 4.3 | 85 |
| 146 | 1.4 | 88 |
| 147 | 0.3 | 90 |
| 148 | 1.2 | 90 |
| 149 | 0.4 | 87 |
| 150 | 1.7 | 88 |
| 151 | 0.2 | 90 |
| 152 | 0.2 | 93 |
| 153 | 0.5 | 92 |
| 154 | 0.4 | 92 |
| 155 | 0.3 | 91 |
| 156 | 0.6 | 89 |
| 157 | 3.1 | 88 |
| 158 | 0.4 | 94 |
| 159 | 20.4 | 97 |
| 160 | 0.6 | 93 |
| 161 | 1.2 | 92 |
| 162 | 1.9 | 93 |
| 163 | 0.8 | 98 |
| 164 | 1.4 | 93 |
| 165 | 1.9 | 96 |
| 166 | 0.6 | 95 |
| 167 | 1.1 | 89 |
| 168 | 0.3 | 95 |
| 169 | 0.3 | 90 |
| 170 | 0.2 | 85 |
| 171 | 0.4 | 88 |
| 172 | 0.4 | 89 |
| 173 | 0.7 | 90 |
| 174 | 2.6 | 86 |
| 175 | 0.3 | 87 |
| 176 | 0.3 | 93 |

TABLE 2-continued

| Compound No. | Degradation $IC_{50}$ (nM) | % Degradation At 0.3 μM |
|---|---|---|
| 177 | 1 | 92 |
| 178 | 1.4 | 95 |
| 179 | 1.4 | 91 |
| 180 | 0.5 | 90 |
| 181 | 0.5 | 91 |
| 182 | 0.6 | 89 |
| 183 | 0.4 | 92 |
| 184 | 0.4 | 90 |
| 185 | 0.5 | 90 |
| 186 | 1 | 92 |
| 187 | 1.6 | 86 |
| 188 | 1.8 | 89 |

It is therefore apparent that the tested compounds have degradation activities for estrogen receptors, with IC50 less than 1 μM and with degradation levels greater than 50%. The compounds of formula (I) can therefore be used for preparing medicaments, especially medicaments which are degraders of estrogen receptors.

Accordingly, also provided herein are medicaments which comprise a compound of the formula (I), or a pharmaceutically acceptable salt thereof.

Herein are also provided the compounds of formula (I) defined above, or pharmaceutically acceptable salts thereof, for use as medicines.

Herein are also provided the compounds of formula (I) defined above, or pharmaceutically acceptable salt thereof, for use in therapy, especially as inhibitors and degraders of estrogen receptors.

Herein are also provided the compounds of formula (I) defined above, or a pharmaceutically acceptable salts thereof, for use in the treatment of ovulatory dysfunction, cancer, endometriosis, osteoporosis, benign prostatic hypertrophy or inflammation.

A particular aspect is a compound of formula (I) defined above, or a pharmaceutically acceptable salt thereof, for use in the treatment of cancer.

In an embodiment, the cancer is a hormone dependent cancer.

In another embodiment, the cancer is an estrogen receptor dependent cancer, particularly the cancer is an estrogen receptor a dependent cancer.

In another embodiment, the cancer is selected from breast, ovarian, endometrial, prostate, uterine, cervical and lung cancer, or a metastasis thereof.

In another embodiment, the metastasis is a cerebral metastasis.

In another embodiment, the cancer is breast cancer. Particularly, the breast cancer is an estrogen receptor positive breast cancer (ERα positive breast cancer).

In another embodiment, the cancer is resistant to anti-hormonal treatment.

In a further embodiment, the compound of formula (I) is as used as single agent or in combination with other agents such as CDK4/6, mTOR or PI3K inhibitors.

According to another aspect, herein is provided a method of treating the pathological conditions indicated above, comprising administering to a subject in need thereof a therapeutically effective amount of a compound of formula (I), or a pharmaceutically acceptable salt thereof. In an embodiment of this method of treatment, the subject is a human.

Herein is also provided the use of a compound of the formula (I), or a pharmaceutically acceptable salt thereof, for the manufacture of a medicament useful in treating any of the pathological conditions indicated above, more particularly useful in treating cancer.

Herein are also provided the pharmaceutical compositions comprising as active principle a compound of formula (I). These pharmaceutical compositions comprise an effective dose of at least one compound of formula (I), or a pharmaceutically acceptable salt thereof, and also at least one pharmaceutically acceptable excipient.

The said excipients are selected, in accordance with the pharmaceutical form and method of administration desired, from the customary excipients, which are known to a person skilled in the art.

In the pharmaceutical compositions for oral, sublingual, subcutaneous, intramuscular, intravenous, topical, local, intra-tracheal, intranasal, transdermal or rectal administration, the active principle of formula (I) above, or its base, acid, zwitterion or salt thereof, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds of formula (I) in creams, gels, ointments or lotions.

As an example, a unit administration form of a compound of formula (I) in tablet form may comprise the following components:

| | |
|---|---|
| Compound of formula (I) | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate. According to usual practice, the dosage that is appropriate for each patient is determined by the doctor according to the mode of administration and the weight and response of the said patient.

The invention claimed is:

1. A compound of formula (I) or a pharmaceutically acceptable salt thereof:

(I)

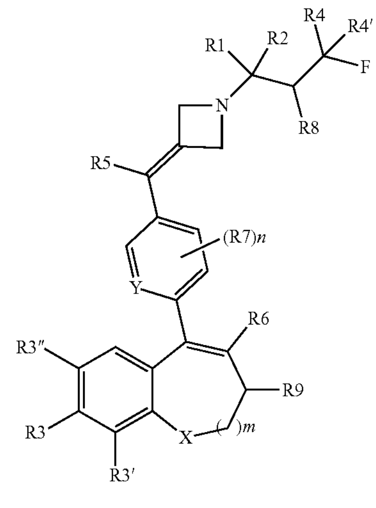

wherein:

R1 and R2 independently represent a hydrogen atom or a deuterium atom;

R3 represents a hydrogen atom, a —COOH group or a —OH group;

R3' and R3" independently represent a hydrogen atom, a methyl group, a methoxy group, a chlorine atom, a fluorine atom or a cyano group;

R4 and R4' independently represent a hydrogen atom or a fluorine atom;

R5 represents a hydrogen atom, a fluorine atom or a $(C_1-C_3)$alkyl group;

R6 represents a group selected from:

a phenyl group, said phenyl group being optionally substituted by 1 to 3 substituents independently selected from a halogen atom; a $(C_1-C_6)$alkyl group, optionally substituted with a cyano group or a —OH group; a $(C_1-C_6)$fluoroalkyl group; a $(C_3-C_6)$cycloalkyl group; a $(C_1-C_6)$alkoxy group; a $(C_1-C_6)$fluoroalkoxy group; a cyano group; a trifluoromethylsulfonyl group; a $(C_1-C_4)$alkylthio group; a $(C_1-C_4)$fluoroalkylthio group; a $(C_1-C_4)$alkylsulfonyl group; and a —OH group;

a fused phenyl group, selected from phenyl groups fused with a $(C_3-C_6)$cycloalkyl, said $(C_3-C_6)$cycloalkyl optionally comprises an unsaturation, and wherein the fused phenyl group is optionally substituted with 1 to 3 substituents independently selected from a $(C_1-C_3)$alkyl group, a hydroxy group, a halogen atom, a $(C_1-C_6)$fluoroalkyl group, and a $(C_1-C_3)$alkoxy group;

a bicyclic group comprising 5 to 12 carbon atoms, optionally comprising 1 to 2 unsaturations; optionally substituted with 1 to 4 substituents independently selected from: a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, and an oxo group;

a heteroaryl group comprising 2 to 9 carbon atoms and comprising from 1 to 3 heteroatoms independently selected from oxygen, nitrogen and sulfur, and at least 5 atoms including carbon atoms and heteroatoms, said heteroaryl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a cyano group, a carbamoyl group, and a —OH group;

a cycloalkyl group comprising 3 to 7 carbon atoms, said cycloalkyl group being saturated or partially saturated and being optionally substituted with 1 to 4 substituents independently selected from:

a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, an oxo group, a $(C_3-C_6)$cycloalkyl group, and a phenyl group, said $(C_3-C_6)$cycloalkyl or phenyl groups being optionally substituted with one or two halogen atom(s) or $(C_1-C_3)$alkyl group(s);

a $(C_3-C_6)$cycloalkyl$(C_1-C_3)$alkyl group, optionally substituted on the cycloalkyl with 1 to 4 substituents independently selected from: a fluorine atom, a —OH group, a $(C_1-C_4)$alkyl group, a $(C_1-C_3)$fluoroalkyl group, a $(C_1-C_3)$fluoroalkoxy group, and an oxo group;

a 3 to 8 membered-heterocycloalkyl group comprising 1 or 2 heteroatoms independently selected from oxygen, nitrogen and sulfur, said heterocycloalkyl group being saturated or partially saturated and being optionally substituted with 1 to 3 substituents independently selected from: a fluorine atom, a $(C_1-C_3)$alkyl group, a $(C_1-C_3)$fluoroalkyl group, a $(C_1-C_3)$fluoroalkoxy group, an oxo group, a $(C_1-C_3)$alkoxy group, and a —OH group;

a $(C_1-C_6)$alkyl group said alkyl group being optionally substituted with 1 to 4 substituents independently selected from: a fluorine atom, a $(C_1-C_3)$alkoxy group, a $(C_1-C_3)$fluoroalkoxy group, and a —OH group; and a phenyl$(C_1-C_2)$alkyl group, said phenyl group being optionally substituted with 1 to 3 substituents independently selected from a halogen atom; a $(C_1-C_3)$alkyl group; a $(C_1-C_3)$fluoroalkyl group; a $(C_1-C_3)$alkoxy group; a $(C_1-C_3)$ fluoroalkoxy group; a cyano group; and a —OH group;

X represents $—CH_2—$, —O— or —S—;

Y represents —CH=, —N= or —CR"=, wherein R" represents a $(C_1-C_3)$alkyl group, a halogen atom, a cyano group or a $(C_1-C_3)$fluoroalkyl group;

R7 independently represents a $(C_1-C_3)$alkyl group, a halogen atom, a cyano group or a $(C_1-C_3)$fluoroalkyl group;

R8 represents a hydrogen atom or a fluorine atom;

R9 represents a hydrogen atom, a $(C_1-C_3)$alkyl group or a cyclopropyl;

n is 0, 1 or 2; and m is 0 or 1.

2. The compound of formula (I) according to claim 1, or a pharmaceutically acceptable salt thereof, wherein R1 and R2 are each a hydrogen atom.

3. The compound of formula (I) according to claim 1, or a pharmaceutically acceptable salt thereof, wherein R3 is —COOH.

4. The compound of formula (I) according to claim 1, or a pharmaceutically acceptable salt thereof, wherein R3' and R3" are each a hydrogen atom.

5. The compound of formula (I) according to claim 1, or a pharmaceutically acceptable salt thereof, wherein R4 and R4' are each a hydrogen atom.

6. The compound of formula (I) according to claim 1, or a pharmaceutically acceptable salt thereof, wherein X is $—CH_2—$.

7. The compound of formula (I) according to claim 1, or a pharmaceutically acceptable salt thereof, wherein R5 is a hydrogen atom.

8. The compound of formula (I) according to claim 1, or a pharmaceutically acceptable salt thereof, wherein R6 is a phenyl group, said phenyl group being optionally substituted with 1 to 3 substituents independently selected from a chlorine atom, a fluorine atom, a methyl group, an ethyl group, a trifluoromethyl group, a cyclopropyl group, a methoxy group, and a cyano group.

9. The compound of formula (I) according to claim 1, or a pharmaceutically acceptable salt thereof, wherein R6 is a fused phenyl group selected from a bicyclo[4.2.0]octatrienyl group, an indanyl group, and a tetrahydronaphthalenyl group, each of which is optionally substituted with one or two fluorine atoms.

10. The compound of formula (I) according to claim 1, or a pharmaceutically acceptable salt thereof, wherein R6 is a bicyclic group selected from a bicyclo[4.1.0]heptanyl, a bicyclo[3.1.0]hexanyl, a spiro[2.3]hexanyl, and a bicyclo[3.2.1]octan-3-yl, each of which is optionally substituted with 1 to 4 substituents independently selected from: a fluorine atom, a —OH group, a ($C_1$-$C_3$)alkyl group, a ($C_1$-$C_3$)fluoroalkyl group, a ($C_1$-$C_3$)alkoxy group, a ($C_1$-$C_3$) fluoroalkoxy group, and an oxo group.

11. The compound of formula (I) according to claim 1, or a pharmaceutically acceptable salt thereof, wherein R6 is a pyridyl group, said pyridyl group being optionally substituted with 1 to 3 substituents independently selected from a halogen atom, a ($C_1$-$C_6$)alkyl group, a ($C_1$-$C_6$)fluoroalkyl group, and a ($C_1$-$C_6$)alkoxy groups.

12. The compound of formula (I) according to claim 1, or a pharmaceutically acceptable salt thereof, wherein R6 is a cycloalkyl chosen from a cyclohexyl or a cyclopropyl group, said cycloalkyl being optionally substituted with 1 to 4 substituents independently selected from:

a fluorine atom, a —OH group, a ($C_1$-$C_3$)alkyl group, a ($C_1$-$C_3$)fluoroalkyl group, a ($C_1$-$C_3$)alkoxy group, a ($C_1$-$C_3$)fluoroalkoxy group, an oxo group, a ($C_3$-$C_6$) cycloalkyl group, and a phenyl group, said ($C_3$-$C_6$) cycloalkyl or phenyl group being optionally substituted with one or two halogen atom(s) or ($C_1$-$C_3$)alkyl group(s).

13. The compound of formula (I) according to claim 1, or a pharmaceutically acceptable salt thereof, wherein R6 represents a cyclobutylmethyl, optionally substituted on the cycloalkyl with 1 to 4 substituents independently selected from: a fluorine atom, a OH group, a ($C_1$-$C_4$)alkyl group, a ($C_1$-$C_3$)fluoroalkyl group, a ($C_1$-$C_3$)fluoroalkoxy group, and an oxo group.

14. The compound of formula (I) according to claim 1, or a pharmaceutically acceptable salt thereof, wherein R6 represents a tetrahydropyranyl group, said tetrahydropyranyl group being optionally substituted with 1 to 3 substituents independently selected from: a fluorine atom, a ($C_1$-$C_3$) alkoxy group, a ($C_1$-$C_3$)fluoroalkyl group, a ($C_1$-$C_3$)fluoroalkoxy group, and a —OH group.

15. The compound of formula (I) according to claim 1, or a pharmaceutically acceptable salt thereof, wherein R6 represents an isobutyl group, said isobutyl group being optionally substituted with 1 to 4 substituents independently selected from: a fluorine atom, a ($C_1$-$C_3$)alkoxy group, a ($C_1$-$C_3$)fluoroalkoxy group, and a —OH group.

16. The compound of formula (I) according to claim 1, or a pharmaceutically acceptable salt thereof, wherein R6 represents a phenyl($C_1$-$C_2$)alkyl group.

17. The compound of formula (I) according to claim 1, or a pharmaceutically acceptable salt thereof, wherein R7 independently represents a methyl group, a cyano group, a trifluoromethyl group or a fluorine atom.

18. The compound of formula (I) according to claim 1, or a pharmaceutically acceptable salt thereof, wherein Y represents —CH═, —N═ or —CR"═, with R" representing a fluorine atom, a cyano group or a trifluoromethyl group.

19. The compound of formula (I) according to claim 1, or a pharmaceutically acceptable salt thereof, wherein m is 1.

20. The compound of formula (I) according to claim 1, or a pharmaceutically acceptable salt thereof, selected from the following compounds:

8-(2,4-dichlorophenyl)-9-(4-((1-(3-fluoropropyl)azetidin-3-ylidene)methyl)phenyl)-6,7-dihydro-5H-benzo[7]annulene-3-carboxylic acid, 8-(3-fluoro-2-methoxypyridin-4-yl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(2-methyl-4-(trifluoromethyl)phenyl)-6,7-dihydro-5H-benzo[7]annulene-3-carboxylic acid, 8-(6-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, 8-(4-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(5-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, 8-(4-fluoro-2,3-dihydro-1H-inden-5-yl)-9-(4-((1-(3-fluoropropyl)azetidin-3-ylidene)methyl)phenyl)-6,7-dihydro-5H-benzo[7]annulene-3-carboxylic acid, 8-(bicyclo[4.2.0]octa-1,3,5-trien-3-yl)-9-(4-((1-(3-fluoropropyl)azetidin-3-ylidene)methyl)phenyl)-6,7-dihydro-5H-benzo[7]annulene-3-carboxylic acid, 8-(1,1-difluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, 8-(2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, 8-(4-fluoro-2-methylphenyl)-9-(2-fluoro-4-((1-(3-fluoropropyl)azetidin-3-ylidene)methyl)phenyl)-6,7-dihydro-5H-benzo[7]annulene-3-carboxylic acid, 8-(7-fluoro-2,3-dihydro-1H-inden-4-yl)-9-(4-((1-(3-fluoropropyl)azetidin-3-ylidene)methyl)phenyl)-6,7-dihydro-5H-benzo[7]annulene-3-carboxylic acid, 8-(3-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(3-methyl-2-(trifluoromethyl)phenyl)-6,7-dihydro-5H-benzo[7]annulene-3-carboxylic acid, 8-(2,4-difluorophenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride, 8-(2,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(2,4-difluorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid hydrochloride, 8-(5-fluoro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid,
9-(4-((1-(3,3-difluoropropyl)azetidin-3-ylidene)methyl)phenyl)-8-(4-fluoro-2-methylphenyl)-6,7-dihydro-5H-benzo[7]annulene-3-carboxylic acid,
8-(2,4-difluorophenyl)-9-(4-((1-(3,3-difluoropropyl)azetidin-3-ylidene)methyl)phenyl)-6,7-dihydro-5H-benzo[7]annulene-3-carboxylic acid,
8-(2,6-difluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(3,4-difluoro-2-methylphenyl)-9-(4-((1-(3,3-difluoropropyl)azetidin-3-ylidene)methyl)phenyl)-6,7-dihydro-5H-benzo[7]annulene-3-carboxylic acid,
8-(3-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(3-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
9-(4-((1-(3,3-difluoropropyl)azetidin-3-ylidene)methyl)phenyl)-8-(4-fluoro-2-(trifluoromethyl)phenyl)-6,7-dihydro-5H-benzo[7]annulene-3-carboxylic acid,
9-(4-((1-(3,3-difluoropropyl)azetidin-3-ylidene)methyl)phenyl)-8-(3-fluoro-2-(trifluoromethyl)phenyl)-6,7-dihydro-5H-benzo[7]annulene-3-carboxylic acid,
8-(2,4-difluorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid,
8-(4-fluoro-2-methylphenyl)-9-(3-fluoro-4-((1-(3-fluoropropyl)azetidin-3-ylidene)methyl)-5-methylphenyl)-6,7-dihydro-5H-benzo[7]annulene-3-carboxylic acid,
8-(3,4-difluoro-2-methylphenyl)-9-(4-((1-(3-fluoropropyl)azetidin-3-ylidene)methyl)phenyl)-6,7-dihydro-5H-benzo[7]annulene-3-carboxylic acid,
8-(4-fluoro-2-methylphenyl)-9-(3-fluoro-4-((1-(3-fluoropropyl)azetidin-3-ylidene)methyl)-2-methylphenyl)-6,7-dihydro-5H-benzo[7]annulene-3-carboxylic acid,
8-(2,4-difluorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid,
8-(5-fluoro-3-methylpyridin-2-yl)-9-(4-((1-(3-fluoropropyl)azetidin-3-ylidene)methyl)phenyl)-6,7-dihydro-5H-benzo[7]annulene-3-carboxylic acid,
9-(4-((1-(3-fluoropropyl)azetidin-3-ylidene)methyl)phenyl)-8-(2,4,6-trifluorophenyl)-6,7-dihydro-5H-benzo[7]annulene-3-carboxylic acid,
8-(4-cyclopropyl-2-fluorophenyl)-9-(4-((1-(3-fluoropropyl)azetidin-3-ylidene)methyl)phenyl)-6,7-dihydro-5H-benzo[7]annulene-3-carboxylic acid,
8-(5-chloro-3-(trifluoromethyl)pyridin-2-yl)-9-(4-((1-(3-fluoropropyl)azetidin-3-ylidene)methyl)phenyl)-6,7-dihydro-5H-benzo[7]annulene-3-carboxylic acid,
9-(3,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid,
8-(4-chloro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(5-fluoro-2-methylphenyl)-9-(4-((1-(3-fluoropropyl)azetidin-3-ylidene)methyl)phenyl)-6,7-dihydro-5H-benzo[7]annulene-3-carboxylic acid,
8-(4-cyclopropyl-2-methylphenyl)-9-(4-((1-(3-fluoropropyl)azetidin-3-ylidene)methyl)phenyl)-6,7-dihydro-5H-benzo[7]annulene-3-carboxylic acid,
8-(2-cyclopropyl-4-fluorophenyl)-9-(4-((1-(3-fluoropropyl)azetidin-3-ylidene)methyl)phenyl)-6,7-dihydro-5H-benzo[7]annulene-3-carboxylic acid,
8-(2-chloro-4-methylphenyl)-9-(4-((1-(3-fluoropropyl)azetidin-3-ylidene)methyl)phenyl)-6,7-dihydro-5H-benzo[7]annulene-3-carboxylic acid,
8-(2-chloro-6-fluorophenyl)-9-(4-((1-(3-fluoropropyl)azetidin-3-ylidene)methyl)phenyl)-6,7-dihydro-5H-benzo[7]annulene-3-carboxylic acid,
9-(2,3-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid,
8-(4-fluoro-2-methylphenyl)-9-(4-((1-(3-fluoropropyl)azetidin-3-ylidene)methyl)-3-methylphenyl)-6,7-dihydro-5H-benzo[7]annulene-3-carboxylic acid hydrochloride,
8-(4-fluoro-2-methylphenyl)-9-(4-((1-(3-fluoropropyl)azetidin-3-ylidene)methyl)-2,5-dimethylphenyl)-6,7-dihydro-5H-benzo[7]annulene-3-carboxylic acid,
9-(3-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid,
8-(3-chloro-2-fluorophenyl)-9-(4-((1-(3-fluoropropyl)azetidin-3-ylidene)methyl)phenyl)-6,7-dihydro-5H-benzo[7]annulene-3-carboxylic acid,
8-(2-fluoro-3-methylphenyl)-9-(4-((1-(3-fluoropropyl)azetidin-3-ylidene)methyl)phenyl)-6,7-dihydro-5H-benzo[7]annulene-3-carboxylic acid,
8-(2-fluoro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(2-chloro-4-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(2,6-difluoro-4-methylphenyl)-9-(4-((1-(3-fluoropropyl)azetidin-3-ylidene)methyl)phenyl)-6,7-dihydro-5H-benzo[7]annulene-3-carboxylic acid,
9-(2,6-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid,
8-(2,4-difluorophenyl)-9-(3-fluoro-4-((1-(3-fluoropropyl)azetidin-3-ylidene)methyl)phenyl)-6,7-dihydro-5H-benzo[7]annulene-3-carboxylic acid,
8-(2,4-difluorophenyl)-9-(4-((1-(3-fluoropropyl)azetidin-3-ylidene)methyl)phenyl)-6,7-dihydro-5H-benzo[7]annulene-3-carboxylic acid,
8-(2,3-difluorophenyl)-9-(4-((1-(3-fluoropropyl)azetidin-3-ylidene)methyl)phenyl)-6,7-dihydro-5H-benzo[7]annulene-3-carboxylic acid,
8-(2-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid,
8-(2-fluoro-4-methylphenyl)-9-(4-((1-(3-fluoropropyl)azetidin-3-ylidene)methyl)phenyl)-6,7-dihydro-5H-benzo[7]annulene-3-carboxylic acid,
8-(4-chloro-2-fluorophenyl)-9-(4-((1-(3-fluoropropyl)azetidin-3-ylidene)methyl)phenyl)-6,7-dihydro-5H-benzo[7]annulene-3-carboxylic acid,
9-(3,5-difluoro-4-((1-(3-fluoropropyl)azetidin-3-ylidene)methyl)phenyl)-8-(2,4-difluorophenyl)-6,7-dihydro-5H-benzo[7]annulene-3-carboxylic acid,
9-(4-((1-(3-fluoropropyl)azetidin-3-ylidene)methyl)phenyl)-8-(tetrahydro-2H-pyran-4-yl)-6,7-dihydro-5H-benzo[7]annulene-3-carboxylic acid, 8-(4-fluoro-2-methylphenyl)-9-(5-fluoro-4-((1-(3-fluoropropyl)azetidin-3-ylidene)methyl)-2-methylphenyl)-6,7-dihydro-5H-benzo[7]annulene-3-carboxylic acid hydrochloride, 8-(4-fluoro-2-methylphenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride, 8-(2,4-dichlorophenyl)-9-(3-fluoro-4-((1-(3-fluoropropyl)azetidin-3-ylidene)methyl)-2-methylphenyl)-6,7-dihydro-5H-benzo[7]annulene-3-carboxylic acid, 8-(2,4-dichlorophenyl)-9-(4-((1-(3-fluoropropyl)azetidin-3-ylidene)methyl)-3-methylphenyl)-6,7-dihydro-5H-benzo[7]annulene-3-carboxylic acid, 9-(2,5-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid hydrochloride, 8-(2,4-dichlorophenyl)-9-(2-fluoro-4-((1-(3-fluoropropyl)azetidin-3-ylidene)methyl)-6-methylphenyl)-6,7-dihydro-5H-benzo[7]annulene-3-carboxylic acid hydrochloride, 8-(4-fluoro-2-methylphenyl)-9-(2-fluoro-4-((1-(3-fluoropropyl)azetidin-3-ylidene)methyl)-3-methylphenyl)-6,7-dihydro-5H-benzo[7]annulene-3-carboxylic acid, 9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid, 9-(3-fluoro-4-((1-(3-fluoropropyl)azetidin-3-ylidene)methyl)phenyl)-8-(2-fluoro-4-methylphenyl)-6,7-dihydro-5H-benzo[7]annulene-3-carboxylic acid, 9-(4-((1-(3-fluoropropyl)azetidin-3-ylidene)methyl)phenyl)-8-(4-methyl-2-(trifluoromethyl)phenyl)-6,7-dihydro-5H-benzo[7]annulene-3-carboxylic acid, 8-(2,4-dichlorophenyl)-9-(3-fluoro-4-((1-(3-fluoropropyl)azetidin-3-ylidene)methyl)-5-methylphenyl)-6,7-dihydro-5H-benzo[7]annulene-3-carboxylic acid hydrochloride, 8-(3-chloro-2-methylphenyl)-9-(4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(2,6-difluoro-4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(2-fluoro-4-((1-(3-fluoropropyl)azetidin-3-ylidene)methyl)-3-methylphenyl)-6,7-dihydro-5H-benzo[7]annulene-3-carboxylic acid hydrochloride, 8-(2-chloro-4-methoxyphenyl)-9-(4-((1-(3-fluoropropyl)azetidin-3-ylidene)methyl)phenyl)-6,7-dihydro-5H-benzo[7]annulene-3-carboxylic acid, 8-(2-chloro-3-methylphenyl)-9-(4-((1-(3-fluoropropyl)azetidin-3-ylidene)methyl)phenyl)-6,7-dihydro-5H-benzo[7]annulene-3-carboxylic acid, 8-(2,4-dimethylphenyl)-9-(4-((1-(3-fluoropropyl)azetidin-3-ylidene)methyl)phenyl)-6,7-dihydro-5H-benzo[7]annulene-3-carboxylic acid, 8-(2-chloro-3-fluorophenyl)-9-(4-((1-(3-fluoropropyl)azetidin-3-ylidene)methyl)phenyl)-6,7-dihydro-5H-benzo[7]annulene-3-carboxylic acid, 8-(2-chloro-4-fluorophenyl)-9-(4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylic acid hydrochloride, 8-(4-chloro-3-fluoro-2-methylphenyl)-9-(4-((1-(3-fluoropropyl)azetidin-3-ylidene)methyl)phenyl)-6,7-dihydro-5H-benzo[7]annulene-3-carboxylic acid, 8-(4-chloro-2,3-dimethylphenyl)-9-(4-((1-(3-fluoropropyl)azetidin-3-ylidene)methyl)phenyl)-6,7-dihydro-5H-benzo[7]annulene-3-carboxylic acid, 8-(4-chloro-2,6-dimethylphenyl)-9-(4-((1-(3-fluoropropyl)azetidin-3-ylidene)methyl)phenyl)-6,7-dihydro-5H-benzo[7]annulene-3-carboxylic acid, 8-(4-cyano-2-methylphenyl)-9-(4-((1-(3-fluoropropyl)azetidin-3-ylidene)methyl)phenyl)-6,7-dihydro-5H-benzo[7]annulene-3-carboxylic acid, 8-(3-fluoro-2-methylphenyl)-9-(4-((1-(3-fluoropropyl)azetidin-3-ylidene)methyl)phenyl)-6,7-dihydro-5H-benzo[7]annulene-3-carboxylic acid, 8-(2-ethylphenyl)-9-(4-((1-(3-fluoropropyl)azetidin-3-ylidene)methyl)phenyl)-6,7-dihydro-5H-benzo[7]annulene-3-carboxylic acid, 8-(4-fluoro-2,3-dimethylphenyl)-9-(4-((1-(3-fluoropropyl)azetidin-3-ylidene)methyl)phenyl)-6,7-dihydro-5H-benzo[7]annulene-3-carboxylic acid, 8-(2-cyano-3-methylphenyl)-9-(4-((1-(3-fluoropropyl)azetidin-3-ylidene)methyl)phenyl)-6,7-dihydro-5H-benzo[7]annulene-3-carboxylic acid, 8-(4-chloro-2-methylphenyl)-9-(4-((1-(3-fluoropropyl)azetidin-3-ylidene)methyl)phenyl)-6,7-dihydro-5H-benzo[7]annulene-3-carboxylic acid, 8-(4-fluoro-2,6-dimethylphenyl)-9-(4-((1-(3-fluoropropyl)azetidin-3-ylidene)methyl)phenyl)-6,7-dihydro-5H-benzo[7]annulene-3-carboxylic acid, 8-(3-cyano-2-methylphenyl)-9-(4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(2,5-difluoro-4-((1-(3-fluoropropyl)azetidin-3-ylidene)methyl)phenyl)-6,7-dihydro-5H-benzo[7]annulene-3-carboxylic acid hydrochloride, 8-(2,4-dichlorophenyl)-9-(4-((1-(3-fluoropropyl)azetidin-3-ylidene)methyl)-2-methylphenyl)-6,7-dihydro-5H-benzo[7]annulene-3-carboxylic acid hydrochloride, 8-(2,3-dimethylphenyl)-9-(4-((1-(3-fluoropropyl)azetidin-3-ylidene)methyl)phenyl)-6,7-dihydro-5H-benzo[7]annulene-3-carboxylic acid, 8-(4-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(2-ethyl-4-fluorophenyl)-9-(4-((1-(3-fluoropropyl)azetidin-3-ylidene)methyl)phenyl)-6,7-dihydro-5H-benzo[7]annulene-3-carboxylic acid, 8-(2,6-dimethylphenyl)-9-(4-((1-(3-fluoropropyl)azetidin-3-ylidene)methyl)phenyl)-6,7-dihydro-5H-benzo[7]annulene-3-carboxylic acid, 8-(4-fluoro-2-methylphenyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(o-tolyl)-6,7-dihydro-5H-benzo[7]annulene-3-carboxylic acid, 9-(4-((1-(3-fluoropropyl)azetidin-3-ylidene)methyl)phenyl)-8-isobutyl-6,7-dihydro-5H-benzo[7]annulene-3-carboxylic acid, 8-(2,4-dichlorophenyl)-9-(2-fluoro-4-((1-(3-fluoropropyl)azetidin-3-ylidene)methyl)phenyl)-6,7-dihydro-5H-benzo[7]annulene-3-carboxylic acid hydrochloride, 8-(2,4-dichlorophenyl)-9-(4-(1-(1-(3-fluoropropyl)azetidin-3-ylidene)ethyl)phenyl)-6,7-dihydro-5H-benzo[7]annulene-3-carboxylic acid, 8-(2,4-dichlorophenyl)-9-(3-fluoro-4-((1-(3-fluoropropyl)azetidin-3-ylidene)methyl)phenyl)-6,7-dihydro-5H-benzo[7]annulene-3-carboxylic acid hydrochloride, 8-(2,4-dichlorophenyl)-9-(4-((1-(3-fluoropropyl)azetidin-3-ylidene)methyl)-3,5-dimethylphenyl)-6,7-dihydro-5H-benzo[7]annulene-3-carboxylic acid hydrochloride, 8-(2,4-dichlorophenyl)-9-(3,5-difluoro-4-((1-(3-fluoropropyl)azetidin-3-ylidene)methyl)phenyl)-6,7-dihydro-5H-benzo[7]annulene-3-carboxylic acid, 6-(2,4-dichlorophenyl)-5-(4-((1-(3-fluoropropyl)azetidin-3-ylidene)methyl)phenyl)-7,8-dihydronaphthalene-2-carboxylic acid hydrochloride, 8-(3-chloro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, 8-(4-fluoro-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, 8-(2,4-dichlorophenyl)-9-(4-((1-(3,3,3-trifluoropropyl)azetidin-3-ylidene)methyl)phenyl)-6,7-dihydro-5H-benzo[7]annulene-3-carboxylic acid, 8-(3-methyl-2-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, 8-(4-chloro-3-fluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid, 8-(3,4-difluoro-2-methylphenyl)-9-(4-((1-(3,3,3-trifluoropropyl)azetidin-3-ylidene)methyl)phenyl)-6,7-dihydro-5H-benzo[7]annulene-3-carboxylic acid, 8-(2-methyl-4-(trifluoromethyl)phenyl)-9-(4-((1-(3,3,3-trifluoropropyl)azetidin-3-ylidene)methyl)phenyl)-6,7-dihydro-5H-benzo[7]annulene-3-carboxylic acid, 4-(2,4-dichlorophenyl)-5-(4-((1-(3-fluoropropyl)azetidin-3-ylidene)methyl)phenyl)-2,3-dihydrobenzo[b]oxepine-8-carboxylic acid hydrochloride, 4-(2,4-dichlorophenyl)-5-[4-[[1-(3-fluoropropyl)azetidin-3-ylidene]methyl]phenyl]-2,3-dihydro-1-benzothiepine-8-carboxylic acid;hydrochloride, 9-(4-((1-(3,3-difluoropropyl)azetidin-3-ylidene)methyl)phenyl)-8-(3-methyl-2-(trifluoromethyl)phenyl)-6,7-dihydro-5H-benzo[7]annulene-3-carboxylic acid, 8-(2,4-dichlorophenyl)-9-(4-((1-(3,3-difluoropropyl-1,1-d2)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(3-methyl-2-(trifluoromethyl)phenyl)-6,7-dihydro-5H-benzo[7]annulene-3-carboxylic acid, 9-(4-((1-(3-fluoropropyl)azetidin-3-ylidene)methyl)phenyl)-8-(5-methyl-2-(trifluoromethyl)phenyl)-6,7-dihydro-5H-benzo[7]annulene-3-carboxylic acid, 3-(4-(8-(2-chlorophenyl)-6,7-dihydro-5H-benzo[7]annulen-9-yl)benzylidene)-1-(3-fluoropropyl)azetidine, 8-(2-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(4-((1-(3-fluoropropyl-1,1-d2)azetidin-3-ylidene)methyl)phenyl)-6,7-dihydro-5H-benzo[7]annulene-3-carboxylic acid, 8-(2-chloro-5-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(2,4-difluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(5-chloro-3-(trifluoromethyl)pyridin-2-yl)-9-(4-((1-(3,3-difluoropropyl)azetidin-3-ylidene)methyl)phenyl)-6,7-dihydro-5H-benzo[7]annulene-3-carboxylic acid, 8-(3-chloro-2-methylphenyl)-9-(4-((1-(3,3-difluoropropyl)azetidin-3-ylidene)methyl)phenyl)-6,7-dihydro-5H-benzo[7]annulene-3-carboxylic acid, 8-(4-chloro-3-fluoro-2-methylphenyl)-9-(4-((1-(3,3-difluoropropyl)azetidin-3-ylidene)methyl)phenyl)-6,7-dihydro-5H-benzo[7]annulene-3-carboxylic acid, 8-(4-chloro-2-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, 9-(4-((1-(3,3-difluoropropyl)azetidin-3-ylidene)methyl)phenyl)-8-(2-fluoro-3-(trifluoromethyl)phenyl)-6,7-dihydro-5H-benzo[7]annulene-3-carboxylic acid, 9-(4-((1-(3,3-difluoropropyl)azetidin-3-ylidene)methyl)phenyl)-8-(4-fluoro-2,3-dimethylphenyl)-6,7-dihydro-5H-benzo[7]annulene-3-carboxylic acid, 8-(2-chloro-3-methylphenyl)-9-(4-((1-(3,3-difluoropropyl)azetidin-3-ylidene)methyl)phenyl)-6,7-dihydro-5H-benzo[7]annulene-3-carboxylic acid, 8-(4-chloro-2-methylphenyl)-9-(4-((1-(3,3-difluoropropyl)azetidin-3-ylidene)methyl)phenyl)-6,7-dihydro-5H-benzo[7]annulene-3-carboxylic acid, 8-(2-chloro-3-(trifluoromethyl)phenyl)-9-(4-((1-(3,3-difluoropropyl)azetidin-3-ylidene)methyl)phenyl)-6,7-dihydro-5H-benzo[7]annulene-3-carboxylic acid, 9-(4-((1-(3,3-difluoropropyl)azetidin-3-ylidene)methyl)phenyl)-8-(2-methyl-3-(trifluoromethyl)phenyl)-6,7-dihydro-5H-benzo[7]annulene-3-carboxylic acid, 9-(4-((1-(3-fluoropropyl)azetidin-3-ylidene)methyl)phenyl)-8-(2,3,4-trifluorophenyl)-6,7-dihydro-5H-benzo[7]annulene-3-carboxylic acid, 9-(4-((1-(3-fluoropropyl)azetidin-3-ylidene)methyl)phenyl)-8-(2-methyl-5-(trifluoromethyl)phenyl)-6,7-dihydro-5H-benzo[7]annulene-3-carboxylic acid, 9-(4-((1-(3-fluoropropyl)azetidin-3-ylidene)methyl)phenyl)-8-(2-methoxy-5-(trifluoromethyl)phenyl)-6,7-dihydro-5H-benzo[7]annulene-3-carboxylic acid, 8-(4-fluoro-2-methylphenyl)-9-(4-((1-(3-fluoropropyl)azetidin-3-ylidene)methyl)-2-(trifluoromethyl)phenyl)-6,7-dihydro-5H-benzo[7]annulene-3-carboxylic acid, 9-(2-cyano-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, 8-(2-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(4-cyclopropyl-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, Sodium 8-(2,4-difluorophenyl)-9-(2-fluoro-4-((1-(3-fluoropropyl)azetidin-3-ylidene)methyl)phenyl)-6,7-dihydro-5H-benzo[7]annulene-3-carboxylate, 8-(3-chloro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(4-methyl-3-(trifluoromethyl)phenyl)-6,7-dihydro-5H-benzo[7]annulene-3-carboxylic acid, 9-(4-((1-(3-fluoropropyl)azetidin-3-ylidene)methyl)phenyl)-8-(3-methyl-5-(trifluoromethyl)phenyl)-6,7-dihydro-5H-benzo[7]annulene-3-carboxylic acid, 8-(3,4-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(2-chloro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(4-methoxy-3-(trifluoromethyl)phenyl)-6,7-dihydro-5H-benzo[7]annulene-3-carboxylic acid, 8-(4-ethoxy-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(3-methoxy-5-(trifluoromethyl)phenyl)-6,7-dihydro-5H-benzo[7]annulene-3-carboxylic acid, 8-(2,5-bis(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 9-(2,3-difluoro-4-((1-(3-fluoropropyl)azetidin-3-ylidene)methyl)phenyl)-8-(4-fluoro-2-methylphenyl)-6,7-dihydro-5H-benzo[7]annulene-3-carboxylic acid, 8-(5-fluoro-2-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(4-fluoro-3-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(3-fluoro-5-(trifluoromethyl)phenyl)-9-(4-((1-(3-fluoropropyl)azetidin-3-ylidene)methyl)phenyl)-6,7-dihydro-5H-benzo[7]annulene-3-carboxylic acid, 8-(5-fluoro-2-methoxypyridin-4-yl)-9-(4-((1-(3-fluoropropyl)azetidin-3-ylidene)methyl)phenyl)-6,7-dihydro-5H-benzo[7]annulene-3-carboxylic acid, 8-(4-fluoro-2-methylphenyl)-9-(4-((1-(3-fluoropropyl)azetidin-3-ylidene)methyl)-3-(trifluoromethyl)phenyl)-6,7-dihydro-5H-benzo[7]annulene-3-carboxylic acid, 8-(2,4-dichlorophenyl)-9-(3-fluoro-5-((1-(3-fluoropropyl)azetidin-3-ylidene)methyl)pyridin-2-yl)-6,7-dihydro-5H-benzo[7]annulene-3-carboxylic acid, 8-(2,4-dichlorophenyl)-9-(5-((1-(3-fluoropropyl)azetidin-3-ylidene)methyl)pyridin-2-yl)-6,7-dihydro-5H-benzo[7]annulene-3-carboxylic acid, trifluoroacetic acid, 9-(4-((1-(3,3-difluoropropyl)azetidin-3-ylidene)methyl)phenyl)-8-(5-fluoro-2,3-dihydro-1H-inden-4-yl)-6,7-dihydro-5H-benzo[7]annulene-3-carboxylic acid, 9-(4-((1-(3,3-difluoropropyl)azetidin-3-ylidene)methyl)phenyl)-8-(4-fluoro-2,3-dihydro-1H-inden-5-yl)-6,7-dihydro-5H-benzo[7]annulene-3-carboxylic acid, 9-(4-((1-(3,3-difluoropropyl)azetidin-3-ylidene)methyl)phenyl)-8-(6-fluoro-2,3-dihydro-1H-inden-4-yl)-6,7-dihydro-5H-benzo[7]annulene-3-carboxylic acid, 9-(4-((1-(3,3-difluoropropyl)azetidin-3-ylidene)methyl)phenyl)-8-(2,3-dihydro-1H-inden-4-yl)-6,7-dihydro-5H-benzo[7]annulene-3-carboxylic acid, 8-(1,1-difluoro-2,3-dihydro-1H-inden-4-yl)-9-(4-((1-(3,3-difluoropropyl)azetidin-3-ylidene)methyl)phenyl)-6,7-dihydro-5H-benzo[7]annulene-3-carboxylic acid, 9-(4-((1-(3,3-difluoropropyl)azetidin-3-ylidene)methyl)phenyl)-8-(7-fluoro-2,3-dihydro-1H-inden-4-yl)-6,7-dihydro-5H-benzo[7]annulene-3-carboxylic acid, 8-(2,4-dichlorophenyl)-9-(4-((1-(3-fluoropropyl)azetidin-3-ylidene)methyl)phenyl)-7-methyl-6,7-dihydro-5H-benzo[7]annulene-3-carboxylic acid, 8-benzyl-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-phenethyl-6,7-dihydro-5H-benzo[7]annulene-3-carboxylic acid, 8-(cyclobutylmethyl)-9-(4-((1-(3-fluoropropyl)azetidin-3-ylidene)methyl)phenyl)-6,7-dihydro-5H-benzo[7]annulene-3-carboxylic acid, 8-(2,4-dichlorophenyl)-9-(4-((1-(3-fluoropropyl)azetidin-3-ylidene)methyl)phenyl)-6,7-dihydro-5H-benzo[7]annulen-3-ol, 8-(3,3-dimethylcyclohexyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-((trans)-2-phenylcyclopropyl)-6,7-dihydro-5H-benzo[7]annulene-3-carboxylic acid, 8-((1R,6S,7r)-bicyclo[4.1.0]heptan-7-yl)-9-(4-((1-(3-fluoropropyl)azetidin-3-ylidene)methyl)phenyl)-6,7-dihydro-5H-benzo[7]annulene-3-carboxylic acid, 8-(bicyclo[3.1.0]hexan-1-yl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(spiro[2.3]hexan-1-yl)-6,7-dihydro-5H-benzo[7]annulene-3-carboxylic acid, 9-(4-((1-(3-fluoropropyl)azetidin-3-ylidene)methyl)phenyl)-8-(5,6,7,8-tetrahydronaphthalen-1-yl)-6,7-dihydro-5H-benzo[7]annulene-3-carboxylic acid-(7-7), 8-(bicyclo[3.2.1]octan-3-yl)-9-(4-((1-(3-fluoropropyl)azetidin-3-ylidene)methyl)phenyl)-6,7-dihydro-5H-benzo[7]annulene-3-carboxylic acid, 8-(4-chlorophenyl)-9-(4-((1-(3-fluoropropyl)azetidin-3-ylidene)methyl)phenyl)-7-methyl-6,7-dihydro-5H-benzo[7]annulene-3-carboxylic acid, 8-(3-chlorophenyl)-9-(4-((1-(3-fluoropropyl)azetidin-3-ylidene)methyl)phenyl)-6,7-dihydro-5H-benzo[7]annulene-3-carboxylic acid, 8-(4-chlorophenyl)-9-(4-((1-(3-fluoropropyl)azetidin-3-ylidene)methyl)phenyl)-6,7-dihydro-5H-benzo[7]annulene-3-carboxylic acid, 9-(4-((1-(3-fluoropropyl)azetidin-3-ylidene)methyl)phenyl)-8-(3-(trifluoromethyl)phenyl)-6,7-dihydro-5H-benzo[7]annulene-3-carboxylic acid hydrochloride, 9-(4-((1-(3-fluoropropyl)azetidin-3-ylidene)methyl)phenyl)-8-(2-(trifluoromethyl)phenyl)-6,7-dihydro-5H-benzo[7]annulene-3-carboxylic acid hydrochloride, 9-(4-((1-(3-fluoropropyl)azetidin-3-ylidene)methyl)phenyl)-8-(4-(trifluoromethyl)phenyl)-6,7-dihydro-5H-benzo[7]annulene-3-carboxylic acid hydrochloride, 8-(3,3-dimethylcyclohexyl)-9-(3-fluoro-5-((1-(3-fluoropropyl)azetidin-3-ylidene)methyl)pyridin-2-yl)-6,7-dihydro-5H-benzo[7]annulene-3-carboxylic acid, 8-(trans-2-(4,4-difluorocyclohexyl)cyclopropyl)-9-(4-((1-(3-fluoropropyl)azetidin-3-ylidene)methyl)phenyl)-6,7-dihydro-5H-benzo[7]annulene-3-carboxylic acid, and 9-(3-fluoro-5-((1-(3-fluoropropyl)azetidin-3-ylidene)methyl)pyridin-2-yl)-8-(4-methylcyclohexyl)-6,7-dihydro-5H-benzo[7]annulene-3-carboxylic acid.

21. A compound of formula 1F, or a pharmaceutically acceptable salt thereof,

1F

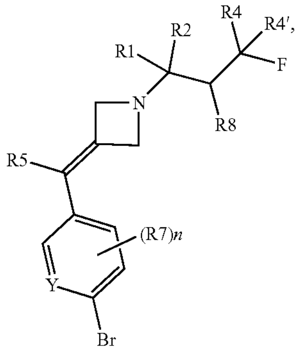

wherein R1, R2, R4, R4', R5, R7, R8, Y and n are as defined in claim 1.

22. A process for preparing the compound of formula (I) according to claim 1, or a pharmaceutically acceptable salt thereof, wherein a compound of formula 1K

1K

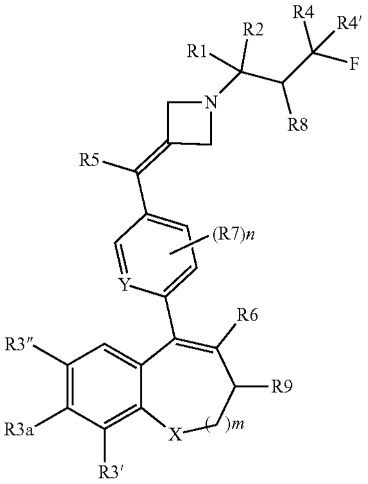

wherein R1, R2, R3', R3", R4, R4', R5, R6, R7, R8, R9, m, n, X and Y are as defined in claim 1 and R3a is a carboxylic ester or a protected OH, is converted to the compound of formula (I) in a first step, in the presence of a source of hydroxide ions, said first step being optionally preceded by a step for obtaining compound 1K, wherein a compound of formula 1T

1T

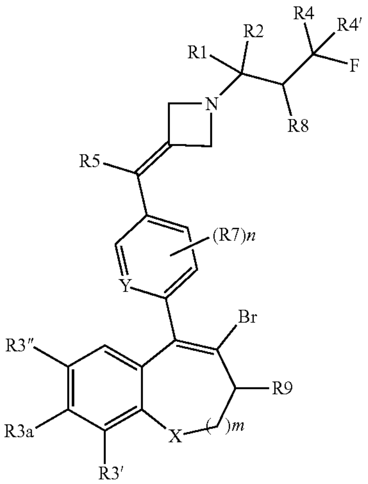

wherein R1, R2, R3', R3", R4, R4', R5, R7, R8, R9, m, n, X and Y are as defined in claim 1 and R3a is as defined above, is subjected to a Suzuki coupling with a boronic reagent $R6B(OR')_2$ or $R6BF_3K$, wherein $—B(OR')_2$ is a boronic acid or a pinacolate ester and R6 is as defined in claim 1.

23. A pharmaceutical composition comprising a compound of formula (I) according to claim 1, or a pharmaceutically acceptable salt thereof, and at least one pharmaceutically acceptable excipient.

24. A method of inhibiting and/or degrading an estrogen receptor, comprising administering to a subject in need thereof a compound of formula (I) according to claim 1, or a pharmaceutically acceptable salt thereof.

25. A method of treating a disease or condition, comprising administering to the subject a compound of formula (I) according to claim 1, or a pharmaceutically acceptable salt thereof, wherein the disease or condition is chosen from ovulatory dysfunction, cancer, endometriosis, osteoporosis, benign prostatic hypertrophy and inflammation.

26. The method according to claim 25, wherein the disease or condition is cancer.

* * * * *